(12) United States Patent
Brennan et al.

(10) Patent No.: US 8,129,117 B2
(45) Date of Patent: Mar. 6, 2012

(54) GENETIC MARKERS FOR ASSESSING RISK OF DEVELOPING BIPOLAR DISORDER

(75) Inventors: Mark David Brennan, Jeffersonville, IN (US); Timothy Lynn Ramsey, Shelbyville, KY (US)

(73) Assignee: SureGene LLC, Louisville, KY (US)

( * ) Notice: Subject to any disclaimer, the term of this patent is extended or adjusted under 35 U.S.C. 154(b) by 0 days.

(21) Appl. No.: 12/612,521

(22) Filed: Nov. 4, 2009

(65) Prior Publication Data
US 2010/0120046 A1    May 13, 2010

Related U.S. Application Data

(63) Continuation of application No. PCT/US2009/058459, filed on Sep. 25, 2009.

(60) Provisional application No. 61/100,176, filed on Sep. 25, 2008.

(51) Int. Cl.
C12Q 1/68    (2006.01)
C07H 21/04    (2006.01)
C12P 19/34    (2006.01)

(52) U.S. Cl. ............ 435/6.11; 536/24.3; 435/91.2

(58) Field of Classification Search .......... None
See application file for complete search history.

(56) References Cited

FOREIGN PATENT DOCUMENTS
WO    2006-072075    7/2006

OTHER PUBLICATIONS

Zuchner (Genetics in Medicine (2007) vol. 9, pp. 332-340).*
Le-Niculescu et al (Curent opinion in Pharamacology (2010) vol. 10, pp. 594-600).*
DB SNP rs22991100 (reproduced below (http://www.ncbi.nlm.nih.gov/projects/SNP/snp_ref.cgi?rs=2291100, downloaded Sep. 2, 2011).*
Braff et al., "Advances in endophenotyping schizophrenia," World Psychiatry, vol. 7(1), pp. 11-18 (2008).
Liu et al., "HTF9C gene of 22q11.21 region associates with schizophrenia having deficit-sustained attention," Psychiatr. Genet., vol. 17(6), pp. 333-338 (2007).
Pinhiero et al., "AKT1 and neurocognition in schizophrenia," Aust. N.Z.J. Psychiatry, vol. 41(2), pp. 169-177 (2007).
Stephens et al., "Association of the 5'-upstream regulatory region of the alpha7 nicotinic acetylcholine receptor subunit gene (CHRNA7) with schizophrenia," Schizophr. Res., vol. 109(1-3), pp. 102-112, Epub. (2009).
O'Donovan et al., "Identification of loci associated with schizophrenia by genome-wide association and follow-up," Nat. Genet., 40(9):1053-1055 (2008).
International Search Report issued in PCT/US2009/058459 on Aug. 24, 2010.
International Search Report issued in PCT/US2009/058487 on Aug. 13, 2010.
International Search Report issued in PCT/US2009/058483 on Aug. 13, 2010.

* cited by examiner

*Primary Examiner* — Steven Pohnert
(74) *Attorney, Agent, or Firm* — Fish & Richardson P.C.

(57) ABSTRACT

This document provides methods and materials related to genetic markers of Bipolar Disorder (BD) and Schizophrenia (SZ). For example, methods for using such genetic markers to assess risk of developing BD and/or SZ are provided, as are methods for making a differential diagnosis between BD and SZ.

17 Claims, No Drawings

GENETIC MARKERS FOR ASSESSING RISK OF DEVELOPING BIPOLAR DISORDER

CLAIM OF PRIORITY

This application is a continuation of International Patent Application No. PCT/US2009/058459, filed Sep. 25, 2009, which claims the benefit of U.S. Provisional Application Ser. No. 61/100,176, filed on Sep. 25, 2008, which are incorporated by reference in their entirety herein.

FEDERALLY SPONSORED RESEARCH OR DEVELOPMENT

This invention was made with government support under Grant No. R43 MH078437 awarded by the National Institutes of Health. The government has certain rights in the invention.

TECHNICAL FIELD

This invention relates to genetic markers of Bipolar Disorder (BD). For example, this document provides methods of using such genetic markers for assessing risk of developing BD.

BACKGROUND

The schizophrenia spectrum disorders include schizophrenia (SZ), schizotypal personality disorder (SPD), and schizoaffective disorder (SD). Schizophrenia (SZ) is considered a clinical syndrome, and is probably a constellation of several pathologies. Substantial heterogeneity is seen between cases, which is thought to reflect multiple overlapping etiologic factors, including both genetic and environmental contributions. SD is characterized by the presence of affective (depressive or manic) symptoms and schizophrenic symptoms within the same, uninterrupted episode of illness. SPD is characterized by a pervasive pattern of social and interpersonal deficits marked by acute discomfort with, and reduced capacity for, close relationships as well as by cognitive or perceptual distortions and eccentricities of behavior, beginning by early adulthood and present in a variety of contexts.

Bipolar Disorder (BD), which is also known as manic-depression or manic-depressive disorder, is characterized by mood that alternates between two emotional extremes, or poles: the sadness of depression and the euphoria of mania. BD includes the following clinical disorders: Bipolar I disorder, Bipolar II disorder, Bipolar mania, and Bipolar depression.

Both schizophrenia and bipolar disorder can be classified as psychotic disorders. Indeed, BD and SZ are clinical classifications rather than actual diseases. The two diagnoses share many common features, with BD subjects often suffering in particular from extensive delusions similar to those seen in SZ. Similarly, SZ patients often have substantial affective symptoms such as mania and depression. Indeed, BD and SZ can be considered two ends of a continuum of mental illness, with BD diagnosis focused more on affective symptoms (e.g., mania and depression) and SZ more focus on positive symptoms (e.g., hallucinations). The diagnosis given to a patient often depends on the symptoms presented at time of diagnosis, which may or may not reflect the full extent of that patient's disease.

Differential diagnosis represents a tremendous area of unmet medical need. One area in particular in which this unmet need is evident is choice of medication. Two prime examples are the use of SSRI antidepressants to treat affective symptoms in SZ (which would be counter-indicated in patients with a high BD vs SZ index) and antipsychotic treatment for some BD subjects. Other examples could include the addition of cognitive enhancers for subjects diagnosed with BD but scoring high for diagnosis of SZ vs BD.

Various genes and chromosomes have been implicated in etiology of SZ and BD. Many studies have suggested the presence of one or more important genes relating to SZ and BD on most or all of the autosomes (Williams et al., *Hum. Mol. Genet.* 8:1729-1739 (1999); Middleton et al., *Am. J. Hum. Genet.* 74:886-897 (2004); Matsuoka et al., *Synapse* 62:1-7 (2008); Fallin et al., *Am. J. Hum. Genet.* 77:918-936 (2005); Sklar et al., *Mol. Psychiatry* 13:558-569 (2008); Sun et al., *Am. J. Med. Genet. B Neuropsychiatr. Genet.* (2008); Badner et al., *Mol. Psychiatry* 7:405-411 (2002); Bennett et al., *Mol. Psychiatry* 7:189-200 (2002); Cooper-Casey et al., *Mol. Psychiatry* 10:651-656 (2005); Devlin et al., *Mol. Psychiatry* 7:689-694 (2002); Fallin et al., *Am. J. Hum. Genet.* 73:601-611 (2003); Ginns et al., *Proc. Natl. Acad. Sci. U.S.A* 95:15531-15536 (1998); Jablensky, *Mol. Psychiatry* (2006); Kirov et al., *J. Clin. Invest.* 115:1440-1448 (2005); Norton et al., *Curr. Opin. Psychiatry* 19:158-164 (2006); Owen et al., *Mol. Psychiatry* 9:14-27 (2004)) However, none of these prior studies have used high resolution genetic association methods to systematically compare genes involved in psychosis, SZ and BD. Neither have any of these studies demonstrated that genetic polymorphisms in the genes defined herein are important, in particular in the genetic etiology of psychosis, or BD.

Due to the severity of these disorders, especially the negative impact of a psychotic episode on a patient, and the diminishing recovery after each psychotic episode, there is a need to more conclusively identify individuals who have or are at risk of developing bipolar disorder (BD) or schizophrenia spectrum disorders in order to, for example, confirm clinical diagnoses, allow for prophylactic therapies, determine optimal therapies, and provide genetic counseling for prospective parents with a personal or family history of the disorder.

SUMMARY

This disclosure provides methods for identifying subjects who have or are at risk of developing psychosis, as well as making a differential diagnosis in subjects suspected of having either bipolar disorder (BD) or a schizophrenia spectrum disorder (SSD), e.g., SZ, based on detecting genetic variants in genes involved in a number of pathways including: glutamate signaling and metabolism, cell adhesion, cytoskeletal architecture, vesicle formation, and trafficking, G-protein coupled receptors, carrier proteins and transporters, cell cycle modulators, neuronal development, calcium/calmodulin signaling, neuropeptide signaling, and several additional genes identified by virtue of their interaction with genes in high impact pathways and their expression in the central nervous system. This disclosure also provides methods and materials relating to determining the genetic risk of developing BD. For example, the allelic and genotypic variants identified as described herein can be used for assessing genetic risk of BD or for making a differential diagnosis between BD and SZ. Specifically, the invention includes methods based on evaluation of SNPs for genes relating to psychosis or BD.

In one aspect, this document features methods for making a differential diagnosis between bipolar disorder (BD) and schizophrenia (SZ) in a human subject. The methods can include determining the identity of at least one allele of a single nucleotide polymorphism (SNP) listed in Table 1 and comparing the identity of the allele in the subject with a reference allele, wherein the reference allele is either an allele associated with BD (OR>1) or an allele associated with SZ (OR<1); and wherein the presence of an allele in the subject that is the same as a reference allele that is associated with BD indicates that the subject has an increased risk of developing BD, and the presence of an allele in the subject that is the same as a reference allele that is associated with SZ indicates that the subject has an increased risk of developing SZ. The SNP can be selected from the group consisting of SEQ ID NO:2701, 154, 2409, 371, 378, 515, 509, 2878, 576, and 957.

In another aspect, this document features methods for diagnosing, or determining risk of developing, psychosis, e.g., psychosis associated with bipolar disorder (BD) or schizophrenia (SZ), in a human subject. The methods can include determining the identity of at least one allele of a SNP listed in Table 2 and comparing the identity of the allele in the subject with a reference allele, wherein the reference allele is associated with psychosis; and wherein the presence of an allele in the subject that the same as the reference allele indicates that the subject has psychosis or has an increased risk of developing psychosis. The SNP can be selected from the group consisting of SEQ ID NOs: 906, 2591, 1285, 904, 951, 50, 1127, 112, and 268. Determining the identity of an allele can include obtaining a sample comprising DNA from the subject, and determining identity of the nucleotide at the polymorphic site. Determining the identity of the nucleotide can include contacting the sample with a probe specific for a selected allele of the polymorphism. Determining also can include detecting the formation of complexes between the probe and the selected allele of the polymorphism, wherein the formation of complexes between the probe and the test marker indicates the presence of the selected allele in the sample. Determining the identity of an allele can comprise determining the identity of the nucleotide at position 31 of one of SEQ ID NOs: 1-3141.

The subject can be a patient (i.e., a human patient) having or suspected of having BD or SZ. The subject can have one or more risk factors associated with BD or SZ. The risk factors associated with BD or SZ can include one or more of: a relative afflicted with BD or SZ; and a genetically based phenotypic trait associated with risk for a BD or SZ. The subject can have exhibited or presently be exhibiting symptoms of psychosis. The methods can further include selecting or excluding a subject for enrollment in a clinical trial based on the identity of the allele. The methods can further include stratifying a subject population for analysis of a clinical trial based on the identity of the allele in the subjects. The methods can further include confirming a diagnosis of a SZ or BD using psychometric instruments. The methods can further comprise selecting a treatment for BD if the allele in the subject is the same as a reference allele in a subject who has BD, or selecting a treatment for SZ if an allele in the subject is the same as a reference allele in a subject who has SZ. The methods can further include administering the selected treatment to the subject. In some embodiments, the treatment is a standard treatment for BD or SZ, e.g., a pharmaceutical treatment or psychotherapy.

The methods can further include recording the identity of the allele in a tangible medium. The tangible medium can comprise a computer-readable disk, a solid state memory device, or an optical storage device.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

This document provides methods for assessing genetic risk for developing bipolar disorder and/or schizophrenia (SZ) based on evaluation of single nucleotide polymorphisms (SNPs). As described herein, bioinformatic and genetic analyses provided evidence of association of the disclosed SNPs and genotypes with these disorders. Specific allelic and genotypic variants identified herein can be used to assess genetic risk and to assist with differential diagnosis.

Definitions

As used herein, an "allele" is one of a pair or series of genetic variants of a polymorphism at a specific genomic location. A "BD risk allele" is an allele that is associated with increased risk of developing BD. A "BD allele" is an allele that is statistically more often associated with BD than with SZ in patients with psychosis. An "SZ allele" is an allele that is statistically more often associated with SZ than with BD in patients with psychosis. For example, using Table 1, Those SNPs that are high (OR>1) are BD alleles by this definition. Those that are low (OR<1) would be SZ alleles by this definition As used herein, "genotype" refers to the diploid combination of alleles for a given genetic polymorphism. A homozygous subject carries two copies of the same allele and a heterozygous subject carries two different alleles.

As used herein, "genetic model" refers to the manner in which an allele influences risk or differential diagnosis. In a "dominant model" the allele impacts the clinical state to the same extent whether present in one copy or two copies, i.e. whether homozygous or heterozygous. In a "recessive model" the allele impacts the clinical state only when homozygous. In an "additive model" the allele impacts the clinical state in proportion to the number of copies present, i.e. the homozygous state has twice the impact of the heterozygous state.

As used herein, a "haplotype" is one or a set of signature genetic changes (polymorphisms) that are normally grouped closely together on the DNA strand, and are usually inherited as a group; the polymorphisms are also referred to herein as "markers." A "haplotype" as used herein is information regarding the presence or absence of one or more genetic markers in a given chromosomal region in a subject. A haplotype can consist of a variety of genetic markers, including indels (insertions or deletions of the DNA at particular locations on the chromosome); single nucleotide polymorphisms (SNPs) in which a particular nucleotide is changed; microsatellites; and minisatellites.

Microsatellites (sometimes referred to as a variable number of tandem repeats or VNTRs) are short segments of DNA that have a repeated sequence, usually about 2 to 5 nucleotides long (e.g., CACACA), that tend to occur in non-coding DNA. Changes in the microsatellites sometimes occur during the genetic recombination of sexual reproduction, increasing or decreasing the number of repeats found at an allele, changing the length of the allele. Microsatellite markers are stable, polymorphic, easily analyzed and occur regularly throughout the genome, making them especially suitable for genetic analysis.

"Copy number variation" (CNV), as used herein, refers to variation from the normal diploid condition for a gene or polymorphism. Individual segments of human chromosomes can be deleted or duplicated such that the subject's two chromosome carry fewer than two copies of the gene or polymorphism (a deletion or deficiency) or two or more copies (a duplication).

"Linkage disequilibrium" refers to when the observed frequencies of haplotypes in a population does not agree with haplotype frequencies predicted by multiplying together the frequency of individual genetic markers in each haplotype.

The term "chromosome" as used herein refers to a gene carrier of a cell that is derived from chromatin and comprises DNA and protein components (e.g., histones). The conventional internationally recognized individual human genome chromosome numbering identification system is employed herein. The size of an individual chromosome can vary from one type to another with a given multi-chromosomal genome and from one genome to another. In the case of the human genome, the entire DNA mass of a given chromosome is usually greater than about 100,000,000 base pairs. For example, the size of the entire human genome is about $3\times10^9$ base pairs.

The term "gene" refers to a DNA sequence in a chromosome that codes for a product (either RNA or its translation product, a polypeptide). A gene contains a coding region and includes regions preceding and following the coding region (termed respectively "leader" and "trailer"). The coding region is comprised of a plurality of coding segments ("exons") and intervening sequences ("introns") between individual coding segments.

The term "probe" refers to an oligonucleotide. A probe can be single stranded at the time of hybridization to a target. As used herein, probes include primers, i.e., oligonucleotides that can be used to prime a reaction, e.g., a PCR reaction.

The term "label" or "label containing moiety" refers in a moiety capable of detection, such as a radioactive isotope or group containing same, and nonisotopic labels, such as enzymes, biotin, avidin, streptavidin, digoxygenin, luminescent agents, dyes, haptens, and the like. Luminescent agents, depending upon the source of exciting energy, can be classified as radioluminescent, chemiluminescent, bioluminescent, and photoluminescent (including fluorescent and phosphorescent). A probe described herein can be bound, e.g., chemically bound to label-containing moieties or can be suitable to be so bound. The probe can be directly or indirectly labeled.

The term "direct label probe" (or "directly labeled probe") refers to a nucleic acid probe whose label after hybrid formation with a target is detectable without further reactive processing of hybrid. The term "indirect label probe" (or "indirectly labeled probe") refers to a nucleic acid probe whose label after hybrid formation with a target is further reacted in subsequent processing with one or more reagents to associate therewith one or more moieties that finally result in a detectable entity.

The terms "target," "DNA target," or "DNA target region" refers to a nucleotide sequence that occurs at a specific chromosomal location. Each such sequence or portion is preferably at least partially, single stranded (e.g., denatured) at the time of hybridization. When the target nucleotide sequences are located only in a single region or fraction of a given chromosome, the term "target region" is sometimes used.

Targets for hybridization can be derived from specimens which include, but are not limited to, chromosomes or regions of chromosomes in normal, diseased or malignant human cells, either interphase or at any state of meiosis or mitosis, and either extracted or derived from living or postmortem tissues, organs or fluids; germinal cells including sperm and egg cells, or cells from zygotes, fetuses, or embryos, or chorionic or amniotic cells, or cells from any other germinating body; cells grown in vitro, from either long-term or short-term culture, and either normal, immortalized or transformed; inter- or intraspecific hybrids of different types of cells or differentiation states of these cells; individual chromosomes or portions of chromosomes, or translocated, deleted or other damaged chromosomes, isolated by any of a number of means known to those with skill in the art, including libraries of such chromosomes cloned and propagated in prokaryotic or other cloning vectors, or amplified in vitro by means well known to those with skill; or any forensic material, including but not limited to blood, or other samples.

The term "hybrid" refers to the product of a hybridization procedure between a probe and a target.

The term "hybridizing conditions" has general reference to the combinations of conditions that are employable in a given hybridization procedure to produce hybrids, such conditions typically involving controlled temperature, liquid phase, and contact between a probe (or probe composition) and a target. Conveniently and preferably, at least one denaturation step precedes a step wherein a probe or probe composition is contacted with a target. Guidance for performing hybridization reactions can be found in Ausubel et al., *Current Protocols in Molecular Biology*, John Wiley & Sons, N.Y. (2003), 6.3.1-6.3.6. Aqueous and nonaqueous methods are described in that reference and either can be used. Hybridization conditions referred to herein are a 50% formamide, 2×SSC wash for 10 minutes at 45° C. followed by a 2×SSC wash for 10 minutes at 37° C.

Calculations of "identity" between two sequences can be performed as follows. The sequences are aligned for optimal comparison purposes (e.g., gaps can be introduced in one or both of a first and a second nucleic acid sequence for optimal alignment and non-identical sequences can be disregarded for comparison purposes). The length of a sequence aligned for comparison purposes is at least 30% (e.g., at least 40%, 50%, 60%, 70%, 80%, 90% or 100%) of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In some embodiments, the percent identity between two nucleotide sequences is determined using the GAP program in the GCG software package, using a Blossum 62 scoring matrix with a gap penalty of 12, a gap extend penalty of 4, and a frameshift gap penalty of 5.

As used herein, the term "substantially identical" is used to refer to a first nucleotide sequence that contains a sufficient number of identical nucleotides to a second nucleotide sequence such that the first and second nucleotide sequences have similar activities. Nucleotide sequences that are substantially identical are at least 80% (e.g., 85%, 90%, 95%, 97% or more) identical.

The term "nonspecific binding DNA" refers to DNA which is complementary to DNA segments of a probe, which DNA occurs in at least one other position in a genome, outside of a selected chromosomal target region within that genome. An example of nonspecific binding DNA comprises a class of DNA repeated segments whose members commonly occur in more than one chromosome or chromosome region. Such common repetitive segments tend to hybridize to a greater extent than other DNA segments that are present in probe composition.

As used herein, the term "stratification" refers to the creation of a distinction between subjects on the basis of a characteristic or characteristics of the subjects. Generally, in the context of clinical trials, the distinction is used to distinguish responses or effects in different sets of patients distinguished according to the stratification parameters. In some embodiments, stratification includes distinction of subject groups based on the presence or absence of particular alleles or genotypes described herein. The stratification can be performed, e.g., in the course of analysis, or can be used in creation of distinct groups or in other ways.

Methods of Differential Diagnosis (BD vs SZ) and Evaluation of Risk of Developing BD+SZ Described herein are a variety of methods for the diagnosis or determination of susceptibility to BD and SZ. "Susceptibility" does not necessarily mean that the subject will develop BD or SZ, but rather that the subject is, in a statistical sense, more likely to develop BD or SZ than an average member of the population (i.e., has an increased risk of developing BD or SZ). As used herein, susceptibility to BD or SZ exists if the subject has an allele or genotype associated with an increased risk of BD or SZ as described herein. Ascertaining whether the subject has such an allele or genotype is included in the concept of diagnosing susceptibility to BD or SZ as used herein. Such determination is useful, for example, for purposes of genetic counseling. Thus, the methods described herein can include obtaining a genotype associated with an increased risk of BD or SZ as described herein for the subject.

Additionally described herein are a variety of methods for the differential diagnosis of BD versus SZ. Differential diagnosis in this context means increased or decreased likelihood of being diagnosed with BD instead of SZ. Differential diagnosis does not necessarily mean that the subject will develop BD, but rather that the subject, in a statistical sense, has an increased or decreased likelihood of being diagnosed with BD instead of SZ. As used herein, differential diagnosis of BD exists if the subject has an allele or genotype associated with an increased or decreased likelihood of being diagnosed with BD versus SZ, as described herein. Ascertaining whether the subject has such an allele or genotype is included in the concept of differential diagnosis for BD and/or SZ as used herein. Such determination is useful, for example, for purposes of genetic counseling or selecting appropriate first line therapy. Thus, the methods described herein can include detecting the presence or identity of an allele or genotype associated with an increased or decreased likelihood of being diagnosed with BD and/or SZ as described herein for the subject. In some embodiments, the subject is exhibiting or has exhibited symptoms associate with psychosis.

As used herein, "determining the identity of an allele" includes obtaining information regarding the identity, presence or absence of one or more specific alleles in a subject. Determining the identity of an allele can, but need not, include obtaining a sample comprising DNA from a subject, and/or assessing the identity, presence or absence of one or more genetic markers in the sample. The individual or organization who determines the identity of the allele need not actually carry out the physical analysis of a sample from a subject; the methods can include using information obtained by analysis of the sample by a third party. Thus the methods can include steps that occur at more than one site. For example, a sample can be obtained from a subject at a first site, such as at a health care provider, or at the subject's home in the case of a self-testing kit. The sample can be analyzed at the same or a second site, e.g., at a laboratory or other testing facility.

Determining the identity of an allele can also include or consist of reviewing a subject's medical history, where the medical history includes information regarding the identity, presence or absence of one or more response alleles in the subject, e.g., results of a genetic test.

In some embodiments, to determine the identity of an allele or presence/absence of an allele or genotype described herein, a biological sample that includes nucleated cells (such as blood, a cheek swab or mouthwash) is prepared and analyzed for the presence or absence of preselected markers. Such diagnoses may be performed by diagnostic laboratories, or, alternatively, diagnostic kits can be manufactured and sold to health care providers or to private individuals for self-diagnosis. Diagnostic or prognostic tests can be performed as described herein or using well known techniques, such as described in U.S. Pat. No. 5,800,998.

Results of these tests, and optionally interpretive information, can be returned to the subject, the health care provider or to a third party payor. The results can be used in a number of ways. The information can be, e.g., communicated to the tested subject, e.g., with a prognosis and optionally interpretive materials that help the subject understand the test results and prognosis. The information can be used, e.g., by a health care provider, to determine whether to administer a specific drug, or whether a subject should be assigned to a specific category, e.g., a category associated with a specific disease endophenotype, or with drug response or non-response. The information can be used, e.g., by a third party payor such as a healthcare payer (e.g., insurance company or HMO) or other agency, to determine whether or not to reimburse a health care provider for services to the subject, or whether to approve the provision of services to the subject. For example, the healthcare payer may decide to reimburse a health care provider for treatments for BD if the subject has BD or has an increased risk of developing BD. The presence or absence of the allele or genotype in a patient may be ascertained by using any of the methods described herein.

Alleles and Genotypes Associated with BD and SZ, or BD vs SZ

This document provides methods for assessing genetic risk based on evaluation of single nucleotide polymorphisms (SNPs) for genes relating to risk of developing Bipolar Disorder (BD) or differential diagnosis between BD and SZ. Tables 1-2 and Table A list exemplary SNPs that can be used in the present methods. One of skill in the art will appreciate that additional variants can be identified via TDT using families with multiple affected individuals and verified by Case/Control comparisons, e.g., using the methods and markers described herein. Using the SNP markers described herein, one can determine the alleles, genotypes or haplotypes in these genes relating to diagnosis or genetic risk of developing BD and/or SZ. These alleles and genotypes can then be used to determine risk of developing BD and SZ, or for making a differential diagnosis between BD and SZ. The allelic and genotypic variants thus identified can be used for diagnosis and for assessing genetic risk.

Markers in Linkage disequilibrium (LD)

Linkage disequilibrium (LD) is a measure of the degree of association between alleles in a population. One of skill in the art will appreciate that alleles involving markers in LD with the polymorphisms described herein can also be used in a similar manner to those described herein. Methods of calculating LD are known in the art (see, e.g., Morton et al., *Proc. Natl. Acad. Sci. USA* 98(9):5217-21 (2001); Tapper et al., *Proc. Natl. Acad. Sci. USA* 102(33):11835-11839 (2005); Maniatis et al., *Proc. Natl. Acad. Sci. USA* 99:2228-2233 (2002)). Thus, in some cases, the methods can include analysis of polymorphisms that are in LD with a polymorphism described herein. Methods are known in the art for identifying such polymorphisms; for example, the International HapMap Project provides a public database that can be used, see hapmap.org, as well as The International HapMap Consortium, *Nature* 426:789-796 (2003), and The International HapMap Consortium, *Nature* 437:1299-1320 (2005). Generally, it will be desirable to use a HapMap constructed using data from individuals who share ethnicity with the subject. For example, a HapMap for African Americans would ideally be used to identify markers in LD with an exemplary marker described herein for use in genotyping a subject of African American descent.

Alternatively, methods described herein can include analysis of polymorphisms that show a correlation coefficient ($r^2$) of value $\geq 0.5$ with the markers described herein. Results can be obtained from on line public resources such as HapMap.org on the World Wide Web. The correlation coefficient is a measure of LD, and reflects the degree to which alleles at two loci (for example, two SNPs) occur together, such that an allele at one SNP position can predict the correlated allele at a second SNP position, in the case where $r^2$ is >0.5.

Identifying Additional Genetic Markers

In general, genetic markers can be identified using any of a number of methods well known in the art. For example, numerous polymorphisms in the regions described herein are known to exist and are available in public databases, which can be searched using methods and algorithms known in the art. Alternately, polymorphisms can be identified by sequencing either genomic DNA or cDNA in the region in which it is desired to find a polymorphism. According to one approach, primers are designed to amplify such a region, and DNA from a subject is obtained and amplified. The DNA is sequenced, and the sequence (referred to as a "subject sequence" or "test sequence") is compared with a reference sequence, which can represent the "normal" or "wild type" sequence, or the "affected" sequence. In some embodiments, a reference sequence can be from, for example, the human draft genome sequence, publicly available in various databases, or a sequence deposited in a database such as GenBank. In some embodiments, the reference sequence is a composite of ethnically diverse individuals.

In general, if sequencing reveals a difference between the sequenced region and the reference sequence, a polymorphism has been identified. The fact that a difference in nucleotide sequence is identified at a particular site that determines that a polymorphism exists at that site. In most instances, particularly in the case of SNPs, only two polymorphic variants will exist at any location. However, in the case of SNPs, up to four variants may exist since there are four naturally occurring nucleotides in DNA. Other polymorphisms, such as insertions and deletions, may have more than four alleles.

The methods described herein can also include determining the presence or absence of other markers known or suspected to be associated with risk of BD and/or SZ, or differentially inherited in BD versus SZ. In some embodiments, the methods include determining the presence or absence of one or more other markers that are or may be associated with BD or SZ, e.g., in one or more genes, e.g., e.g., as described in WO 2009/092032, WO 2009/089120, WO 2009/082743, US2006/0177851, and US2009/0012371 incorporated herein in their entirety. See also, e.g., OMIM entry no. 181500 (SCZD).

Methods of Determining the Identity of an Allele or Obtaining a Genotype

The methods described herein include determining the identity, presence or absence of alleles or genotypes associated with diagnosis or risk of developing BD and/or SZ, or differentially associated with BD versus SZ. In some embodiments, an association with BD is determined by the statistical likelihood of the presence of an allele or genotype in an individual with BD, e.g., an unrelated individual or a first or second-degree relation of the subject, and optionally the statistical likelihood of the absence of the same allele or genotype in an unaffected reference individual, e.g., an unrelated individual or a first or second-degree relation of the subject. In some embodiments, a differential association with BD versus SZ is determined by the statistical likelihood of the presence of the same genotype in both the subject and an affected reference individual, e.g., an unrelated individual or a first or second-degree relation of the subject, and the absence of the genotype in an unaffected reference individual. For example, an association with BD versus SZ is determined by the statistical likelihood of the presence of an allele or genotype in an individual with BD and the statistical likelihood of the absence of the same allele or genotype in a reference individual affected with SZ; likewise, an association with SZ versus BD is determined by the statistical likelihood of the presence of an allele or genotype in an individual with SZ and the statistical likelihood of the absence of the same allele or genotype in a reference individual affected with BD. Thus the methods can include obtaining and analyzing a sample from a suitable reference individual.

Samples that are suitable for use in the methods described herein contain genetic material, e.g., genomic DNA (gDNA). Genomic DNA is typically extracted from biological samples such as blood or mucosal scrapings of the lining of the mouth, but can be extracted from other biological samples including urine or expectorant. The sample itself will typically consist of nucleated cells (e.g., blood or buccal cells) or tissue removed from the subject. The subject can be an adult, child, fetus, or embryo. In some embodiments, the sample is obtained prenatally, either from a fetus or embryo or from the mother (e.g., from fetal or embryonic cells in the maternal circulation). Methods and reagents are known in the art for obtaining, processing, and analyzing samples. In some embodiments, the sample is obtained with the assistance of a health care provider, e.g., to draw blood. In some embodiments, the sample is obtained without the assistance of a health care provider, e.g., where the sample is obtained non-invasively, such as a sample comprising buccal cells that is obtained using a buccal swab or brush, or a mouthwash sample.

In some cases, a biological sample may be processed for DNA isolation. For example, DNA in a cell or tissue sample can be separated from other components of the sample. Cells can be harvested from a biological sample using standard techniques known in the art. For example, cells can be harvested by centrifuging a cell sample and resuspending the pelleted cells. The cells can be resuspended in a buffered solution such as phosphate-buffered saline (PBS). After centrifuging the cell suspension to obtain a cell pellet, the cells can be lysed to extract DNA, e.g., gDNA. See, e.g., Ausubel et al., 2003, supra. The sample can be concentrated and/or purified to isolate DNA. All samples obtained from a subject, including those subjected to any sort of further processing, are considered to be obtained from the subject. Routine methods can be used to extract genomic DNA from a biological sample, including, for example, phenol extraction. Alternatively, genomic DNA can be extracted with kits such as the QIAamp® Tissue Kit (Qiagen, Chatsworth, Calif.) and the Wizard® Genomic DNA purification kit (Promega). Non-limiting examples of sources of samples include urine, blood, and tissue.

The absence or presence of an allele or genotype associated with BD and/or SZ as described herein can be determined using methods known in the art. For example, gel electrophoresis, capillary electrophoresis, size exclusion chromatography, sequencing, and/or arrays can be used to detect the presence or absence of the allele or genotype. Amplification of nucleic acids, where desirable, can be accomplished using methods known in the art, e.g., PCR. In one example, a sample (e.g., a sample comprising genomic DNA), is obtained from a subject. The DNA in the sample is then examined to identify or detect the presence of an allele or genotype as described herein. The allele or genotype can be identified or determined by any method described herein, e.g., by sequencing or by hybridization of the gene in the genomic DNA, RNA, or cDNA to a nucleic acid probe, e.g., a DNA probe (which includes cDNA and oligonucleotide probes) or an RNA probe. The nucleic acid probe can be designed to specifically or preferentially hybridize with a particular polymorphic variant.

Other methods of nucleic acid analysis can include direct manual sequencing (Church and Gilbert, *Proc. Natl. Acad. Sci. USA* 81:1991-1995 (1988); Sanger et al., *Proc. Natl. Acad. Sci. USA* 74:5463-5467 (1977); Beavis et al., U.S. Pat. No. 5,288,644); automated fluorescent sequencing; single-stranded conformation polymorphism assays (SSCP) (Schafer et al., *Nat. Biotechnol.* 15:33-39 (1995)); clamped denaturing gel electrophoresis (CDGE); two-dimensional gel electrophoresis (2DGE or TDGE); conformational sensitive gel electrophoresis (CSGE); denaturing gradient gel electrophoresis (DGGE) (Sheffield et al., *Proc. Natl. Acad. Sci. USA* 86:232-236 (1989)); denaturing high performance liquid chromatography (DHPLC, Underhill et al., *Genome Res.* 7:996-1005 (1997)); infrared matrix-assisted laser desorption/ionization (IR-MALDI) mass spectrometry (WO 99/57318); mobility shift analysis (Orita et al., *Proc. Natl. Acad. Sci. USA* 86:2766-2770 (1989)); restriction enzyme analysis (Flavell et al., *Cell* 15:25 (1978); Geever et al., *Proc. Natl. Acad. Sci. USA* 78:5081 (1981)); quantitative real-time PCR (Raca et al., *Genet Test* 8(4):387-94 (2004)); heteroduplex analysis; chemical mismatch cleavage (CMC) (Cotton et al., *Proc. Natl. Acad. Sci. USA* 85:4397-4401 (1985)); RNase protection assays (Myers et al., *Science* 230:1242 (1985)); use of polypeptides that recognize nucleotide mismatches, e.g., *E. coli* mutS protein; allele-specific PCR, and combinations of such methods. See, e.g., Gerber et al., U.S. Patent Publication No. 2004/0014095 which is incorporated herein by reference in its entirety.

Sequence analysis can also be used to detect specific polymorphic variants. For example, polymorphic variants can be detected by sequencing exons, introns, 5' untranslated sequences, or 3' untranslated sequences. A sample comprising DNA or RNA is obtained from the subject. PCR or other appropriate methods can be used to amplify a portion encompassing the polymorphic site, if desired. The sequence is then ascertained, using any standard method, and the presence of a polymorphic variant is determined. Real-time pyrophosphate DNA sequencing is yet another approach to detection of polymorphisms and polymorphic variants (Alderborn et al., *Genome Research* 10(8):1249-1258 (2000)). Additional methods include, for example, PCR amplification in combination with denaturing high performance liquid chromatography (dHPLC) (Underhill et al., *Genome Research* 7(10): 996-1005 (1997)).

In order to detect polymorphisms and/or polymorphic variants, it will frequently be desirable to amplify a portion of genomic DNA (gDNA) encompassing the polymorphic site. Such regions can be amplified and isolated by PCR using oligonucleotide primers designed based on genomic and/or cDNA sequences that flank the site. PCR refers to procedures in which target nucleic acid (e.g., genomic DNA) is amplified in a manner similar to that described in U.S. Pat. No. 4,683, 195, and subsequent modifications of the procedure described therein. Generally, sequence information from the ends of the region of interest or beyond are used to design oligonucleotide primers that are identical or similar in sequence to opposite strands of a potential template to be amplified. See e.g., *PCR Primer: A Laboratory Manual*, Dieffenbach and Dveksler, (Eds.); McPherson et al., *PCR Basics: From Background to Bench* (Springer Verlag, 2000); Mattila et al., *Nucleic Acids Res.*, 19:4967 (1991); Eckert et al., *PCR Methods and Applications*, 1:17 (1991); PCR (eds. McPherson et al., IRL Press, Oxford); and U.S. Pat. No. 4,683,202. Other amplification methods that may be employed include the ligase chain reaction (LCR) (Wu and Wallace, *Genomics* 4:560 (1989), Landegren et al., *Science* 241:1077 (1988), transcription amplification (Kwoh et al., *Proc. Natl. Acad. Sci. USA* 86:1173 (1989)), self-sustained sequence replication (Guatelli et al., *Proc. Nat. Acad. Sci. USA* 87:1874 (1990)), and nucleic acid based sequence amplification (NASBA). Guidelines for selecting primers for PCR amplification are well known in the art. See, e.g., McPherson et al., *PCR Basics: From Background to Bench*, Springer-Verlag, 2000. A variety of computer programs for designing primers are available, e.g., 'Oligo' (National Biosciences, Inc, Plymouth Minn.), MacVector (Kodak/IBI), and the GCG suite of sequence analysis programs (Genetics Computer Group, Madison, Wis. 53711).

In some cases, PCR conditions and primers can be developed that amplify a product only when the variant allele is present or only when the wild type allele is present (MSPCR or allele-specific PCR). For example, patient DNA and a control can be amplified separately using either a wild type primer or a primer specific for the variant allele. Each set of reactions is then examined for the presence of amplification products using standard methods to visualize the DNA. For example, the reactions can be electrophoresed through an agarose gel and the DNA visualized by staining with ethidium bromide or other DNA intercalating dye. In DNA samples from heterozygous patients, reaction products would be detected in each reaction.

Real-time quantitative PCR can also be used to determine copy number. Quantitative PCR permits both detection and quantification of specific DNA sequence in a sample as an absolute number of copies or as a relative amount when normalized to DNA input or other normalizing genes. A key feature of quantitative PCR is that the amplified DNA product is quantified in real-time as it accumulates in the reaction after each amplification cycle. Methods of quantification can include the use of fluorescent dyes that intercalate with double-stranded DNA, and modified DNA oligonucleotide probes that fluoresce when hybridized with a complementary DNA. Methods of quantification can include determining the intensity of fluorescence for fluorescently tagged molecular probes attached to a solid surface such as a microarray.

The first report of extensive copy number variation (CNV) in the human genome used intensity analysis of microarray data to document numerous examples of genes that vary in copy number (Redon et al., Nature 444(7118):444-54 (2006)). Subsequent studies have shown that certain copy number variants are associated with complex genetic diseases such as SZ (Walsh et al., Science 320(5875):539-43 (2008); and Stone et al., Nature 455(7210):237-41 (2008)).

In some embodiments, a peptide nucleic acid (PNA) probe can be used instead of a nucleic acid probe in the hybridization methods described above. PNA is a DNA mimetic with a peptide-like, inorganic backbone, e.g., N-(2-aminoethyl)glycine units, with an organic base (A, G, C, T or U) attached to the glycine nitrogen via a methylene carbonyl linker (see, e.g., Nielsen et al., *Bioconjugate Chemistry*, The American Chemical Society, 5:1 (1994)). The PNA probe can be designed to specifically hybridize to a nucleic acid comprising a polymorphic variant conferring susceptibility to or indicative of the presence of SZ.

In some cases, allele-specific oligonucleotides can also be used to detect the presence of a polymorphic variant. For example, polymorphic variants can be detected by performing allele-specific hybridization or allele-specific restriction digests. Allele specific hybridization is an example of a method that can be used to detect sequence variants, including complete genotypes of a subject (e.g., a mammal such as a human). See Stoneking et al., *Am. J. Hum. Genet.* 48:370-382 (1991); and Prince et al., *Genome Res.* 11:152-162 (2001). An "allele-specific oligonucleotide" (also referred to herein as an "allele-specific oligonucleotide probe") is an oligonucleotide that is specific for particular a polymorphism can be prepared using standard methods (see Ausubel et al., *Current Protocols in Molecular Biology*, supra). Allele-specific oligonucleotide probes typically can be approximately 10-50 base pairs, preferably approximately 15-30 base pairs, that specifically hybridizes to a nucleic acid region that contains a polymorphism. Hybridization conditions are selected such that a nucleic acid probe can specifically bind to the sequence of interest, e.g., the variant nucleic acid sequence. Such hybridizations typically are performed under high stringency as some sequence variants include only a single nucleotide difference. In some cases, dot-blot hybridization of amplified oligonucleotides with allele-specific oligonucleotide (ASO) probes can be performed. See, for example, Saiki et al., *Nature* (London) 324:163-166 (1986).

In some embodiments, allele-specific restriction digest analysis can be used to detect the existence of a polymorphic variant of a polymorphism, if alternate polymorphic variants of the polymorphism result in the creation or elimination of a restriction site. Allele-specific restriction digests can be performed in the following manner. A sample containing genomic DNA is obtained from the individual and genomic DNA is isolated for analysis. For nucleotide sequence variants that introduce a restriction site, restriction digest with the particular restriction enzyme can differentiate the alleles. In some cases, polymerase chain reaction (PCR) can be used to amplify a region comprising the polymorphic site, and restriction fragment length polymorphism analysis is conducted (see Ausubel et al., *Current Protocols in Molecular Biology*, supra). The digestion pattern of the relevant DNA fragment indicates the presence or absence of a particular polymorphic variant of the polymorphism and is therefore indicative of the presence or absence of susceptibility to BD and/or SZ. For sequence variants that do not alter a common restriction site, mutagenic primers can be designed that introduce a restriction site when the variant allele is present or when the wild type allele is present. For example, a portion of a nucleic acid can be amplified using the mutagenic primer and a wild type primer, followed by digest with the appropriate restriction endonuclease.

In some embodiments, fluorescence polarization template-directed dye-terminator incorporation (FP-TDI) is used to determine which of multiple polymorphic variants of a polymorphism is present in a subject (Chen et al., *Genome Research* 9(5):492-498 (1999)). Rather than involving use of allele-specific probes or primers, this method employs primers that terminate adjacent to a polymorphic site, so that extension of the primer by a single nucleotide results in incorporation of a nucleotide complementary to the polymorphic variant at the polymorphic site.

In some cases, DNA containing an amplified portion may be dot-blotted, using standard methods (see Ausubel et al., *Current Protocols in Molecular Biology*, supra), and the blot contacted with the oligonucleotide probe. The presence of specific hybridization of the probe to the DNA is then detected. Specific hybridization of an allele-specific oligonucleotide probe (specific for a polymorphic variant indicative of susceptibility to BD and/or SZ) to DNA from the subject is indicative of susceptibility to BD and/or SZ.

The methods can include determining the genotype of a subject with respect to both copies of the polymorphic site present in the genome. For example, the complete genotype may be characterized as −/−, as −/+, or as +/+, where a minus sign indicates the presence of the reference or wild type sequence at the polymorphic site, and the plus sign indicates the presence of a polymorphic variant other than the reference sequence. If multiple polymorphic variants exist at a site, this can be appropriately indicated by specifying which ones are present in the subject. Any of the detection means described herein can be used to determine the genotype of a subject with respect to one or both copies of the polymorphism present in the subject's genome.

Methods of nucleic acid analysis to detect polymorphisms and/or polymorphic variants can include, e.g., microarray analysis. Hybridization methods, such as Southern analysis, Northern analysis, or in situ hybridizations, can also be used (see Ausubel et al., *Current Protocols in Molecular Biology*, eds., John Wiley & Sons (2003)). To detect microdeletions, fluorescence in situ hybridization (FISH) using DNA probes that are directed to a putatively deleted region in a chromosome can be used. For example, probes that detect all or a part of a microsatellite marker can be used to detect microdeletions in the region that contains that marker.

In some embodiments, it is desirable to employ methods that can detect the presence of multiple polymorphisms (e.g., polymorphic variants at a plurality of polymorphic sites) in parallel or substantially simultaneously. Oligonucleotide arrays represent one suitable means for doing so. Other methods, including methods in which reactions (e.g., amplification, hybridization) are performed in individual vessels, e.g., within individual wells of a multi-well plate or other vessel may also be performed so as to detect the presence of multiple polymorphic variants (e.g., polymorphic variants at a plurality of polymorphic sites) in parallel or substantially simultaneously according to certain embodiments.

Nucleic acid probes can be used to detect and/or quantify the presence of a particular target nucleic acid sequence within a sample of nucleic acid sequences, e.g., as hybridization probes, or to amplify a particular target sequence within a sample, e.g., as a primer. Probes have a complimentary nucleic acid sequence that selectively hybridizes to the target nucleic acid sequence. In order for a probe to hybridize to a target sequence, the hybridization probe must have sufficient identity with the target sequence, i.e., at least 70% (e.g., 80%, 90%, 95%, 98% or more) identity to the target sequence. The probe sequence must also be sufficiently long so that the probe exhibits selectivity for the target sequence over non-target sequences. For example, the probe will be at least 20 (e.g., 25, 30, 35, 50, 100, 200, 300, 400, 500, 600, 700, 800, 900 or more) nucleotides in length. In some embodiments, the probes are not more than 30, 50, 100, 200, 300, 500, 750, or 1000 nucleotides in length. Probes are typically about 20 to about $1 \times 10^6$ nucleotides in length. Probes include primers, which generally refers to a single-stranded oligonucleotide probe that can act as a point of initiation of template-directed DNA synthesis using methods such as PCR (polymerase chain reaction), LCR (ligase chain reaction), etc., for amplification of a target sequence.

The probe can be a test probe such as a probe that can be used to detect polymorphisms in a region described herein (e.g., polymorphisms as described herein). For example, the probe can hybridize to an allele described herein. In some embodiments, the probe can bind to another marker sequence associated with SZ, SPD, SD or BD as described herein.

Control probes can also be used. For example, a probe that binds a less variable sequence, e.g., repetitive DNA associated with a centromere of a chromosome, can be used as a control. Probes that hybridize with various centromeric DNA and locus-specific DNA are available commercially, for example, from Vysis, Inc. (Downers Grove, Ill.), Molecular Probes, Inc. (Eugene, Oreg.), or from Cytocell (Oxfordshire, UK). Probe sets are available commercially such from Applied Biosystems, e.g., the Assays-on-Demand SNP kits Alternatively, probes can be synthesized, e.g., chemically or in vitro, or made from chromosomal or genomic DNA through standard techniques. For example, sources of DNA that can be used include genomic DNA, cloned DNA sequences, somatic cell hybrids that contain one, or a part of one, human chromosome along with the normal chromosome complement of the host, and chromosomes purified by flow cytometry or microdissection. The region of interest can be isolated through cloning, or by site-specific amplification via the polymerase chain reaction (PCR). See, for example, Nath and Johnson, *Biotechnic. Histochem.* 73(1):6-22 (1998); Wheeless et al., *Cytometry* 17:319-326 (1994); and U.S. Pat. No. 5,491,224.

In some embodiments, the probes are labeled, e.g., by direct labeling, with a fluorophore, an organic molecule that fluoresces after absorbing light of lower wavelength/higher energy. A directly labeled fluorophore allows the probe to be visualized without a secondary detection molecule. After covalently attaching a fluorophore to a nucleotide, the nucleotide can be directly incorporated into the probe with standard techniques such as nick translation, random priming, and PCR labeling. Alternatively, deoxycytidine nucleotides within the probe can be transaminated with a linker. The fluorophore then is covalently attached to the transaminated deoxycytidine nucleotides. See, e.g., U.S. Pat. No. 5,491,224.

Fluorophores of different colors can be chosen such that each probe in a set can be distinctly visualized. For example, a combination of the following fluorophores can be used: 7-amino-4-methylcoumarin-3-acetic acid (AMCA), TEXAS RED™ (Molecular Probes, Inc., Eugene, Oreg.), 5-(and-6)-carboxy-X-rhodamine, lissamine rhodamine B, 5-(and-6)-carboxyfluorescein, fluorescein-5-isothiocyanate (FITC), 7-diethylaminocoumarin-3-carboxylic acid, tetramethylrhodamine-5-(and-6)-isothiocyanate, 5-(and-6)-carboxytetramethylrhodamine, 7-hydroxycoumarin-3-carboxylic acid, 6-[fluorescein 5-(and-6)-carboxamido]hexanoic acid, N-(4, 4-difluoro-5,7-dimethyl-4-bora-3a,4a diaza-3-indacenepropionic acid, eosin-5-isothiocyanate, erythrosin-5-isothiocyanate, and CASCADE™ blue acetylazide (Molecular Probes, Inc., Eugene, Oreg.). Fluorescently labeled probes can be viewed with a fluorescence microscope and an appropriate filter for each fluorophore, or by using dual or triple band-pass filter sets to observe multiple fluorophores. See, for example, U.S. Pat. No. 5,776,688. Alternatively, techniques such as flow cytometry can be used to examine the hybridization pattern of the probes. Fluorescence-based arrays are also known in the art.

In other embodiments, the probes can be indirectly labeled with, e.g., biotin or digoxygenin, or labeled with radioactive isotopes such as $^{32}P$ and $^{3}H$. For example, a probe indirectly labeled with biotin can be detected by avidin conjugated to a detectable marker. For example, avidin can be conjugated to an enzymatic marker such as alkaline phosphatase or horseradish peroxidase. Enzymatic markers can be detected in standard colorimetric reactions using a substrate and/or a catalyst for the enzyme. Catalysts for alkaline phosphatase include 5-bromo-4-chloro-3-indolylphosphate and nitro blue tetrazolium. Diaminobenzoate can be used as a catalyst for horseradish peroxidase.

In another aspect, this document features arrays that include a substrate having a plurality of addressable areas, and methods of using them. At least one area of the plurality includes a nucleic acid probe that binds specifically to a sequence comprising a polymorphism listed in Tables 1-2 or Table A, and can be used to detect the absence or presence of said polymorphism, e.g., one or more SNPs, microsatellites, minisatellites, or indels, as described herein, to determine or identify an allele or genotype. For example, the array can include one or more nucleic acid probes that can be used to detect a polymorphism listed in Tables 1-2 or Table A. In some embodiments, the array further includes at least one area that includes a nucleic acid probe that can be used to specifically detect another marker associated with BD and/or SZ as described herein. In some embodiments, the probes are nucleic acid capture probes.

Generally, microarray hybridization is performed by hybridizing a nucleic acid of interest (e.g., a nucleic acid encompassing a polymorphic site) with the array and detecting hybridization using nucleic acid probes. In some cases, the nucleic acid of interest is amplified prior to hybridization. Hybridization and detecting are generally carried out according to standard methods. See, e.g., Published PCT Application Nos. WO 92/10092 and WO 95/11995, and U.S. Pat. No. 5,424,186. For example, the array can be scanned to determine the position on the array to which the nucleic acid hybridizes. The hybridization data obtained from the scan is typically in the form of fluorescence intensities as a function of location on the array.

Arrays can be formed on substrates fabricated with materials such as paper, glass, plastic (e.g., polypropylene, nylon, or polystyrene), polyacrylamide, nitrocellulose, silicon, optical fiber, or any other suitable solid or semisolid support, and can be configured in a planar (e.g., glass plates, silicon chips) or three dimensional (e.g., pins, fibers, beads, particles, microtiter wells, capillaries) configuration. Methods for generating arrays are known in the art and include, e.g., photolithographic methods (see, e.g., U.S. Pat. Nos. 5,143,854; 5,510,270; and 5,527,681), mechanical methods (e.g., directed-flow methods as described in U.S. Pat. No. 5,384, 261), pin-based methods (e.g., as described in U.S. Pat. No. 5,288,514), and bead-based techniques (e.g., as described in PCT US/93/04145). The array typically includes oligonucleotide hybridization probes capable of specifically hybridizing to different polymorphic variants. Oligonucleotide probes that exhibit differential or selective binding to polymorphic sites may readily be designed by one of ordinary skill in the art. For example, an oligonucleotide that is perfectly complementary to a sequence that encompasses a polymorphic site (i.e., a sequence that includes the polymorphic site, within it or at one end) will generally hybridize preferentially to a nucleic acid comprising that sequence, as opposed to a nucleic acid comprising an alternate polymorphic variant.

Oligonucleotide probes forming an array may be attached to a substrate by any number of techniques, including, without limitation, (i) in situ synthesis (e.g., high-density oligonucleotide arrays) using photolithographic techniques; (ii) spotting/printing at medium to low density on glass, nylon or nitrocellulose; (iii) by masking, and (iv) by dot-blotting on a nylon or nitrocellulose hybridization membrane. Oligonucleotides can be immobilized via a linker, including by covalent, ionic, or physical linkage. Linkers for immobilizing nucleic acids and polypeptides, including reversible or cleavable linkers, are known in the art. See, for example, U.S. Pat. No. 5,451,683 and WO98/20019. Alternatively, oligonucleotides can be non-covalently immobilized on a substrate by hybridization to anchors, by means of magnetic beads, or in a fluid phase such as in microtiter wells or capillaries. Immobilized oligonucleotide probes are typically about 20 nucleotides in length, but can vary from about 10 nucleotides to about 1000 nucleotides in length.

Arrays can include multiple detection blocks (i.e., multiple groups of probes designed for detection of particular polymorphisms). Such arrays can be used to analyze multiple different polymorphisms. Detection blocks may be grouped within a single array or in multiple, separate arrays so that varying conditions (e.g., conditions optimized for particular polymorphisms) may be used during the hybridization. For example, it may be desirable to provide for the detection of those polymorphisms that fall within G-C rich stretches of a genomic sequence, separately from those falling in A-T rich segments. General descriptions of using oligonucleotide arrays for detection of polymorphisms can be found, for example, in U.S. Pat. Nos. 5,858,659 and 5,837,832. In addition to oligonucleotide arrays, cDNA arrays may be used similarly in certain embodiments.

The methods described herein can include providing an array as described herein; contacting the array with a sample (e.g., a portion of genomic DNA that includes at least a portion of a human chromosome) and/or optionally, a different portion of genomic DNA (e.g., a portion that includes a different portion of a human chromosome, e.g., including another region associated with BD and/or SZ), and detecting binding of a nucleic acid from the sample to the array. Optionally, the method includes amplifying nucleic acid from the sample, e.g., genomic DNA that includes a portion of a human chromosome described herein, and, optionally, a region that includes another region associated with BD and/or SZ, prior to or during contact with the array.

In some aspects, the methods described herein can include using an array that can ascertain differential expression patterns or copy numbers of one or more genes in samples from normal and affected individuals (see, e.g., Redon et al., *Nature* 444(7118):444-54 (2006)). For example, arrays of probes to a marker described herein can be used to measure polymorphisms between DNA from a subject having BD and/or SZ, and control DNA, e.g., DNA obtained from an individual that does not have BD and/or SZ, and has no risk factors for BD and/or SZ. Since the clones on the array contain sequence tags, their positions on the array are accurately known relative to the genomic sequence. Different hybridization patterns between DNA from an individual afflicted with BD and/or SZ and DNA from a normal individual at areas in the array corresponding to markers as described herein, and, optionally, one or more other regions associated with BD and/or SZ, are indicative of a risk of BD and/or SZ. Methods for array production, hybridization, and analysis are described, e.g., in Snijders et al., *Nat. Genetics* 29:263-264 (2001); Klein et al., *Proc. Natl. Acad. Sci. USA* 96:4494-4499 (1999); Albertson et al., *Breast Cancer Research and Treatment* 78:289-298 (2003); and Snijders et al., "BAC microarray based comparative genomic hybridization," in: Zhao et al. (eds), *Bacterial Artificial Chromosomes: Methods and Protocols*, Methods in Molecular Biology, Humana Press, 2002.

In another aspect, this document provides methods of determining the absence or presence of an allele or genotype associated with BD and/or SZ as described herein, using an array described above. The methods can include providing a two dimensional array having a plurality of addresses, each address of the plurality being positionally distinguishable from each other address of the plurality having a unique nucleic acid capture probe, contacting the array with a first sample from a test subject who is suspected of having or being at risk for BD and/or SZ, and comparing the binding of the first sample with one or more references, e.g., binding of a sample from a subject who is known to have BD and/or SZ, and/or binding of a sample from a subject who is unaffected, e.g., a control sample from a subject who neither has, nor has any risk factors for BD and/or SZ. In some embodiments, the methods can include contacting the array with a second sample from a subject who has BD and/or SZ; and comparing the binding of the first sample with the binding of the second sample. In some embodiments, the methods can include contacting the array with a third sample from a cell or subject that does not have BD and/or SZ and is not at risk for BD and/or SZ; and comparing the binding of the first sample with the binding of the third sample. In some embodiments, the second and third samples are from first or second-degree relatives of the test subject. In the case of a nucleic acid hybridization, binding with a capture probe at an address of the plurality, can be detected by any method known in the art, e.g., by detection of a signal generated from a label attached to the nucleic acid.

Bipolar Disorder and Schizophrenia Spectrum Disorders

The methods described herein can be used to determine a differential diagnosis based on the presence or absence of an allele or genotype associated with BD or with a schizophrenia spectrum disorder (SSD). The SSDs include schizophrenia (SZ), schizotypal personality disorder (SPD), and schizoaffective disorder (SD). Methods for diagnosing SSDs are known in the art, see, e.g., the *Diagnostic and Statistical Manual of Mental Disorders—Fourth Edition* ("DSM-IV"). See also, e.g., WO 2009/092032, incorporated herein by reference.

Bipolar Disorder, which is also known as manic-depression or manic-depressive disorder, is characterized by mood that alternates between two emotional extremes, or poles: the sadness of depression and the euphoria of mania (see symptoms of mania below).

People with bipolar disorder experience a wide range of feelings depending on the phase of the illness is present. Between these emotional swings, there are periods when a person's mood is quite normal. During the depressed phase of bipolar illness, the individual will have the same symptoms as those found in major depressive disorder, and the symptoms can be severe. The individual may have despondent mood, a loss of energy, feelings of worthlessness or guilt, or problems with concentration. Thoughts of suicide are not uncommon. In fact, 10% to 15% of those with bipolar disorder may die by suicide.

During the manic phase, the individual experiences mood that is extremely elevated, expansive, or irritable. Mania can seriously impair one's normal judgment, and the individual may not be able to realize the harm of his or her behavior and may even lose touch with reality. The individual becomes euphoric, ideas come much too fast, and concentration is nearly impossible. The individual's judgment is impaired, and he or she may behave recklessly without a sense of consequence. If a person with bipolar disorder experiences a severe manic episode, he or she may be abusive to children, spouses, or engage in other violent behaviors. When this happens, people often need to be hospitalized for their own safety and for the safety of others. There may also be problems with attendance and performance at school or work, as well as significant difficulties in personal relationships.

There are two types of bipolar disorder. Bipolar I Disorder is diagnosed when a person has had at least one manic or mixed episode, often along with a major depressive episode. It affects equal numbers of men and women in approximately 0.4% to 1.6% of the population. Bipolar II Disorder is diagnosed when a person has had a major depressive episode along with at least one hypomanic episode. It affects more women than men in about 0.5% of the population. Bipolar I disorder affects equal numbers of males and females, however there does appear to be a gender difference in the onset of the illness. Females are more likely to experience a first episode of depression, while males tend to have a first episode that is manic. Women who have bipolar I or II disorder and who have children may be at a higher risk of experiencing bipolar episodes within several months of giving birth. Of adolescents who have recurrent major depressive episodes, about 10%-15% of them will likely develop bipolar disorder. People who have immediate relatives with bipolar I disorder have a higher risk of developing a mood disorder themselves. For these people, the rate of developing bipolar II disorder or major depression is 4%-24% and bipolar I disorder is 1%-5%.

The cycles of bipolar disorder may be different for each person. Oftentimes a person may first experience depression. Depression may then be replaced with manic symptoms, and the cycle between depression and mania may continue for days, weeks, or months. Between phases of depression and mania some people return to their normal mood. Some others have several periods of either depression or mania. Still others may experience several bouts of depression with infrequent phases of hypomania, or repeated manic episodes with occasional depressive periods. A portion of people, roughly 10% to 20% may only experience mania, while others can have both depression and mania at the same time. For at least 90% of those who have bipolar disorder the condition is recurrent. They will experience future symptoms of the cycles of mania and depression. Approximately 60%-70% of manic episodes may happen just before or after a depressive episode, and this pattern may happen in a particular way for each person. Most people return to a regular level of functioning between episodes, while some (about 20%-30%) may continue to have some problems with mood stability and social and occupational functioning.

Diagnostic Criteria of Bipolar I Disorder

Diagnostic criteria for bipolar I disorder are known in the art. The following is summarized from the *Diagnostic and Statistical Manual of Mental Disorders—Fourth Edition*.

A. A person experiences a current or recent episode that is manic, hypomanic, mixed, or depressed.
  1. To be a manic episode, for at least one week a person's mood must be out of the ordinary and continuously heightened, exaggerated, or irritable.
  2. At least three of the following seven symptoms have been significant and enduring. If the mood is only irritable, then four symptoms are required.
    a. Self-esteem is excessive or grandiose.
    b. The need for sleep is greatly reduced.
    c. Talks much more than usual.
    d. Thoughts and ideas are continuous and without a pattern or focus.
    e. Easily distracted by unimportant things.
    f. An increase in purposeful activity or productivity, or behaving and feeling agitated.
    g. Reckless participation in enjoyable activities that create a high risk for negative consequences (e.g., extensive spending sprees, sexual promiscuity).
  3. The person's symptoms do not indicate a mixed episode.
  4. The person's symptoms are a cause of great distress or difficulty in functioning at home, work, or other important areas. Or, the symptoms require the person to be hospitalized to protect the person from harming himself/herself or others. Or, the symptoms include psychotic features (hallucinations, delusions).
  5. The person's symptoms are not caused by substance use (e.g., alcohol, drugs, medication), or a medical disorder.
B. Unless this is a first single manic episode there has been at least one manic, mixed, hypomanic, or depressive episode.
  1. For a major depressive episode a person must have experienced at least five of the nine symptoms below for the same two weeks or more, for most of the time almost every day, and this is a change from his/her prior level of functioning. One of the symptoms must be either (a) depressed mood, or (b) loss of interest.
    a. Depressed mood. For children and adolescents, this may be irritable mood.
    b. A significantly reduced level of interest or pleasure in most or all activities.
    c. A considerable loss or gain of weight (e.g., 5% or more change of weight in a month when not dieting). This may also be an increase or decrease in appetite. For children, they may not gain an expected amount of weight.
    d. Difficulty falling or staying asleep (insomnia), or sleeping more than usual (hypersomnia).
    e. Behavior that is agitated or slowed down. Others should be able to observe this.
    f. Feeling fatigued, or diminished energy.
    g. Thoughts of worthlessness or extreme guilt (not about being ill).
    h. Ability to think, concentrate, or make decisions is reduced.
    i. Frequent thoughts of death or suicide (with or without a specific plan), or attempt of suicide.
  2. The persons' symptoms do not indicate a mixed episode.
  3. The person's symptoms are a cause of great distress or difficulty in functioning at home, work, or other important areas.
  4. The person's symptoms are not caused by substance use (e.g., alcohol, drugs, medication), or a medical disorder.
  5. The person's symptoms are not due to normal grief or bereavement over the death of a loved one, they continue for more than two months, or they include great difficulty in functioning, frequent thoughts of worthlessness, thoughts of suicide, symptoms that are psychotic, or behavior that is slowed down (psychomotor retardation).

C. Another disorder does not better explain the episode.

Diagnostic Criteria of Bipolar II Disorder

Diagnostic criteria for bipolar II disorder are known in the art. The following is summarized from the *Diagnostic and Statistical Manual of Mental Disorders—Fourth Edition*.

A. The person currently has, or in the past has had at least one major depressive episode:
  1. For a major depressive episode a person must have experienced at least five of the nine symptoms below for the same two weeks or more, for most of the time almost every day, and this is a change from his/her prior level of functioning. One of the symptoms must be either (a) depressed mood, or (b) loss of interest.
     a. Depressed mood. For children and adolescents, this may be irritable mood.
     b. A significantly reduced level of interest or pleasure in most or all activities.
     c. A considerable loss or gain of weight (e.g., 5% or more change of weight in a month when not dieting). This may also be an increase or decrease in appetite. For children, they may not gain an expected amount of weight.
     d. Difficulty falling or staying asleep (insomnia), or sleeping more than usual (hypersomnia).
     e. Behavior that is agitated or slowed down. Others should be able to observe this.
     f. Feeling fatigued, or diminished energy.
     g. Thoughts of worthlessness or extreme guilt (not about being ill).
     h. Ability to think, concentrate, or make decisions is reduced.
     i. Frequent thoughts of death or suicide (with or without a specific plan), or attempt of suicide.
  2. The persons' symptoms do not indicate a mixed episode.
  3. The person's symptoms are a cause of great distress or difficulty in functioning at home, work, or other important areas.
  4. The person's symptoms are not caused by substance use (e.g., alcohol, drugs, medication), or a medical disorder.
  5. The person's symptoms are not due to normal grief or bereavement over the death of a loved one, they continue for more than two months, or they include great difficulty in functioning, frequent thoughts of worthlessness, thoughts of suicide, symptoms that are psychotic, or behavior that is slowed down (psychomotor retardation).

B. The person currently has, or in the past has had at least one hypomanic episode:
  1. For a hypomanic episode a person's mood must be out of the ordinary and continuously heightened, exaggerated, or irritable for at least four days.
  2. At least three of the following seven symptoms have been significant and enduring. If the mood is only irritable, then four symptoms are required.
     a. Self-esteem is excessive or grandiose.
     b. The need for sleep is greatly reduced.
     c. Talks much more than usual.
     d. Thoughts and ideas are continuous and without a pattern or focus.
     e. Easily distracted by unimportant things.
     f. An increase in purposeful activity or productivity, or behaving and feeling agitated.
     g. Reckless participation in enjoyable activities that create a high risk for negative consequences (e.g., extensive spending sprees, sexual promiscuity).
  3. The episode is a substantial change for the person and uncharacteristic of his or her usual functioning.
  4. The changes of functioning and mood can be observed by others.
  5. The person's symptoms are NOT severe enough to cause difficulty in functioning at home, work, or other important areas; the symptoms neither require the person to be hospitalized, nor are there any psychotic features.
  6. The person's symptoms are not caused by substance use (e.g., alcohol, drugs, medication), or a medical disorder.

C. The person has never experienced a manic or mixed episode.

D. Another disorder does not better explain the episode.

E. The symptoms are a cause of great distress or difficulty in functioning at home, work, or other important areas.

Communicating Risk Assessment

This document also provides methods and materials to assist medical or research professionals in determining whether or not a subject has or is at risk for developing BD and/or SZ. Medical professionals can be, for example, doctors, nurses, medical laboratory technologists, and pharmacists. Research professionals can be, for example, principle investigators, research technicians, postdoctoral trainees, and graduate students. A professional can be assisted by (1) determining whether specific polymorphic variants are present in a biological sample from a subject, and (2) communicating information about polymorphic variants to that professional.

After information about specific polymorphic variants is reported, a medical professional can take one or more actions that can affect patient care. For example, a medical professional can record information in the patient's medical record regarding the diagnosis or risk of the patient to develop BD and/or SZ. In some cases, a medical professional can record information regarding risk assessment, or otherwise transform the patient's medical record, to reflect the patient's current medical condition. In some cases, a medical professional can review and evaluate a patient's entire medical record and assess multiple treatment strategies for clinical intervention of a patient's condition.

A medical professional can initiate or modify treatment after receiving information regarding a patient's diagnosis of or risk of developing BD and/or SZ, for example. In some cases, a medical professional can recommend a change in therapy. In some cases, a medical professional can enroll a patient in a clinical trial for, by way of example, detecting correlations between an allele or genotype as described herein and any measurable or quantifiable parameter relating to the outcome of the treatment as described above.

A medical professional can communicate information regarding a patient's diagnosis of or risk of developing BD and/or SZ to a patient or a patient's family. In some cases, a medical professional can provide a patient and/or a patient's family with information regarding BD and/or SZ diagnosis and risk assessment information, including treatment options, prognosis, and referrals to specialists. In some cases, a medical professional can provide a copy of a patient's medical records to a specialist.

A research professional can apply information regarding a subject's diagnosis of or risk of developing BD and/or SZ to advance scientific research. For example, a researcher can compile data on wild specific polymorphic variants. In some cases, a research professional can obtain a subject's allele(s) or genotype as described herein to evaluate a subject's enrollment, or continued participation, in a research study or clinical trial. In some cases, a research professional can communicate information regarding a subject's diagnosis of or risk of developing BD and/or SZ to a medical professional. In some cases, a research professional can refer a subject to a medical professional.

Any appropriate method can be used to communicate information to another person (e.g., a professional). For example, information can be given directly or indirectly to a professional. For example, a laboratory technician can input a patient's polymorphic variant allele(s) or genotype as described herein into a computer-based record. In some cases, information is communicated by making an physical alteration to medical or research records. For example, a medical professional can make a permanent notation or flag a medical record for communicating the risk assessment to other medical professionals reviewing the record. In addition, any type of communication can be used to communicate the risk assessment information. For example, mail, e-mail, telephone, and face-to-face interactions can be used. The information also can be communicated to a professional by making that information electronically available to the professional. For example, the information can be communicated to a professional by placing the information on a computer database such that the professional can access the information. In addition, the information can be communicated to a hospital, clinic, or research facility serving as an agent for the professional.

Articles of Manufacture

Also provided herein are articles of manufacture comprising a probe that hybridizes with a region of human chromosome as described herein and can be used to detect a polymorphism described herein. For example, any of the probes for detecting polymorphisms described herein can be combined with packaging material to generate articles of manufacture or kits. The kit can include one or more other elements including: instructions for use; and other reagents such as a label or an agent useful for attaching a label to the probe. Instructions for use can include instructions for diagnostic applications of the probe for making a diagnosis of or assessing risk of BD and/or SZ in a method described herein. Other instructions can include instructions for attaching a label to the probe, instructions for performing in situ analysis with the probe, and/or instructions for obtaining a sample to be analyzed from a subject. In some cases, the kit can include a labeled probe that hybridizes to a region of human chromosome as described herein.

The kit can also include one or more additional reference or control probes that hybridize to the same chromosome or another chromosome or portion thereof that can have an abnormality associated with a particular endophenotype. A kit that includes additional probes can further include labels, e.g., one or more of the same or different labels for the probes. In other embodiments, the additional probe or probes provided with the kit can be a labeled probe or probes. When the kit further includes one or more additional probe or probes, the kit can further provide instructions for the use of the additional probe or probes. Kits for use in self-testing can also be provided. Such test kits can include devices and instructions that a subject can use to obtain a biological sample (e.g., buccal cells, blood) without the aid of a health care provider. For example, buccal cells can be obtained using a buccal swab or brush, or using mouthwash.

Kits as provided herein can also include a mailer (e.g., a postage paid envelope or mailing pack) that can be used to return the sample for analysis, e.g., to a laboratory. The kit can include one or more containers for the sample, or the sample can be in a standard blood collection vial. The kit can also include one or more of an informed consent form, a test requisition form, and instructions on how to use the kit in a method described herein. Methods for using such kits are also included herein. One or more of the forms (e.g., the test requisition form) and the container holding the sample can be coded, for example, with a bar code for identifying the subject who provided the sample.

Databases and Reports

Also provided herein are databases that include a list of polymorphisms as described herein, and wherein the list is largely or entirely limited to polymorphisms identified as useful for determining a diagnosis or susceptibility to BD and/or SZ as described herein. The list is stored, e.g., on a flat file or computer-readable medium. The databases can further include information regarding one or more subjects, e.g., whether a subject is affected or unaffected, clinical information such as endophenotype, age of onset of symptoms, any treatments administered and outcomes (e.g., data relevant to pharmacogenomics, diagnostics or theranostics), and other details, e.g., about the disorder in the subject, or environmental or other genetic factors. The databases can be used to detect correlations between a particular allele or genotype and the information regarding the subject.

The methods described herein can also include the generation of reports, e.g., for use by a patient, care giver, payor, or researcher, that include information regarding a subject's response allele(s), and optionally further information such as treatments administered, treatment history, medical history, predicted response, and actual response. The reports can be recorded in a tangible medium, e.g., a computer-readable disk, a solid state memory device, or an optical storage device.

Engineered Cells

Also provided herein are engineered cells that harbor one or more polymorphism described herein, e.g., one or more polymorphisms associated with BD and/or SZ. Such cells are useful for studying the effect of a polymorphism on physiological function, and for identifying and/or evaluating potential therapeutic agents such as anti-psychotics for the treatment of BD and/or SZ.

As one example, included herein are cells in which one of the various alleles of the genes described herein has been re-created that is associated with an increased risk of BD and/or SZ. Methods are known in the art for generating cells, e.g., by homologous recombination between the endogenous gene and an exogenous DNA molecule introduced into a cell, e.g., a cell of an animal. In some cases, the cells can be used to generate transgenic animals using methods known in the art.

The cells are preferably mammalian cells (e.g., neuronal type cells) in which an endogenous gene has been altered to include a polymorphism as described herein. Techniques such as targeted homologous recombinations, can be used to insert the heterologous DNA as described in, e.g., Chappel, U.S. Pat. No. 5,272,071; WO 91/06667, published in May 16, 1991.

EXAMPLES

The invention is further described in the following examples, which do not limit the scope of the invention described in the claims.

Example 1

Genotypes and Alleles that Contribute to Differential Diagnosis of BD Versus SZ

Genotyping and phenotype data were obtained from the Genetic Analysis Information Network (GAIN) Database found at ncbi.nlm.nih.gov through dbGaP, at accession number PHS000017.v1.p1. Genotypes and associated phenotype data for the GAIN Genome-Wide Association Study of Schizophrenia were provided by P. Gejman, and genotyping of these samples was provided through the Genetic Association Information Network (GAIN). Data for 1018 BD cases, 1172 SZ cases and 1378 neurologically normal controls with Caucasian ancestry were evaluated for the GAIN sample.

To determine the significance of the relationship between each allele or genotype and diagnosis of either BD or SZ or BD vs SZ, Golden Helix's SNP and Variation Suite (SVS™) was used to determine a p-value using a trend/correlations test. This test showed the p-value for the dependent variable value having any correlation with or "trend", which depends on the (possibly PCA-corrected) count value of the genotype. (See below.) For case/control dependent variables, a "case" was considered to have a value of one, and a "control" was considered to have a value of zero. For the genotype predictor variable, the count values were as follows where the minor allele "D" is the allele shown in the table:

Additive Model: The count of the minor allele D, which is zero within genotype dd, one within genotype Dd, and two within genotype DD, where d is the major allele.

Dominant Model: The count is one for genotypes DD and Dd and zero for genotype dd.

Recessive Model: The count is one for genotype DD and zero for genotypes Dd and dd.

Table 1 lists alleles and genotypes influencing differential diagnosis for BD versus SZ. 1018 BD cases and 1170 SZ cases were used to identify these polymorphisms. In brief, each BD case was coded as a 1 (or case) and each SZ case was coded as 0 (or control). The Genetic Association Information Network (GAIN), a partnership between the NIH and private companies, provided genome wide genotyping data for SZ and BP (database of Genotype and Phenotype (dbGaP). National Institutes of Health 2008, available on the NCBI website). Using this coding and genotypes and phenotypes provided by GAIN, case control analysis was performed using various genetic models (recessive, dominant and additive) in Golden Helix's SNP and Variation Suite v 7.0 (SVS™). Table 1 lists the gene, SEQ ID NO:, NCBI RS number, test allele, genetic model, odds ratio (OR), and p-value for the comparison. In this example, an OR greater than 1 indicates that the subject has a greater likelihood of a BD diagnosis than a SZ diagnosis. Similarly, an OR less than 1 indicates that the subject has a lower likelihood of a BD diagnosis than a SZ diagnosis.

TABLE 1

Alleles and Genotypes Influencing Likelihood of Bipolar vs. Schizophrenia Diagnoses

| Gene | SEQ ID NO: | NCBI RS# | Allele | Model | P | Odds Ratio |
|---|---|---|---|---|---|---|
| KIF1B | 1 | 1555849 | G | RECESSIVE | 0.0168627 | 0.72 |
| PRDM2 | 2 | 876931 | C | DOMINANT | 0.0174243 | 1.25 |
| RP1-21O18.1 | 3 | 12035178 | G | ADDITIVE | 0.0068159 | 0.81 |
| RP1-21O18.1 | 4 | 6663699 | G | ADDITIVE | 0.0217698 | 0.86 |
| EPHB2 | 9 | 309473 | T | RECESSIVE | 0.0303631 | 1.25 |
| EPHB2 | 10 | 309471 | G | RECESSIVE | 0.0174109 | 1.28 |
| CLIC4 | 11 | 3131502 | A | RECESSIVE | 0.0372989 | 1.38 |
| CLIC4 | 12 | 9259 | C | RECESSIVE | 0.0162138 | 1.43 |
| AGBL4-C1ORF165 | 19 | 3122291 | T | RECESSIVE | 0.0056129 | 0.71 |
| AGBL4-C1ORF165 | 20 | 3121512 | C | RECESSIVE | 0.0178332 | 0.77 |
| AGBL4-C1ORF165 | 21 | 3118215 | A | RECESSIVE | 0.0347862 | 0.78 |
| AGBL4-C1ORF165 | 22 | 3118223 | G | RECESSIVE | 0.0270175 | 0.77 |
| AGBL4-C1ORF165 | 23 | 3121273 | G | RECESSIVE | 0.0354423 | 0.79 |
| AGBL4-C1ORF165 | 24 | 3127556 | G | RECESSIVE | 0.0312224 | 0.78 |
| AGBL4-C1ORF165 | 25 | 3121518 | A | RECESSIVE | 0.0227865 | 0.76 |
| AGBL4-C1ORF165 | 26 | 6669433 | A | RECESSIVE | 0.0349819 | 0.78 |
| AGBL4-C1ORF165 | 27 | 7520773 | T | RECESSIVE | 0.0050132 | 0.68 |
| SLC6A17 | 41 | 495959 | T | ADDITIVE | 0.0121511 | 0.88 |
| SLC16A4 | 42 | 10857820 | A | RECESSIVE | 0.0103223 | 1.32 |
| SLC16A4 | 43 | 4498805 | G | ADDITIVE | 0.0243463 | 0.86 |
| KCNA10 | 45 | 3748731 | A | ADDITIVE | 0.0188446 | 1.16 |
| SLC22A15 | 52 | 2488433 | T | ADDITIVE | 0.0096888 | 1.38 |
| SLC22A15 | 54 | 3748743 | A | ADDITIVE | 0.0148878 | 1.42 |
| CGN | 59 | 1547832 | A | DOMINANT | 0.0148568 | 0.78 |
| CGN | 60 | 10788807 | G | DOMINANT | 0.0154457 | 0.78 |
| CGN | 62 | 1418823 | T | DOMINANT | 0.0375351 | 0.70 |
| ATF6 | 63 | 905594 | T | ADDITIVE | 0.0234906 | 0.86 |
| ATF6 | 64 | 2070151 | T | DOMINANT | 0.0499978 | 0.78 |
| ATF6 | 65 | 1553443 | C | DOMINANT | 0.0315353 | 0.75 |
| ATF6 | 67 | 12405111 | A | ADDITIVE | 0.0338357 | 0.78 |
| ATF6 | 69 | 7530997 | A | DOMINANT | 0.0370491 | 0.77 |
| ATF6 | 70 | 12401299 | G | ADDITIVE | 0.0486075 | 0.82 |
| ATF6 | 71 | 16856629 | G | ADDITIVE | 0.0437555 | 0.80 |
| ATF6 | 72 | 7552420 | C | ADDITIVE | 0.0486075 | 0.82 |
| ATF6 | 73 | 12028953 | T | DOMINANT | 0.0489870 | 0.78 |
| ATF6 | 74 | 10918214 | G | ADDITIVE | 0.0491995 | 0.87 |
| ATF6 | 75 | 10918215 | G | ADDITIVE | 0.0491995 | 0.87 |
| ATF6 | 76 | 10753686 | A | ADDITIVE | 0.0491995 | 0.87 |
| ATF6 | 77 | 4657124 | G | ADDITIVE | 0.0409751 | 0.86 |
| ATF6 | 78 | 4657125 | C | ADDITIVE | 0.0491995 | 0.87 |
| FAM78B | 85 | 12030964 | T | DOMINANT | 0.0345563 | 0.82 |
| FAM78B | 86 | 10494453 | A | RECESSIVE | 0.0286683 | 0.67 |
| FAM78B | 87 | 9787101 | T | RECESSIVE | 0.0303146 | 0.68 |
| FAM78B | 88 | 715421 | A | RECESSIVE | 0.0149449 | 0.64 |

TABLE 1-continued

Alleles and Genotypes Influencing Likelihood of Bipolar vs. Schizophrenia Diagnoses

| Gene | SEQ ID NO: | NCBI RS# | Allele | Model | P | Odds Ratio |
|---|---|---|---|---|---|---|
| FAM78B | 89 | 10800198 | C | RECESSIVE | 0.0175647 | 0.65 |
| DPT | 90 | 511187 | G | ADDITIVE | 0.0264861 | 0.88 |
| SEC16B | 91 | 1889981 | A | ADDITIVE | 0.0217462 | 1.16 |
| CACNA1E | 96 | 199960 | T | DOMINANT | 0.0290569 | 0.83 |
| CACNA1E | 97 | 3766983 | C | DOMINANT | 0.0438431 | 0.83 |
| CACNA1E | 98 | 4652675 | G | DOMINANT | 0.0193933 | 0.82 |
| CACNA1E | 99 | 3845444 | G | DOMINANT | 0.0461923 | 0.84 |
| CACNA1E | 100 | 3843280 | G | ADDITIVE | 0.0219374 | 0.84 |
| CACNA1E | 101 | 704329 | A | RECESSIVE | 0.0256218 | 1.26 |
| CACNA1E | 102 | 546191 | T | ADDITIVE | 0.0134889 | 0.89 |
| PLA2G4A | 121 | 6662687 | A | RECESSIVE | 0.0323279 | 0.78 |
| KCNH1 | 122 | 1340128 | C | ADDITIVE | 0.0287026 | 0.87 |
| KCNH1 | 124 | 1777256 | A | ADDITIVE | 0.0433741 | 0.90 |
| KCNH1 | 128 | 17267442 | T | RECESSIVE | 0.0218244 | 0.69 |
| KCNK2 | 131 | 10864143 | A | RECESSIVE | 0.0246322 | 1.39 |
| USH2A | 142 | 17025416 | T | RECESSIVE | 0.0304882 | 4.73 |
| ESRRG | 143 | 12027901 | C | DOMINANT | 0.0438998 | 0.81 |
| SLC35F3 | 145 | 6688304 | A | ADDITIVE | 0.0075880 | 0.82 |
| SLC35F3 | 146 | 1463501 | G | ADDITIVE | 0.0136990 | 0.84 |
| SLC35F3 | 147 | 1563693 | G | ADDITIVE | 0.0092743 | 0.83 |
| SLC35F3 | 148 | 9435569 | T | ADDITIVE | 0.0075579 | 0.82 |
| SLC35F3 | 149 | 6674291 | C | ADDITIVE | 0.0107637 | 0.85 |
| SLC35F3 | 150 | 480993 | T | RECESSIVE | 0.0463714 | 0.76 |
| GNG4 | 151 | 508208 | G | ADDITIVE | 0.0133270 | 0.88 |
| GNG4 | 152 | 7554426 | G | DOMINANT | 0.0266180 | 1.22 |
| GNG4 | 153 | 7554532 | G | DOMINANT | 0.0336946 | 1.21 |
| RYR2 | 154 | 6684412 | C | DOMINANT | 0.0000058 | 1.49 |
| RYR2 | 155 | 884641 | T | ADDITIVE | 0.0242126 | 0.84 |
| CHRM3 | 159 | 12097526 | T | DOMINANT | 0.0021341 | 0.77 |
| FMN2 | 160 | 897662 | T | DOMINANT | 0.0069240 | 0.79 |
| FMN2 | 161 | 10926188 | G | DOMINANT | 0.0074822 | 0.79 |
| FMN2 | 165 | 10495466 | A | ADDITIVE | 0.0270938 | 1.34 |
| RGS7 | 166 | 2815871 | T | RECESSIVE | 0.0099288 | 2.30 |
| PLD5 | 167 | 2343119 | A | DOMINANT | 0.0046930 | 1.30 |
| PLD5 | 168 | 7542270 | G | DOMINANT | 0.0215593 | 1.23 |
| C2ORF46 | 169 | 11684514 | T | DOMINANT | 0.0205265 | 1.31 |
| C2ORF46 | 170 | 7577544 | G | DOMINANT | 0.0039917 | 1.38 |
| C2ORF46 | 171 | 11677028 | G | DOMINANT | 0.0068260 | 1.36 |
| DDEF2 | 172 | 11686324 | T | DOMINANT | 0.0173768 | 1.23 |
| DDEF2 | 173 | 2356779 | A | DOMINANT | 0.0098345 | 1.25 |
| DDEF2 | 174 | 2666218 | G | DOMINANT | 0.0130585 | 1.24 |
| DDEF2 | 175 | 6431996 | C | DOMINANT | 0.0139985 | 1.24 |
| DDEF2 | 176 | 16866981 | G | RECESSIVE | 0.0219219 | 1.34 |
| DDEF2 | 177 | 17627209 | G | ADDITIVE | 0.0219751 | 1.15 |
| DDEF2 | 178 | 10177742 | A | RECESSIVE | 0.0262729 | 1.33 |
| DDEF2 | 179 | 4610024 | G | RECESSIVE | 0.0393906 | 1.29 |
| DDEF2 | 180 | 17673165 | G | ADDITIVE | 0.0405321 | 1.14 |
| DDEF2 | 181 | 6743955 | C | RECESSIVE | 0.0301506 | 1.32 |
| DDEF2 | 182 | 10172687 | T | RECESSIVE | 0.0296340 | 1.32 |
| DDEF2 | 183 | 6736216 | G | RECESSIVE | 0.0219219 | 1.34 |
| DDEF2 | 184 | 13414373 | G | RECESSIVE | 0.0365651 | 1.31 |
| DDEF2 | 185 | 3811599 | C | RECESSIVE | 0.0310306 | 1.32 |
| DDEF2 | 186 | 4627537 | T | RECESSIVE | 0.0463321 | 1.29 |
| DDEF2 | 187 | 17522163 | A | ADDITIVE | 0.0344479 | 1.17 |
| DDEF2 | 188 | 10181704 | T | RECESSIVE | 0.0350575 | 1.31 |
| DDEF2 | 189 | 4392227 | G | ADDITIVE | 0.0345107 | 1.17 |
| DDEF2 | 190 | 13424953 | T | RECESSIVE | 0.0196379 | 1.35 |
| DDEF2 | 191 | 4599081 | G | RECESSIVE | 0.0294499 | 2.38 |
| KLHL29 | 198 | 6742888 | C | ADDITIVE | 0.0348988 | 0.88 |
| KLHL29 | 199 | 7564616 | G | ADDITIVE | 0.0438533 | 0.88 |
| KLHL29 | 200 | 893430 | G | ADDITIVE | 0.0328464 | 0.92 |
| KLHL29 | 201 | 747345 | A | ADDITIVE | 0.0428263 | 0.90 |
| KLHL29 | 202 | 737565 | A | ADDITIVE | 0.0321218 | 0.93 |
| KLHL29 | 203 | 747344 | G | ADDITIVE | 0.0405452 | 0.93 |
| KLHL29 | 204 | 6726802 | A | ADDITIVE | 0.0093161 | 0.86 |
| KLHL29 | 205 | 7573494 | G | ADDITIVE | 0.0330346 | 0.91 |
| KLHL29 | 206 | 7570872 | G | ADDITIVE | 0.0110811 | 0.87 |
| KLHL29 | 207 | 6544857 | C | ADDITIVE | 0.0109959 | 0.86 |
| KLHL29 | 208 | 10178369 | A | RECESSIVE | 0.0078072 | 0.59 |
| KLHL29 | 209 | 11125053 | G | RECESSIVE | 0.0431439 | 0.75 |
| ASXL2 | 211 | 7599961 | C | DOMINANT | 0.0448173 | 1.19 |
| ASXL2 | 212 | 12987707 | A | DOMINANT | 0.0494199 | 1.21 |
| CIB4 | 213 | 11694917 | T | RECESSIVE | 0.0346178 | 7.09 |
| BRE | 219 | 10168171 | A | DOMINANT | 0.0052977 | 0.77 |
| BRE | 220 | 10180107 | T | DOMINANT | 0.0028722 | 0.76 |

TABLE 1-continued

Alleles and Genotypes Influencing Likelihood of Bipolar vs. Schizophrenia Diagnoses

| Gene | SEQ ID NO: | NCBI RS# | Allele | Model | P | Odds Ratio |
|---|---|---|---|---|---|---|
| BRE | 221 | 6738887 | C | ADDITIVE | 0.0484749 | 0.89 |
| BRE | 222 | 12617913 | C | DOMINANT | 0.0403340 | 0.83 |
| CRIM1 | 231 | 848532 | C | ADDITIVE | 0.0300993 | 1.10 |
| CRIM1 | 232 | 848531 | A | ADDITIVE | 0.0304785 | 1.10 |
| CRIM1 | 236 | 3755197 | A | RECESSIVE | 0.0362269 | 1.33 |
| PLEKHH2 | 258 | 6753626 | T | DOMINANT | 0.0468983 | 0.80 |
| PLEKHH2 | 259 | 7570252 | A | DOMINANT | 0.0433193 | 0.84 |
| PLEKHH2 | 260 | 10165660 | C | DOMINANT | 0.0058234 | 0.79 |
| C2ORF34 | 265 | 1067343 | A | RECESSIVE | 0.0337422 | 1.46 |
| C2ORF34 | 269 | 1067378 | A | RECESSIVE | 0.0419640 | 1.44 |
| C2ORF34 | 270 | 1067375 | C | RECESSIVE | 0.0332333 | 1.47 |
| C2ORF34 | 271 | 1067374 | G | RECESSIVE | 0.0414616 | 1.45 |
| C2ORF34 | 276 | 1067348 | T | RECESSIVE | 0.0405977 | 1.49 |
| C2ORF34 | 280 | 1067402 | T | RECESSIVE | 0.0311285 | 1.52 |
| C2ORF34 | 282 | 698792 | A | RECESSIVE | 0.0404097 | 1.50 |
| C2ORF34 | 284 | 698793 | C | RECESSIVE | 0.0497570 | 1.41 |
| C2ORF34 | 299 | 1377906 | G | RECESSIVE | 0.0180084 | 1.38 |
| C2ORF34 | 300 | 7609431 | C | RECESSIVE | 0.0101792 | 1.41 |
| C2ORF34 | 301 | 4953101 | T | RECESSIVE | 0.0476874 | 1.32 |
| C2ORF34 | 302 | 10188972 | T | RECESSIVE | 0.0489810 | 1.31 |
| PRKCE | 309 | 4953294 | A | ADDITIVE | 0.0493338 | 1.10 |
| EPAS1 | 313 | 13006131 | G | RECESSIVE | 0.0402451 | 0.81 |
| PSME4 | 314 | 805316 | C | RECESSIVE | 0.0400115 | 1.40 |
| ACYP2 | 315 | 10186140 | C | RECESSIVE | 0.0264937 | 0.21 |
| CCDC85A | 316 | 13432055 | C | RECESSIVE | 0.0100911 | 1.50 |
| COMMD1 | 317 | 11885927 | A | RECESSIVE | 0.0241086 | 0.41 |
| AAK1 | 322 | 4852272 | T | DOMINANT | 0.0303217 | 0.83 |
| AAK1 | 323 | 2312213 | G | DOMINANT | 0.0460414 | 0.84 |
| AAK1 | 324 | 3821277 | G | DOMINANT | 0.0377504 | 0.83 |
| AAK1 | 325 | 4852868 | T | DOMINANT | 0.0488927 | 0.84 |
| AAK1 | 326 | 6736776 | T | RECESSIVE | 0.0027341 | 0.61 |
| CTNNA2 | 328 | 3795994 | A | RECESSIVE | 0.0330763 | 1.28 |
| CTNNA2 | 329 | 4541274 | C | RECESSIVE | 0.0476626 | 1.28 |
| NAP5 | 346 | 12478698 | C | DOMINANT | 0.0005561 | 0.74 |
| NAP5 | 349 | 7559118 | C | RECESSIVE | 0.0229795 | 1.70 |
| RAB3GAP1 | 354 | 2305594 | G | ADDITIVE | 0.0430480 | 0.81 |
| LRP1B | 359 | 2171169 | A | ADDITIVE | 0.0158790 | 0.83 |
| LRP1B | 360 | 3749010 | T | ADDITIVE | 0.0126393 | 0.78 |
| LRP1B | 361 | 12691587 | A | RECESSIVE | 0.0082097 | 1.35 |
| LRP1B | 362 | 1525600 | T | RECESSIVE | 0.0231176 | 1.30 |
| LRP1B | 363 | 1525598 | A | RECESSIVE | 0.0217906 | 1.30 |
| LRP1B | 365 | 352973 | A | DOMINANT | 0.0320322 | 0.83 |
| LRP1B | 371 | 2029142 | A | DOMINANT | 0.0001309 | 0.70 |
| LRP1B | 372 | 4662370 | T | DOMINANT | 0.0232464 | 0.82 |
| LRP1B | 373 | 1900933 | A | DOMINANT | 0.0011840 | 0.73 |
| LRP1B | 374 | 10928134 | C | DOMINANT | 0.0174066 | 0.81 |
| LRP1B | 375 | 7558803 | A | DOMINANT | 0.0005023 | 0.71 |
| LRP1B | 376 | 1449478 | C | DOMINANT | 0.0005212 | 0.71 |
| LRP1B | 377 | 13418304 | A | DOMINANT | 0.0299440 | 0.78 |
| LRP1B | 378 | 11680286 | A | DOMINANT | 0.0001878 | 0.69 |
| LRP1B | 379 | 1375613 | T | RECESSIVE | 0.0098351 | 1.30 |
| LRP1B | 380 | 12691633 | T | DOMINANT | 0.0117205 | 0.76 |
| LRP1B | 381 | 2290140 | T | DOMINANT | 0.0082539 | 0.79 |
| KYNU | 383 | 351685 | C | RECESSIVE | 0.0264489 | 2.52 |
| KYNU | 384 | 352892 | T | RECESSIVE | 0.0349849 | 0.76 |
| ARHGAP15 | 385 | 11681284 | C | RECESSIVE | 0.0329951 | 0.74 |
| ARHGAP15 | 386 | 6732131 | A | RECESSIVE | 0.0062475 | 0.68 |
| ARHGAP15 | 387 | 11694505 | G | RECESSIVE | 0.0058840 | 0.62 |
| ARHGAP15 | 388 | 6745691 | G | RECESSIVE | 0.0040745 | 0.67 |
| ARHGAP15 | 389 | 6750323 | C | RECESSIVE | 0.0031136 | 0.67 |
| ARHGAP15 | 390 | 4662343 | A | RECESSIVE | 0.0145068 | 0.72 |
| ARHGAP15 | 391 | 16823036 | A | DOMINANT | 0.0392608 | 1.20 |
| ARHGAP15 | 392 | 16823114 | A | DOMINANT | 0.0470151 | 1.19 |
| ARHGAP15 | 393 | 10928200 | T | DOMINANT | 0.0406542 | 1.20 |
| KCNJ3 | 399 | 12995382 | C | DOMINANT | 0.0487689 | 1.19 |
| PKP4 | 400 | 6437186 | T | DOMINANT | 0.0342404 | 7.11 |
| PKP4 | 401 | 2528575 | A | DOMINANT | 0.0403036 | 1.20 |
| PLA2R1 | 402 | 6432570 | T | DOMINANT | 0.0103076 | 0.78 |
| PLA2R1 | 403 | 3828324 | C | DOMINANT | 0.0296821 | 0.81 |
| SCN3A | 411 | 17829626 | A | DOMINANT | 0.0403437 | 0.61 |
| SCN2A | 413 | 4667810 | G | DOMINANT | 0.0020017 | 1.32 |
| SCN2A | 414 | 4667485 | C | DOMINANT | 0.0035559 | 1.31 |
| SCN2A | 415 | 10181853 | T | DOMINANT | 0.0019952 | 1.32 |
| SCN1A | 416 | 1824551 | C | RECESSIVE | 0.0282465 | 0.75 |
| SCN1A | 417 | 1841549 | C | RECESSIVE | 0.0321010 | 0.64 |

TABLE 1-continued

Alleles and Genotypes Influencing Likelihood of Bipolar vs. Schizophrenia Diagnoses

| Gene | SEQ ID NO: | NCBI RS# | Allele | Model | P | Odds Ratio |
|---|---|---|---|---|---|---|
| SCN1A | 418 | 7607543 | C | RECESSIVE | 0.0339116 | 0.65 |
| SCN1A | 419 | 1461197 | A | RECESSIVE | 0.0386158 | 0.76 |
| SCN1A | 420 | 1824549 | G | RECESSIVE | 0.0283570 | 0.75 |
| SCN1A | 421 | 1381105 | G | RECESSIVE | 0.0314593 | 0.75 |
| SCN9A | 422 | 4303728 | A | RECESSIVE | 0.0169081 | 0.19 |
| SCN7A | 426 | 3579 | A | DOMINANT | 0.0076308 | 0.74 |
| SCN7A | 427 | 13397124 | T | DOMINANT | 0.0155437 | 0.80 |
| SCN7A | 428 | 13029092 | T | DOMINANT | 0.0027898 | 0.74 |
| SCN7A | 429 | 13017982 | C | DOMINANT | 0.0021760 | 0.74 |
| SCN7A | 430 | 13022308 | A | DOMINANT | 0.0235060 | 0.80 |
| SCN7A | 431 | 2593529 | C | DOMINANT | 0.0036914 | 0.75 |
| PDE1A | 433 | 12693301 | G | DOMINANT | 0.0027198 | 0.77 |
| PDE1A | 434 | 12988258 | A | DOMINANT | 0.0169140 | 0.81 |
| PDE1A | 435 | 6736414 | T | DOMINANT | 0.0018837 | 0.76 |
| PDE1A | 436 | 6718589 | T | DOMINANT | 0.0079529 | 0.79 |
| PDE1A | 437 | 6719036 | A | DOMINANT | 0.0017120 | 0.75 |
| PDE1A | 439 | 1430158 | C | RECESSIVE | 0.0462373 | 0.74 |
| NAB1 | 441 | 16832766 | A | RECESSIVE | 0.0084389 | <.2 |
| TMEFF2 | 442 | 10497725 | C | DOMINANT | 0.0468195 | 1.19 |
| TMEFF2 | 443 | 13004835 | G | RECESSIVE | 0.0187116 | 1.26 |
| TMEFF2 | 444 | 17433337 | A | DOMINANT | 0.0138373 | 0.79 |
| PARD3B | 450 | 1861763 | C | RECESSIVE | 0.0402838 | 0.55 |
| PARD3B | 451 | 1019357 | G | RECESSIVE | 0.0103151 | 0.45 |
| PARD3B | 452 | 236843 | G | DOMINANT | 0.0273232 | 1.23 |
| NRP2 | 457 | 849565 | C | RECESSIVE | 0.0031073 | 1.92 |
| PIP5K3 | 458 | 6746926 | A | DOMINANT | 0.0076853 | 1.28 |
| ERBB4 | 459 | 12992319 | A | DOMINANT | 0.0400316 | 0.84 |
| IRS1 | 462 | 2288587 | C | DOMINANT | 0.0077855 | 0.67 |
| IRS1 | 463 | 16822570 | G | DOMINANT | 0.0077855 | 0.67 |
| IRS1 | 464 | 16822574 | T | ADDITIVE | 0.0429294 | 0.75 |
| IRS1 | 465 | 10205233 | T | ADDITIVE | 0.0131742 | 0.69 |
| IRS1 | 466 | 10181778 | T | ADDITIVE | 0.0014551 | 0.63 |
| IRS1 | 467 | 13414359 | G | RECESSIVE | 0.0185113 | 0.25 |
| IRS1 | 468 | 2396427 | G | RECESSIVE | 0.0434814 | 0.29 |
| COL4A4 | 469 | 1054413 | A | DOMINANT | 0.0093344 | 0.79 |
| COL4A4 | 470 | 10187726 | T | RECESSIVE | 0.0499004 | 1.22 |
| COL4A4 | 471 | 4423583 | T | DOMINANT | 0.0104595 | 0.79 |
| COL4A4 | 472 | 10182307 | A | DOMINANT | 0.0101423 | 0.79 |
| COL4A4 | 473 | 10933165 | G | DOMINANT | 0.0159812 | 0.80 |
| COL4A4 | 474 | 6740108 | C | DOMINANT | 0.0084746 | 0.78 |
| COL4A4 | 475 | 1949807 | G | DOMINANT | 0.0039806 | 0.77 |
| COL4A4 | 476 | 2272198 | T | DOMINANT | 0.0088794 | 0.79 |
| COL4A4 | 477 | 10176882 | T | DOMINANT | 0.0153786 | 0.80 |
| COL4A4 | 478 | 13423714 | G | DOMINANT | 0.0109821 | 0.79 |
| COL4A4 | 479 | 2276593 | A | DOMINANT | 0.0121443 | 0.79 |
| COL4A4 | 480 | 10166736 | A | DOMINANT | 0.0102444 | 0.79 |
| COL4A4 | 481 | 13383070 | A | DOMINANT | 0.0046153 | 0.77 |
| COL4A3 | 483 | 6436672 | A | DOMINANT | 0.0484551 | 1.26 |
| COL4A3 | 484 | 4673188 | T | DOMINANT | 0.0419728 | 1.25 |
| COL4A3 | 485 | 6436674 | A | DOMINANT | 0.0221612 | 1.31 |
| COL4A3 | 486 | 7587228 | C | DOMINANT | 0.0347568 | 1.26 |
| COL4A3 | 487 | 10188531 | C | DOMINANT | 0.0221612 | 1.31 |
| DNER | 488 | 207671 | G | RECESSIVE | 0.0221000 | 1.27 |
| DNER | 490 | 7584721 | A | DOMINANT | 0.0306237 | 1.29 |
| DNER | 491 | 10170426 | T | DOMINANT | 0.0179298 | 1.30 |
| DNER | 492 | 11695348 | A | DOMINANT | 0.0208254 | 1.32 |
| ECEL1 | 493 | 2678505 | G | RECESSIVE | 0.0264454 | 0.21 |
| SAG | 495 | 13427703 | G | DOMINANT | 0.0220575 | 0.78 |
| CENTG2 | 499 | 1962550 | G | ADDITIVE | 0.0450037 | 0.89 |
| CNTN6 | 501 | 9840388 | C | RECESSIVE | 0.0244837 | 0.79 |
| CNTN6 | 506 | 3772274 | T | ADDITIVE | 0.0304668 | 1.20 |
| CNTN6 | 508 | 2291101 | T | ADDITIVE | 0.0416503 | 1.15 |
| CNTN6 | 509 | 2291100 | C | ADDITIVE | 0.0003121 | 0.85 |
| CNTN6 | 510 | 17038463 | G | DOMINANT | 0.0381322 | 1.36 |
| CNTN6 | 511 | 3845158 | T | DOMINANT | 0.0285379 | 1.21 |
| CNTN6 | 512 | 3816445 | G | DOMINANT | 0.0364712 | 1.23 |
| CNTN4 | 513 | 11129148 | T | ADDITIVE | 0.0247728 | 0.89 |
| CNTN4 | 514 | 2134356 | C | ADDITIVE | 0.0101235 | 0.88 |
| CNTN4 | 515 | 899540 | G | DOMINANT | 0.0002858 | 1.42 |
| CNTN4 | 516 | 2616585 | T | DOMINANT | 0.0103108 | 1.27 |
| CNTN4 | 517 | 9837469 | G | DOMINANT | 0.0287880 | 0.81 |
| CNTN4 | 520 | 4685542 | C | ADDITIVE | 0.0499516 | 1.15 |
| CNTN4 | 521 | 9837045 | A | DOMINANT | 0.0224299 | 1.24 |
| CNTN4 | 522 | 9843087 | T | DOMINANT | 0.0407710 | 1.20 |
| ITPR1 | 526 | 304014 | A | DOMINANT | 0.0460660 | 0.84 |

TABLE 1-continued

Alleles and Genotypes Influencing Likelihood of Bipolar vs. Schizophrenia Diagnoses

| Gene | SEQ ID NO: | NCBI RS# | Allele | Model | P | Odds Ratio |
|---|---|---|---|---|---|---|
| ITPR1 | 527 | 13080068 | A | RECESSIVE | 0.0234785 | <.2 |
| ITPR1 | 528 | 902985 | C | RECESSIVE | 0.0389873 | <.2 |
| ITPR1 | 529 | 9818111 | A | RECESSIVE | 0.0236952 | <.2 |
| ITPR1 | 530 | 3792489 | A | RECESSIVE | 0.0339749 | 0.74 |
| IRAK2 | 532 | 778041 | A | ADDITIVE | 0.0238947 | 1.14 |
| IRAK2 | 533 | 708035 | T | ADDITIVE | 0.0196761 | 1.14 |
| SLC6A11 | 535 | 1485142 | C | RECESSIVE | 0.0092762 | 0.53 |
| SLC6A1 | 536 | 1062246 | G | DOMINANT | 0.0301978 | 0.83 |
| SLC6A6 | 537 | 11713355 | A | DOMINANT | 0.0495407 | 0.84 |
| FBXL2 | 539 | 9880596 | C | DOMINANT | 0.0014283 | 1.32 |
| CLASP2 | 540 | 4679039 | C | RECESSIVE | 0.0114555 | 0.72 |
| CLASP2 | 541 | 6772776 | T | RECESSIVE | 0.0498543 | 0.78 |
| CLASP2 | 542 | 8179967 | C | ADDITIVE | 0.0147798 | 0.87 |
| CLASP2 | 543 | 6807542 | G | ADDITIVE | 0.0266431 | 0.90 |
| ULK4 | 553 | 2293301 | G | RECESSIVE | 0.0428999 | 3.55 |
| ULK4 | 554 | 2293300 | C | RECESSIVE | 0.0248408 | 3.94 |
| ULK4 | 555 | 9838277 | G | RECESSIVE | 0.0430861 | 3.55 |
| ULK4 | 556 | 12493870 | C | RECESSIVE | 0.0430861 | 3.55 |
| ULK4 | 557 | 9820239 | T | RECESSIVE | 0.0397738 | 1.52 |
| ULK4 | 559 | 1386601 | G | RECESSIVE | 0.0459956 | 1.26 |
| ULK4 | 560 | 9832048 | A | RECESSIVE | 0.0411133 | 1.23 |
| ZNF445 | 561 | 9311357 | G | RECESSIVE | 0.0462402 | 1.33 |
| CAMKV | 564 | 2883059 | C | RECESSIVE | 0.0170760 | 1.32 |
| SEMA3F | 565 | 2624842 | G | RECESSIVE | 0.0015687 | 2.76 |
| SEMA3F | 566 | 11711407 | A | RECESSIVE | 0.0018287 | 1.39 |
| CACNA2D2 | 567 | 762895 | C | RECESSIVE | 0.0018308 | 2.65 |
| CACNA2D2 | 568 | 2298955 | C | RECESSIVE | 0.0013825 | 2.64 |
| CACNA2D2 | 569 | 734767 | C | RECESSIVE | 0.0012152 | 2.67 |
| CACNA2D2 | 570 | 2236964 | G | RECESSIVE | 0.0073441 | 2.31 |
| CACNA2D2 | 571 | 916217 | T | RECESSIVE | 0.0100097 | 2.30 |
| CACNA2D2 | 572 | 2236967 | A | RECESSIVE | 0.0236960 | 2.06 |
| CACNA2D2 | 573 | 743757 | G | RECESSIVE | 0.0048367 | 2.39 |
| CACNA2D2 | 574 | 2236975 | C | RECESSIVE | 0.0043747 | 2.48 |
| CACNA2D2 | 575 | 12492113 | A | RECESSIVE | 0.0077768 | 2.49 |
| CACNA2D2 | 576 | 6786523 | T | RECESSIVE | 0.0003940 | 3.05 |
| CACNA2D2 | 577 | 12494849 | G | RECESSIVE | 0.0003948 | 3.05 |
| CACNA2D2 | 578 | 1467913 | T | RECESSIVE | 0.0003948 | 3.05 |
| CACNA2D2 | 579 | 754298 | C | RECESSIVE | 0.0304486 | 2.10 |
| ERC2 | 587 | 11712729 | C | RECESSIVE | 0.0260858 | 1.43 |
| FHIT | 591 | 11707783 | G | ADDITIVE | 0.0482246 | 0.82 |
| FHIT | 592 | 6446100 | T | DOMINANT | 0.0035376 | 0.77 |
| FHIT | 593 | 2736802 | A | DOMINANT | 0.0392613 | 0.81 |
| FHIT | 594 | 212015 | T | ADDITIVE | 0.0203327 | 0.81 |
| FHIT | 595 | 13066381 | T | DOMINANT | 0.0083825 | 0.80 |
| FHIT | 596 | 802778 | A | ADDITIVE | 0.0214893 | 0.80 |
| FHIT | 597 | 802779 | C | ADDITIVE | 0.0432879 | 0.82 |
| FHIT | 598 | 17062392 | C | DOMINANT | 0.0186053 | 1.23 |
| FHIT | 601 | 7650786 | T | RECESSIVE | 0.0483484 | 1.24 |
| FHIT | 602 | 2142296 | G | ADDITIVE | 0.0252880 | 0.88 |
| PTPRG | 603 | 1388613 | C | RECESSIVE | 0.0291650 | 0.66 |
| CADPS | 604 | 304209 | G | DOMINANT | 0.0406227 | 0.84 |
| SYNPR | 612 | 1812207 | A | DOMINANT | 0.0082602 | 1.26 |
| SYNPR | 613 | 1505595 | A | RECESSIVE | 0.0459095 | 1.58 |
| ROBO2 | 624 | 4683968 | G | DOMINANT | 0.0446194 | 1.20 |
| ROBO1 | 626 | 329812 | C | RECESSIVE | 0.0164134 | 1.39 |
| ROBO1 | 627 | 162262 | T | RECESSIVE | 0.0084565 | 1.43 |
| ROBO1 | 628 | 1455833 | A | RECESSIVE | 0.0493273 | 0.73 |
| ROBO1 | 629 | 7631406 | T | RECESSIVE | 0.0109668 | 0.68 |
| ROBO1 | 630 | 12486635 | G | RECESSIVE | 0.0408876 | 0.75 |
| GBE1 | 632 | 9821673 | A | RECESSIVE | 0.0292191 | 0.60 |
| CBLB | 635 | 1443108 | T | RECESSIVE | 0.0351240 | 0.71 |
| CBLB | 636 | 1550711 | G | RECESSIVE | 0.0404819 | 0.79 |
| CBLB | 637 | 7638504 | C | DOMINANT | 0.0101111 | 0.77 |
| CBLB | 638 | 12497428 | G | DOMINANT | 0.0135723 | 0.77 |
| CBLB | 639 | 9838755 | C | DOMINANT | 0.0122254 | 0.77 |
| KALRN | 644 | 13321072 | C | DOMINANT | 0.0396312 | 0.78 |
| KALRN | 645 | 2008839 | A | DOMINANT | 0.0354175 | 0.77 |
| KALRN | 646 | 1822995 | A | ADDITIVE | 0.0345649 | 1.24 |
| KALRN | 647 | 10433406 | A | ADDITIVE | 0.0211886 | 1.24 |
| KALRN | 648 | 2289843 | A | ADDITIVE | 0.0148873 | 1.26 |
| KALRN | 649 | 3729581 | T | DOMINANT | 0.0351293 | 1.23 |
| ZXDC | 651 | 1043803 | A | DOMINANT | 0.0333425 | 0.83 |
| ZXDC | 652 | 1687462 | C | DOMINANT | 0.0266341 | 0.82 |
| CPNE4 | 654 | 9289393 | T | RECESSIVE | 0.0302037 | 1.26 |
| CPNE4 | 655 | 16838031 | A | ADDITIVE | 0.0008895 | 1.44 |

TABLE 1-continued

Alleles and Genotypes Influencing Likelihood of Bipolar vs. Schizophrenia Diagnoses

| Gene | SEQ ID NO: | NCBI RS# | Allele | Model | P | Odds Ratio |
|---|---|---|---|---|---|---|
| CPNE4 | 656 | 17297521 | G | DOMINANT | 0.0130424 | 1.30 |
| CPNE4 | 657 | 6806898 | T | ADDITIVE | 0.0109104 | 1.26 |
| EPHB1 | 671 | 3772637 | T | DOMINANT | 0.0037323 | 1.28 |
| SPSB4 | 672 | 9816809 | T | DOMINANT | 0.0476394 | 1.26 |
| SPSB4 | 673 | 11915229 | C | DOMINANT | 0.0496640 | 1.26 |
| SERPINI1 | 675 | 2229697 | A | DOMINANT | 0.0434861 | 0.80 |
| SLC7A14 | 676 | 7648588 | A | DOMINANT | 0.0475929 | 0.83 |
| TNIK | 681 | 6445006 | A | RECESSIVE | 0.0017287 | 0.52 |
| PLD1 | 682 | 380929 | A | ADDITIVE | 0.0362956 | 1.11 |
| PLD1 | 683 | 397176 | T | ADDITIVE | 0.0318479 | 1.12 |
| PLD1 | 684 | 431196 | C | ADDITIVE | 0.0322453 | 1.12 |
| PLD1 | 685 | 406484 | A | ADDITIVE | 0.0339780 | 1.11 |
| PLD1 | 686 | 405910 | T | ADDITIVE | 0.0195401 | 1.11 |
| PLD1 | 687 | 360413 | A | ADDITIVE | 0.0143963 | 1.15 |
| PLD1 | 688 | 187229 | T | ADDITIVE | 0.0118656 | 1.17 |
| PLD1 | 689 | 181715 | A | ADDITIVE | 0.0093281 | 1.19 |
| PLD1 | 690 | 360401 | T | ADDITIVE | 0.0114614 | 1.18 |
| NLGN1 | 703 | 6779415 | A | DOMINANT | 0.0412066 | 1.22 |
| NLGN1 | 705 | 9815572 | A | ADDITIVE | 0.0466970 | 1.17 |
| NLGN1 | 706 | 7614469 | C | RECESSIVE | 0.0177892 | 1.62 |
| IL1RAP | 710 | 4140708 | G | RECESSIVE | 0.0320163 | 1.40 |
| IL1RAP | 711 | 3774001 | G | RECESSIVE | 0.0214074 | 1.44 |
| IL1RAP | 712 | 3773999 | C | RECESSIVE | 0.0175931 | 1.45 |
| IL1RAP | 713 | 9990231 | C | RECESSIVE | 0.0048588 | 1.61 |
| IL1RAP | 714 | 10212103 | C | RECESSIVE | 0.0173303 | 1.46 |
| IL1RAP | 716 | 10513860 | A | RECESSIVE | 0.0307056 | 4.72 |
| IL1RAP | 717 | 6444452 | T | RECESSIVE | 0.0167183 | 5.33 |
| CENTB2 | 718 | 2410839 | G | DOMINANT | 0.0200194 | 1.24 |
| SLC2A9 | 721 | 13142273 | T | RECESSIVE | 0.0300284 | >5 |
| SLC2A9 | 722 | 3733589 | T | RECESSIVE | 0.0300284 | >5 |
| SLC2A9 | 723 | 16891926 | T | RECESSIVE | 0.0291182 | >5 |
| SLC2A9 | 724 | 13101772 | A | RECESSIVE | 0.0300161 | >5 |
| LDB2 | 726 | 1501132 | T | RECESSIVE | 0.0003835 | 0.33 |
| LDB2 | 727 | 6449255 | A | RECESSIVE | 0.0174593 | 0.55 |
| LDB2 | 728 | 1501141 | T | RECESSIVE | 0.0285595 | 0.57 |
| SOD3 | 740 | 12649653 | A | RECESSIVE | 0.0401569 | 0.73 |
| PI4K2B | 741 | 7654358 | G | RECESSIVE | 0.0424119 | 1.27 |
| N4BP2 | 745 | 1625495 | C | RECESSIVE | 0.0459815 | 0.56 |
| LIMCH1 | 754 | 4610372 | G | DOMINANT | 0.0063646 | 1.29 |
| LIMCH1 | 756 | 4861118 | A | DOMINANT | 0.0464618 | 1.20 |
| LIMCH1 | 759 | 1105886 | T | DOMINANT | 0.0081667 | 1.26 |
| LIMCH1 | 760 | 10026359 | T | DOMINANT | 0.0006576 | 1.37 |
| LIMCH1 | 761 | 13146318 | T | DOMINANT | 0.0093573 | 1.25 |
| LIMCH1 | 762 | 10805090 | C | DOMINANT | 0.0115515 | 1.24 |
| LIMCH1 | 763 | 13113314 | T | DOMINANT | 0.0122260 | 1.27 |
| LIMCH1 | 764 | 2304651 | A | RECESSIVE | 0.0225626 | 0.13 |
| LIMCH1 | 765 | 7674006 | C | RECESSIVE | 0.0388071 | <.2 |
| LPHN3 | 768 | 950313 | C | RECESSIVE | 0.0124420 | 0.53 |
| LPHN3 | 769 | 1124974 | A | RECESSIVE | 0.0449070 | 0.62 |
| NPFFR2 | 772 | 4574375 | G | ADDITIVE | 0.0358307 | 0.66 |
| NPFFR2 | 773 | 4379029 | G | ADDITIVE | 0.0361672 | 0.66 |
| NPFFR2 | 774 | 7657617 | A | ADDITIVE | 0.0498153 | 0.68 |
| NPFFR2 | 775 | 4276256 | T | ADDITIVE | 0.0490012 | 0.68 |
| NPFFR2 | 776 | 9884712 | A | ADDITIVE | 0.0369620 | 0.66 |
| NPFFR2 | 777 | 10938003 | A | ADDITIVE | 0.0362230 | 0.66 |
| NPFFR2 | 778 | 10033980 | C | ADDITIVE | 0.0358307 | 0.66 |
| NPFFR2 | 779 | 4472109 | T | ADDITIVE | 0.0186600 | 0.62 |
| NPFFR2 | 780 | 11733404 | A | ADDITIVE | 0.0183936 | 1.15 |
| NPFFR2 | 781 | 2137735 | A | DOMINANT | 0.0086958 | 1.25 |
| NPFFR2 | 782 | 7673208 | C | ADDITIVE | 0.0054932 | 1.18 |
| NPFFR2 | 783 | 2365797 | T | ADDITIVE | 0.0207231 | 1.13 |
| SCARB2 | 784 | 17001532 | A | RECESSIVE | 0.0073559 | 2.31 |
| SCARB2 | 785 | 17001533 | C | RECESSIVE | 0.0073559 | 2.31 |
| SCD5 | 790 | 10014168 | C | RECESSIVE | 0.0137208 | 1.48 |
| GPRIN3 | 791 | 6844815 | G | RECESSIVE | 0.0344083 | 0.77 |
| GPRIN3 | 794 | 12498405 | T | RECESSIVE | 0.0326299 | 1.25 |
| GPRIN3 | 795 | 6839114 | C | RECESSIVE | 0.0318186 | 1.25 |
| GRID2 | 796 | 1993030 | T | RECESSIVE | 0.0084799 | 0.60 |
| UNC5C | 811 | 2220105 | G | RECESSIVE | 0.0256000 | 1.40 |
| UNC5C | 814 | 13121737 | C | DOMINANT | 0.0140151 | 0.80 |
| UNC5C | 815 | 13134684 | T | ADDITIVE | 0.0299021 | 0.90 |
| UNC5C | 816 | 4103379 | G | DOMINANT | 0.0193420 | 0.80 |
| UNC5C | 817 | 6834411 | G | DOMINANT | 0.0202948 | 0.80 |
| UNC5C | 818 | 4519799 | G | RECESSIVE | 0.0304882 | 4.73 |
| ADH1C | 820 | 2851255 | G | RECESSIVE | 0.0281527 | 0.69 |

TABLE 1-continued

Alleles and Genotypes Influencing Likelihood of Bipolar vs. Schizophrenia Diagnoses

| Gene | SEQ ID NO: | NCBI RS# | Allele | Model | P | Odds Ratio |
|---|---|---|---|---|---|---|
| PPP3CA | 826 | 2659524 | A | RECESSIVE | 0.0464225 | 0.64 |
| PAPSS1 | 827 | 9569 | A | RECESSIVE | 0.0327436 | 0.66 |
| PAPSS1 | 828 | 2522421 | G | RECESSIVE | 0.0138444 | 0.12 |
| PAPSS1 | 829 | 2522422 | A | RECESSIVE | 0.0139557 | 0.12 |
| PAPSS1 | 830 | 2522423 | T | RECESSIVE | 0.0088063 | 0.11 |
| PAPSS1 | 831 | 757170 | T | RECESSIVE | 0.0225406 | 0.13 |
| PAPSS1 | 832 | 2726198 | G | RECESSIVE | 0.0141927 | 0.12 |
| PAPSS1 | 833 | 2340454 | T | RECESSIVE | 0.0034834 | <.2 |
| PAPSS1 | 834 | 2522431 | C | RECESSIVE | 0.0139557 | 0.12 |
| COL25A1 | 838 | 17233629 | A | DOMINANT | 0.0208133 | 1.22 |
| COL25A1 | 839 | 4256292 | G | DOMINANT | 0.0276724 | 1.21 |
| COL25A1 | 840 | 6857726 | A | ADDITIVE | 0.0281793 | 1.19 |
| ANK2 | 843 | 10488905 | C | DOMINANT | 0.0194020 | 1.25 |
| ANK2 | 844 | 11933707 | G | DOMINANT | 0.0068063 | 1.27 |
| ANK2 | 845 | 10488904 | A | DOMINANT | 0.0098931 | 1.26 |
| ANK2 | 847 | 29355 | G | RECESSIVE | 0.0087407 | 0.32 |
| ANK2 | 848 | 29319 | A | RECESSIVE | 0.0059700 | 0.30 |
| CAMK2D | 850 | 13144613 | G | RECESSIVE | 0.0478159 | 1.30 |
| MAML3 | 856 | 1350036 | T | DOMINANT | 0.0438195 | 1.22 |
| MAML3 | 857 | 2604918 | A | DOMINANT | 0.0139465 | 0.81 |
| MAML3 | 858 | 7698089 | T | RECESSIVE | 0.0079339 | 1.32 |
| MAML3 | 859 | 7656823 | A | RECESSIVE | 0.0089806 | 1.31 |
| MAML3 | 860 | 9996478 | G | RECESSIVE | 0.0093113 | 1.31 |
| MAML3 | 861 | 4863720 | C | RECESSIVE | 0.0079848 | 1.32 |
| MAML3 | 863 | 6858531 | T | RECESSIVE | 0.0498930 | 2.55 |
| MAML3 | 864 | 11947536 | C | RECESSIVE | 0.0078938 | >5 |
| INPP4B | 866 | 336407 | G | ADDITIVE | 0.0099862 | 1.17 |
| INPP4B | 867 | 336402 | T | DOMINANT | 0.0127092 | 1.25 |
| INPP4B | 868 | 336406 | A | DOMINANT | 0.0083762 | 1.27 |
| INPP4B | 869 | 336394 | G | DOMINANT | 0.0047041 | 1.29 |
| INPP4B | 870 | 2636637 | T | DOMINANT | 0.0115457 | 1.26 |
| INPP4B | 871 | 1219269 | T | DOMINANT | 0.0328045 | 1.22 |
| INPP4B | 872 | 2636656 | G | DOMINANT | 0.0493955 | 1.20 |
| INPP4B | 873 | 3102439 | G | DOMINANT | 0.0224570 | 1.24 |
| INPP4B | 874 | 1907119 | G | DOMINANT | 0.0186256 | 1.25 |
| INPP4B | 875 | 2172023 | T | DOMINANT | 0.0200937 | 1.24 |
| INPP4B | 876 | 2636652 | C | ADDITIVE | 0.0109982 | 1.26 |
| DCLK2 | 892 | 11727182 | G | DOMINANT | 0.0322952 | 0.82 |
| CTSO | 894 | 6832480 | T | DOMINANT | 0.0237369 | 1.22 |
| CTSO | 895 | 6536124 | T | DOMINANT | 0.0234800 | 1.22 |
| CTSO | 896 | 10024900 | A | ADDITIVE | 0.0325296 | 1.14 |
| FSTL5 | 904 | 7375994 | A | RECESSIVE | 0.0315844 | 1.69 |
| TLL1 | 910 | 12646597 | T | RECESSIVE | 0.0483031 | 0.79 |
| TLL1 | 911 | 10018177 | T | RECESSIVE | 0.0412312 | 0.75 |
| PALLD | 913 | 10440507 | T | DOMINANT | 0.0486089 | 0.84 |
| PALLD | 914 | 6552874 | A | RECESSIVE | 0.0462259 | 1.35 |
| PALLD | 915 | 10019193 | G | RECESSIVE | 0.0304723 | 1.38 |
| PALLD | 917 | 2710841 | T | DOMINANT | 0.0321971 | 0.83 |
| PALLD | 918 | 4280700 | T | DOMINANT | 0.0338394 | 0.81 |
| PALLD | 919 | 12511925 | T | DOMINANT | 0.0274824 | 0.81 |
| PALLD | 920 | 13122019 | A | RECESSIVE | 0.0407708 | 1.24 |
| PALLD | 921 | 1039386 | G | DOMINANT | 0.0385672 | 0.83 |
| GPM6A | 928 | 2877886 | C | DOMINANT | 0.0050323 | 0.78 |
| GPM6A | 929 | 1021226 | C | ADDITIVE | 0.0380585 | 0.92 |
| ENPP6 | 934 | 9968325 | A | ADDITIVE | 0.0406970 | 1.16 |
| CASP3 | 935 | 12108497 | T | DOMINANT | 0.0111860 | 1.24 |
| SLC6A3 | 936 | 27061 | A | ADDITIVE | 0.0167413 | 0.87 |
| SLC6A3 | 937 | 250682 | G | DOMINANT | 0.0065105 | 0.78 |
| SLC6A3 | 938 | 250681 | A | DOMINANT | 0.0470083 | 0.83 |
| SLC6A3 | 939 | 393795 | A | DOMINANT | 0.0025052 | 0.76 |
| SLC6A3 | 940 | 2937639 | A | RECESSIVE | 0.0240082 | 0.76 |
| SEMA5A | 941 | 1806095 | T | ADDITIVE | 0.0352291 | 1.23 |
| SEMA5A | 942 | 268529 | G | ADDITIVE | 0.0374797 | 1.11 |
| SEMA5A | 945 | 150631 | A | ADDITIVE | 0.0360142 | 0.87 |
| CTNND2 | 946 | 1024497 | A | ADDITIVE | 0.0281941 | 0.87 |
| CTNND2 | 947 | 13358276 | T | ADDITIVE | 0.0019458 | 1.19 |
| CTNND2 | 948 | 32267 | T | DOMINANT | 0.0124904 | 0.79 |
| CTNND2 | 949 | 32264 | T | DOMINANT | 0.0121132 | 0.79 |
| CTNND2 | 952 | 31888 | A | ADDITIVE | 0.0362142 | 0.84 |
| CTNND2 | 953 | 31892 | T | ADDITIVE | 0.0472033 | 0.87 |
| CTNND2 | 954 | 1458482 | T | DOMINANT | 0.0011190 | 1.35 |
| CTNND2 | 955 | 1458483 | T | ADDITIVE | 0.0014734 | 0.81 |
| CTNND2 | 956 | 6884647 | T | DOMINANT | 0.0010565 | 1.35 |
| CTNND2 | 957 | 1542428 | T | DOMINANT | 0.0004697 | 1.38 |
| CTNND2 | 958 | 1379901 | T | DOMINANT | 0.0007729 | 1.36 |

TABLE 1-continued

Alleles and Genotypes Influencing Likelihood of Bipolar vs. Schizophrenia Diagnoses

| Gene | SEQ ID NO: | NCBI RS# | Allele | Model | P | Odds Ratio |
|---|---|---|---|---|---|---|
| DNAH5 | 960 | 13154455 | G | RECESSIVE | 0.0417889 | 1.27 |
| DNAH5 | 961 | 13178616 | C | RECESSIVE | 0.0248029 | 1.32 |
| BASP1 | 964 | 2929726 | A | ADDITIVE | 0.0022115 | 1.16 |
| BASP1 | 965 | 2956564 | G | ADDITIVE | 0.0025794 | 1.13 |
| BASP1 | 966 | 2929710 | C | ADDITIVE | 0.0023921 | 1.13 |
| CDH10 | 968 | 10056470 | C | RECESSIVE | 0.0411944 | 0.50 |
| SLC1A3 | 974 | 2731877 | C | DOMINANT | 0.0461012 | 0.82 |
| SLC1A3 | 975 | 4869680 | G | DOMINANT | 0.0351844 | 0.83 |
| EGFLAM | 976 | 6873748 | C | RECESSIVE | 0.0284958 | 0.34 |
| EGFLAM | 977 | 2589804 | G | RECESSIVE | 0.0058548 | 0.32 |
| EGFLAM | 978 | 2561111 | T | RECESSIVE | 0.0497412 | 0.43 |
| ITGA1 | 979 | 2548494 | T | ADDITIVE | 0.0368558 | 1.19 |
| ITGA1 | 980 | 13189973 | T | ADDITIVE | 0.0394305 | 1.19 |
| ITGA1 | 983 | 10513000 | G | ADDITIVE | 0.0138472 | 0.89 |
| ITGA1 | 986 | 1047481 | G | DOMINANT | 0.0313913 | 1.22 |
| ITGA2 | 988 | 989073 | A | ADDITIVE | 0.0375827 | 1.12 |
| ITGA2 | 989 | 1421937 | C | ADDITIVE | 0.0317117 | 1.12 |
| ITGA2 | 994 | 12521915 | G | RECESSIVE | 0.0343584 | 1.32 |
| PDE4D | 997 | 12654005 | G | DOMINANT | 0.0381491 | 0.83 |
| PDE4D | 998 | 929820 | T | DOMINANT | 0.0479056 | 0.84 |
| PDE4D | 999 | 9292195 | T | ADDITIVE | 0.0404465 | 1.15 |
| PDE4D | 1000 | 35258 | T | RECESSIVE | 0.0398711 | 0.77 |
| PDE4D | 1001 | 294492 | T | RECESSIVE | 0.0080393 | 2.48 |
| PDE4D | 1002 | 295954 | G | RECESSIVE | 0.0337408 | 1.99 |
| PDE4D | 1003 | 295956 | T | RECESSIVE | 0.0222173 | 2.12 |
| PDE4D | 1004 | 17380508 | C | RECESSIVE | 0.0499867 | 0.43 |
| ELOVL7 | 1007 | 6449503 | A | DOMINANT | 0.0493368 | 0.83 |
| ELOVL7 | 1008 | 4482855 | T | DOMINANT | 0.0210430 | 0.80 |
| ELOVL7 | 1009 | 4700394 | A | DOMINANT | 0.0224171 | 0.80 |
| ELOVL7 | 1010 | 4700397 | A | RECESSIVE | 0.0271345 | 1.28 |
| ELOVL7 | 1011 | 17332824 | G | RECESSIVE | 0.0297118 | 1.27 |
| PIK3R1 | 1012 | 706713 | T | RECESSIVE | 0.0495010 | 0.66 |
| TNPO1 | 1015 | 34673 | G | DOMINANT | 0.0424093 | 0.81 |
| TNPO1 | 1016 | 155624 | T | ADDITIVE | 0.0188032 | 0.81 |
| FCHO2 | 1018 | 7712673 | T | ADDITIVE | 0.0260252 | 0.86 |
| FCHO2 | 1019 | 716327 | T | ADDITIVE | 0.0227187 | 0.85 |
| FCHO2 | 1020 | 1156398 | G | ADDITIVE | 0.0244766 | 0.85 |
| FCHO2 | 1021 | 1568712 | G | ADDITIVE | 0.0196452 | 0.85 |
| FCHO2 | 1022 | 2277017 | C | ADDITIVE | 0.0379745 | 0.87 |
| FCHO2 | 1023 | 7727222 | C | ADDITIVE | 0.0064707 | 0.83 |
| PDE8B | 1024 | 1982658 | A | RECESSIVE | 0.0095640 | 0.66 |
| PDE8B | 1025 | 11953611 | C | RECESSIVE | 0.0030521 | 1.64 |
| PDE8B | 1030 | 13178853 | C | RECESSIVE | 0.0344304 | 1.46 |
| PDE8B | 1031 | 398509 | G | RECESSIVE | 0.0406595 | 1.44 |
| PDE8B | 1032 | 335643 | G | RECESSIVE | 0.0073142 | 1.63 |
| SCAMP1 | 1034 | 10942850 | G | DOMINANT | 0.0484655 | 0.82 |
| SCAMP1 | 1035 | 1529497 | T | DOMINANT | 0.0144309 | 0.79 |
| SCAMP1 | 1036 | 11950060 | T | DOMINANT | 0.0146335 | 0.79 |
| SCAMP1 | 1037 | 11949403 | A | DOMINANT | 0.0191555 | 0.79 |
| SCAMP1 | 1038 | 3952231 | G | DOMINANT | 0.0105949 | 0.78 |
| SCAMP1 | 1039 | 9293749 | A | DOMINANT | 0.0144309 | 0.79 |
| SCAMP1 | 1040 | 10474548 | G | RECESSIVE | 0.0114317 | 1.29 |
| SCAMP1 | 1041 | 10065805 | C | DOMINANT | 0.0169067 | 0.79 |
| SCAMP1 | 1042 | 1050674 | G | DOMINANT | 0.0087343 | 0.77 |
| SCAMP1 | 1043 | 10514138 | G | DOMINANT | 0.0097017 | 0.77 |
| CMYA5 | 1050 | 12514461 | G | DOMINANT | 0.0467297 | 1.24 |
| MEF2C | 1052 | 454214 | G | ADDITIVE | 0.0081904 | 1.14 |
| MEF2C | 1053 | 618298 | T | ADDITIVE | 0.0161067 | 1.14 |
| MEF2C | 1054 | 625970 | A | ADDITIVE | 0.0147143 | 1.14 |
| MEF2C | 1055 | 681446 | A | ADDITIVE | 0.0103384 | 1.15 |
| MEF2C | 1056 | 679232 | G | ADDITIVE | 0.0126294 | 1.15 |
| MEF2C | 1057 | 304153 | T | DOMINANT | 0.0022371 | 1.30 |
| MEF2C | 1058 | 304152 | C | DOMINANT | 0.0026481 | 1.30 |
| MEF2C | 1059 | 304151 | C | DOMINANT | 0.0085504 | 1.25 |
| MEF2C | 1060 | 304159 | T | DOMINANT | 0.0021511 | 1.30 |
| GPR98 | 1063 | 7716829 | A | DOMINANT | 0.0390854 | 0.83 |
| GPR98 | 1067 | 1876635 | C | RECESSIVE | 0.0053294 | 0.21 |
| GPR98 | 1069 | 1852731 | C | ADDITIVE | 0.0462196 | 0.86 |
| PJA2 | 1086 | 2963046 | T | RECESSIVE | 0.0407637 | 1.29 |
| PJA2 | 1087 | 2914705 | A | RECESSIVE | 0.0380956 | 1.30 |
| PJA2 | 1089 | 2963029 | C | RECESSIVE | 0.0083230 | 1.44 |
| PJA2 | 1090 | 2963031 | A | RECESSIVE | 0.0215023 | 1.48 |
| PJA2 | 1091 | 2963034 | A | RECESSIVE | 0.0155698 | 1.40 |
| PJA2 | 1092 | 2963013 | C | RECESSIVE | 0.0065274 | 1.58 |
| KCNN2 | 1094 | 1841248 | G | RECESSIVE | 0.0051033 | 0.43 |

TABLE 1-continued

Alleles and Genotypes Influencing Likelihood of Bipolar vs. Schizophrenia Diagnoses

| Gene | SEQ ID NO: | NCBI RS# | Allele | Model | P | Odds Ratio |
|---|---|---|---|---|---|---|
| KCNN2 | 1095 | 6889371 | G | RECESSIVE | 0.0101849 | 0.45 |
| SEMA6A | 1096 | 154599 | G | RECESSIVE | 0.0337687 | 0.61 |
| SEMA6A | 1097 | 154600 | C | RECESSIVE | 0.0488880 | 0.64 |
| VDAC1 | 1110 | 2066944 | T | RECESSIVE | 0.0139245 | 0.51 |
| GRIA1 | 1133 | 1037892 | T | RECESSIVE | 0.0339369 | 0.68 |
| ODZ2 | 1134 | 5024074 | G | DOMINANT | 0.0015007 | 1.42 |
| ODZ2 | 1137 | 1549152 | C | DOMINANT | 0.0358324 | 0.81 |
| ODZ2 | 1138 | 9284975 | T | DOMINANT | 0.0430784 | 0.76 |
| ODZ2 | 1140 | 11952245 | G | DOMINANT | 0.0310791 | 0.83 |
| ODZ2 | 1141 | 11959012 | T | DOMINANT | 0.0200308 | 1.25 |
| ODZ2 | 1143 | 10447203 | A | ADDITIVE | 0.0114402 | 0.87 |
| ODZ2 | 1144 | 11748886 | G | ADDITIVE | 0.0306799 | 0.79 |
| WWC1 | 1146 | 9686714 | C | RECESSIVE | 0.0138956 | 0.12 |
| WWC1 | 1147 | 2085449 | A | ADDITIVE | 0.0147636 | 0.86 |
| WWC1 | 1150 | 888773 | A | ADDITIVE | 0.0147299 | 0.82 |
| KCNIP1 | 1154 | 4867625 | A | RECESSIVE | 0.0084345 | 1.79 |
| STK10 | 1157 | 2172048 | C | RECESSIVE | 0.0266094 | 1.27 |
| EXOC2 | 1162 | 9405242 | A | DOMINANT | 0.0286682 | 0.82 |
| EXOC2 | 1164 | 1766835 | C | RECESSIVE | 0.0130641 | 1.55 |
| EXOC2 | 1165 | 4960092 | G | RECESSIVE | 0.0171303 | 1.65 |
| EXOC2 | 1167 | 1747586 | A | RECESSIVE | 0.0472588 | 1.53 |
| EXOC2 | 1168 | 9328331 | G | RECESSIVE | 0.0476395 | 1.44 |
| JARID2 | 1174 | 2237156 | T | ADDITIVE | 0.0054397 | 1.24 |
| JARID2 | 1175 | 4109434 | T | ADDITIVE | 0.0061261 | 0.88 |
| JARID2 | 1176 | 9383054 | G | ADDITIVE | 0.0043356 | 1.25 |
| JARID2 | 1177 | 2237152 | G | DOMINANT | 0.0007130 | 1.36 |
| JARID2 | 1178 | 2237150 | G | DOMINANT | 0.0038437 | 1.30 |
| JARID2 | 1179 | 4085876 | T | ADDITIVE | 0.0016878 | 1.20 |
| JARID2 | 1180 | 2282827 | C | ADDITIVE | 0.0033568 | 1.17 |
| JARID2 | 1181 | 9476827 | T | ADDITIVE | 0.0010437 | 1.20 |
| JARID2 | 1182 | 2237124 | C | ADDITIVE | 0.0006731 | 1.22 |
| ATXN1 | 1183 | 235146 | C | RECESSIVE | 0.0194869 | 0.78 |
| ATXN1 | 1184 | 235147 | A | DOMINANT | 0.0015523 | 1.35 |
| ATXN1 | 1185 | 2237175 | C | DOMINANT | 0.0033516 | 0.70 |
| SLC17A4 | 1198 | 9358890 | G | DOMINANT | 0.0070529 | 0.66 |
| BTN3A1 | 1214 | 3799378 | G | RECESSIVE | 0.0343668 | 1.51 |
| MSH5 | 1217 | 2299851 | A | ADDITIVE | 0.0063621 | 1.35 |
| MSH5 | 1218 | 707937 | C | RECESSIVE | 0.0160747 | 1.82 |
| KLC4 | 1221 | 9471999 | C | RECESSIVE | 0.0279392 | 0.34 |
| TJAP1 | 1223 | 7755135 | T | DOMINANT | 0.0170193 | 1.30 |
| XPO5 | 1224 | 7769795 | A | ADDITIVE | 0.0440420 | 1.25 |
| XPO5 | 1225 | 7748977 | C | ADDITIVE | 0.0377733 | 1.26 |
| XPO5 | 1226 | 1096699 | A | RECESSIVE | 0.0342656 | 0.73 |
| XPO5 | 1227 | 699937 | T | RECESSIVE | 0.0267710 | 0.72 |
| TMEM63B | 1228 | 1935611 | A | DOMINANT | 0.0021920 | 0.74 |
| ELOVL5 | 1229 | 10948744 | G | DOMINANT | 0.0049312 | 1.28 |
| ELOVL5 | 1230 | 209485 | A | RECESSIVE | 0.0440659 | 0.81 |
| ELOVL5 | 1231 | 1579454 | G | ADDITIVE | 0.0157892 | 0.82 |
| ELOVL5 | 1232 | 9474507 | A | ADDITIVE | 0.0170088 | 0.82 |
| ELOVL5 | 1233 | 9296711 | G | ADDITIVE | 0.0061497 | 0.83 |
| RIMS1 | 1234 | 9360527 | T | DOMINANT | 0.0207283 | 1.24 |
| RIMS1 | 1235 | 2349095 | T | ADDITIVE | 0.0427535 | 1.17 |
| HTR1B | 1236 | 6296 | C | ADDITIVE | 0.0424589 | 0.90 |
| GABRR2 | 1238 | 9294426 | A | ADDITIVE | 0.0405476 | 0.92 |
| GABRR2 | 1239 | 9344920 | T | ADDITIVE | 0.0183365 | 0.86 |
| TRDN | 1244 | 7773653 | T | DOMINANT | 0.0076876 | 1.31 |
| TRDN | 1245 | 1431284 | G | RECESSIVE | 0.0445839 | 0.77 |
| TRDN | 1246 | 17737857 | C | RECESSIVE | 0.0128481 | 0.78 |
| TRDN | 1249 | 6905508 | T | DOMINANT | 0.0214175 | 1.22 |
| TRDN | 1250 | 1570187 | C | DOMINANT | 0.0299527 | 1.21 |
| TRDN | 1251 | 1570186 | T | DOMINANT | 0.0370378 | 1.20 |
| TRDN | 1252 | 1853158 | G | DOMINANT | 0.0219061 | 1.22 |
| TRDN | 1253 | 6915835 | C | DOMINANT | 0.0313070 | 1.21 |
| TRDN | 1254 | 9398739 | T | DOMINANT | 0.0077908 | 1.26 |
| TRDN | 1255 | 7453704 | C | DOMINANT | 0.0440035 | 1.19 |
| TRDN | 1256 | 1853157 | A | DOMINANT | 0.0169131 | 1.23 |
| TRDN | 1257 | 9285452 | G | DOMINANT | 0.0091034 | 1.26 |
| TRDN | 1258 | 1459767 | C | DOMINANT | 0.0127535 | 1.25 |
| NKAIN2 | 1259 | 342660 | A | DOMINANT | 0.0416553 | 0.70 |
| NKAIN2 | 1260 | 342641 | T | DOMINANT | 0.0464314 | 0.72 |
| EYA4 | 1264 | 7454561 | G | RECESSIVE | 0.0330682 | 0.80 |
| PDE7B | 1266 | 7761961 | T | DOMINANT | 0.0279036 | 1.22 |
| PDE7B | 1267 | 6916194 | T | ADDITIVE | 0.0427785 | 1.12 |
| PDE7B | 1268 | 4074263 | T | ADDITIVE | 0.0300311 | 1.42 |
| UTRN | 1275 | 9373430 | A | RECESSIVE | 0.0306231 | 1.32 |

TABLE 1-continued

Alleles and Genotypes Influencing Likelihood of Bipolar vs. Schizophrenia Diagnoses

| Gene | SEQ ID NO: | NCBI RS# | Allele | Model | P | Odds Ratio |
|---|---|---|---|---|---|---|
| SYNE1 | 1276 | 2763031 | T | DOMINANT | 0.0248949 | 0.82 |
| SYNE1 | 1277 | 2635470 | C | DOMINANT | 0.0242862 | 0.82 |
| SYNE1 | 1278 | 2635469 | A | DOMINANT | 0.0378937 | 0.83 |
| SYNE1 | 1279 | 1324452 | T | DOMINANT | 0.0422846 | 0.84 |
| SYNE1 | 1280 | 2763015 | A | RECESSIVE | 0.0149143 | 1.29 |
| SLC22A3 | 1281 | 372665 | C | RECESSIVE | 0.0062916 | 0.68 |
| SLC22A3 | 1282 | 377551 | A | RECESSIVE | 0.0114600 | 0.67 |
| PDE10A | 1293 | 6906719 | A | ADDITIVE | 0.0136527 | 0.82 |
| PDE10A | 1294 | 481701 | C | RECESSIVE | 0.0167779 | 0.39 |
| SDK1 | 1295 | 651245 | A | RECESSIVE | 0.0329166 | 1.29 |
| SDK1 | 1296 | 4723420 | A | DOMINANT | 0.0357213 | 0.82 |
| SDK1 | 1297 | 12701426 | A | RECESSIVE | 0.0399629 | 1.26 |
| NXPH1 | 1305 | 3779355 | A | RECESSIVE | 0.0233636 | 1.38 |
| ETV1 | 1306 | 118020 | G | DOMINANT | 0.0403479 | 1.20 |
| DGKB | 1309 | 6461071 | C | DOMINANT | 0.0136856 | 1.24 |
| DGKB | 1310 | 6461072 | A | DOMINANT | 0.0097236 | 1.25 |
| DGKB | 1312 | 2049447 | C | ADDITIVE | 0.0165858 | 0.83 |
| DGKB | 1313 | 6967001 | C | RECESSIVE | 0.0344874 | 1.70 |
| TSPAN13 | 1317 | 706057 | T | RECESSIVE | 0.0356695 | 1.27 |
| SNX13 | 1318 | 4543441 | A | ADDITIVE | 0.0474867 | 0.88 |
| SNX13 | 1319 | 4544985 | C | ADDITIVE | 0.0438740 | 0.88 |
| STK31 | 1321 | 10950956 | T | DOMINANT | 0.0196026 | 1.24 |
| STK31 | 1322 | 6955786 | G | DOMINANT | 0.0136536 | 1.24 |
| STK31 | 1323 | 13244337 | G | DOMINANT | 0.0122712 | 1.25 |
| STK31 | 1324 | 2158055 | C | RECESSIVE | 0.0227590 | 1.75 |
| STK31 | 1325 | 12667136 | T | RECESSIVE | 0.0297902 | 1.71 |
| SKAP2 | 1327 | 550141 | C | DOMINANT | 0.0302471 | 1.21 |
| SKAP2 | 1328 | 17315929 | T | RECESSIVE | 0.0449551 | 0.68 |
| SKAP2 | 1329 | 1391805 | G | DOMINANT | 0.0115043 | 1.25 |
| CREB5 | 1330 | 2237361 | C | ADDITIVE | 0.0024760 | 0.85 |
| CREB5 | 1331 | 2237364 | G | ADDITIVE | 0.0136271 | 0.83 |
| PLEKHA8 | 1332 | 10951257 | G | DOMINANT | 0.0262302 | 0.81 |
| PLEKHA8 | 1333 | 11975645 | C | DOMINANT | 0.0281621 | 0.81 |
| CRHR2 | 1334 | 973002 | G | ADDITIVE | 0.0383946 | 0.83 |
| BMPER | 1344 | 6968741 | G | RECESSIVE | 0.0266098 | 0.21 |
| EEPD1 | 1346 | 2098368 | C | ADDITIVE | 0.0336799 | 0.85 |
| VPS41 | 1347 | 11765454 | G | ADDITIVE | 0.0058268 | 1.20 |
| VPS41 | 1348 | 6462862 | A | DOMINANT | 0.0358235 | 0.83 |
| VPS41 | 1349 | 2240355 | A | ADDITIVE | 0.0391994 | 0.85 |
| VPS41 | 1350 | 10262154 | T | ADDITIVE | 0.0046053 | 1.19 |
| VPS41 | 1351 | 3801145 | C | DOMINANT | 0.0214666 | 0.82 |
| VPS41 | 1352 | 3779127 | G | ADDITIVE | 0.0029837 | 1.19 |
| VPS41 | 1353 | 10279367 | A | ADDITIVE | 0.0055477 | 1.23 |
| VPS41 | 1354 | 6961672 | C | DOMINANT | 0.0320528 | 0.83 |
| VPS41 | 1355 | 2286080 | C | ADDITIVE | 0.0030299 | 1.20 |
| VPS41 | 1356 | 4723789 | T | ADDITIVE | 0.0043633 | 1.22 |
| VPS41 | 1357 | 6462865 | G | ADDITIVE | 0.0122099 | 1.17 |
| VPS41 | 1358 | 6957565 | C | ADDITIVE | 0.0072009 | 1.15 |
| VPS41 | 1359 | 17618395 | G | ADDITIVE | 0.0110340 | 1.20 |
| VPS41 | 1360 | 4723793 | G | DOMINANT | 0.0067641 | 0.79 |
| VPS41 | 1361 | 17680408 | A | ADDITIVE | 0.0042231 | 1.23 |
| VPS41 | 1362 | 6462868 | G | ADDITIVE | 0.0034174 | 1.20 |
| VPS41 | 1363 | 6946636 | C | ADDITIVE | 0.0066739 | 1.22 |
| VPS41 | 1364 | 10085898 | C | ADDITIVE | 0.0034282 | 1.21 |
| VPS41 | 1365 | 7798033 | C | ADDITIVE | 0.0239792 | 1.17 |
| VPS41 | 1366 | 10951578 | C | ADDITIVE | 0.0151908 | 1.19 |
| VPS41 | 1367 | 10255290 | A | RECESSIVE | 0.0472003 | 1.37 |
| VPS41 | 1368 | 10255854 | T | RECESSIVE | 0.0391532 | 1.39 |
| VPS41 | 1369 | 859522 | G | RECESSIVE | 0.0264937 | 0.21 |
| IGFBP3 | 1370 | 1553009 | A | ADDITIVE | 0.0479207 | 0.87 |
| IGFBP3 | 1371 | 10282088 | A | ADDITIVE | 0.0296121 | 0.84 |
| IGFBP3 | 1372 | 10499637 | A | ADDITIVE | 0.0337505 | 0.86 |
| GRB10 | 1399 | 6976501 | G | DOMINANT | 0.0031246 | 1.31 |
| GRB10 | 1400 | 2329489 | C | DOMINANT | 0.0231994 | 1.22 |
| GRB10 | 1401 | 13311390 | G | DOMINANT | 0.0138341 | 1.24 |
| GRB10 | 1402 | 1978208 | G | DOMINANT | 0.0175505 | 1.25 |
| GRB10 | 1403 | 10265504 | A | DOMINANT | 0.0268050 | 1.21 |
| GRB10 | 1404 | 6968827 | A | DOMINANT | 0.0097772 | 1.26 |
| GRB10 | 1405 | 12536500 | T | DOMINANT | 0.0293983 | 1.21 |
| GRB10 | 1406 | 17134002 | A | DOMINANT | 0.0191867 | 1.23 |
| GRB10 | 1407 | 1019000 | T | DOMINANT | 0.0063420 | 1.27 |
| GRB10 | 1408 | 757774 | G | DOMINANT | 0.0132302 | 1.25 |
| GRB10 | 1409 | 6593164 | C | DOMINANT | 0.0288063 | 1.21 |
| GRB10 | 1410 | 10281065 | A | DOMINANT | 0.0243187 | 1.22 |
| GRB10 | 1411 | 6593174 | T | DOMINANT | 0.0259624 | 1.22 |

TABLE 1-continued

Alleles and Genotypes Influencing Likelihood of Bipolar vs. Schizophrenia Diagnoses

| Gene | SEQ ID NO: | NCBI RS# | Allele | Model | P | Odds Ratio |
|---|---|---|---|---|---|---|
| GRB10 | 1412 | 2876846 | C | DOMINANT | 0.0279213 | 1.21 |
| GRB10 | 1413 | 11238326 | G | DOMINANT | 0.0280415 | 1.21 |
| GRB10 | 1414 | 6963498 | C | DOMINANT | 0.0287868 | 1.21 |
| GRB10 | 1415 | 6593182 | G | DOMINANT | 0.0179188 | 1.25 |
| GRB10 | 1416 | 6943901 | G | DOMINANT | 0.0324424 | 1.21 |
| GRB10 | 1417 | 6971834 | T | DOMINANT | 0.0324424 | 1.21 |
| WBSCR17 | 1419 | 6979579 | C | DOMINANT | 0.0463092 | 0.82 |
| WBSCR17 | 1420 | 648415 | T | ADDITIVE | 0.0281075 | 0.88 |
| WBSCR17 | 1421 | 995497 | T | ADDITIVE | 0.0158683 | 0.83 |
| CALN1 | 1422 | 3801156 | T | DOMINANT | 0.0082123 | 1.31 |
| CALN1 | 1423 | 749585 | T | DOMINANT | 0.0102443 | 1.29 |
| CALN1 | 1424 | 12673109 | T | RECESSIVE | 0.0041836 | 0.47 |
| CALN1 | 1425 | 6963114 | A | RECESSIVE | 0.0087261 | 0.50 |
| CALN1 | 1426 | 10254309 | C | RECESSIVE | 0.0084468 | 0.50 |
| CALN1 | 1427 | 10950297 | C | RECESSIVE | 0.0053872 | 0.48 |
| CALN1 | 1428 | 12666578 | A | RECESSIVE | 0.0090005 | 0.47 |
| CALN1 | 1429 | 10260183 | C | RECESSIVE | 0.0022818 | 0.37 |
| CALN1 | 1430 | 10260420 | C | RECESSIVE | 0.0011975 | 0.34 |
| CALN1 | 1435 | 9638655 | A | DOMINANT | 0.0318496 | 1.22 |
| CALN1 | 1436 | 6946380 | A | RECESSIVE | 0.0477544 | 0.76 |
| MAGI2 | 1441 | 38107 | A | RECESSIVE | 0.0360157 | 1.38 |
| MAGI2 | 1442 | 38111 | G | RECESSIVE | 0.0141213 | 1.38 |
| MAGI2 | 1448 | 860246 | A | DOMINANT | 0.0235468 | 0.82 |
| CACNA2D1 | 1449 | 37068 | C | RECESSIVE | 0.0314903 | 0.76 |
| CACNA2D1 | 1450 | 37076 | G | RECESSIVE | 0.0487669 | 0.77 |
| PCLO | 1451 | 2107828 | A | ADDITIVE | 0.0074065 | 1.18 |
| PCLO | 1452 | 10954694 | C | RECESSIVE | 0.0350386 | 0.76 |
| PCLO | 1453 | 7781142 | A | ADDITIVE | 0.0138359 | 1.14 |
| PCLO | 1454 | 7799260 | C | ADDITIVE | 0.0119021 | 1.15 |
| PCLO | 1455 | 1034780 | C | ADDITIVE | 0.0174271 | 1.17 |
| PCLO | 1456 | 7778238 | C | ADDITIVE | 0.0068488 | 0.82 |
| PCLO | 1457 | 12707567 | G | RECESSIVE | 0.0459516 | 1.30 |
| PCLO | 1458 | 10240976 | A | RECESSIVE | 0.0314341 | 1.27 |
| PPP1R9A | 1466 | 17305991 | T | RECESSIVE | 0.0233510 | 0.78 |
| PPP1R9A | 1467 | 7806304 | C | ADDITIVE | 0.0480923 | 0.89 |
| PPP1R9A | 1468 | 854520 | T | DOMINANT | 0.0495215 | 1.21 |
| PPP1R9A | 1469 | 854521 | C | ADDITIVE | 0.0398185 | 0.85 |
| PPP1R9A | 1470 | 854531 | T | DOMINANT | 0.0403329 | 1.20 |
| PPP1R9A | 1471 | 854532 | T | DOMINANT | 0.0441487 | 1.19 |
| PPP1R9A | 1472 | 854534 | A | DOMINANT | 0.0149600 | 1.25 |
| PPP1R9A | 1473 | 854535 | C | DOMINANT | 0.0182574 | 1.24 |
| PPP1R9A | 1474 | 854537 | A | ADDITIVE | 0.0156679 | 0.85 |
| DYNC1I1 | 1476 | 4729206 | G | ADDITIVE | 0.0045583 | 1.37 |
| DYNC1I1 | 1477 | 2171555 | A | ADDITIVE | 0.0145986 | 1.19 |
| DYNC1I1 | 1478 | 13238456 | C | ADDITIVE | 0.0210332 | 1.19 |
| ZNF3 | 1480 | 6465760 | A | DOMINANT | 0.0475339 | 1.19 |
| ZNF3 | 1481 | 4424195 | G | DOMINANT | 0.0200763 | 1.22 |
| EMID2 | 1482 | 4727494 | G | DOMINANT | 0.0023064 | 0.77 |
| EMID2 | 1483 | 869127 | T | ADDITIVE | 0.0455470 | 0.78 |
| CUX1 | 1486 | 2694166 | A | RECESSIVE | 0.0007876 | 1.97 |
| NRCAM | 1496 | 10262724 | A | RECESSIVE | 0.0467176 | 1.33 |
| KCND2 | 1497 | 10276880 | G | ADDITIVE | 0.0262938 | 1.47 |
| CADPS2 | 1503 | 916982 | G | RECESSIVE | 0.0416549 | 0.71 |
| CADPS2 | 1504 | 2501439 | C | ADDITIVE | 0.0425517 | 1.13 |
| GRM8 | 1512 | 712723 | C | DOMINANT | 0.0250489 | 1.23 |
| GRM8 | 1513 | 10228052 | T | DOMINANT | 0.0385174 | 1.22 |
| GRM8 | 1514 | 11978873 | T | ADDITIVE | 0.0455030 | 0.88 |
| GRM8 | 1515 | 17680718 | C | DOMINANT | 0.0197320 | 1.23 |
| GRM8 | 1516 | 766239 | G | DOMINANT | 0.0197320 | 1.23 |
| GRM8 | 1517 | 2299449 | A | DOMINANT | 0.0210484 | 1.23 |
| GRM8 | 1518 | 2237735 | A | DOMINANT | 0.0210484 | 1.23 |
| GRM8 | 1519 | 2283065 | C | DOMINANT | 0.0163372 | 1.24 |
| GRM8 | 1520 | 2283066 | C | DOMINANT | 0.0201634 | 1.23 |
| GRM8 | 1521 | 12154335 | T | DOMINANT | 0.0426821 | 1.20 |
| GRM8 | 1522 | 2023640 | T | ADDITIVE | 0.0058360 | 1.18 |
| GRM8 | 1523 | 2299523 | A | ADDITIVE | 0.0075430 | 0.81 |
| GRM8 | 1524 | 1018854 | G | ADDITIVE | 0.0051250 | 0.82 |
| GRM8 | 1525 | 2188187 | C | ADDITIVE | 0.0098052 | 1.17 |
| GRM8 | 1526 | 1156652 | G | ADDITIVE | 0.0017295 | 1.16 |
| GRM8 | 1527 | 1156654 | A | ADDITIVE | 0.0022243 | 1.17 |
| GRM8 | 1528 | 11563730 | T | ADDITIVE | 0.0074010 | 1.20 |
| GRM8 | 1529 | 1419442 | T | ADDITIVE | 0.0014619 | 1.28 |
| DGKI | 1532 | 4732255 | T | RECESSIVE | 0.0281503 | 1.31 |
| DGKI | 1533 | 12535157 | A | RECESSIVE | 0.0441275 | 1.30 |
| DGKI | 1534 | 4728415 | G | RECESSIVE | 0.0429775 | 1.28 |

TABLE 1-continued

Alleles and Genotypes Influencing Likelihood of Bipolar vs. Schizophrenia Diagnoses

| Gene | SEQ ID NO: | NCBI RS# | Allele | Model | P | Odds Ratio |
|---|---|---|---|---|---|---|
| DGKI | 1535 | 2113578 | T | ADDITIVE | 0.0293521 | 1.10 |
| DGKI | 1536 | 12707359 | T | RECESSIVE | 0.0042222 | 1.33 |
| DGKI | 1537 | 7793852 | G | RECESSIVE | 0.0034265 | 1.34 |
| CREB3L2 | 1541 | 1020961 | T | DOMINANT | 0.0396712 | 1.20 |
| CREB3L2 | 1542 | 9757 | G | DOMINANT | 0.0238794 | 1.22 |
| CREB3L2 | 1544 | 11972734 | A | DOMINANT | 0.0391734 | 1.20 |
| TBXAS1 | 1546 | 2269997 | T | DOMINANT | 0.0398368 | 1.20 |
| CNTNAP2 | 1547 | 6969607 | C | ADDITIVE | 0.0266035 | 0.88 |
| CNTNAP2 | 1548 | 12703906 | T | ADDITIVE | 0.0343689 | 0.91 |
| CNTNAP2 | 1549 | 7803992 | A | ADDITIVE | 0.0366156 | 1.19 |
| CNTNAP2 | 1550 | 1542566 | G | ADDITIVE | 0.0084223 | 1.16 |
| CNTNAP2 | 1551 | 826811 | C | ADDITIVE | 0.0016559 | 1.19 |
| CNTNAP2 | 1552 | 700309 | A | ADDITIVE | 0.0042302 | 1.16 |
| CNTNAP2 | 1553 | 1525218 | T | ADDITIVE | 0.0071294 | 1.16 |
| CNTNAP2 | 1554 | 11972784 | C | ADDITIVE | 0.0034040 | 1.17 |
| CNTNAP2 | 1555 | 4726861 | A | ADDITIVE | 0.0061281 | 1.19 |
| CNTNAP2 | 1556 | 10242076 | A | ADDITIVE | 0.0416655 | 1.11 |
| CNTNAP2 | 1557 | 2022225 | A | ADDITIVE | 0.0059064 | 1.17 |
| CNTNAP2 | 1558 | 10276608 | G | ADDITIVE | 0.0043470 | 1.17 |
| CNTNAP2 | 1559 | 12703913 | C | ADDITIVE | 0.0041744 | 1.16 |
| CNTNAP2 | 1560 | 7789396 | A | ADDITIVE | 0.0042509 | 1.16 |
| CNTNAP2 | 1561 | 2373133 | G | ADDITIVE | 0.0037206 | 1.16 |
| CNTNAP2 | 1562 | 6947428 | C | ADDITIVE | 0.0032470 | 1.17 |
| CNTNAP2 | 1563 | 10270551 | G | ADDITIVE | 0.0041744 | 1.16 |
| CNTNAP2 | 1564 | 10260458 | T | RECESSIVE | 0.0067884 | 1.58 |
| CNTNAP2 | 1565 | 3915305 | C | ADDITIVE | 0.0034758 | 1.17 |
| CNTNAP2 | 1566 | 4725731 | T | ADDITIVE | 0.0033189 | 1.16 |
| CNTNAP2 | 1567 | 10952682 | G | ADDITIVE | 0.0082219 | 1.14 |
| CNTNAP2 | 1568 | 10952685 | A | ADDITIVE | 0.0041685 | 1.15 |
| CNTNAP2 | 1569 | 4726875 | A | DOMINANT | 0.0054919 | 1.28 |
| CNTNAP2 | 1570 | 1528507 | C | DOMINANT | 0.0038729 | 1.30 |
| CNTNAP2 | 1571 | 2888516 | C | RECESSIVE | 0.0495788 | 0.69 |
| CNTNAP2 | 1572 | 851653 | A | ADDITIVE | 0.0498081 | 0.91 |
| CNTNAP2 | 1573 | 10251347 | G | DOMINANT | 0.0085100 | 1.55 |
| ACCN3 | 1574 | 891507 | T | ADDITIVE | 0.0414271 | 0.83 |
| DPP6 | 1575 | 916513 | G | RECESSIVE | 0.0249396 | 3.08 |
| DPP6 | 1576 | 880730 | A | RECESSIVE | 0.0352403 | 0.72 |
| DPP6 | 1577 | 729269 | T | ADDITIVE | 0.0367995 | 1.16 |
| HTR5A | 1578 | 1657276 | C | RECESSIVE | 0.0487329 | 0.77 |
| HTR5A | 1579 | 1657283 | G | RECESSIVE | 0.0101954 | 0.68 |
| PTPRN2 | 1580 | 221295 | A | RECESSIVE | 0.0227256 | 0.79 |
| PTPRN2 | 1581 | 221300 | C | RECESSIVE | 0.0369780 | 0.81 |
| PTPRN2 | 1582 | 221303 | A | RECESSIVE | 0.0030937 | 0.74 |
| PTPRN2 | 1583 | 4716881 | A | RECESSIVE | 0.0324292 | 0.74 |
| PTPRN2 | 1584 | 13307400 | C | RECESSIVE | 0.0185490 | 0.71 |
| CSMD1 | 1586 | 341724 | C | ADDITIVE | 0.0081167 | 1.22 |
| CSMD1 | 1587 | 688894 | G | DOMINANT | 0.0296692 | 1.22 |
| CSMD1 | 1588 | 11136609 | T | DOMINANT | 0.0212984 | 1.24 |
| CSMD1 | 1589 | 1348267 | C | DOMINANT | 0.0070134 | 0.79 |
| CSMD1 | 1590 | 10092265 | G | DOMINANT | 0.0056497 | 0.79 |
| CSMD1 | 1591 | 7819225 | C | ADDITIVE | 0.0237828 | 0.85 |
| CSMD1 | 1592 | 270054 | A | DOMINANT | 0.0250442 | 0.82 |
| CSMD1 | 1593 | 12543159 | T | ADDITIVE | 0.0102090 | 0.82 |
| CSMD1 | 1594 | 9969557 | T | ADDITIVE | 0.0306538 | 0.88 |
| CSMD1 | 1595 | 7005990 | G | ADDITIVE | 0.0073525 | 0.82 |
| CSMD1 | 1596 | 7014229 | T | ADDITIVE | 0.0165635 | 0.82 |
| MCPH1 | 1598 | 2442633 | G | DOMINANT | 0.0243083 | 0.81 |
| MCPH1 | 1599 | 3020213 | T | DOMINANT | 0.0171547 | 0.81 |
| MCPH1 | 1600 | 2515435 | C | DOMINANT | 0.0397371 | 0.83 |
| MCPH1 | 1602 | 1375668 | G | RECESSIVE | 0.0154748 | 1.42 |
| MCPH1 | 1603 | 4455855 | A | RECESSIVE | 0.0308755 | 1.37 |
| MCPH1 | 1604 | 17624022 | C | ADDITIVE | 0.0022198 | 0.77 |
| MCPH1 | 1605 | 3739391 | A | DOMINANT | 0.0102519 | 0.78 |
| MCPH1 | 1606 | 3739392 | G | ADDITIVE | 0.0135040 | 0.80 |
| MCPH1 | 1607 | 2515514 | A | DOMINANT | 0.0308876 | 0.81 |
| MCPH1 | 1608 | 2912084 | C | ADDITIVE | 0.0313028 | 0.88 |
| ANGPT2 | 1609 | 7825811 | T | RECESSIVE | 0.0427316 | 0.29 |
| SGCZ | 1611 | 10092634 | C | RECESSIVE | 0.0394393 | 1.26 |
| SGCZ | 1612 | 2054356 | G | RECESSIVE | 0.0179649 | 1.34 |
| SGCZ | 1613 | 1551816 | C | RECESSIVE | 0.0224905 | 1.32 |
| SGCZ | 1614 | 1510445 | C | RECESSIVE | 0.0247559 | 0.63 |
| SGCZ | 1615 | 11989868 | C | RECESSIVE | 0.0363739 | 0.67 |
| SGCZ | 1616 | 11990657 | A | RECESSIVE | 0.0313972 | 0.66 |
| SGCZ | 1617 | 11998116 | G | RECESSIVE | 0.0231300 | 0.65 |
| SGCZ | 1618 | 7822045 | A | RECESSIVE | 0.0250617 | 0.67 |

TABLE 1-continued

Alleles and Genotypes Influencing Likelihood of Bipolar vs. Schizophrenia Diagnoses

| Gene | SEQ ID NO: | NCBI RS# | Allele | Model | P | Odds Ratio |
|---|---|---|---|---|---|---|
| SLC7A2 | 1620 | 2588164 | A | ADDITIVE | 0.0366482 | 0.88 |
| ATP6V1B2 | 1627 | 13253777 | G | ADDITIVE | 0.0206804 | 1.15 |
| XPO7 | 1628 | 11135789 | C | DOMINANT | 0.0275765 | 0.83 |
| PPP3CC | 1629 | 7827093 | C | RECESSIVE | 0.0426589 | 0.80 |
| PPP3CC | 1630 | 11778831 | T | RECESSIVE | 0.0414312 | 0.80 |
| PPP3CC | 1631 | 2469757 | T | RECESSIVE | 0.0442273 | 0.80 |
| PPP3CC | 1632 | 2461491 | C | RECESSIVE | 0.0326578 | 0.79 |
| PPP3CC | 1633 | 2469760 | G | RECESSIVE | 0.0401341 | 0.80 |
| PPP3CC | 1634 | 2461481 | A | RECESSIVE | 0.0268717 | 0.78 |
| PPP3CC | 1635 | 1116084 | A | RECESSIVE | 0.0232025 | 0.78 |
| PPP3CC | 1636 | 1482337 | T | RECESSIVE | 0.0474068 | 0.80 |
| SLC25A37 | 1638 | 7826247 | G | RECESSIVE | 0.0133535 | 1.52 |
| UNC5D | 1642 | 7841785 | A | RECESSIVE | 0.0121948 | 0.35 |
| UNC5D | 1643 | 6989128 | A | RECESSIVE | 0.0233071 | 0.40 |
| UNC5D | 1644 | 983270 | A | RECESSIVE | 0.0088917 | 0.34 |
| UNC5D | 1645 | 983273 | G | RECESSIVE | 0.0233071 | 0.40 |
| UNC5D | 1646 | 4739416 | G | RECESSIVE | 0.0027065 | 0.25 |
| UNC5D | 1647 | 10954992 | C | ADDITIVE | 0.0318533 | 0.88 |
| SNTG1 | 1656 | 2450290 | G | RECESSIVE | 0.0077811 | >5 |
| SNTG1 | 1657 | 318861 | G | RECESSIVE | 0.0078474 | >5 |
| SNTG1 | 1659 | 10504093 | G | RECESSIVE | 0.0300981 | >5 |
| SNTG1 | 1661 | 1344326 | G | RECESSIVE | 0.0154496 | >5 |
| SNTG1 | 1662 | 11783503 | G | RECESSIVE | 0.0300981 | >5 |
| SNTG1 | 1664 | 11783631 | T | RECESSIVE | 0.0300284 | >5 |
| SNTG1 | 1667 | 203632 | T | DOMINANT | 0.0386653 | 0.83 |
| SNTG1 | 1671 | 6997739 | C | RECESSIVE | 0.0053340 | 0.50 |
| SNTG1 | 1672 | 4440649 | C | DOMINANT | 0.0359079 | 0.78 |
| LYN | 1674 | 907424 | A | RECESSIVE | 0.0428401 | 1.24 |
| LYN | 1675 | 1877301 | T | RECESSIVE | 0.0371189 | 1.25 |
| LYN | 1676 | 868541 | A | RECESSIVE | 0.0395984 | 1.24 |
| LYN | 1677 | 1027986 | C | RECESSIVE | 0.0368128 | 1.25 |
| LYN | 1678 | 10282821 | A | ADDITIVE | 0.0229134 | 1.15 |
| NKAIN3 | 1682 | 17243191 | T | RECESSIVE | 0.0158950 | 1.51 |
| NKAIN3 | 1683 | 1376759 | A | ADDITIVE | 0.0334432 | 1.09 |
| NKAIN3 | 1685 | 10458307 | T | ADDITIVE | 0.0298413 | 1.17 |
| DEPDC2 | 1690 | 1434764 | A | RECESSIVE | 0.0383367 | 1.29 |
| DEPDC2 | 1691 | 1014663 | C | RECESSIVE | 0.0378064 | 1.30 |
| KCNB2 | 1692 | 13251896 | G | DOMINANT | 0.0148115 | 1.25 |
| KCNB2 | 1693 | 2256431 | A | DOMINANT | 0.0208368 | 1.22 |
| KCNB2 | 1694 | 1972888 | C | DOMINANT | 0.0192951 | 1.22 |
| KCNB2 | 1695 | 2256012 | C | DOMINANT | 0.0409104 | 1.20 |
| KCNB2 | 1696 | 2196904 | C | DOMINANT | 0.0019747 | 1.31 |
| KCNB2 | 1697 | 1899077 | T | DOMINANT | 0.0426818 | 1.19 |
| KCNB2 | 1698 | 1866740 | A | DOMINANT | 0.0199283 | 1.22 |
| KCNB2 | 1699 | 1440355 | C | DOMINANT | 0.0390306 | 1.19 |
| KCNB2 | 1700 | 2247121 | A | DOMINANT | 0.0175706 | 1.23 |
| KCNB2 | 1701 | 2243607 | G | DOMINANT | 0.0235291 | 1.22 |
| KCNB2 | 1702 | 1965805 | G | DOMINANT | 0.0374924 | 1.20 |
| KCNB2 | 1703 | 2919408 | G | DOMINANT | 0.0052564 | 1.28 |
| KCNB2 | 1704 | 4571768 | G | ADDITIVE | 0.0087585 | 1.21 |
| KCNB2 | 1705 | 4307385 | C | ADDITIVE | 0.0262631 | 1.17 |
| KCNB2 | 1706 | 4307386 | C | ADDITIVE | 0.0223659 | 1.13 |
| KCNB2 | 1707 | 10096802 | A | RECESSIVE | 0.0400735 | 1.24 |
| KCNB2 | 1708 | 7006287 | G | RECESSIVE | 0.0417485 | 1.24 |
| MMP16 | 1710 | 10100297 | G | DOMINANT | 0.0093713 | 1.25 |
| MMP16 | 1711 | 4961087 | C | DOMINANT | 0.0061100 | 1.27 |
| MMP16 | 1713 | 4548227 | A | DOMINANT | 0.0052824 | 1.27 |
| ZFPM2 | 1735 | 16873003 | C | RECESSIVE | 0.0291068 | 1.55 |
| ZFPM2 | 1737 | 7823133 | T | RECESSIVE | 0.0399677 | 1.51 |
| ZFPM2 | 1738 | 6992053 | A | RECESSIVE | 0.0399677 | 1.51 |
| ZFPM2 | 1739 | 1481026 | T | RECESSIVE | 0.0310871 | 1.55 |
| CSMD3 | 1742 | 4876279 | T | DOMINANT | 0.0239791 | 1.23 |
| CSMD3 | 1743 | 17628739 | G | DOMINANT | 0.0403819 | 0.83 |
| CSMD3 | 1744 | 17630545 | C | ADDITIVE | 0.0198970 | 0.87 |
| CSMD3 | 1745 | 10505182 | A | ADDITIVE | 0.0162187 | 0.86 |
| CSMD3 | 1746 | 1895016 | G | DOMINANT | 0.0319117 | 1.22 |
| CSMD3 | 1747 | 16883350 | A | DOMINANT | 0.0141110 | 0.79 |
| CSMD3 | 1748 | 929685 | T | ADDITIVE | 0.0127708 | 1.18 |
| CSMD3 | 1749 | 1420859 | T | ADDITIVE | 0.0251957 | 1.15 |
| CSMD3 | 1750 | 1492678 | A | DOMINANT | 0.0040323 | 0.76 |
| CSMD3 | 1751 | 3950676 | A | DOMINANT | 0.0032317 | 0.76 |
| CSMD3 | 1752 | 4876281 | G | RECESSIVE | 0.0130176 | 1.27 |
| CSMD3 | 1753 | 4876468 | T | DOMINANT | 0.0029974 | 0.75 |
| CSMD3 | 1754 | 4563913 | T | DOMINANT | 0.0043788 | 0.76 |
| CSMD3 | 1755 | 4556111 | T | ADDITIVE | 0.0266173 | 1.12 |

TABLE 1-continued

Alleles and Genotypes Influencing Likelihood of Bipolar vs. Schizophrenia Diagnoses

| Gene | SEQ ID NO: | NCBI RS# | Allele | Model | P | Odds Ratio |
|---|---|---|---|---|---|---|
| CSMD3 | 1756 | 1873746 | T | DOMINANT | 0.0040320 | 0.76 |
| CSMD3 | 1757 | 6994009 | A | RECESSIVE | 0.0080830 | 1.30 |
| CSMD3 | 1758 | 9886643 | C | RECESSIVE | 0.0071703 | 1.30 |
| CSMD3 | 1759 | 12676848 | A | RECESSIVE | 0.0090360 | 1.29 |
| CSMD3 | 1760 | 9649933 | A | RECESSIVE | 0.0112562 | 1.28 |
| CSMD3 | 1761 | 1492660 | A | ADDITIVE | 0.0325255 | 1.10 |
| CSMD3 | 1765 | 1513520 | G | RECESSIVE | 0.0237756 | 0.79 |
| FBXO32 | 1768 | 4870855 | A | ADDITIVE | 0.0396670 | 0.78 |
| FER1L6 | 1777 | 6981430 | G | DOMINANT | 0.0380371 | 1.21 |
| MTSS1 | 1778 | 2013845 | G | ADDITIVE | 0.0125099 | 0.87 |
| MTSS1 | 1779 | 9771920 | T | RECESSIVE | 0.0433217 | 0.52 |
| MTSS1 | 1780 | 919544 | A | ADDITIVE | 0.0082588 | 0.82 |
| MTSS1 | 1781 | 3901290 | C | RECESSIVE | 0.0032857 | 2.47 |
| DDEF1 | 1785 | 2670886 | C | RECESSIVE | 0.0066020 | 0.35 |
| ADCY8 | 1786 | 6986982 | A | RECESSIVE | 0.0136146 | 0.46 |
| ADCY8 | 1787 | 11776982 | C | RECESSIVE | 0.0225496 | 0.50 |
| ADCY8 | 1788 | 7461448 | A | RECESSIVE | 0.0219152 | 0.50 |
| COL22A1 | 1790 | 7017524 | A | DOMINANT | 0.0234086 | 0.79 |
| COL22A1 | 1791 | 10875432 | G | RECESSIVE | 0.0327652 | 1.45 |
| COL22A1 | 1792 | 7818881 | C | ADDITIVE | 0.0282287 | 1.13 |
| COL22A1 | 1793 | 10090299 | C | ADDITIVE | 0.0199321 | 1.14 |
| COL22A1 | 1794 | 7838300 | C | ADDITIVE | 0.0226159 | 1.16 |
| COL22A1 | 1795 | 7838450 | C | ADDITIVE | 0.0330791 | 1.16 |
| COL22A1 | 1796 | 9324497 | G | ADDITIVE | 0.0286441 | 1.15 |
| COL22A1 | 1797 | 2292927 | T | RECESSIVE | 0.0073296 | 1.84 |
| COL22A1 | 1798 | 4736221 | T | RECESSIVE | 0.0010171 | 2.31 |
| COL22A1 | 1799 | 7006103 | C | RECESSIVE | 0.0006843 | 2.36 |
| COL22A1 | 1800 | 1879047 | T | RECESSIVE | 0.0010017 | 2.31 |
| KCNK9 | 1801 | 885724 | C | DOMINANT | 0.0271704 | 0.82 |
| PTP4A3 | 1802 | 7464176 | T | ADDITIVE | 0.0235240 | 1.18 |
| SMARCA2 | 1803 | 13288443 | G | DOMINANT | 0.0257316 | 0.79 |
| SMARCA2 | 1804 | 7035991 | T | DOMINANT | 0.0367617 | 0.80 |
| SMARCA2 | 1806 | 7858344 | T | DOMINANT | 0.0118075 | 0.76 |
| SMARCA2 | 1807 | 10965113 | C | DOMINANT | 0.0238185 | 0.80 |
| SMARCA2 | 1809 | 3818385 | T | DOMINANT | 0.0158222 | 0.77 |
| SLC1A1 | 1811 | 7045401 | G | RECESSIVE | 0.0038336 | 0.71 |
| SLC1A1 | 1813 | 4742013 | C | ADDITIVE | 0.0463596 | 0.75 |
| ADAMTSL1 | 1815 | 563805 | C | RECESSIVE | 0.0287211 | 1.89 |
| ASAH3L | 1816 | 2383096 | A | DOMINANT | 0.0218034 | 0.81 |
| KIAA1797 | 1817 | 10738564 | G | DOMINANT | 0.0338537 | 1.22 |
| KIAA1797 | 1818 | 7848159 | G | DOMINANT | 0.0283309 | 1.23 |
| KIAA1797 | 1820 | 17685673 | T | RECESSIVE | 0.0332263 | 1.29 |
| KIAA1797 | 1822 | 16938162 | C | RECESSIVE | 0.0191739 | 1.33 |
| KIAA1797 | 1823 | 10511687 | G | RECESSIVE | 0.0234244 | 1.33 |
| KIAA1797 | 1824 | 7025868 | G | ADDITIVE | 0.0234769 | 1.21 |
| KIAA1797 | 1825 | 6475483 | T | ADDITIVE | 0.0446537 | 1.16 |
| KIAA1797 | 1826 | 2383169 | C | ADDITIVE | 0.0326291 | 1.17 |
| KIAA1797 | 1827 | 2383170 | A | ADDITIVE | 0.0228506 | 1.20 |
| KIAA1797 | 1828 | 10738569 | A | ADDITIVE | 0.0316246 | 1.19 |
| KIAA1797 | 1829 | 4278230 | G | RECESSIVE | 0.0022173 | 0.73 |
| IFT74 | 1830 | 7035755 | G | ADDITIVE | 0.0186187 | 0.81 |
| IFT74 | 1831 | 7039400 | A | ADDITIVE | 0.0346589 | 0.82 |
| IFT74 | 1832 | 17756299 | C | DOMINANT | 0.0151261 | 0.74 |
| IFT74 | 1833 | 7857669 | A | ADDITIVE | 0.0144243 | 0.80 |
| IFT74 | 1835 | 17694631 | C | ADDITIVE | 0.0118149 | 0.78 |
| IFT74 | 1836 | 2095405 | C | ADDITIVE | 0.0108959 | 0.80 |
| TEK | 1837 | 1591355 | G | ADDITIVE | 0.0082850 | 0.80 |
| TEK | 1838 | 4601425 | T | RECESSIVE | 0.0014039 | 0.66 |
| PIP5K1B | 1841 | 4744726 | G | DOMINANT | 0.0314778 | 1.23 |
| PIP5K1B | 1842 | 1414949 | C | DOMINANT | 0.0244834 | 1.24 |
| PIP5K1B | 1843 | 11144133 | T | RECESSIVE | 0.0239211 | 0.79 |
| PIP5K1B | 1845 | 872077 | A | ADDITIVE | 0.0012371 | 0.76 |
| MAMDC2 | 1846 | 3015182 | C | ADDITIVE | 0.0415595 | 1.19 |
| MAMDC2 | 1847 | 3015189 | G | ADDITIVE | 0.0366178 | 1.19 |
| MAMDC2 | 1848 | 3015213 | A | ADDITIVE | 0.0424673 | 1.19 |
| MAMDC2 | 1849 | 3015223 | A | ADDITIVE | 0.0127180 | 1.26 |
| MAMDC2 | 1850 | 2182731 | C | ADDITIVE | 0.0104016 | 1.20 |
| TRPM3 | 1851 | 2275242 | G | ADDITIVE | 0.0427214 | 1.11 |
| TRPM3 | 1852 | 1415229 | A | ADDITIVE | 0.0374724 | 1.12 |
| TRPM3 | 1853 | 6560161 | G | ADDITIVE | 0.0439742 | 1.17 |
| TRPM3 | 1854 | 1337028 | T | ADDITIVE | 0.0286367 | 1.18 |
| TRPM3 | 1855 | 7022926 | G | ADDITIVE | 0.0339566 | 1.18 |
| TRPM3 | 1856 | 10868916 | C | ADDITIVE | 0.0338369 | 0.85 |
| TRPM6 | 1869 | 539079 | G | RECESSIVE | 0.0210478 | 4.08 |
| TRPM6 | 1870 | 506973 | C | RECESSIVE | 0.0329027 | 3.26 |

TABLE 1-continued

Alleles and Genotypes Influencing Likelihood of Bipolar vs. Schizophrenia Diagnoses

| Gene | SEQ ID NO: | NCBI RS# | Allele | Model | P | Odds Ratio |
|---|---|---|---|---|---|---|
| TRPM6 | 1871 | 2274924 | G | ADDITIVE | 0.0168181 | 1.22 |
| TRPM6 | 1872 | 3750425 | T | RECESSIVE | 0.0331844 | 3.25 |
| TRPM6 | 1873 | 12004677 | G | ADDITIVE | 0.0111713 | 1.22 |
| NTRK2 | 1884 | 1439054 | C | RECESSIVE | 0.0432386 | 0.33 |
| NTRK2 | 1886 | 1212171 | C | RECESSIVE | 0.0319888 | 0.79 |
| NTRK2 | 1887 | 1187329 | A | RECESSIVE | 0.0341744 | 0.79 |
| NTRK2 | 1888 | 3780632 | C | RECESSIVE | 0.0032326 | 0.67 |
| NTRK2 | 1889 | 10116453 | A | RECESSIVE | 0.0050538 | 0.62 |
| NTRK2 | 1890 | 7867174 | C | RECESSIVE | 0.0015349 | 0.65 |
| NTRK2 | 1891 | 1936435 | T | RECESSIVE | 0.0154401 | 0.70 |
| NTRK2 | 1892 | 7038866 | A | ADDITIVE | 0.0110408 | 0.90 |
| NTRK2 | 1893 | 1539676 | A | RECESSIVE | 0.0104620 | 0.68 |
| NTRK2 | 1894 | 2799482 | C | RECESSIVE | 0.0061924 | 0.69 |
| NTRK2 | 1895 | 2799483 | C | RECESSIVE | 0.0061924 | 0.69 |
| NTRK2 | 1896 | 1778913 | T | RECESSIVE | 0.0142011 | 1.62 |
| NTRK2 | 1897 | 10512154 | A | RECESSIVE | 0.0410501 | 1.49 |
| NTRK2 | 1898 | 9314735 | G | RECESSIVE | 0.0244377 | 1.58 |
| DAPK1 | 1899 | 6560011 | C | RECESSIVE | 0.0389489 | 0.79 |
| DAPK1 | 1900 | 11141934 | A | RECESSIVE | 0.0396753 | <.2 |
| DAPK1 | 1901 | 3128501 | G | RECESSIVE | 0.0199596 | 1.31 |
| SHC3 | 1903 | 9410299 | C | DOMINANT | 0.0305083 | 0.81 |
| ZNF169 | 1910 | 3118766 | C | RECESSIVE | 0.0379430 | 0.76 |
| GABBR2 | 1912 | 1435253 | T | ADDITIVE | 0.0416995 | 0.85 |
| GABBR2 | 1913 | 970388 | C | DOMINANT | 0.0148177 | 0.81 |
| GABBR2 | 1914 | 7850445 | G | DOMINANT | 0.0293185 | 0.83 |
| GRIN3A | 1915 | 9299345 | T | ADDITIVE | 0.0144311 | 0.78 |
| GRIN3A | 1916 | 10819954 | A | RECESSIVE | 0.0212699 | 0.65 |
| GRIN3A | 1917 | 10819959 | C | RECESSIVE | 0.0157693 | 0.63 |
| GRIN3A | 1918 | 1323421 | T | DOMINANT | 0.0302447 | 1.23 |
| GRIN3A | 1919 | 7849782 | C | RECESSIVE | 0.0088792 | 0.76 |
| GRIN3A | 1920 | 2146801 | T | DOMINANT | 0.0474707 | 1.19 |
| GRIN3A | 1921 | 1853447 | T | RECESSIVE | 0.0169973 | 0.62 |
| GRIN3A | 1922 | 12708308 | C | RECESSIVE | 0.0093364 | 0.60 |
| GRIN3A | 1923 | 4742823 | A | DOMINANT | 0.0370507 | 1.22 |
| GRIN3A | 1924 | 2485534 | A | RECESSIVE | 0.0107954 | 0.77 |
| GRIN3A | 1925 | 2506362 | C | DOMINANT | 0.0267598 | 1.24 |
| GRIN3A | 1926 | 10760802 | T | RECESSIVE | 0.0040421 | 0.74 |
| GRIN3A | 1927 | 4278209 | T | RECESSIVE | 0.0042671 | 0.74 |
| GRIN3A | 1928 | 2786720 | C | DOMINANT | 0.0030816 | 1.34 |
| PALM2 | 1937 | 10816929 | A | ADDITIVE | 0.0366808 | 1.12 |
| SVEP1 | 1938 | 4978934 | C | ADDITIVE | 0.0408891 | 0.90 |
| SVEP1 | 1939 | 10817042 | T | RECESSIVE | 0.0053090 | 0.65 |
| RGS3 | 1944 | 4979253 | G | DOMINANT | 0.0161113 | 0.81 |
| RGS3 | 1945 | 12337340 | C | RECESSIVE | 0.0194267 | 3.56 |
| ZNF618 | 1946 | 10121424 | T | DOMINANT | 0.0251012 | 1.21 |
| DFNB31 | 1956 | 10817625 | A | RECESSIVE | 0.0420573 | 1.24 |
| DFNB31 | 1957 | 10982246 | A | RECESSIVE | 0.0388448 | 1.23 |
| DFNB31 | 1958 | 1535964 | C | RECESSIVE | 0.0448325 | 1.27 |
| DFNB31 | 1959 | 10817635 | A | DOMINANT | 0.0146594 | 0.78 |
| DFNB31 | 1960 | 10817636 | A | DOMINANT | 0.0258219 | 0.80 |
| PAPPA | 1961 | 1475215 | A | RECESSIVE | 0.0186419 | 1.36 |
| ASTN2 | 1965 | 1876475 | A | DOMINANT | 0.0273090 | 0.82 |
| ASTN2 | 1966 | 767432 | A | RECESSIVE | 0.0101445 | 1.42 |
| ASTN2 | 1967 | 1475057 | T | DOMINANT | 0.0052805 | 0.78 |
| ASTN2 | 1968 | 1542987 | C | DOMINANT | 0.0063019 | 0.78 |
| ASTN2 | 1969 | 1885242 | A | DOMINANT | 0.0425887 | 0.83 |
| ASTN2 | 1970 | 803926 | C | RECESSIVE | 0.0167959 | 1.27 |
| ASTN2 | 1971 | 803929 | A | RECESSIVE | 0.0167959 | 1.27 |
| ASTN2 | 1972 | 2900132 | G | DOMINANT | 0.0273053 | 0.83 |
| ASTN2 | 1973 | 811689 | T | DOMINANT | 0.0363152 | 0.83 |
| ASTN2 | 1974 | 803939 | G | RECESSIVE | 0.0132340 | 1.29 |
| ASTN2 | 1975 | 10983314 | T | DOMINANT | 0.0176569 | 0.81 |
| ASTN2 | 1976 | 10759876 | A | RECESSIVE | 0.0325558 | 0.60 |
| ASTN2 | 1977 | 3849144 | G | RECESSIVE | 0.0359050 | 0.61 |
| ASTN2 | 1981 | 1928993 | C | ADDITIVE | 0.0227890 | 0.91 |
| ASTN2 | 1982 | 1928995 | G | RECESSIVE | 0.0192020 | 0.78 |
| ASTN2 | 1986 | 10739492 | A | ADDITIVE | 0.0380223 | 0.87 |
| ASTN2 | 1987 | 7032028 | T | RECESSIVE | 0.0165675 | 0.77 |
| ASTN2 | 1988 | 17419611 | T | DOMINANT | 0.0112128 | 1.28 |
| CDK5RAP2 | 1990 | 3849113 | C | RECESSIVE | 0.0356542 | 0.15 |
| CDK5RAP2 | 1991 | 10760103 | G | ADDITIVE | 0.0329487 | 0.77 |
| TTLL11 | 1997 | 13299260 | T | RECESSIVE | 0.0443712 | 0.82 |
| LHX6 | 2001 | 7859776 | T | DOMINANT | 0.0298107 | 0.83 |
| DENND1A | 2002 | 7047077 | T | RECESSIVE | 0.0056382 | 0.65 |
| DENND1A | 2003 | 7044960 | T | RECESSIVE | 0.0305607 | 0.70 |

TABLE 1-continued

Alleles and Genotypes Influencing Likelihood of Bipolar vs. Schizophrenia Diagnoses

| Gene | SEQ ID NO: | NCBI RS# | Allele | Model | P | Odds Ratio |
|---|---|---|---|---|---|---|
| DENND1A | 2004 | 3829851 | C | RECESSIVE | 0.0304882 | 4.73 |
| DENND1A | 2005 | 17212242 | C | DOMINANT | 0.0381496 | 1.23 |
| DENND1A | 2006 | 10760290 | T | RECESSIVE | 0.0073319 | 0.66 |
| DENND1A | 2007 | 10986026 | T | RECESSIVE | 0.0193819 | 0.70 |
| DENND1A | 2008 | 10986064 | T | RECESSIVE | 0.0082638 | 0.53 |
| DENND1A | 2009 | 1346643 | G | RECESSIVE | 0.0384185 | 0.70 |
| DENND1A | 2010 | 12377523 | A | RECESSIVE | 0.0380315 | 0.73 |
| DENND1A | 2011 | 670961 | A | DOMINANT | 0.0165799 | 1.28 |
| DENND1A | 2012 | 623640 | C | DOMINANT | 0.0213830 | 1.33 |
| DENND1A | 2013 | 630991 | A | ADDITIVE | 0.0354109 | 1.22 |
| NEK6 | 2014 | 4838141 | T | RECESSIVE | 0.0176925 | 0.75 |
| NEK6 | 2015 | 4838142 | T | RECESSIVE | 0.0173032 | 0.75 |
| NEK6 | 2016 | 7020077 | T | RECESSIVE | 0.0374866 | 0.39 |
| ABL1 | 2018 | 11244112 | T | RECESSIVE | 0.0104563 | 1.56 |
| ABL1 | 2019 | 2791728 | A | RECESSIVE | 0.0103761 | 1.56 |
| ABL1 | 2020 | 2583845 | A | RECESSIVE | 0.0101904 | 1.56 |
| ABL1 | 2021 | 2855160 | T | ADDITIVE | 0.0482647 | 1.11 |
| ABL1 | 2022 | 2789764 | T | RECESSIVE | 0.0060805 | 1.60 |
| ABL1 | 2023 | 2253070 | A | RECESSIVE | 0.0084280 | 1.57 |
| ABL1 | 2024 | 2253084 | T | RECESSIVE | 0.0133269 | 1.54 |
| ABL1 | 2025 | 2855166 | G | RECESSIVE | 0.0080620 | 1.58 |
| ABL1 | 2026 | 10793970 | C | RECESSIVE | 0.0095570 | 1.58 |
| ABL1 | 2027 | 2260323 | C | RECESSIVE | 0.0035922 | 0.39 |
| TSC1 | 2028 | 2072058 | A | RECESSIVE | 0.0218350 | 1.27 |
| TSC1 | 2029 | 1076160 | A | ADDITIVE | 0.0031707 | 1.20 |
| TSC1 | 2030 | 2106346 | C | ADDITIVE | 0.0038176 | 1.18 |
| VAV2 | 2034 | 3780737 | T | ADDITIVE | 0.0373574 | 1.21 |
| VAV2 | 2035 | 7038256 | T | DOMINANT | 0.0491421 | 1.23 |
| VAV2 | 2036 | 7025939 | C | DOMINANT | 0.0484149 | 1.23 |
| VAV2 | 2037 | 7852459 | C | ADDITIVE | 0.0374513 | 1.20 |
| KCNT1 | 2038 | 497547 | G | RECESSIVE | 0.0181664 | 8.29 |
| INPP5E | 2039 | 3812591 | C | RECESSIVE | 0.0392248 | 0.67 |
| NOTCH1 | 2040 | 3124596 | G | RECESSIVE | 0.0381242 | 0.81 |
| CACNA1B | 2047 | 2606356 | C | RECESSIVE | 0.0373269 | 0.70 |
| PRKCQ | 2050 | 7098118 | G | RECESSIVE | 0.0322084 | 0.80 |
| MYO3A | 2066 | 12413819 | G | ADDITIVE | 0.0465566 | 1.12 |
| MYO3A | 2067 | 10828913 | A | RECESSIVE | 0.0251933 | 0.79 |
| MYO3A | 2068 | 1339814 | T | ADDITIVE | 0.0285389 | 0.91 |
| MYO3A | 2069 | 1416860 | T | ADDITIVE | 0.0394525 | 0.91 |
| MYO3A | 2070 | 7899567 | A | ADDITIVE | 0.0356197 | 0.91 |
| MYO3A | 2071 | 11014934 | G | ADDITIVE | 0.0329156 | 0.90 |
| MYO3A | 2072 | 12246202 | C | ADDITIVE | 0.0336769 | 0.89 |
| MYO3A | 2073 | 12263990 | G | ADDITIVE | 0.0156424 | 0.89 |
| MYO3A | 2074 | 7095559 | A | ADDITIVE | 0.0254709 | 0.89 |
| MYO3A | 2075 | 12258453 | T | ADDITIVE | 0.0211277 | 0.89 |
| SLC18A3 | 2076 | 7072155 | A | ADDITIVE | 0.0302690 | 0.86 |
| SLC18A3 | 2077 | 3810947 | A | ADDITIVE | 0.0020366 | 0.61 |
| PRKG1 | 2078 | 6479874 | T | RECESSIVE | 0.0168037 | 0.48 |
| PRKG1 | 2079 | 1904701 | A | RECESSIVE | 0.0439780 | 1.24 |
| PRKG1 | 2080 | 1904693 | C | RECESSIVE | 0.0044438 | 0.74 |
| PRKG1 | 2081 | 1904692 | T | RECESSIVE | 0.0050777 | 0.74 |
| PRKG1 | 2082 | 7893773 | T | ADDITIVE | 0.0160324 | 0.91 |
| PRKG1 | 2083 | 1904683 | A | RECESSIVE | 0.0365828 | 0.79 |
| PRKG1 | 2087 | 10466032 | A | ADDITIVE | 0.0215148 | 1.12 |
| PRKG1 | 2088 | 7898110 | C | ADDITIVE | 0.0140078 | 1.13 |
| PCDH15 | 2089 | 7894926 | G | DOMINANT | 0.0278962 | 0.83 |
| PCDH15 | 2110 | 11004864 | A | RECESSIVE | 0.0029424 | 0.61 |
| PCDH15 | 2111 | 11004899 | C | ADDITIVE | 0.0265588 | 0.89 |
| PCDH15 | 2112 | 11817318 | T | RECESSIVE | 0.0075861 | 0.64 |
| PCDH15 | 2113 | 16907523 | G | RECESSIVE | 0.0055983 | 0.63 |
| ANK3 | 2114 | 4948381 | C | RECESSIVE | 0.0163307 | 1.42 |
| ANK3 | 2117 | 2393614 | T | DOMINANT | 0.0227626 | 1.22 |
| ANK3 | 2118 | 11814110 | A | DOMINANT | 0.0059685 | 1.28 |
| JMJD1C | 2121 | 10733789 | C | RECESSIVE | 0.0036418 | 1.53 |
| JMJD1C | 2122 | 10761739 | C | RECESSIVE | 0.0310920 | 1.27 |
| JMJD1C | 2123 | 10761741 | T | RECESSIVE | 0.0170313 | 1.31 |
| JMJD1C | 2125 | 10740118 | C | RECESSIVE | 0.0307258 | 1.27 |
| CTNNA3 | 2127 | 4746541 | G | ADDITIVE | 0.0377940 | 0.86 |
| CTNNA3 | 2128 | 10509256 | A | DOMINANT | 0.0105834 | 0.79 |
| CTNNA3 | 2130 | 1903881 | A | ADDITIVE | 0.0400313 | 0.84 |
| CTNNA3 | 2131 | 6480141 | T | ADDITIVE | 0.0172475 | 0.84 |
| CTNNA3 | 2132 | 10996932 | C | ADDITIVE | 0.0201696 | 0.84 |
| CTNNA3 | 2133 | 1462817 | A | ADDITIVE | 0.0458365 | 0.87 |
| CTNNA3 | 2134 | 1471383 | A | ADDITIVE | 0.0437793 | 0.88 |
| CTNNA3 | 2135 | 2893985 | C | ADDITIVE | 0.0403465 | 0.90 |

TABLE 1-continued

Alleles and Genotypes Influencing Likelihood of Bipolar vs. Schizophrenia Diagnoses

| Gene | SEQ ID NO: | NCBI RS# | Allele | Model | P | Odds Ratio |
|---|---|---|---|---|---|---|
| CTNNA3 | 2136 | 4578273 | T | RECESSIVE | 0.0343268 | 0.53 |
| CTNNA3 | 2138 | 12569810 | G | ADDITIVE | 0.0435631 | 0.87 |
| CTNNA3 | 2139 | 10997042 | G | ADDITIVE | 0.0449482 | 0.87 |
| CTNNA3 | 2145 | 6480253 | A | DOMINANT | 0.0370978 | 0.82 |
| CTNNA3 | 2146 | 1904633 | A | DOMINANT | 0.0239466 | 0.82 |
| CTNNA3 | 2147 | 2127595 | A | DOMINANT | 0.0242748 | 0.82 |
| CTNNA3 | 2148 | 7078583 | T | DOMINANT | 0.0272915 | 0.82 |
| CTNNA3 | 2149 | 1904653 | T | DOMINANT | 0.0316871 | 0.82 |
| CTNNA3 | 2150 | 1947842 | A | DOMINANT | 0.0389275 | 0.83 |
| CTNNA3 | 2151 | 10823003 | C | DOMINANT | 0.0204615 | 0.81 |
| CTNNA3 | 2152 | 7907339 | T | DOMINANT | 0.0146015 | 0.80 |
| CTNNA3 | 2153 | 1904645 | G | DOMINANT | 0.0209166 | 0.81 |
| CTNNA3 | 2156 | 10997759 | A | ADDITIVE | 0.0133316 | 0.82 |
| CTNNA3 | 2157 | 7076484 | A | ADDITIVE | 0.0270663 | 0.85 |
| CTNNA3 | 2158 | 4522060 | G | ADDITIVE | 0.0127013 | 0.83 |
| CTNNA3 | 2159 | 7076356 | A | ADDITIVE | 0.0213460 | 0.85 |
| CTNNA3 | 2160 | 7893446 | C | ADDITIVE | 0.0208959 | 0.87 |
| CTNNA3 | 2161 | 3125312 | A | DOMINANT | 0.0251542 | 0.82 |
| CTNNA3 | 2162 | 7072543 | G | ADDITIVE | 0.0115815 | 0.83 |
| CDH23 | 2163 | 2305210 | A | DOMINANT | 0.0449191 | 1.19 |
| KCNMA1 | 2164 | 846606 | T | DOMINANT | 0.0476626 | 1.20 |
| KCNMA1 | 2165 | 2569360 | C | ADDITIVE | 0.0027201 | 1.25 |
| KCNMA1 | 2166 | 2569361 | C | ADDITIVE | 0.0028000 | 1.25 |
| KCNMA1 | 2167 | 4980107 | C | ADDITIVE | 0.0034214 | 1.28 |
| KCNMA1 | 2168 | 10762731 | G | ADDITIVE | 0.0050389 | 1.25 |
| KCNMA1 | 2169 | 4980113 | C | ADDITIVE | 0.0082204 | 1.25 |
| KCNMA1 | 2170 | 10762732 | T | ADDITIVE | 0.0088407 | 1.23 |
| KCNMA1 | 2171 | 7086316 | G | RECESSIVE | 0.0044008 | 1.98 |
| KCNMA1 | 2172 | 10762740 | G | RECESSIVE | 0.0047376 | 1.73 |
| KCNMA1 | 2177 | 7078525 | T | RECESSIVE | 0.0298495 | 2.10 |
| KCNMA1 | 2178 | 11002054 | G | RECESSIVE | 0.0443400 | 1.87 |
| KCNMA1 | 2179 | 7071433 | A | ADDITIVE | 0.0146885 | 0.83 |
| KCNMA1 | 2180 | 7071575 | C | ADDITIVE | 0.0088199 | 0.80 |
| KCNMA1 | 2181 | 10824547 | T | DOMINANT | 0.0046037 | 0.75 |
| KCNMA1 | 2182 | 2673464 | A | ADDITIVE | 0.0258129 | 1.21 |
| NRG3 | 2183 | 11191281 | G | DOMINANT | 0.0223381 | 0.82 |
| NRG3 | 2187 | 474496 | G | ADDITIVE | 0.0141283 | 0.88 |
| NRG3 | 2188 | 495978 | A | RECESSIVE | 0.0424455 | 0.76 |
| SORBS1 | 2189 | 3193970 | G | ADDITIVE | 0.0403484 | 0.87 |
| SORBS1 | 2191 | 7904517 | C | DOMINANT | 0.0481906 | 0.84 |
| SORBS1 | 2192 | 4918918 | T | DOMINANT | 0.0465045 | 0.84 |
| SORBS1 | 2195 | 7086071 | A | RECESSIVE | 0.0402730 | 0.81 |
| PIK3AP1 | 2200 | 563654 | A | ADDITIVE | 0.0485542 | 1.20 |
| SLIT1 | 2201 | 2817688 | G | DOMINANT | 0.0477908 | 0.84 |
| SLIT1 | 2204 | 877825 | A | RECESSIVE | 0.0068247 | 1.49 |
| SLIT1 | 2205 | 1253425 | T | RECESSIVE | 0.0044443 | 1.53 |
| SORCS3 | 2206 | 10786806 | T | DOMINANT | 0.0230872 | 0.81 |
| SORCS3 | 2207 | 10884026 | G | DOMINANT | 0.0466766 | 0.83 |
| SORCS3 | 2212 | 2451484 | T | DOMINANT | 0.0204182 | 1.22 |
| SORCS3 | 2213 | 2451492 | T | DOMINANT | 0.0448306 | 1.19 |
| SORCS3 | 2214 | 2451498 | C | DOMINANT | 0.0394798 | 1.20 |
| VTI1A | 2218 | 10509963 | A | ADDITIVE | 0.0364346 | 1.15 |
| VTI1A | 2219 | 10885352 | A | ADDITIVE | 0.0312111 | 1.16 |
| ATRNL1 | 2220 | 1264764 | C | RECESSIVE | 0.0423769 | 1.44 |
| ATRNL1 | 2221 | 2165988 | A | RECESSIVE | 0.0263977 | 1.49 |
| ATRNL1 | 2222 | 659351 | C | ADDITIVE | 0.0425307 | 0.92 |
| ATRNL1 | 2226 | 11197258 | A | RECESSIVE | 0.0241968 | 1.27 |
| ATRNL1 | 2227 | 17724227 | G | RECESSIVE | 0.0486980 | 1.22 |
| ATRNL1 | 2229 | 11197299 | G | RECESSIVE | 0.0420227 | 1.23 |
| ATRNL1 | 2230 | 2804192 | A | DOMINANT | 0.0465215 | 0.83 |
| ATRNL1 | 2232 | 2804204 | T | DOMINANT | 0.0452295 | 0.82 |
| ATRNL1 | 2233 | 2804207 | C | DOMINANT | 0.0446262 | 0.82 |
| ATRNL1 | 2234 | 1590734 | G | DOMINANT | 0.0220684 | 0.80 |
| ATRNL1 | 2235 | 1590733 | G | DOMINANT | 0.0271440 | 0.81 |
| ATRNL1 | 2236 | 10787584 | T | DOMINANT | 0.0300612 | 0.81 |
| ATRNL1 | 2237 | 11197337 | T | DOMINANT | 0.0247875 | 0.80 |
| ATRNL1 | 2238 | 2804249 | G | DOMINANT | 0.0261977 | 0.81 |
| ATRNL1 | 2239 | 2420098 | G | DOMINANT | 0.0258332 | 0.81 |
| ATRNL1 | 2240 | 2615886 | T | DOMINANT | 0.0213907 | 0.81 |
| GRK5 | 2245 | 12783252 | A | DOMINANT | 0.0293098 | 1.26 |
| ATE1 | 2246 | 9971131 | G | RECESSIVE | 0.0322772 | 1.28 |
| ATE1 | 2247 | 1693688 | C | RECESSIVE | 0.0110052 | 1.39 |
| ATE1 | 2248 | 1696853 | T | RECESSIVE | 0.0190620 | 1.32 |
| ATE1 | 2249 | 2935718 | C | RECESSIVE | 0.0165139 | 1.33 |
| ATE1 | 2250 | 1693687 | C | RECESSIVE | 0.0213620 | 1.31 |

TABLE 1-continued

Alleles and Genotypes Influencing Likelihood of Bipolar vs. Schizophrenia Diagnoses

| Gene | SEQ ID NO: | NCBI RS# | Allele | Model | P | Odds Ratio |
|---|---|---|---|---|---|---|
| ATE1 | 2251 | 7086628 | G | ADDITIVE | 0.0298710 | 1.12 |
| ATE1 | 2253 | 753455 | C | ADDITIVE | 0.0240211 | 0.81 |
| ATE1 | 2254 | 3862129 | C | RECESSIVE | 0.0160747 | 1.82 |
| ATE1 | 2255 | 11200201 | C | RECESSIVE | 0.0250409 | 1.70 |
| ATE1 | 2257 | 7907871 | A | RECESSIVE | 0.0077470 | 2.10 |
| ATE1 | 2258 | 12245528 | C | RECESSIVE | 0.0170905 | 1.78 |
| ATE1 | 2259 | 11818001 | A | RECESSIVE | 0.0154840 | 1.79 |
| ATE1 | 2260 | 10510101 | A | RECESSIVE | 0.0127797 | 1.82 |
| ATE1 | 2261 | 12253283 | A | RECESSIVE | 0.0121793 | 1.82 |
| ATE1 | 2262 | 11200257 | A | RECESSIVE | 0.0126460 | 1.82 |
| ATE1 | 2263 | 11200260 | T | RECESSIVE | 0.0126460 | 1.82 |
| EBF3 | 2264 | 11016947 | T | ADDITIVE | 0.0249669 | 0.87 |
| DEAF1 | 2267 | 10902209 | A | RECESSIVE | 0.0407650 | 1.49 |
| CEND1 | 2268 | 11823172 | A | ADDITIVE | 0.0447735 | 1.12 |
| TRIM21 | 2280 | 2599586 | G | ADDITIVE | 0.0496600 | 1.09 |
| GALNTL4 | 2282 | 12224023 | C | RECESSIVE | 0.0315983 | 0.76 |
| GALNTL4 | 2283 | 901553 | C | DOMINANT | 0.0400766 | 0.84 |
| GALNTL4 | 2284 | 11021956 | C | ADDITIVE | 0.0036817 | 1.23 |
| GALNTL4 | 2285 | 7484121 | A | ADDITIVE | 0.0262693 | 1.12 |
| SPON1 | 2291 | 2697852 | G | RECESSIVE | 0.0314548 | 1.43 |
| SPON1 | 2292 | 1969542 | C | RECESSIVE | 0.0068803 | 1.46 |
| SPON1 | 2303 | 12283632 | A | RECESSIVE | 0.0211452 | 1.43 |
| SPON1 | 2304 | 11023067 | G | RECESSIVE | 0.0314589 | 1.39 |
| SPON1 | 2309 | 1864658 | C | RECESSIVE | 0.0225521 | 1.38 |
| SPON1 | 2310 | 4757244 | A | RECESSIVE | 0.0161609 | 1.41 |
| SPON1 | 2311 | 2303974 | A | RECESSIVE | 0.0392525 | 1.34 |
| SERGEF | 2319 | 999420 | T | ADDITIVE | 0.0259634 | 0.91 |
| SERGEF | 2320 | 4757589 | C | ADDITIVE | 0.0241152 | 0.88 |
| SERGEF | 2321 | 2299634 | C | DOMINANT | 0.0470294 | 1.20 |
| IGSF22 | 2322 | 9705036 | T | RECESSIVE | 0.0454089 | 0.73 |
| IGSF22 | 2325 | 4537730 | A | DOMINANT | 0.0307116 | 1.20 |
| PTPN5 | 2326 | 4757710 | A | DOMINANT | 0.0068522 | 1.26 |
| PTPN5 | 2327 | 4757711 | T | DOMINANT | 0.0101211 | 1.25 |
| PTPN5 | 2328 | 11024782 | T | DOMINANT | 0.0108359 | 1.24 |
| PTPN5 | 2329 | 4757718 | G | RECESSIVE | 0.0044080 | 1.45 |
| NAV2 | 2331 | 1559665 | G | RECESSIVE | 0.0079769 | 1.30 |
| NAV2 | 2333 | 1035700 | T | RECESSIVE | 0.0146450 | 1.28 |
| NAV2 | 2339 | 12807015 | T | RECESSIVE | 0.0466472 | 0.81 |
| LRRC4C | 2362 | 976933 | G | ADDITIVE | 0.0151178 | 0.83 |
| LRRC4C | 2363 | 7925066 | T | ADDITIVE | 0.0223300 | 0.84 |
| LRRC4C | 2364 | 1452478 | G | ADDITIVE | 0.0137950 | 0.77 |
| LRRC4C | 2365 | 6485190 | A | ADDITIVE | 0.0341935 | 0.81 |
| LRRC4C | 2366 | 721587 | A | ADDITIVE | 0.0202120 | 0.76 |
| LRRC4C | 2367 | 1470817 | G | ADDITIVE | 0.0230646 | 0.83 |
| LRRC4C | 2368 | 1452474 | C | ADDITIVE | 0.0215748 | 0.84 |
| LRRC4C | 2369 | 1452473 | C | ADDITIVE | 0.0292250 | 0.79 |
| LRRC4C | 2370 | 10837372 | T | ADDITIVE | 0.0142079 | 0.77 |
| LRRC4C | 2371 | 1452466 | C | ADDITIVE | 0.0290746 | 0.79 |
| LRRC4C | 2373 | 10501227 | G | ADDITIVE | 0.0128450 | 0.77 |
| LRRC4C | 2374 | 1452485 | A | ADDITIVE | 0.0172530 | 0.79 |
| PHACS | 2376 | 16937817 | G | ADDITIVE | 0.0225850 | 0.83 |
| PHACS | 2379 | 7950395 | T | ADDITIVE | 0.0093959 | 0.83 |
| PHACS | 2382 | 11037858 | A | RECESSIVE | 0.0140017 | 1.64 |
| SYT13 | 2383 | 2863174 | C | RECESSIVE | 0.0224882 | 2.71 |
| SYT13 | 2384 | 6485604 | T | RECESSIVE | 0.0224882 | 2.71 |
| SYT13 | 2385 | 6416130 | A | ADDITIVE | 0.0451255 | 1.15 |
| SYT13 | 2386 | 12362429 | G | ADDITIVE | 0.0337908 | 1.17 |
| SYT13 | 2387 | 12362444 | G | ADDITIVE | 0.0365689 | 1.17 |
| SYT13 | 2388 | 1000665 | C | DOMINANT | 0.0097587 | 1.28 |
| SYT13 | 2389 | 7124508 | T | DOMINANT | 0.0192891 | 1.24 |
| CTNND1 | 2390 | 576859 | A | RECESSIVE | 0.0449124 | 0.73 |
| CTNND1 | 2391 | 2956981 | A | DOMINANT | 0.0262929 | 1.23 |
| CTNND1 | 2392 | 11570181 | C | DOMINANT | 0.0375459 | 1.21 |
| CTNND1 | 2393 | 606499 | G | DOMINANT | 0.0419198 | 1.21 |
| CTNND1 | 2394 | 1786438 | T | DOMINANT | 0.0220739 | 1.24 |
| CTNND1 | 2395 | 585337 | C | DOMINANT | 0.0490368 | 1.20 |
| CTNND1 | 2396 | 10750870 | A | DOMINANT | 0.0437290 | 1.20 |
| DLG2 | 2397 | 1075719 | G | ADDITIVE | 0.0463368 | 0.90 |
| DLG2 | 2398 | 10501540 | G | ADDITIVE | 0.0071038 | 0.85 |
| DLG2 | 2399 | 11233641 | G | DOMINANT | 0.0091873 | 0.80 |
| DLG2 | 2400 | 7116939 | C | DOMINANT | 0.0180733 | 0.82 |
| DLG2 | 2401 | 10898133 | A | ADDITIVE | 0.0138623 | 0.83 |
| DLG2 | 2402 | 6592120 | G | ADDITIVE | 0.0238984 | 0.86 |
| DLG2 | 2403 | 7113167 | C | ADDITIVE | 0.0169090 | 0.85 |
| DLG2 | 2404 | 515618 | C | ADDITIVE | 0.0351546 | 0.89 |

TABLE 1-continued

Alleles and Genotypes Influencing Likelihood of Bipolar vs. Schizophrenia Diagnoses

| Gene | SEQ ID NO: | NCBI RS# | Allele | Model | P | Odds Ratio |
|---|---|---|---|---|---|---|
| DLG2 | 2405 | 635823 | G | ADDITIVE | 0.0224424 | 0.88 |
| DLG2 | 2406 | 489567 | C | ADDITIVE | 0.0339389 | 0.92 |
| DLG2 | 2407 | 1367980 | G | ADDITIVE | 0.0001342 | 1.25 |
| DLG2 | 2408 | 4480567 | C | ADDITIVE | 0.0001111 | 1.26 |
| DLG2 | 2409 | 2060147 | G | ADDITIVE | 0.0000526 | 1.28 |
| DLG2 | 2410 | 983590 | T | ADDITIVE | 0.0002851 | 1.26 |
| DLG2 | 2411 | 11233711 | T | ADDITIVE | 0.0007972 | 1.26 |
| DLG2 | 2412 | 12225388 | A | ADDITIVE | 0.0006237 | 1.26 |
| DLG2 | 2413 | 10898148 | A | ADDITIVE | 0.0003065 | 1.34 |
| DLG2 | 2414 | 12222455 | A | ADDITIVE | 0.0012133 | 1.23 |
| DLG2 | 2415 | 10898152 | C | ADDITIVE | 0.0009121 | 1.18 |
| DLG2 | 2416 | 7950988 | T | ADDITIVE | 0.0007903 | 1.25 |
| DLG2 | 2417 | 1945309 | A | ADDITIVE | 0.0042119 | 1.24 |
| DLG2 | 2418 | 10898301 | A | ADDITIVE | 0.0422705 | 0.90 |
| OPCML | 2424 | 1894193 | C | DOMINANT | 0.0428955 | 0.83 |
| OPCML | 2425 | 7119286 | T | RECESSIVE | 0.0349083 | 1.23 |
| OPCML | 2426 | 10791288 | G | RECESSIVE | 0.0423356 | 0.80 |
| OPCML | 2427 | 2155777 | A | RECESSIVE | 0.0480178 | 1.73 |
| TSPAN9 | 2434 | 650180 | T | RECESSIVE | 0.0274779 | 0.77 |
| TSPAN9 | 2435 | 544668 | G | RECESSIVE | 0.0448808 | 0.79 |
| TMEM16B | 2436 | 2159952 | A | ADDITIVE | 0.0117685 | 0.84 |
| TMEM16B | 2438 | 3782652 | G | DOMINANT | 0.0205163 | 0.79 |
| TMEM16B | 2439 | 735393 | A | ADDITIVE | 0.0048766 | 0.83 |
| TMEM16B | 2440 | 2277403 | G | DOMINANT | 0.0328471 | 0.81 |
| TMEM16B | 2441 | 11832095 | A | DOMINANT | 0.0051263 | 0.78 |
| TMEM16B | 2442 | 11063875 | T | DOMINANT | 0.0038849 | 0.78 |
| PIK3C2G | 2461 | 4471494 | C | DOMINANT | 0.0312098 | 0.76 |
| PIK3C2G | 2462 | 7968533 | C | DOMINANT | 0.0267659 | 0.75 |
| PIK3C2G | 2464 | 10841059 | A | DOMINANT | 0.0326190 | 0.83 |
| ITPR2 | 2466 | 9442 | T | DOMINANT | 0.0464723 | 0.84 |
| ITPR2 | 2467 | 2570 | C | DOMINANT | 0.0243506 | 0.82 |
| ITPR2 | 2468 | 7955049 | G | DOMINANT | 0.0290689 | 0.82 |
| CNOT2 | 2476 | 7312236 | C | RECESSIVE | 0.0187919 | 0.66 |
| KCNC2 | 2478 | 4309217 | A | RECESSIVE | 0.0489126 | 1.34 |
| KCNC2 | 2479 | 4131954 | T | RECESSIVE | 0.0463830 | 1.36 |
| KCNC2 | 2480 | 2471653 | T | ADDITIVE | 0.0255763 | 1.12 |
| NAV3 | 2481 | 300447 | C | DOMINANT | 0.0466417 | 1.19 |
| NAV3 | 2482 | 2694667 | A | ADDITIVE | 0.0174834 | 1.18 |
| NAV3 | 2483 | 1375287 | C | DOMINANT | 0.0454615 | 1.19 |
| GAS2L3 | 2484 | 35716 | A | DOMINANT | 0.0078126 | 0.78 |
| GAS2L3 | 2485 | 35714 | T | DOMINANT | 0.0151061 | 0.79 |
| GAS2L3 | 2486 | 35711 | G | DOMINANT | 0.0155281 | 0.80 |
| CHST11 | 2488 | 2453161 | G | RECESSIVE | 0.0303619 | 0.71 |
| CHST11 | 2490 | 2642109 | T | RECESSIVE | 0.0322027 | 0.74 |
| CHST11 | 2491 | 1565815 | T | RECESSIVE | 0.0076800 | 0.66 |
| CHST11 | 2492 | 1038968 | C | RECESSIVE | 0.0117274 | 0.69 |
| CHST11 | 2493 | 2696006 | T | RECESSIVE | 0.0076488 | 0.66 |
| CHST11 | 2494 | 2463017 | C | RECESSIVE | 0.0052053 | 0.65 |
| CHST11 | 2495 | 2468082 | G | RECESSIVE | 0.0199536 | 0.72 |
| CHST11 | 2496 | 2468083 | A | RECESSIVE | 0.0209249 | 0.69 |
| KIAA1853 | 2497 | 7134748 | G | DOMINANT | 0.0081069 | 0.80 |
| KIAA1853 | 2498 | 7298308 | C | DOMINANT | 0.0183467 | 0.81 |
| KIAA1853 | 2499 | 11064675 | C | RECESSIVE | 0.0344640 | 1.43 |
| KIAA1853 | 2500 | 7136574 | T | DOMINANT | 0.0268004 | 0.82 |
| KIAA1853 | 2501 | 4075945 | T | DOMINANT | 0.0335334 | 0.78 |
| KIAA1853 | 2502 | 4075946 | T | RECESSIVE | 0.0013569 | 1.38 |
| PLA2G1B | 2503 | 5637 | A | ADDITIVE | 0.0455980 | 0.87 |
| RIMBP2 | 2504 | 7132917 | A | DOMINANT | 0.0315735 | 0.69 |
| STX2 | 2507 | 1554807 | T | ADDITIVE | 0.0488395 | 1.13 |
| STX2 | 2508 | 7975825 | C | ADDITIVE | 0.0443082 | 1.14 |
| STX2 | 2509 | 4619189 | T | DOMINANT | 0.0275395 | 1.23 |
| STX2 | 2510 | 7956851 | C | ADDITIVE | 0.0391212 | 1.14 |
| KIAA1545 | 2511 | 3751309 | G | DOMINANT | 0.0019743 | 1.37 |
| KIAA1545 | 2512 | 11208 | C | DOMINANT | 0.0287632 | 1.22 |
| MTIF3 | 2513 | 2892058 | G | DOMINANT | 0.0254705 | 0.58 |
| MTIF3 | 2514 | 17085657 | C | DOMINANT | 0.0390401 | 0.63 |
| UBL3 | 2516 | 11618361 | A | RECESSIVE | 0.0202510 | 0.77 |
| N4BP2L2 | 2517 | 206335 | C | RECESSIVE | 0.0320207 | 0.79 |
| NBEA | 2520 | 1148328 | C | DOMINANT | 0.0464549 | 1.30 |
| NBEA | 2521 | 2247674 | A | DOMINANT | 0.0475123 | 1.28 |
| NBEA | 2522 | 2243774 | C | DOMINANT | 0.0173986 | 1.25 |
| NBEA | 2523 | 499570 | A | DOMINANT | 0.0449816 | 1.28 |
| NBEA | 2525 | 9315346 | T | DOMINANT | 0.0266363 | 0.82 |
| NBEA | 2526 | 7333195 | T | DOMINANT | 0.0225556 | 0.82 |
| NBEA | 2527 | 3794394 | G | DOMINANT | 0.0195103 | 0.81 |

TABLE 1-continued

Alleles and Genotypes Influencing Likelihood of Bipolar vs. Schizophrenia Diagnoses

| Gene | SEQ ID NO: | NCBI RS# | Allele | Model | P | Odds Ratio |
|---|---|---|---|---|---|---|
| TRPC4 | 2528 | 7319022 | A | DOMINANT | 0.0378172 | 1.21 |
| TRPC4 | 2529 | 1556541 | C | DOMINANT | 0.0048620 | 1.29 |
| TRPC4 | 2530 | 12858218 | A | RECESSIVE | 0.0252777 | 0.79 |
| TRPC4 | 2531 | 9548043 | G | DOMINANT | 0.0015744 | 1.32 |
| TRPC4 | 2532 | 1759875 | G | DOMINANT | 0.0182381 | 0.80 |
| KPNA3 | 2536 | 9526614 | G | DOMINANT | 0.0059645 | 0.78 |
| PCDH17 | 2538 | 9527675 | G | RECESSIVE | 0.0155568 | 1.37 |
| PCDH17 | 2539 | 9527676 | G | RECESSIVE | 0.0111272 | 1.38 |
| PCDH17 | 2540 | 2592866 | A | DOMINANT | 0.0392094 | 1.21 |
| PCDH17 | 2541 | 17175693 | A | DOMINANT | 0.0243714 | 1.23 |
| PCDH20 | 2542 | 9539153 | T | RECESSIVE | 0.0101180 | 0.57 |
| LMO7 | 2545 | 579540 | C | ADDITIVE | 0.0227271 | 1.24 |
| LMO7 | 2546 | 2273996 | T | ADDITIVE | 0.0331422 | 1.17 |
| SLAIN1 | 2547 | 2813740 | T | ADDITIVE | 0.0261869 | 0.84 |
| SLAIN1 | 2548 | 9530678 | A | ADDITIVE | 0.0182447 | 0.83 |
| SLAIN1 | 2549 | 9593251 | T | ADDITIVE | 0.0113857 | 0.90 |
| SLAIN1 | 2550 | 7997533 | G | ADDITIVE | 0.0047501 | 0.80 |
| SLAIN1 | 2551 | 9600917 | C | ADDITIVE | 0.0045485 | 0.82 |
| SLAIN1 | 2552 | 1279446 | C | ADDITIVE | 0.0063095 | 0.85 |
| GPC5 | 2554 | 9523304 | A | RECESSIVE | 0.0068650 | 1.37 |
| GPC5 | 2555 | 7322734 | A | RECESSIVE | 0.0073729 | 1.37 |
| GPC5 | 2556 | 4142965 | C | RECESSIVE | 0.0133525 | 1.31 |
| GPC5 | 2557 | 9523312 | G | RECESSIVE | 0.0057670 | 1.38 |
| GPC5 | 2558 | 8002779 | G | RECESSIVE | 0.0079325 | 1.36 |
| GPC5 | 2561 | 17267257 | C | RECESSIVE | 0.0359110 | 1.34 |
| GPC5 | 2563 | 10507993 | G | ADDITIVE | 0.0409083 | 1.12 |
| GPC6 | 2566 | 9561374 | T | ADDITIVE | 0.0252836 | 1.11 |
| GPC6 | 2567 | 3899317 | A | DOMINANT | 0.0470229 | 0.83 |
| GPC6 | 2568 | 1330620 | A | DOMINANT | 0.0292062 | 0.83 |
| GPC6 | 2569 | 9589816 | A | DOMINANT | 0.0490167 | 0.84 |
| GPC6 | 2570 | 4394948 | C | DOMINANT | 0.0233102 | 0.82 |
| GPC6 | 2571 | 7987964 | T | DOMINANT | 0.0191043 | 0.82 |
| GPC6 | 2572 | 7993501 | C | DOMINANT | 0.0251535 | 0.82 |
| GPC6 | 2573 | 9584153 | C | DOMINANT | 0.0226752 | 0.82 |
| GPC6 | 2574 | 9561444 | T | ADDITIVE | 0.0342887 | 0.86 |
| GPC6 | 2575 | 885192 | G | ADDITIVE | 0.0383759 | 0.85 |
| GPC6 | 2576 | 3759423 | A | ADDITIVE | 0.0404510 | 0.87 |
| GPC6 | 2577 | 3759422 | A | ADDITIVE | 0.0317214 | 0.85 |
| GPC6 | 2578 | 4486746 | T | ADDITIVE | 0.0304719 | 0.87 |
| GPC6 | 2579 | 9556328 | T | ADDITIVE | 0.0342887 | 0.86 |
| GPC6 | 2580 | 7317144 | A | ADDITIVE | 0.0284312 | 0.85 |
| GPC6 | 2581 | 2150124 | T | ADDITIVE | 0.0198515 | 0.85 |
| GPC6 | 2582 | 2892667 | G | ADDITIVE | 0.0185626 | 0.87 |
| GPC6 | 2583 | 1411507 | C | ADDITIVE | 0.0183944 | 0.86 |
| GPC6 | 2584 | 1983987 | A | ADDITIVE | 0.0168726 | 0.85 |
| GPC6 | 2585 | 2183430 | T | ADDITIVE | 0.0232996 | 0.85 |
| GPC6 | 2586 | 1411513 | T | ADDITIVE | 0.0201909 | 0.85 |
| GPC6 | 2587 | 9301916 | C | ADDITIVE | 0.0136589 | 0.87 |
| GPC6 | 2588 | 9524268 | T | ADDITIVE | 0.0203651 | 0.87 |
| GPC6 | 2589 | 9301957 | A | RECESSIVE | 0.0278119 | 0.66 |
| NALCN | 2601 | 7992226 | G | RECESSIVE | 0.0147207 | 1.42 |
| NALCN | 2602 | 570252 | C | RECESSIVE | 0.0092784 | 1.30 |
| FGF14 | 2614 | 12870187 | T | RECESSIVE | 0.0144408 | 0.73 |
| TTC5 | 2616 | 4981948 | C | ADDITIVE | 0.0220117 | 1.21 |
| TTC5 | 2617 | 3737220 | A | ADDITIVE | 0.0147145 | 1.20 |
| TTC5 | 2618 | 4981951 | C | ADDITIVE | 0.0450037 | 1.17 |
| TTC5 | 2619 | 1953552 | A | ADDITIVE | 0.0374421 | 0.84 |
| TTC5 | 2620 | 2318864 | G | DOMINANT | 0.0292801 | 1.21 |
| TTC5 | 2621 | 3742945 | A | DOMINANT | 0.0472652 | 1.19 |
| TTC5 | 2622 | 10873395 | T | DOMINANT | 0.0347043 | 1.20 |
| TEP1 | 2623 | 1760904 | C | ADDITIVE | 0.0020357 | 1.21 |
| TEP1 | 2624 | 1713458 | T | DOMINANT | 0.0048196 | 1.32 |
| TEP1 | 2625 | 1760903 | T | ADDITIVE | 0.0024041 | 1.27 |
| TEP1 | 2626 | 1713440 | T | RECESSIVE | 0.0225677 | 1.34 |
| NOVA1 | 2630 | 8008779 | C | RECESSIVE | 0.0409157 | 0.61 |
| SLC25A21 | 2633 | 7359156 | G | DOMINANT | 0.0248664 | 0.82 |
| SLC25A21 | 2634 | 1884777 | T | ADDITIVE | 0.0250316 | 1.25 |
| GNG2 | 2644 | 8014746 | G | ADDITIVE | 0.0124262 | 0.82 |
| GNG2 | 2645 | 8019331 | A | ADDITIVE | 0.0232918 | 0.85 |
| GNG2 | 2646 | 8008081 | A | ADDITIVE | 0.0324350 | 0.86 |
| DAAM1 | 2651 | 10873113 | T | RECESSIVE | 0.0181338 | 0.53 |
| DAAM1 | 2652 | 10483710 | A | RECESSIVE | 0.0259872 | 0.55 |
| PPP2R5E | 2663 | 6573522 | A | RECESSIVE | 0.0329840 | 1.41 |
| PPP2R5E | 2664 | 2754223 | G | RECESSIVE | 0.0468080 | 1.37 |
| PPP2R5E | 2666 | 964954 | G | RECESSIVE | 0.0214470 | 1.44 |

TABLE 1-continued

Alleles and Genotypes Influencing Likelihood of Bipolar vs. Schizophrenia Diagnoses

| Gene | SEQ ID NO: | NCBI RS# | Allele | Model | P | Odds Ratio |
|---|---|---|---|---|---|---|
| PPP2R5E | 2667 | 1255771 | G | RECESSIVE | 0.0163658 | 1.53 |
| PPP2R5E | 2670 | 7156393 | T | RECESSIVE | 0.0304882 | 4.73 |
| RGS6 | 2671 | 8003168 | A | ADDITIVE | 0.0272940 | 0.85 |
| RGS6 | 2672 | 11629078 | G | ADDITIVE | 0.0102800 | 0.86 |
| RGS6 | 2674 | 12894979 | G | DOMINANT | 0.0192980 | 0.79 |
| RGS6 | 2675 | 10149098 | G | DOMINANT | 0.0067421 | 0.79 |
| RGS6 | 2676 | 4903003 | G | DOMINANT | 0.0232287 | 0.80 |
| RGS6 | 2677 | 2139594 | G | DOMINANT | 0.0372164 | 0.82 |
| RGS6 | 2678 | 8007922 | G | DOMINANT | 0.0371972 | 0.82 |
| RGS6 | 2679 | 740337 | C | DOMINANT | 0.0402133 | 0.83 |
| RGS6 | 2680 | 2681754 | A | DOMINANT | 0.0263361 | 0.81 |
| RGS6 | 2681 | 2283380 | T | ADDITIVE | 0.0044408 | 0.84 |
| RGS6 | 2682 | 4903024 | T | RECESSIVE | 0.0037284 | 0.64 |
| RGS6 | 2683 | 2074953 | G | ADDITIVE | 0.0110725 | 0.86 |
| RGS6 | 2684 | 2239272 | G | ADDITIVE | 0.0110812 | 0.90 |
| KCNK10 | 2688 | 17771758 | G | RECESSIVE | 0.0230278 | 0.72 |
| KCNK10 | 2689 | 2223933 | C | RECESSIVE | 0.0225705 | 0.72 |
| KCNK10 | 2690 | 1950279 | T | RECESSIVE | 0.0225705 | 0.72 |
| KCNK10 | 2691 | 11628680 | G | RECESSIVE | 0.0238746 | 0.72 |
| KCNK10 | 2692 | 11844638 | T | RECESSIVE | 0.0138222 | 0.70 |
| KCNK10 | 2693 | 17698533 | C | RECESSIVE | 0.0010514 | 0.60 |
| KCNK10 | 2694 | 12185033 | T | ADDITIVE | 0.0298994 | 0.92 |
| KCNK13 | 2695 | 12432204 | G | ADDITIVE | 0.0082331 | 1.22 |
| KCNK13 | 2696 | 12894287 | T | DOMINANT | 0.0070356 | 1.27 |
| KCNK13 | 2697 | 12885846 | T | ADDITIVE | 0.0181878 | 1.16 |
| CCDC88C | 2700 | 1970912 | T | RECESSIVE | 0.0427118 | 1.25 |
| CCDC88C | 2701 | 17127245 | A | ADDITIVE | 0.0000056 | 1.98 |
| CCDC88C | 2702 | 1046311 | C | RECESSIVE | 0.0126923 | 0.51 |
| CCDC88C | 2703 | 8015982 | C | RECESSIVE | 0.0354492 | 0.67 |
| CCDC88C | 2704 | 10131741 | G | RECESSIVE | 0.0461950 | 0.68 |
| CCDC88C | 2705 | 8008996 | T | RECESSIVE | 0.0344292 | 0.66 |
| CCDC88C | 2706 | 8007791 | A | RECESSIVE | 0.0354492 | 0.67 |
| CCDC88C | 2709 | 11160006 | C | DOMINANT | 0.0137069 | 1.26 |
| ATP10A | 2711 | 12592145 | T | RECESSIVE | 0.0186787 | 0.25 |
| ATP10A | 2712 | 17555920 | T | RECESSIVE | 0.0300942 | >5 |
| ATP10A | 2713 | 17116015 | A | RECESSIVE | 0.0423953 | 0.33 |
| ATP10A | 2714 | 17555995 | C | RECESSIVE | 0.0299790 | >5 |
| ATP10A | 2715 | 2066703 | T | RECESSIVE | 0.0411497 | 0.23 |
| ATP10A | 2716 | 11637231 | G | RECESSIVE | 0.0308049 | 0.73 |
| ATP10A | 2717 | 9888671 | T | RECESSIVE | 0.0272411 | 0.45 |
| RYR3 | 2718 | 2596229 | A | DOMINANT | 0.0252864 | 1.24 |
| RYR3 | 2719 | 1560968 | G | DOMINANT | 0.0080819 | 1.28 |
| RYR3 | 2720 | 2676085 | A | DOMINANT | 0.0242734 | 1.22 |
| RYR3 | 2721 | 2676087 | A | DOMINANT | 0.0031600 | 1.34 |
| RYR3 | 2722 | 2164249 | C | DOMINANT | 0.0138068 | 1.26 |
| RYR3 | 2723 | 2596159 | T | DOMINANT | 0.0075480 | 1.29 |
| RYR3 | 2724 | 2596163 | G | DOMINANT | 0.0077911 | 1.28 |
| RYR3 | 2726 | 2082753 | A | DOMINANT | 0.0165656 | 1.25 |
| RYR3 | 2727 | 2572175 | A | DOMINANT | 0.0361360 | 1.23 |
| RYR3 | 2728 | 2572169 | A | DOMINANT | 0.0327803 | 1.22 |
| RYR3 | 2729 | 2596175 | A | DOMINANT | 0.0311287 | 1.23 |
| RYR3 | 2731 | 11853872 | A | DOMINANT | 0.0228117 | 0.76 |
| RYR3 | 2733 | 6495228 | G | DOMINANT | 0.0099332 | 1.28 |
| C15ORF41 | 2735 | 7183415 | C | RECESSIVE | 0.0249613 | 3.08 |
| RASGRP1 | 2746 | 17651741 | A | DOMINANT | 0.0290584 | 1.21 |
| UNC13C | 2749 | 2163195 | A | DOMINANT | 0.0074064 | 0.79 |
| UNC13C | 2750 | 2115825 | A | DOMINANT | 0.0296225 | 0.80 |
| UNC13C | 2751 | 8024845 | G | DOMINANT | 0.0017932 | 0.76 |
| UNC13C | 2752 | 1897013 | G | ADDITIVE | 0.0259308 | 0.83 |
| UNC13C | 2753 | 1864416 | T | ADDITIVE | 0.0235201 | 0.83 |
| UNC13C | 2754 | 11636356 | T | ADDITIVE | 0.0215324 | 0.83 |
| UNC13C | 2755 | 934192 | A | ADDITIVE | 0.0133643 | 0.82 |
| UNC13C | 2767 | 9920150 | G | RECESSIVE | 0.0411190 | 2.84 |
| NEDD4 | 2768 | 10518828 | A | RECESSIVE | 0.0234715 | 0.13 |
| CGNL1 | 2771 | 17820281 | A | RECESSIVE | 0.0053568 | 0.60 |
| GRINL1A | 2772 | 9920308 | A | RECESSIVE | 0.0328098 | 0.78 |
| GRINL1A | 2773 | 9920106 | T | ADDITIVE | 0.0126832 | 0.87 |
| GRINL1A | 2774 | 16953342 | C | RECESSIVE | 0.0412209 | 0.79 |
| GRINL1A | 2775 | 16977629 | T | DOMINANT | 0.0086808 | 0.69 |
| GRINL1A | 2776 | 16977631 | C | DOMINANT | 0.0143872 | 0.77 |
| ADAM10 | 2779 | 2414607 | A | ADDITIVE | 0.0252614 | 1.19 |
| CLK3 | 2781 | 2068982 | A | DOMINANT | 0.0351073 | 0.80 |
| ARNT2 | 2786 | 7172548 | T | RECESSIVE | 0.0339851 | 0.70 |
| ARNT2 | 2787 | 4459508 | A | RECESSIVE | 0.0222836 | 0.67 |
| AKAP13 | 2790 | 17623915 | C | RECESSIVE | 0.0382878 | 1.55 |

TABLE 1-continued

Alleles and Genotypes Influencing Likelihood of Bipolar vs. Schizophrenia Diagnoses

| Gene | SEQ ID NO: | NCBI RS# | Allele | Model | P | Odds Ratio |
|---|---|---|---|---|---|---|
| AKAP13 | 2803 | 8041467 | A | RECESSIVE | 0.0362968 | 0.75 |
| AKAP13 | 2806 | 11638762 | T | DOMINANT | 0.0384566 | 1.21 |
| AKAP13 | 2809 | 338515 | C | RECESSIVE | 0.0413126 | 0.23 |
| SV2B | 2816 | 2239994 | A | DOMINANT | 0.0147181 | 0.77 |
| SLCO3A1 | 2817 | 8037251 | T | RECESSIVE | 0.0417847 | 1.39 |
| SLCO3A1 | 2818 | 207970 | T | ADDITIVE | 0.0381480 | 1.13 |
| SLCO3A1 | 2819 | 7175812 | C | RECESSIVE | 0.0047319 | 0.35 |
| IGF1R | 2823 | 1574213 | A | RECESSIVE | 0.0270750 | 0.63 |
| IGF1R | 2824 | 11854132 | A | RECESSIVE | 0.0238766 | 0.68 |
| IGF1R | 2825 | 7170035 | G | RECESSIVE | 0.0201919 | 0.61 |
| A2BP1 | 2828 | 12445131 | C | RECESSIVE | 0.0445886 | 2.61 |
| A2BP1 | 2832 | 12600141 | T | DOMINANT | 0.0068865 | 0.79 |
| A2BP1 | 2833 | 7191740 | C | ADDITIVE | 0.0280927 | 0.85 |
| A2BP1 | 2834 | 17144423 | T | DOMINANT | 0.0421914 | 0.83 |
| A2BP1 | 2835 | 2079753 | T | DOMINANT | 0.0075058 | 0.79 |
| TMC5 | 2837 | 1985395 | C | RECESSIVE | 0.0063044 | 0.66 |
| TMC5 | 2838 | 7198723 | C | RECESSIVE | 0.0496953 | 0.66 |
| GOT2 | 2842 | 30842 | T | DOMINANT | 0.0187610 | 1.22 |
| GOT2 | 2843 | 257634 | C | DOMINANT | 0.0091372 | 1.26 |
| GOT2 | 2844 | 257637 | T | DOMINANT | 0.0086536 | 1.26 |
| GOT2 | 2845 | 171786 | T | DOMINANT | 0.0066105 | 1.27 |
| GOT2 | 2846 | 257621 | C | DOMINANT | 0.0092573 | 1.26 |
| GOT2 | 2847 | 185397 | T | DOMINANT | 0.0076979 | 1.26 |
| GOT2 | 2848 | 11076262 | G | DOMINANT | 0.0133323 | 1.24 |
| GOT2 | 2849 | 6499976 | A | DOMINANT | 0.0121080 | 1.24 |
| GOT2 | 2850 | 1595181 | A | DOMINANT | 0.0065869 | 1.27 |
| GOT2 | 2851 | 10852565 | C | DOMINANT | 0.0139807 | 1.24 |
| GOT2 | 2852 | 4784986 | T | DOMINANT | 0.0134433 | 1.24 |
| GOT2 | 2853 | 6416775 | C | DOMINANT | 0.0491326 | 1.21 |
| PLCG2 | 2858 | 9646328 | G | RECESSIVE | 0.0203369 | 0.77 |
| MPHOSPH6 | 2859 | 12149621 | T | DOMINANT | 0.0320370 | 0.82 |
| MPHOSPH6 | 2860 | 4889467 | C | ADDITIVE | 0.0142780 | 0.89 |
| MPHOSPH6 | 2861 | 2081257 | G | RECESSIVE | 0.0154834 | 0.34 |
| MPHOSPH6 | 2862 | 4889476 | G | ADDITIVE | 0.0065039 | 0.88 |
| MPHOSPH6 | 2863 | 2967355 | A | ADDITIVE | 0.0477083 | 0.91 |
| MPHOSPH6 | 2864 | 2967370 | A | RECESSIVE | 0.0162193 | 0.74 |
| MPHOSPH6 | 2865 | 1862820 | C | RECESSIVE | 0.0253166 | 0.75 |
| MPHOSPH6 | 2866 | 2911391 | G | RECESSIVE | 0.0218882 | 0.74 |
| MPHOSPH6 | 2867 | 2967337 | C | RECESSIVE | 0.0392984 | 0.53 |
| CDH13 | 2868 | 12325628 | G | ADDITIVE | 0.0393312 | 0.88 |
| CDH13 | 2870 | 9940179 | A | DOMINANT | 0.0396491 | 1.20 |
| KIAA0182 | 2875 | 3815794 | T | RECESSIVE | 0.0145556 | 1.37 |
| KIAA0182 | 2876 | 736845 | T | ADDITIVE | 0.0008466 | 0.80 |
| KIAA0182 | 2877 | 9940601 | A | ADDITIVE | 0.0081450 | 0.87 |
| KIAA0182 | 2878 | 1049868 | C | RECESSIVE | 0.0003614 | 0.54 |
| KIAA0182 | 2879 | 1053328 | A | RECESSIVE | 0.0030174 | 1.50 |
| GAS7 | 2880 | 1558226 | G | DOMINANT | 0.0349526 | 0.82 |
| DNAH9 | 2882 | 2286305 | T | DOMINANT | 0.0191343 | 0.80 |
| RAB11FIP4 | 2884 | 9901334 | T | ADDITIVE | 0.0147545 | 0.85 |
| CA10 | 2887 | 11655715 | T | RECESSIVE | 0.0182340 | 0.44 |
| MSI2 | 2893 | 1477065 | G | RECESSIVE | 0.0245468 | 0.72 |
| MSI2 | 2894 | 4608395 | C | RECESSIVE | 0.0461877 | 0.65 |
| DNAH17 | 2897 | 7211232 | T | RECESSIVE | 0.0028899 | 0.15 |
| HRNBP3 | 2900 | 4313838 | C | RECESSIVE | 0.0180130 | 0.75 |
| HRNBP3 | 2901 | 4313839 | C | RECESSIVE | 0.0259572 | 0.76 |
| PTPRM | 2911 | 1470323 | T | RECESSIVE | 0.0136419 | 0.73 |
| PTPRM | 2912 | 11081352 | T | RECESSIVE | 0.0027436 | 0.65 |
| PTPRM | 2913 | 2156236 | T | RECESSIVE | 0.0077796 | 0.70 |
| PTPRM | 2914 | 5000485 | T | RECESSIVE | 0.0039162 | 0.68 |
| PTPRM | 2915 | 1942958 | T | RECESSIVE | 0.0065194 | 0.69 |
| PTPRM | 2916 | 8088354 | A | RECESSIVE | 0.0033035 | 0.67 |
| PTPRM | 2917 | 649598 | T | RECESSIVE | 0.0079161 | 0.70 |
| PTPRM | 2918 | 623258 | T | RECESSIVE | 0.0056093 | 0.70 |
| PTPRM | 2920 | 619379 | C | RECESSIVE | 0.0126593 | 0.72 |
| PTPRM | 2921 | 502843 | T | RECESSIVE | 0.0253166 | 0.75 |
| PTPRM | 2922 | 552448 | T | RECESSIVE | 0.0089282 | 0.70 |
| PTPRM | 2923 | 507445 | T | RECESSIVE | 0.0183559 | 0.74 |
| OSBPL1A | 2929 | 6508259 | A | ADDITIVE | 0.0014763 | 1.24 |
| CHST9 | 2932 | 4800787 | T | DOMINANT | 0.0105520 | 1.25 |
| CHST9 | 2933 | 2162412 | A | ADDITIVE | 0.0084702 | 1.15 |
| CHST9 | 2934 | 9949654 | C | ADDITIVE | 0.0105674 | 1.15 |
| CHST9 | 2935 | 9965371 | C | ADDITIVE | 0.0141501 | 1.23 |
| CHST9 | 2936 | 1426879 | G | ADDITIVE | 0.0351731 | 1.13 |
| CHST9 | 2937 | 4800797 | G | ADDITIVE | 0.0091123 | 1.16 |
| CHST9 | 2938 | 9948409 | A | ADDITIVE | 0.0303283 | 1.10 |

TABLE 1-continued

Alleles and Genotypes Influencing Likelihood of Bipolar vs. Schizophrenia Diagnoses

| Gene | SEQ ID NO: | NCBI RS# | Allele | Model | P | Odds Ratio |
|---|---|---|---|---|---|---|
| KIAA0427 | 2942 | 8095607 | A | ADDITIVE | 0.0332070 | 1.27 |
| KIAA0427 | 2949 | 1319945 | G | RECESSIVE | 0.0326970 | 0.42 |
| DCC | 2951 | 17383821 | G | RECESSIVE | 0.0163221 | 1.42 |
| DCC | 2954 | 9964026 | G | ADDITIVE | 0.0398037 | 1.16 |
| DCC | 2959 | 8084200 | A | DOMINANT | 0.0412987 | 0.83 |
| DCC | 2964 | 9953546 | G | RECESSIVE | 0.0483463 | 2.57 |
| DCC | 2965 | 1394466 | A | RECESSIVE | 0.0256019 | 1.26 |
| DCC | 2966 | 17504520 | G | RECESSIVE | 0.0280368 | 1.26 |
| DCC | 2967 | 11876282 | G | RECESSIVE | 0.0321682 | 1.25 |
| DCC | 2968 | 11876941 | G | RECESSIVE | 0.0392771 | 1.24 |
| DCC | 2969 | 2270954 | A | RECESSIVE | 0.0357727 | 1.94 |
| NEDD4L | 2970 | 7243469 | G | DOMINANT | 0.0412457 | 0.77 |
| NEDD4L | 2971 | 4941312 | T | DOMINANT | 0.0404941 | 0.77 |
| NEDD4L | 2972 | 17064338 | C | DOMINANT | 0.0289103 | 0.76 |
| CCBE1 | 2974 | 895005 | T | DOMINANT | 0.0369089 | 1.20 |
| TXNDC10 | 2975 | 507533 | C | ADDITIVE | 0.0460221 | 1.21 |
| TXNDC10 | 2976 | 12605752 | A | RECESSIVE | 0.0283574 | 0.27 |
| TXNDC10 | 2977 | 7227089 | T | RECESSIVE | 0.0284949 | 0.27 |
| TXNDC10 | 2978 | 1477992 | G | RECESSIVE | 0.0331144 | 0.14 |
| TXNDC10 | 2979 | 309228 | A | RECESSIVE | 0.0279392 | 0.34 |
| TXNDC10 | 2980 | 309251 | C | RECESSIVE | 0.0406452 | 0.36 |
| TXNDC10 | 2981 | 309242 | G | RECESSIVE | 0.0087933 | 0.29 |
| TXNDC10 | 2982 | 590974 | T | DOMINANT | 0.0480823 | 1.19 |
| DOK6 | 2983 | 9947842 | C | RECESSIVE | 0.0143136 | 0.51 |
| DOK6 | 2995 | 4438406 | C | DOMINANT | 0.0044738 | 1.30 |
| LDLR | 3001 | 2738456 | C | RECESSIVE | 0.0433496 | 0.75 |
| RNF24 | 3005 | 241611 | T | DOMINANT | 0.0004744 | 0.74 |
| RNF24 | 3006 | 241612 | A | DOMINANT | 0.0009164 | 0.75 |
| RNF24 | 3007 | 6084530 | C | DOMINANT | 0.0163967 | 0.81 |
| PRNT | 3009 | 2245220 | T | RECESSIVE | 0.0374102 | 0.81 |
| PRNT | 3010 | 2756262 | A | ADDITIVE | 0.0170211 | 0.91 |
| PRNT | 3011 | 2422932 | A | DOMINANT | 0.0057154 | 1.27 |
| PRNT | 3012 | 6084858 | C | RECESSIVE | 0.0489977 | 0.80 |
| PRNT | 3013 | 730999 | T | RECESSIVE | 0.0394947 | 0.79 |
| PLCB1 | 3021 | 6055577 | A | RECESSIVE | 0.0167900 | 1.77 |
| PLCB1 | 3022 | 2235212 | A | RECESSIVE | 0.0331976 | 1.49 |
| PLCB1 | 3023 | 6055601 | A | RECESSIVE | 0.0212322 | 1.65 |
| PLCB1 | 3024 | 13044527 | A | RECESSIVE | 0.0432858 | 1.36 |
| PLCB1 | 3025 | 6039117 | T | RECESSIVE | 0.0489716 | 1.35 |
| PLCB4 | 3028 | 6056454 | G | ADDITIVE | 0.0159695 | 0.86 |
| PLCB4 | 3029 | 4816126 | A | ADDITIVE | 0.0314437 | 0.84 |
| PLCB4 | 3030 | 2145266 | C | ADDITIVE | 0.0193561 | 0.85 |
| PLCB4 | 3031 | 2208295 | C | ADDITIVE | 0.0116134 | 0.83 |
| PLCB4 | 3032 | 6086808 | T | DOMINANT | 0.0355663 | 0.82 |
| JAG1 | 3036 | 3790158 | A | RECESSIVE | 0.0152506 | >5 |
| JAG1 | 3037 | 3748477 | T | RECESSIVE | 0.0152506 | >5 |
| JAG1 | 3038 | 3748478 | T | RECESSIVE | 0.0152506 | >5 |
| MACROD2 | 3040 | 459322 | C | ADDITIVE | 0.0377449 | 0.92 |
| MACROD2 | 3042 | 4814383 | G | RECESSIVE | 0.0026275 | 0.51 |
| MACROD2 | 3044 | 1233763 | C | RECESSIVE | 0.0153543 | 0.61 |
| MACROD2 | 3045 | 1233769 | G | RECESSIVE | 0.0336831 | 0.63 |
| MACROD2 | 3047 | 175810 | G | RECESSIVE | 0.0239964 | 0.57 |
| MACROD2 | 3048 | 175805 | T | RECESSIVE | 0.0464941 | 0.62 |
| PTPRT | 3052 | 6016664 | G | DOMINANT | 0.0474778 | 1.19 |
| PTPRT | 3053 | 6029979 | T | DOMINANT | 0.0496507 | 1.19 |
| PTPRT | 3054 | 6016798 | C | RECESSIVE | 0.0216889 | 0.77 |
| PTPRT | 3055 | 2076082 | A | RECESSIVE | 0.0254923 | 0.77 |
| PTPRT | 3056 | 6065482 | C | RECESSIVE | 0.0271959 | 0.78 |
| PTPRT | 3057 | 6030395 | T | RECESSIVE | 0.0330898 | 1.43 |
| PTGIS | 3064 | 12625166 | T | RECESSIVE | 0.0300284 | >5 |
| BMP7 | 3066 | 162313 | A | RECESSIVE | 0.0457414 | 2.24 |
| BMP7 | 3068 | 1015985 | A | RECESSIVE | 0.0457414 | 2.24 |
| GNAS | 3071 | 7121 | T | DOMINANT | 0.0144299 | 1.27 |
| CDH4 | 3073 | 1891490 | A | ADDITIVE | 0.0135434 | 1.13 |
| CDH4 | 3074 | 3752252 | G | DOMINANT | 0.0086970 | 1.26 |
| CDH4 | 3075 | 1970546 | A | ADDITIVE | 0.0035930 | 1.21 |
| CDH4 | 3086 | 6061845 | G | ADDITIVE | 0.0156651 | 0.88 |
| CDH4 | 3087 | 1891572 | T | DOMINANT | 0.0372843 | 0.83 |
| CDH4 | 3088 | 17811544 | G | DOMINANT | 0.0279199 | 0.82 |
| CDH4 | 3089 | 6142875 | T | DOMINANT | 0.0249437 | 0.82 |
| NCAM2 | 3090 | 2226806 | C | RECESSIVE | 0.0022837 | 1.42 |
| NCAM2 | 3091 | 2826349 | G | RECESSIVE | 0.0183510 | 1.44 |
| NCAM2 | 3092 | 2826351 | A | RECESSIVE | 0.0203522 | 1.43 |
| NCAM2 | 3094 | 11702660 | A | RECESSIVE | 0.0344979 | 7.10 |
| NCAM2 | 3095 | 232490 | C | DOMINANT | 0.0133412 | 0.81 |

TABLE 1-continued

Alleles and Genotypes Influencing Likelihood of Bipolar vs. Schizophrenia Diagnoses

| Gene | SEQ ID NO: | NCBI RS# | Allele | Model | P | Odds Ratio |
|---|---|---|---|---|---|---|
| NCAM2 | 3096 | 232491 | T | DOMINANT | 0.0081579 | 0.79 |
| NCAM2 | 3097 | 2826815 | T | DOMINANT | 0.0017598 | 0.76 |
| NCAM2 | 3098 | 232509 | T | ADDITIVE | 0.0078224 | 0.81 |
| NCAM2 | 3099 | 232516 | A | DOMINANT | 0.0163957 | 0.81 |
| NCAM2 | 3100 | 2826818 | G | DOMINANT | 0.0015795 | 0.76 |
| NCAM2 | 3101 | 232424 | T | DOMINANT | 0.0064791 | 0.79 |
| NCAM2 | 3102 | 2826826 | A | DOMINANT | 0.0026054 | 0.77 |
| NCAM2 | 3103 | 232446 | G | DOMINANT | 0.0060568 | 0.79 |
| NCAM2 | 3104 | 2847461 | T | DOMINANT | 0.0017547 | 0.76 |
| NCAM2 | 3105 | 2826830 | G | ADDITIVE | 0.0115585 | 0.81 |
| NCAM2 | 3106 | 3787603 | G | ADDITIVE | 0.0111789 | 0.82 |
| SLC37A1 | 3113 | 12483006 | A | RECESSIVE | 0.0195839 | 1.73 |
| SLC37A1 | 3116 | 1788421 | G | DOMINANT | 0.0073634 | 0.79 |
| PDE9A | 3117 | 2269139 | T | RECESSIVE | 0.0363891 | 1.93 |
| PDE9A | 3118 | 2269143 | A | RECESSIVE | 0.0319822 | 2.04 |
| PDE9A | 3119 | 2269173 | G | ADDITIVE | 0.0048662 | 0.89 |
| ASPHD2 | 3121 | 11913750 | C | DOMINANT | 0.0310367 | 0.73 |
| ASPHD2 | 3122 | 16982107 | T | DOMINANT | 0.0360544 | 0.74 |
| TTLL1 | 3124 | 5996268 | C | ADDITIVE | 0.0470533 | 0.78 |
| EFCAB6 | 3125 | 137746 | C | RECESSIVE | 0.0364594 | 1.93 |
| EFCAB6 | 3126 | 137767 | T | RECESSIVE | 0.0254356 | 2.01 |
| EFCAB6 | 3127 | 137801 | A | RECESSIVE | 0.0333977 | 2.26 |
| EFCAB6 | 3128 | 1013039 | C | RECESSIVE | 0.0494874 | 1.87 |
| EFCAB6 | 3129 | 5764302 | G | RECESSIVE | 0.0254356 | 2.01 |
| SULT4A1 | 3130 | 5764318 | C | RECESSIVE | 0.0175703 | 0.50 |
| SULT4A1 | 3131 | 2066915 | C | ADDITIVE | 0.0262448 | 1.13 |
| SULT4A1 | 3133 | 2285162 | A | RECESSIVE | 0.0311834 | 0.69 |
| SULT4A1 | 3134 | 2285166 | T | RECESSIVE | 0.0307734 | 0.68 |
| SULT4A1 | 3135 | 2285167 | A | RECESSIVE | 0.0080914 | 0.46 |
| SULT4A1 | 3137 | 5764367 | T | RECESSIVE | 0.0352891 | 0.69 |
| RIBC2 | 3138 | 5765397 | A | RECESSIVE | 0.0330656 | 1.26 |
| RIBC2 | 3139 | 2092101 | G | RECESSIVE | 0.0292451 | 1.27 |
| RIBC2 | 3140 | 5764751 | C | RECESSIVE | 0.0338442 | 1.24 |
| RIBC2 | 3141 | 5765425 | A | RECESSIVE | 0.0188752 | 1.30 |

Example 2

Genotypes and Alleles that Contribute to Risk of BD or SZ

The same methods described above in Example 1 to identify SNPs that were differentially associated with BD or SZ. Specifically, this analysis examined alleles that contributed to a diagnosis of either BD or SZ. For example, a given SNP could enhance likelihood of diagnosis of both BD and SZ. Those SNPs that contribute to the likelihood of diagnosis of both diseases may be those SNPs that contribute the overlapping symptom pattern between BD and SZ, e.g. SNPs that contribute to mania, depression, or delusions.

Table 2 lists alleles and genotypes influencing a diagnosis of, or risk of developing, BD or SZ. 640 BD cases, and a randomly selected subset of 640 SZ cases, and 1378 neurologically normal controls were used to identify these alleles and genotypes. Briefly, BD cases and SZ cases were both considered cases and were coded as a 1 (or case) and each control was coded as 0. Combining BD and SZ in this manner identifies those SNPs that contribute to a diagnosis of, or risk of developing, broadly defined serious psychiatric illness (psychosis). Using this coding and genotypes provided by GAIN, case control analysis was performed using various genetic models (recessive, dominant and additive) in Golden Helix's SNP and Variation Suite v 7.0 (SVS™). Table 2 lists the gene, SEQ ID NO:, NCBI RS number, test allele, genetic model, odds ratio, and p-value for the comparison. In this example, an OR greater than 1 indicates that the subject has a greater likelihood of a BD or SZ diagnosis. Similarly, an OR less than 1 indicates that the subject has a lower likelihood of a BD or SZ diagnosis.

TABLE 2

Alleles and Genotypes Influencing Likelihood of Diagnosis of Bipolar or Schizophrenia

| Gene | SEQ ID NO: | NCBI RS# | Allele | Model | P | Odds Ratio |
|---|---|---|---|---|---|---|
| RP1-21O18.1 | 5 | 1000313 | G | ADDITIVE | 0.023031 | 1.13 |
| RP1-21O18.1 | 6 | 4501834 | C | ADDITIVE | 0.010524 | 1.14 |
| RP1-21O18.1 | 7 | 10803349 | A | ADDITIVE | 0.007056 | 1.15 |
| RP1-21O18.1 | 8 | 4661575 | T | RECESSIVE | 0.002888 | 1.45 |
| AGBL4-C1ORF165 | 13 | 11205538 | C | DOMINANT | 0.003952 | 1.23 |
| AGBL4-C1ORF165 | 14 | 7520784 | A | DOMINANT | 0.005937 | 1.21 |
| AGBL4-C1ORF165 | 15 | 10888622 | G | DOMINANT | 0.010006 | 1.20 |
| AGBL4-C1ORF165 | 16 | 4926759 | C | DOMINANT | 0.015223 | 1.19 |
| AGBL4-C1ORF165 | 17 | 1934368 | C | DOMINANT | 0.020949 | 1.18 |
| AGBL4-C1ORF165 | 19 | 3122291 | T | DOMINANT | 0.001607 | 1.25 |
| AGBL4-C1ORF165 | 20 | 3121512 | C | DOMINANT | 0.001749 | 1.27 |

TABLE 2-continued

Alleles and Genotypes Influencing Likelihood of Diagnosis of Bipolar or Schizophrenia

| Gene | SEQ ID NO: | NCBI RS# | Allele | Model | P | Odds Ratio |
|---|---|---|---|---|---|---|
| AGBL4-C1ORF165 | 21 | 3118215 | A | ADDITIVE | 0.004611 | 1.23 |
| AGBL4-C1ORF165 | 22 | 3118223 | G | ADDITIVE | 0.003490 | 1.23 |
| AGBL4-C1ORF165 | 23 | 3121273 | G | ADDITIVE | 0.001892 | 1.23 |
| AGBL4-C1ORF165 | 24 | 3127556 | G | ADDITIVE | 0.003664 | 1.22 |
| AGBL4-C1ORF165 | 25 | 3121518 | A | ADDITIVE | 0.003788 | 1.21 |
| AGBL4-C1ORF165 | 26 | 6669433 | A | ADDITIVE | 0.004697 | 1.23 |
| AGBL4-C1ORF165 | 27 | 7520773 | T | RECESSIVE | 0.004313 | 1.38 |
| LRP8 | 28 | 17785382 | G | RECESSIVE | 0.000489 | 0.71 |
| LRP8 | 29 | 5177 | C | ADDITIVE | 0.002955 | 0.89 |
| LRP8 | 30 | 11206127 | A | DOMINANT | 0.001922 | 0.79 |
| LRP8 | 31 | 869987 | T | DOMINANT | 0.001601 | 0.79 |
| LRP8 | 32 | 869988 | C | DOMINANT | 0.001625 | 0.79 |
| LRP8 | 33 | 2297660 | A | ADDITIVE | 0.003823 | 0.89 |
| LRP8 | 34 | 2297657 | A | RECESSIVE | 0.004002 | 0.75 |
| LRP8 | 35 | 4623641 | T | RECESSIVE | 0.022652 | 0.79 |
| PRKACB | 39 | 589373 | A | ADDITIVE | 0.045631 | 1.15 |
| SLC6A17 | 40 | 17671169 | A | ADDITIVE | 0.044442 | 1.11 |
| SLC6A17 | 41 | 495959 | T | ADDITIVE | 0.015930 | 0.82 |
| SLC16A4 | 43 | 4498805 | G | ADDITIVE | 0.026757 | 0.83 |
| SLC16A4 | 44 | 2271885 | C | ADDITIVE | 0.047401 | 1.32 |
| SYT6 | 46 | 611514 | A | RECESSIVE | 0.011843 | 0.80 |
| NGF | 47 | 7523654 | T | ADDITIVE | 0.000414 | 1.31 |
| NGF | 48 | 11102924 | G | DOMINANT | 0.001940 | 1.27 |
| NGF | 49 | 10776799 | G | DOMINANT | 0.000102 | 1.34 |
| NGF | 50 | 4332358 | T | DOMINANT | 0.000031 | 1.34 |
| NGF | 51 | 17033706 | A | DOMINANT | 0.000303 | 1.33 |
| SLC22A15 | 53 | 2488432 | T | DOMINANT | 0.043650 | 0.87 |
| PTGFRN | 56 | 12090536 | G | RECESSIVE | 0.009209 | 0.71 |
| PTGFRN | 57 | 7552382 | G | RECESSIVE | 0.012344 | 0.73 |
| PTGFRN | 58 | 3829881 | A | DOMINANT | 0.007166 | 1.24 |
| CGN | 60 | 10788807 | G | DOMINANT | 0.049612 | 0.85 |
| ATF6 | 63 | 905594 | T | ADDITIVE | 0.009476 | 0.83 |
| ATF6 | 66 | 1875762 | T | ADDITIVE | 0.001909 | 0.80 |
| ATF6 | 68 | 10918029 | A | ADDITIVE | 0.000629 | 0.71 |
| ATF6 | 79 | 2499854 | G | ADDITIVE | 0.045617 | 0.88 |
| OLFML2B | 80 | 4657130 | G | RECESSIVE | 0.001979 | 0.72 |
| OLFML2B | 81 | 4657131 | A | RECESSIVE | 0.001212 | 0.70 |
| OLFML2B | 82 | 2490420 | G | RECESSIVE | 0.002385 | 0.71 |
| OLFML2B | 83 | 4657132 | G | RECESSIVE | 0.000790 | 0.71 |
| OLFML2B | 84 | 6691548 | C | RECESSIVE | 0.000739 | 0.70 |
| CACNA1E | 92 | 553042 | C | DOMINANT | 0.005496 | 1.22 |
| CACNA1E | 93 | 486708 | T | DOMINANT | 0.009729 | 1.20 |
| CACNA1E | 94 | 17441683 | A | ADDITIVE | 0.015582 | 1.21 |
| CACNA1E | 95 | 17494681 | T | ADDITIVE | 0.014240 | 1.23 |
| LAMC1 | 103 | 6658501 | A | DOMINANT | 0.000552 | 0.76 |
| LAMC1 | 104 | 4652772 | G | DOMINANT | 0.001674 | 0.78 |
| LAMC1 | 105 | 3935384 | G | DOMINANT | 0.000298 | 0.75 |
| LAMC1 | 106 | 10797829 | A | DOMINANT | 0.000298 | 0.75 |
| LAMC1 | 107 | 10911232 | T | RECESSIVE | 0.003177 | 1.32 |
| LAMC1 | 108 | 12091137 | A | DOMINANT | 0.000146 | 0.75 |
| LAMC1 | 109 | 12086466 | T | DOMINANT | 0.000103 | 0.74 |
| LAMC1 | 110 | 10797838 | A | DOMINANT | 0.000079 | 0.74 |
| LAMC1 | 111 | 10797839 | T | DOMINANT | 0.000065 | 0.74 |
| LAMC1 | 112 | 10752898 | T | DOMINANT | 0.000043 | 0.73 |
| LAMC1 | 113 | 10797842 | G | DOMINANT | 0.000062 | 0.73 |
| LAMC1 | 114 | 6424888 | A | DOMINANT | 0.000122 | 0.74 |
| LAMC1 | 115 | 20563 | A | DOMINANT | 0.000133 | 0.75 |
| LAMC1 | 116 | 3768617 | A | RECESSIVE | 0.002595 | 1.32 |
| LAMC1 | 117 | 7518957 | A | DOMINANT | 0.000063 | 0.74 |
| LAMC1 | 118 | 1360704 | G | RECESSIVE | 0.001865 | 1.33 |
| LAMC1 | 119 | 2274984 | C | DOMINANT | 0.000253 | 0.75 |
| LAMC1 | 120 | 2027085 | A | DOMINANT | 0.000180 | 0.75 |
| KCNH1 | 123 | 1340127 | C | DOMINANT | 0.017478 | 0.83 |
| KCNH1 | 129 | 7537388 | C | RECESSIVE | 0.041062 | 1.56 |
| KCNK2 | 132 | 4655272 | A | DOMINANT | 0.006028 | 1.24 |
| KCNK2 | 133 | 10494994 | A | DOMINANT | 0.013011 | 1.20 |
| KCNK2 | 134 | 12038695 | C | DOMINANT | 0.008288 | 1.22 |
| KCNK2 | 135 | 11120519 | A | ADDITIVE | 0.002214 | 1.28 |
| KCNK2 | 137 | 11120527 | T | DOMINANT | 0.003193 | 1.24 |
| USH2A | 138 | 11120538 | A | DOMINANT | 0.005019 | 1.23 |
| USH2A | 139 | 6674743 | T | DOMINANT | 0.006689 | 1.22 |
| USH2A | 140 | 2677117 | A | DOMINANT | 0.024546 | 1.17 |
| USH2A | 141 | 2677111 | C | DOMINANT | 0.009890 | 1.20 |
| ESRRG | 143 | 12027901 | C | DOMINANT | 0.019424 | 1.23 |
| ESRRG | 144 | 7529655 | A | RECESSIVE | 0.019137 | 0.60 |
| RYR2 | 156 | 16835170 | C | RECESSIVE | 0.021686 | 1.31 |

TABLE 2-continued

Alleles and Genotypes Influencing Likelihood of Diagnosis of Bipolar or Schizophrenia

| Gene | SEQ ID NO: | NCBI RS# | Allele | Model | P | Odds Ratio |
|---|---|---|---|---|---|---|
| RYR2 | 157 | 2779397 | C | DOMINANT | 0.017430 | 0.84 |
| RYR2 | 158 | 2779400 | A | DOMINANT | 0.022488 | 0.85 |
| FMN2 | 162 | 12122068 | C | ADDITIVE | 0.005347 | 0.80 |
| FMN2 | 163 | 10926223 | C | ADDITIVE | 0.010874 | 0.80 |
| FMN2 | 164 | 12130718 | A | ADDITIVE | 0.011256 | 0.86 |
| KCNF1 | 192 | 2884310 | G | ADDITIVE | 0.045453 | 1.11 |
| NAG | 193 | 3805093 | C | ADDITIVE | 0.048493 | 0.87 |
| NAG | 194 | 10206116 | C | ADDITIVE | 0.032081 | 0.86 |
| HS1BP3 | 195 | 3732157 | A | ADDITIVE | 0.012752 | 1.19 |
| HS1BP3 | 196 | 1047176 | T | DOMINANT | 0.005932 | 1.22 |
| HS1BP3 | 197 | 7586298 | T | ADDITIVE | 0.027521 | 1.18 |
| ASXL2 | 210 | 6747116 | C | DOMINANT | 0.009733 | 1.22 |
| CIB4 | 213 | 11694917 | T | ADDITIVE | 0.034547 | 0.79 |
| DPYSL5 | 215 | 12991828 | G | DOMINANT | 0.039784 | 0.86 |
| DPYSL5 | 216 | 6756245 | C | DOMINANT | 0.047309 | 0.86 |
| BRE | 217 | 6706209 | C | DOMINANT | 0.018802 | 0.84 |
| BRE | 221 | 6738887 | C | DOMINANT | 0.044436 | 0.87 |
| CRIM1 | 224 | 2160367 | C | RECESSIVE | 0.024909 | 1.22 |
| CRIM1 | 225 | 711252 | T | DOMINANT | 0.016634 | 0.83 |
| CRIM1 | 226 | 848556 | T | DOMINANT | 0.000503 | 0.76 |
| CRIM1 | 227 | 848553 | C | DOMINANT | 0.022784 | 0.83 |
| CRIM1 | 228 | 848552 | G | DOMINANT | 0.011423 | 0.82 |
| CRIM1 | 229 | 848547 | G | DOMINANT | 0.015172 | 0.82 |
| CRIM1 | 230 | 3770852 | A | DOMINANT | 0.001510 | 0.80 |
| CRIM1 | 233 | 3770833 | A | DOMINANT | 0.003501 | 0.81 |
| CRIM1 | 234 | 2293254 | G | DOMINANT | 0.011868 | 0.83 |
| CRIM1 | 235 | 2287082 | T | DOMINANT | 0.001615 | 0.80 |
| CRIM1 | 236 | 3755197 | A | DOMINANT | 0.003015 | 0.81 |
| CRIM1 | 237 | 11681392 | T | DOMINANT | 0.000473 | 0.78 |
| FEZ2 | 238 | 10189344 | C | DOMINANT | 0.001795 | 0.80 |
| FEZ2 | 239 | 10172196 | A | DOMINANT | 0.000792 | 0.79 |
| FEZ2 | 240 | 3770811 | T | DOMINANT | 0.000125 | 0.76 |
| FEZ2 | 241 | 1533949 | T | DOMINANT | 0.001063 | 0.79 |
| FEZ2 | 242 | 1533948 | C | DOMINANT | 0.000233 | 0.77 |
| FEZ2 | 243 | 1533946 | G | DOMINANT | 0.000165 | 0.76 |
| FEZ2 | 244 | 13406184 | C | DOMINANT | 0.000122 | 0.76 |
| FEZ2 | 245 | 17488036 | G | DOMINANT | 0.000220 | 0.77 |
| FEZ2 | 246 | 2022211 | G | DOMINANT | 0.000419 | 0.77 |
| FEZ2 | 247 | 10197570 | T | DOMINANT | 0.001223 | 0.79 |
| FEZ2 | 248 | 11691767 | T | DOMINANT | 0.000737 | 0.79 |
| FEZ2 | 249 | 10469898 | G | DOMINANT | 0.001462 | 0.80 |
| FEZ2 | 250 | 5003670 | C | DOMINANT | 0.006521 | 0.82 |
| CDC42EP3 | 252 | 15628 | T | ADDITIVE | 0.032228 | 1.21 |
| SLC8A1 | 253 | 6544318 | A | ADDITIVE | 0.017655 | 0.81 |
| SLC8A1 | 254 | 759384 | C | ADDITIVE | 0.023659 | 0.84 |
| SLC8A1 | 255 | 4952609 | G | ADDITIVE | 0.023271 | 0.87 |
| HAAO | 256 | 13398984 | T | RECESSIVE | 0.049160 | 0.72 |
| HAAO | 257 | 4564826 | A | ADDITIVE | 0.003779 | 0.88 |
| C2ORF34 | 261 | 786613 | G | DOMINANT | 0.000401 | 1.28 |
| C2ORF34 | 262 | 786616 | G | DOMINANT | 0.008815 | 1.20 |
| C2ORF34 | 263 | 786626 | C | DOMINANT | 0.000284 | 1.29 |
| C2ORF34 | 264 | 786624 | T | DOMINANT | 0.000304 | 1.29 |
| C2ORF34 | 265 | 1067343 | A | DOMINANT | 0.007403 | 1.21 |
| C2ORF34 | 266 | 1067386 | G | DOMINANT | 0.000931 | 1.26 |
| C2ORF34 | 267 | 1067383 | G | DOMINANT | 0.006617 | 1.21 |
| C2ORF34 | 268 | 1584885 | C | ADDITIVE | 0.000081 | 1.32 |
| C2ORF34 | 269 | 1067378 | A | DOMINANT | 0.008498 | 1.21 |
| C2ORF34 | 270 | 1067375 | C | DOMINANT | 0.009726 | 1.20 |
| C2ORF34 | 271 | 1067374 | G | DOMINANT | 0.007631 | 1.21 |
| C2ORF34 | 272 | 1067367 | A | DOMINANT | 0.001689 | 1.25 |
| C2ORF34 | 273 | 1065786 | T | DOMINANT | 0.000625 | 1.27 |
| C2ORF34 | 274 | 1067355 | C | DOMINANT | 0.010313 | 1.20 |
| C2ORF34 | 275 | 1085447 | T | DOMINANT | 0.000515 | 1.28 |
| C2ORF34 | 276 | 1067348 | T | DOMINANT | 0.007260 | 1.21 |
| C2ORF34 | 277 | 1067347 | C | DOMINANT | 0.000360 | 1.29 |
| C2ORF34 | 278 | 1067406 | C | DOMINANT | 0.000404 | 1.29 |
| C2ORF34 | 279 | 1067404 | A | DOMINANT | 0.002957 | 1.24 |
| C2ORF34 | 280 | 1067402 | T | DOMINANT | 0.005635 | 1.22 |
| C2ORF34 | 281 | 1067397 | A | DOMINANT | 0.012315 | 1.20 |
| C2ORF34 | 282 | 698792 | A | DOMINANT | 0.010748 | 1.20 |
| C2ORF34 | 283 | 786419 | G | DOMINANT | 0.000789 | 1.27 |
| C2ORF34 | 284 | 698793 | C | DOMINANT | 0.007146 | 1.21 |
| C2ORF34 | 285 | 2166453 | G | ADDITIVE | 0.000143 | 1.28 |
| C2ORF34 | 286 | 698809 | A | DOMINANT | 0.015551 | 1.19 |
| C2ORF34 | 287 | 698823 | G | DOMINANT | 0.001215 | 1.26 |
| C2ORF34 | 288 | 698824 | C | DOMINANT | 0.000552 | 1.28 |

TABLE 2-continued

Alleles and Genotypes Influencing Likelihood of Diagnosis of Bipolar or Schizophrenia

| Gene | SEQ ID NO: | NCBI RS# | Allele | Model | P | Odds Ratio |
|---|---|---|---|---|---|---|
| C2ORF34 | 289 | 698827 | G | DOMINANT | 0.003581 | 1.23 |
| C2ORF34 | 290 | 698828 | T | DOMINANT | 0.006854 | 1.21 |
| C2ORF34 | 291 | 698832 | C | DOMINANT | 0.004858 | 1.22 |
| C2ORF34 | 292 | 698833 | T | DOMINANT | 0.004272 | 1.22 |
| C2ORF34 | 293 | 786406 | T | DOMINANT | 0.003550 | 1.23 |
| C2ORF34 | 294 | 11888605 | A | DOMINANT | 0.010202 | 1.21 |
| C2ORF34 | 295 | 3862996 | G | DOMINANT | 0.000228 | 1.31 |
| C2ORF34 | 296 | 1011798 | C | ADDITIVE | 0.003870 | 1.22 |
| C2ORF34 | 297 | 729310 | A | DOMINANT | 0.003360 | 1.24 |
| C2ORF34 | 298 | 2341457 | A | DOMINANT | 0.006713 | 1.22 |
| C2ORF34 | 299 | 1377906 | G | DOMINANT | 0.045305 | 1.15 |
| C2ORF34 | 300 | 7609431 | C | DOMINANT | 0.045594 | 1.15 |
| C2ORF34 | 301 | 4953101 | T | DOMINANT | 0.009825 | 1.20 |
| C2ORF34 | 303 | 13383854 | G | DOMINANT | 0.003965 | 1.24 |
| C2ORF34 | 304 | 6721746 | A | RECESSIVE | 0.002125 | 0.52 |
| C2ORF34 | 305 | 7603180 | G | RECESSIVE | 0.019588 | 0.61 |
| C2ORF34 | 306 | 11679997 | T | RECESSIVE | 0.005864 | 0.56 |
| PRKCE | 307 | 2881068 | C | ADDITIVE | 0.031005 | 0.88 |
| PRKCE | 308 | 4952792 | C | RECESSIVE | 0.012801 | 0.77 |
| PRKCE | 310 | 12989656 | T | DOMINANT | 0.029417 | 1.17 |
| EPAS1 | 311 | 1374749 | A | DOMINANT | 0.002654 | 0.79 |
| EPAS1 | 312 | 10178633 | A | DOMINANT | 0.009113 | 0.81 |
| EPAS1 | 313 | 13006131 | G | RECESSIVE | 0.041003 | 1.18 |
| AAK1 | 321 | 2312207 | T | DOMINANT | 0.013618 | 0.82 |
| CTNNA2 | 327 | 2566539 | T | ADDITIVE | 0.032627 | 0.89 |
| CTNNA2 | 332 | 7577376 | G | RECESSIVE | 0.042889 | 1.83 |
| CTNNA2 | 333 | 17018760 | T | RECESSIVE | 0.027435 | 1.95 |
| CTNNA2 | 334 | 1443897 | C | RECESSIVE | 0.047455 | 1.84 |
| CTNNA2 | 335 | 7576232 | T | RECESSIVE | 0.036371 | 1.90 |
| CTNNA2 | 336 | 7570531 | C | RECESSIVE | 0.030140 | 1.97 |
| CTNNA2 | 337 | 961408 | G | RECESSIVE | 0.047146 | 1.84 |
| CTNNA2 | 338 | 1446107 | G | RECESSIVE | 0.019905 | 2.17 |
| CTNNA2 | 339 | 1446108 | A | RECESSIVE | 0.019950 | 2.17 |
| CTNNA2 | 341 | 1965834 | T | ADDITIVE | 0.037994 | 1.13 |
| CTNNA2 | 342 | 1965833 | G | RECESSIVE | 0.031176 | 1.74 |
| CTNNA2 | 343 | 2165975 | T | RECESSIVE | 0.039586 | 1.91 |
| CTNNA2 | 344 | 6738092 | C | RECESSIVE | 0.039410 | 1.92 |
| INPP4A | 345 | 17446058 | G | DOMINANT | 0.020841 | 1.18 |
| NAP5 | 346 | 12478698 | C | ADDITIVE | 0.046440 | 0.85 |
| NAP5 | 347 | 10174856 | C | ADDITIVE | 0.035515 | 1.08 |
| NAP5 | 348 | 1437904 | T | ADDITIVE | 0.047914 | 1.07 |
| NAP5 | 350 | 13421559 | G | RECESSIVE | 0.020681 | 1.59 |
| RAB3GAP1 | 351 | 10186594 | G | DOMINANT | 0.018167 | 1.21 |
| RAB3GAP1 | 352 | 17293519 | G | DOMINANT | 0.026159 | 1.20 |
| RAB3GAP1 | 353 | 2874739 | T | DOMINANT | 0.022042 | 1.21 |
| RAB3GAP1 | 355 | 3739028 | G | DOMINANT | 0.036625 | 1.58 |
| ZRANB3 | 356 | 1898524 | T | DOMINANT | 0.040695 | 1.48 |
| LRP1B | 357 | 1492388 | T | RECESSIVE | 0.005578 | 1.34 |
| LRP1B | 358 | 12479163 | A | RECESSIVE | 0.007088 | 1.46 |
| LRP1B | 364 | 972485 | A | ADDITIVE | 0.023486 | 1.17 |
| LRP1B | 366 | 1369528 | G | ADDITIVE | 0.020164 | 0.86 |
| LRP1B | 367 | 6429927 | G | DOMINANT | 0.012980 | 1.20 |
| LRP1B | 368 | 13408365 | A | DOMINANT | 0.013165 | 1.20 |
| LRP1B | 369 | 10165154 | C | DOMINANT | 0.015857 | 1.19 |
| LRP1B | 370 | 13418027 | T | DOMINANT | 0.041922 | 1.17 |
| FMNL2 | 395 | 1155779 | C | ADDITIVE | 0.035232 | 0.86 |
| FMNL2 | 396 | 1370504 | G | RECESSIVE | 0.019686 | 1.49 |
| FMNL2 | 397 | 10193104 | A | RECESSIVE | 0.019152 | 1.48 |
| PLA2R1 | 403 | 3828324 | C | RECESSIVE | 0.028752 | 0.83 |
| PLA2R1 | 404 | 3792189 | C | DOMINANT | 0.001395 | 1.26 |
| PLA2R1 | 405 | 4665138 | T | RECESSIVE | 0.006305 | 0.80 |
| PLA2R1 | 406 | 17241282 | C | RECESSIVE | 0.001488 | 0.75 |
| PLA2R1 | 407 | 17830904 | G | RECESSIVE | 0.007897 | 0.80 |
| KCNH7 | 408 | 9287822 | C | RECESSIVE | 0.030714 | 0.57 |
| KCNH7 | 409 | 9807929 | T | RECESSIVE | 0.016298 | 0.54 |
| KCNH7 | 410 | 4091356 | T | RECESSIVE | 0.012100 | 0.54 |
| SCN2A | 412 | 353128 | G | RECESSIVE | 0.004556 | 1.35 |
| SCN1A | 416 | 1824551 | C | RECESSIVE | 0.008412 | 1.34 |
| SCN1A | 418 | 7607543 | C | RECESSIVE | 0.047154 | 1.40 |
| SCN1A | 419 | 1461197 | A | RECESSIVE | 0.006218 | 1.35 |
| SCN1A | 420 | 1824549 | G | RECESSIVE | 0.012012 | 1.32 |
| SCN1A | 421 | 1381105 | G | RECESSIVE | 0.014105 | 1.31 |
| SCN9A | 423 | 6756630 | A | RECESSIVE | 0.024679 | 1.78 |
| SCN9A | 424 | 3924001 | T | ADDITIVE | 0.008161 | 0.94 |
| SCN9A | 425 | 6747673 | T | RECESSIVE | 0.025748 | 0.83 |
| CERKL | 432 | 1967351 | C | RECESSIVE | 0.003041 | 0.74 |

TABLE 2-continued

Alleles and Genotypes Influencing Likelihood of Diagnosis of Bipolar or Schizophrenia

| Gene | SEQ ID NO: | NCBI RS# | Allele | Model | P | Odds Ratio |
|---|---|---|---|---|---|---|
| PDE1A | 438 | 16823124 | A | ADDITIVE | 0.001819 | 1.20 |
| PDE1A | 439 | 1430158 | C | ADDITIVE | 0.039304 | 1.18 |
| PDE1A | 440 | 10497597 | T | ADDITIVE | 0.003065 | 1.25 |
| TMEFF2 | 442 | 10497725 | C | RECESSIVE | 0.015237 | 1.31 |
| TMEFF2 | 445 | 4853492 | T | DOMINANT | 0.011412 | 1.20 |
| TMEFF2 | 446 | 10191803 | T | DOMINANT | 0.011724 | 1.20 |
| ALS2 | 447 | 6731583 | C | DOMINANT | 0.034680 | 1.19 |
| ABI2 | 448 | 10197623 | T | RECESSIVE | 0.004368 | 1.53 |
| PARD3B | 453 | 17626122 | C | DOMINANT | 0.008669 | 0.82 |
| PARD3B | 454 | 12469145 | C | DOMINANT | 0.019983 | 0.84 |
| ERBB4 | 460 | 10210330 | T | ADDITIVE | 0.025685 | 1.14 |
| ERBB4 | 461 | 4672668 | G | ADDITIVE | 0.032214 | 1.14 |
| COL4A4 | 482 | 13382950 | C | DOMINANT | 0.015788 | 1.21 |
| DNER | 489 | 6733289 | G | ADDITIVE | 0.031550 | 1.09 |
| SAG | 496 | 2241874 | A | RECESSIVE | 0.006025 | 0.75 |
| SAG | 497 | 2241873 | C | RECESSIVE | 0.008788 | 0.76 |
| CENTG2 | 498 | 2292708 | T | ADDITIVE | 0.027226 | 0.85 |
| CENTG2 | 500 | 10929160 | T | RECESSIVE | 0.028919 | 1.23 |
| CNTN6 | 502 | 3902672 | G | DOMINANT | 0.040582 | 0.85 |
| CNTN6 | 505 | 155390 | G | ADDITIVE | 0.009897 | 0.78 |
| CNTN6 | 507 | 155391 | C | ADDITIVE | 0.007737 | 0.77 |
| CNTN4 | 518 | 2063896 | A | ADDITIVE | 0.036403 | 0.92 |
| CNTN4 | 519 | 12494838 | G | RECESSIVE | 0.014353 | 0.73 |
| CNTN4 | 523 | 163574 | A | ADDITIVE | 0.000838 | 1.36 |
| CNTN4 | 524 | 163352 | G | DOMINANT | 0.029184 | 1.18 |
| ITPR1 | 525 | 304041 | G | ADDITIVE | 0.039812 | 1.06 |
| IRAK2 | 531 | 696041 | A | RECESSIVE | 0.013603 | 1.83 |
| SLC6A1 | 536 | 1062246 | G | RECESSIVE | 0.012815 | 0.76 |
| GADL1 | 538 | 1494730 | C | DOMINANT | 0.040974 | 0.86 |
| FBXL2 | 539 | 9880596 | C | ADDITIVE | 0.029534 | 1.12 |
| CLASP2 | 544 | 7624319 | G | RECESSIVE | 0.018826 | 1.31 |
| CLASP2 | 545 | 7641020 | G | RECESSIVE | 0.033987 | 1.21 |
| ARPP-21 | 546 | 9811585 | G | DOMINANT | 0.010468 | 1.20 |
| ARPP-21 | 547 | 2278758 | A | RECESSIVE | 0.002872 | 0.40 |
| ARPP-21 | 548 | 2012153 | G | RECESSIVE | 0.000352 | 0.74 |
| ARPP-21 | 549 | 7621692 | T | RECESSIVE | 0.016503 | 0.48 |
| ARPP-21 | 550 | 6550367 | C | RECESSIVE | 0.007170 | 0.80 |
| ARPP-21 | 551 | 2305234 | A | RECESSIVE | 0.011295 | 0.47 |
| STAC | 552 | 17186340 | T | RECESSIVE | 0.037390 | 2.57 |
| CAMKV | 564 | 2883059 | C | RECESSIVE | 0.003731 | 0.77 |
| CACNA2D3 | 581 | 1467179 | A | DOMINANT | 0.004411 | 1.24 |
| CACNA2D3 | 582 | 1467178 | T | DOMINANT | 0.002068 | 1.26 |
| CACNA2D3 | 583 | 3773580 | T | DOMINANT | 0.002278 | 1.24 |
| CACNA2D3 | 584 | 17054677 | A | ADDITIVE | 0.006768 | 1.27 |
| CACNA2D3 | 585 | 3773569 | A | DOMINANT | 0.001038 | 1.27 |
| FLNB | 588 | 12488636 | C | RECESSIVE | 0.027938 | 1.29 |
| FLNB | 589 | 7373012 | G | RECESSIVE | 0.006274 | 0.71 |
| FHIT | 590 | 639244 | C | DOMINANT | 0.017999 | 0.84 |
| FHIT | 599 | 2736823 | T | DOMINANT | 0.040257 | 0.86 |
| CADPS | 606 | 1812677 | G | ADDITIVE | 0.019052 | 1.12 |
| CADPS | 607 | 1398623 | G | DOMINANT | 0.004679 | 1.24 |
| CADPS | 608 | 304233 | G | ADDITIVE | 0.014797 | 1.14 |
| CADPS | 609 | 526163 | A | ADDITIVE | 0.023865 | 1.10 |
| CADPS | 610 | 9854059 | T | ADDITIVE | 0.043479 | 1.08 |
| SYNPR | 611 | 6809418 | T | DOMINANT | 0.020076 | 1.19 |
| PRICKLE2 | 614 | 696016 | A | RECESSIVE | 0.004590 | 2.69 |
| PRICKLE2 | 615 | 696017 | A | RECESSIVE | 0.008484 | 2.44 |
| PRICKLE2 | 616 | 704398 | G | RECESSIVE | 0.001129 | 3.04 |
| PRICKLE2 | 617 | 697288 | T | RECESSIVE | 0.001166 | 3.18 |
| MAGI1 | 618 | 2222582 | T | ADDITIVE | 0.024962 | 0.94 |
| MAGI1 | 619 | 9859408 | T | ADDITIVE | 0.014405 | 1.18 |
| MAGI1 | 621 | 264705 | A | ADDITIVE | 0.033436 | 1.16 |
| FAM19A1 | 622 | 17140779 | G | ADDITIVE | 0.025219 | 0.86 |
| FAM19A1 | 623 | 11707519 | G | DOMINANT | 0.013989 | 1.25 |
| ROBO2 | 625 | 9882239 | C | ADDITIVE | 0.004971 | 1.25 |
| ROBO1 | 631 | 4564923 | T | ADDITIVE | 0.027376 | 1.12 |
| EPHA6 | 634 | 4571251 | T | ADDITIVE | 0.039238 | 1.39 |
| PLCXD2 | 640 | 9870533 | A | RECESSIVE | 0.032427 | 0.59 |
| PLCXD2 | 641 | 6807632 | T | ADDITIVE | 0.026521 | 1.43 |
| KALRN | 643 | 6438827 | G | RECESSIVE | 0.044675 | >5 |
| CPNE4 | 653 | 9843898 | C | RECESSIVE | 0.029620 | 1.34 |
| EPHB1 | 658 | 9819372 | A | RECESSIVE | 0.019239 | 0.77 |
| SERPINI1 | 675 | 2229697 | A | DOMINANT | 0.047086 | 1.21 |
| SLC7A14 | 677 | 12496334 | C | ADDITIVE | 0.035840 | 0.85 |
| SLC7A14 | 678 | 17289598 | G | ADDITIVE | 0.031139 | 0.84 |
| TNIK | 679 | 6781167 | A | ADDITIVE | 0.029134 | 1.18 |

TABLE 2-continued

Alleles and Genotypes Influencing Likelihood of Diagnosis of Bipolar or Schizophrenia

| Gene | SEQ ID NO: | NCBI RS# | Allele | Model | P | Odds Ratio |
|---|---|---|---|---|---|---|
| TNIK | 681 | 6445006 | A | RECESSIVE | 0.022127 | 0.71 |
| PLD1 | 688 | 187229 | T | DOMINANT | 0.049571 | 0.87 |
| PLD1 | 689 | 181715 | A | DOMINANT | 0.034263 | 0.86 |
| PLD1 | 690 | 360401 | T | DOMINANT | 0.046942 | 0.87 |
| PLD1 | 691 | 9822322 | T | DOMINANT | 0.015150 | 1.20 |
| PLD1 | 692 | 6781853 | C | DOMINANT | 0.014711 | 1.20 |
| PLD1 | 693 | 9881788 | G | DOMINANT | 0.009027 | 1.22 |
| PLD1 | 694 | 4894707 | T | DOMINANT | 0.013833 | 1.20 |
| PLD1 | 695 | 3774039 | T | DOMINANT | 0.015297 | 1.20 |
| PLD1 | 696 | 2290479 | G | DOMINANT | 0.011224 | 1.20 |
| PLD1 | 697 | 2290480 | A | ADDITIVE | 0.011886 | 1.16 |
| PLD1 | 698 | 7649974 | G | DOMINANT | 0.030944 | 1.18 |
| PLD1 | 699 | 6794454 | C | ADDITIVE | 0.002987 | 1.22 |
| PLD1 | 700 | 6769838 | G | RECESSIVE | 0.004606 | 0.77 |
| PLD1 | 701 | 13089252 | T | RECESSIVE | 0.001562 | 0.75 |
| NLGN1 | 702 | 1948162 | G | DOMINANT | 0.018084 | 0.83 |
| HTR3D | 707 | 7430671 | G | ADDITIVE | 0.025876 | 1.08 |
| LEPREL1 | 709 | 1447948 | A | RECESSIVE | 0.043390 | 0.70 |
| IL1RAP | 715 | 4624606 | A | ADDITIVE | 0.020796 | 0.87 |
| SLC2A9 | 719 | 7674711 | C | ADDITIVE | 0.017265 | 1.23 |
| SLC2A9 | 720 | 16890905 | T | ADDITIVE | 0.011312 | 1.24 |
| KCNIP4 | 735 | 16869851 | C | DOMINANT | 0.001438 | 1.30 |
| KCNIP4 | 736 | 2114474 | T | ADDITIVE | 0.022544 | 1.19 |
| KCNIP4 | 737 | 7689421 | A | ADDITIVE | 0.023300 | 1.17 |
| KCNIP4 | 738 | 7694208 | G | ADDITIVE | 0.044093 | 1.17 |
| KCNIP4 | 739 | 17623902 | A | RECESSIVE | 0.014218 | 0.76 |
| UBE2K | 744 | 7697939 | G | ADDITIVE | 0.024586 | 0.86 |
| LIMCH1 | 746 | 17528515 | C | DOMINANT | 0.019809 | 0.85 |
| LIMCH1 | 747 | 13134348 | A | RECESSIVE | 0.041170 | 1.52 |
| LIMCH1 | 748 | 6838113 | T | ADDITIVE | 0.002631 | 1.15 |
| LIMCH1 | 749 | 6447080 | G | ADDITIVE | 0.002666 | 1.16 |
| LIMCH1 | 750 | 6447081 | G | ADDITIVE | 0.002651 | 1.16 |
| LIMCH1 | 751 | 7671360 | T | ADDITIVE | 0.002916 | 1.14 |
| LIMCH1 | 752 | 7674935 | C | ADDITIVE | 0.036953 | 1.05 |
| LIMCH1 | 753 | 4266323 | T | ADDITIVE | 0.002949 | 1.15 |
| LIMCH1 | 754 | 4610372 | G | ADDITIVE | 0.000509 | 1.21 |
| LIMCH1 | 755 | 7683275 | G | ADDITIVE | 0.025159 | 1.10 |
| LIMCH1 | 756 | 4861118 | A | ADDITIVE | 0.001559 | 1.17 |
| LIMCH1 | 757 | 6838196 | C | ADDITIVE | 0.007764 | 1.14 |
| LIMCH1 | 758 | 6447088 | C | ADDITIVE | 0.002957 | 1.11 |
| LIMCH1 | 764 | 2304651 | A | DOMINANT | 0.042200 | 1.23 |
| LIMCH1 | 765 | 7674006 | C | DOMINANT | 0.011887 | 1.33 |
| LPHN3 | 766 | 10008326 | A | ADDITIVE | 0.022975 | 1.10 |
| LPHN3 | 767 | 1397548 | A | ADDITIVE | 0.029744 | 1.07 |
| SHROOM3 | 786 | 3821979 | A | RECESSIVE | 0.000811 | 0.34 |
| SHROOM3 | 787 | 12640170 | T | RECESSIVE | 0.004293 | 0.72 |
| SHROOM3 | 788 | 10013334 | T | RECESSIVE | 0.003336 | 0.42 |
| SHROOM3 | 789 | 11734394 | A | RECESSIVE | 0.007616 | 0.73 |
| GPRIN3 | 792 | 7653897 | A | DOMINANT | 0.018616 | 0.83 |
| GPRIN3 | 793 | 7690986 | G | DOMINANT | 0.033546 | 0.85 |
| GRID2 | 798 | 7668740 | T | RECESSIVE | 0.035881 | 0.79 |
| GRID2 | 802 | 2164314 | A | RECESSIVE | 0.032472 | 1.35 |
| GRID2 | 803 | 13123140 | C | RECESSIVE | 0.005195 | 1.29 |
| GRID2 | 804 | 4693331 | C | RECESSIVE | 0.004350 | 1.29 |
| GRID2 | 805 | 7671794 | A | RECESSIVE | 0.016565 | 1.33 |
| GRID2 | 806 | 11932367 | A | RECESSIVE | 0.018157 | 1.29 |
| GRID2 | 807 | 6837139 | C | DOMINANT | 0.030403 | 0.86 |
| UNC5C | 812 | 4529060 | A | DOMINANT | 0.039558 | 1.17 |
| UNC5C | 813 | 10856918 | G | DOMINANT | 0.005559 | 1.22 |
| UNC5C | 814 | 13121737 | C | DOMINANT | 0.001643 | 1.27 |
| UNC5C | 815 | 13134684 | T | DOMINANT | 0.000460 | 1.28 |
| UNC5C | 816 | 4103379 | G | DOMINANT | 0.001489 | 1.28 |
| UNC5C | 817 | 6834411 | G | DOMINANT | 0.001254 | 1.28 |
| UNC5C | 819 | 13148787 | A | DOMINANT | 0.000128 | 1.31 |
| PPP3CA | 821 | 2732507 | G | RECESSIVE | 0.033517 | 0.83 |
| PPP3CA | 822 | 2851048 | C | RECESSIVE | 0.039359 | 0.83 |
| PPP3CA | 823 | 2851062 | G | RECESSIVE | 0.003730 | 0.78 |
| PPP3CA | 824 | 2141145 | T | DOMINANT | 0.016846 | 1.21 |
| PPP3CA | 825 | 1405686 | T | DOMINANT | 0.021504 | 1.20 |
| COL25A1 | 835 | 11098004 | T | ADDITIVE | 0.033780 | 0.88 |
| COL25A1 | 836 | 1563004 | G | ADDITIVE | 0.022397 | 0.86 |
| ANK2 | 842 | 1026975 | G | DOMINANT | 0.024160 | 1.19 |
| ANK2 | 846 | 11942005 | G | ADDITIVE | 0.032895 | 1.15 |
| ANK2 | 847 | 29355 | G | ADDITIVE | 0.021642 | 1.23 |
| ANK2 | 848 | 29319 | A | ADDITIVE | 0.022271 | 1.21 |
| PRSS12 | 851 | 4834679 | T | DOMINANT | 0.009389 | 1.36 |

TABLE 2-continued

Alleles and Genotypes Influencing Likelihood of Diagnosis of Bipolar or Schizophrenia

| Gene | SEQ ID NO: | NCBI RS# | Allele | Model | P | Odds Ratio |
|---|---|---|---|---|---|---|
| PRSS12 | 852 | 1514657 | A | DOMINANT | 0.023109 | 1.31 |
| PRSS12 | 853 | 2892812 | C | DOMINANT | 0.041795 | 1.27 |
| MAML3 | 854 | 6831959 | A | RECESSIVE | 0.003586 | 1.28 |
| MAML3 | 857 | 2604918 | A | RECESSIVE | 0.015325 | 0.77 |
| MAML3 | 862 | 6830177 | A | DOMINANT | 0.030418 | 1.17 |
| INPP4B | 878 | 13138212 | T | RECESSIVE | 0.018785 | 0.78 |
| INPP4B | 879 | 1497389 | T | RECESSIVE | 0.010774 | 0.76 |
| INPP4B | 880 | 881611 | G | RECESSIVE | 0.013646 | 0.78 |
| INPP4B | 881 | 6820463 | T | RECESSIVE | 0.005003 | 0.71 |
| INPP4B | 882 | 17715707 | G | RECESSIVE | 0.007255 | 0.72 |
| POU4F2 | 883 | 2174304 | A | ADDITIVE | 0.007872 | 0.81 |
| POU4F2 | 884 | 10010958 | T | ADDITIVE | 0.008797 | 0.82 |
| POU4F2 | 885 | 6821387 | A | ADDITIVE | 0.013700 | 0.87 |
| POU4F2 | 886 | 1104532 | A | ADDITIVE | 0.012404 | 0.83 |
| POU4F2 | 887 | 6835151 | A | ADDITIVE | 0.008051 | 0.81 |
| POU4F2 | 888 | 1394279 | C | ADDITIVE | 0.013437 | 0.82 |
| DCLK2 | 891 | 12374344 | T | ADDITIVE | 0.032894 | 0.88 |
| CTSO | 893 | 6854827 | G | DOMINANT | 0.034372 | 1.16 |
| CTSO | 894 | 6832480 | T | DOMINANT | 0.023229 | 1.18 |
| CTSO | 895 | 6536124 | T | DOMINANT | 0.020871 | 1.18 |
| FSTL5 | 897 | 6824038 | T | ADDITIVE | 0.043324 | 0.87 |
| FSTL5 | 898 | 1023957 | C | ADDITIVE | 0.042148 | 0.87 |
| FSTL5 | 899 | 13121013 | A | ADDITIVE | 0.038681 | 0.89 |
| FSTL5 | 900 | 17459954 | T | ADDITIVE | 0.041918 | 0.89 |
| FSTL5 | 901 | 2872800 | A | RECESSIVE | 0.015723 | 0.82 |
| FSTL5 | 902 | 7699959 | A | RECESSIVE | 0.004355 | 0.78 |
| FSTL5 | 903 | 10031537 | T | RECESSIVE | 0.000485 | 0.74 |
| FSTL5 | 904 | 7375994 | A | RECESSIVE | 0.000021 | 0.48 |
| FSTL5 | 905 | 13113862 | A | RECESSIVE | 0.000106 | 0.50 |
| FSTL5 | 906 | 4301062 | C | RECESSIVE | 0.000016 | 0.50 |
| FSTL5 | 907 | 4574362 | C | RECESSIVE | 0.003856 | 0.78 |
| FSTL5 | 908 | 13101933 | T | RECESSIVE | 0.000176 | 0.44 |
| FSTL5 | 909 | 4691039 | T | RECESSIVE | 0.001018 | 0.64 |
| PALLD | 922 | 6817551 | A | RECESSIVE | 0.003843 | 0.65 |
| PALLD | 923 | 3733656 | T | RECESSIVE | 0.000789 | 0.62 |
| PALLD | 924 | 10023864 | A | RECESSIVE | 0.002252 | 0.63 |
| PALLD | 925 | 1531254 | A | RECESSIVE | 0.008089 | 0.67 |
| PALLD | 926 | 11733251 | A | RECESSIVE | 0.005134 | 0.66 |
| PALLD | 927 | 10518037 | T | RECESSIVE | 0.002405 | 0.63 |
| ODZ3 | 930 | 10520541 | G | DOMINANT | 0.016402 | 0.83 |
| ODZ3 | 931 | 4862087 | G | DOMINANT | 0.012773 | 0.83 |
| ODZ3 | 932 | 17329750 | C | DOMINANT | 0.010690 | 0.82 |
| SEMA5A | 944 | 150633 | C | RECESSIVE | 0.024356 | 0.78 |
| CTNND2 | 947 | 13358276 | T | RECESSIVE | 0.000844 | 0.73 |
| CTNND2 | 950 | 27520 | C | RECESSIVE | 0.000179 | 1.38 |
| CTNND2 | 951 | 2530215 | C | RECESSIVE | 0.000031 | 1.43 |
| DNAH5 | 959 | 17203442 | G | RECESSIVE | 0.019214 | 0.59 |
| MYO10 | 963 | 10045328 | A | DOMINANT | 0.015841 | 1.75 |
| BASP1 | 964 | 2929726 | A | ADDITIVE | 0.004630 | 1.11 |
| BASP1 | 965 | 2956564 | G | ADDITIVE | 0.006795 | 1.10 |
| BASP1 | 966 | 2929710 | C | ADDITIVE | 0.007172 | 1.09 |
| CDH10 | 967 | 7719252 | G | DOMINANT | 0.008975 | 0.83 |
| CDH10 | 969 | 1395025 | C | DOMINANT | 0.005616 | 0.82 |
| C1QTNF3 | 971 | 840391 | G | RECESSIVE | 0.031427 | 0.81 |
| C1QTNF3 | 972 | 840381 | G | DOMINANT | 0.012639 | 1.19 |
| C1QTNF3 | 973 | 299620 | G | DOMINANT | 0.003622 | 0.81 |
| ITGA1 | 980 | 13189973 | T | RECESSIVE | 0.037140 | 0.69 |
| ITGA1 | 981 | 4865747 | T | RECESSIVE | 0.006946 | 0.49 |
| ITGA1 | 982 | 17209947 | A | RECESSIVE | 0.010415 | 0.51 |
| ITGA1 | 983 | 10513000 | G | RECESSIVE | 0.026389 | 0.74 |
| ITGA1 | 984 | 10513001 | G | RECESSIVE | 0.041671 | 0.76 |
| ITGA1 | 985 | 6886404 | C | RECESSIVE | 0.023463 | 0.73 |
| ITGA1 | 987 | 16876270 | C | ADDITIVE | 0.010615 | 1.52 |
| ITGA2 | 989 | 1421937 | C | RECESSIVE | 0.043339 | 0.76 |
| ITGA2 | 990 | 3212528 | A | RECESSIVE | 0.004249 | 3.74 |
| ITGA2 | 991 | 3212544 | T | RECESSIVE | 0.004262 | 3.74 |
| ITGA2 | 992 | 3212545 | A | RECESSIVE | 0.004271 | 3.74 |
| ITGA2 | 993 | 2303125 | G | RECESSIVE | 0.001769 | 4.68 |
| ITGA2 | 994 | 12521915 | G | RECESSIVE | 0.025294 | 0.79 |
| ITGA2 | 995 | 3212634 | C | RECESSIVE | 0.005785 | 4.05 |
| ITGA2 | 996 | 2303120 | A | RECESSIVE | 0.001769 | 4.68 |
| PIK3R1 | 1013 | 6881033 | G | RECESSIVE | 0.002456 | 0.78 |
| FCHO2 | 1017 | 6877485 | T | RECESSIVE | 0.028029 | 0.68 |
| PDE8B | 1026 | 6896093 | G | DOMINANT | 0.033112 | 0.86 |
| PDE8B | 1027 | 17671243 | A | DOMINANT | 0.026875 | 0.86 |
| PDE8B | 1028 | 11742730 | G | DOMINANT | 0.043594 | 0.87 |

TABLE 2-continued

Alleles and Genotypes Influencing Likelihood of Diagnosis of Bipolar or Schizophrenia

| Gene | SEQ ID NO: | NCBI RS# | Allele | Model | P | Odds Ratio |
|---|---|---|---|---|---|---|
| PDE8B | 1029 | 11750661 | A | DOMINANT | 0.027770 | 0.86 |
| PDE8B | 1033 | 335635 | C | RECESSIVE | 0.007356 | 0.80 |
| CMYA5 | 1044 | 12654905 | G | DOMINANT | 0.010558 | 1.28 |
| CMYA5 | 1045 | 6880680 | G | DOMINANT | 0.011159 | 1.27 |
| CMYA5 | 1046 | 1541813 | G | DOMINANT | 0.004662 | 1.22 |
| CMYA5 | 1047 | 7719553 | A | DOMINANT | 0.000659 | 1.28 |
| CMYA5 | 1048 | 7734306 | T | DOMINANT | 0.000642 | 1.28 |
| CMYA5 | 1049 | 1991483 | G | DOMINANT | 0.003242 | 1.23 |
| CMYA5 | 1051 | 259064 | C | RECESSIVE | 0.002122 | 2.51 |
| MEF2C | 1052 | 454214 | G | DOMINANT | 0.040096 | 1.17 |
| MEF2C | 1053 | 618298 | T | DOMINANT | 0.034471 | 1.17 |
| MEF2C | 1054 | 625970 | A | DOMINANT | 0.036148 | 1.17 |
| MEF2C | 1055 | 681446 | A | DOMINANT | 0.040327 | 1.17 |
| MEF2C | 1056 | 679232 | G | DOMINANT | 0.042695 | 1.17 |
| GPR98 | 1061 | 27657 | T | RECESSIVE | 0.002882 | 2.39 |
| GPR98 | 1062 | 40205 | C | RECESSIVE | 0.007956 | 2.11 |
| GPR98 | 1064 | 10070074 | C | RECESSIVE | 0.030660 | 0.80 |
| GPR98 | 1065 | 2460177 | G | DOMINANT | 0.021205 | 1.18 |
| GPR98 | 1066 | 2222244 | A | DOMINANT | 0.005160 | 1.22 |
| GPR98 | 1068 | 16869425 | C | RECESSIVE | 0.018577 | 2.67 |
| GPR98 | 1069 | 1852731 | C | RECESSIVE | 0.009231 | 2.75 |
| FBXL17 | 1070 | 288180 | T | RECESSIVE | 0.000857 | 0.48 |
| FBXL17 | 1071 | 288173 | C | RECESSIVE | 0.008117 | 0.57 |
| FBXL17 | 1072 | 288172 | G | RECESSIVE | 0.001858 | 0.50 |
| FBXL17 | 1073 | 288146 | A | RECESSIVE | 0.011604 | 0.65 |
| FBXL17 | 1074 | 288144 | A | RECESSIVE | 0.001779 | 0.50 |
| FBXL17 | 1075 | 288139 | T | RECESSIVE | 0.013779 | 0.66 |
| FBXL17 | 1076 | 286753 | T | RECESSIVE | 0.011156 | 0.65 |
| FBXL17 | 1077 | 289227 | C | RECESSIVE | 0.003804 | 0.53 |
| FBXL17 | 1078 | 34428 | T | RECESSIVE | 0.005606 | 0.56 |
| FBXL17 | 1079 | 286769 | T | RECESSIVE | 0.008358 | 0.61 |
| FBXL17 | 1080 | 17385448 | T | RECESSIVE | 0.009082 | 0.60 |
| PJA2 | 1081 | 1862204 | C | DOMINANT | 0.001308 | 1.27 |
| PJA2 | 1082 | 784291 | T | DOMINANT | 0.002544 | 1.25 |
| PJA2 | 1083 | 11738695 | C | DOMINANT | 0.002528 | 1.25 |
| PJA2 | 1084 | 246103 | G | DOMINANT | 0.006431 | 1.22 |
| PJA2 | 1085 | 2963024 | C | DOMINANT | 0.005544 | 1.22 |
| PJA2 | 1086 | 2963046 | T | DOMINANT | 0.008465 | 1.21 |
| PJA2 | 1087 | 2914705 | A | DOMINANT | 0.005301 | 1.22 |
| PJA2 | 1088 | 2963028 | C | DOMINANT | 0.004163 | 1.24 |
| PJA2 | 1089 | 2963029 | C | DOMINANT | 0.005706 | 1.22 |
| PJA2 | 1090 | 2963031 | A | DOMINANT | 0.001640 | 1.25 |
| PJA2 | 1091 | 2963034 | A | DOMINANT | 0.004623 | 1.22 |
| PJA2 | 1092 | 2963013 | C | DOMINANT | 0.005696 | 1.22 |
| PJA2 | 1093 | 12514259 | C | DOMINANT | 0.018478 | 1.19 |
| ADAMTS19 | 1098 | 13158524 | A | ADDITIVE | 0.025048 | 1.10 |
| ADAMTS19 | 1099 | 1017201 | T | ADDITIVE | 0.033907 | 1.11 |
| ADAMTS19 | 1100 | 1972624 | T | ADDITIVE | 0.011041 | 1.10 |
| ADAMTS19 | 1101 | 30710 | T | ADDITIVE | 0.009705 | 1.09 |
| ADAMTS19 | 1102 | 30671 | C | ADDITIVE | 0.005393 | 1.11 |
| ADAMTS19 | 1103 | 25820 | A | ADDITIVE | 0.001422 | 1.14 |
| ADAMTS19 | 1104 | 30669 | G | ADDITIVE | 0.013109 | 1.11 |
| ADAMTS19 | 1105 | 30665 | G | ADDITIVE | 0.002654 | 1.11 |
| ADAMTS19 | 1106 | 30664 | G | ADDITIVE | 0.007485 | 1.10 |
| ADAMTS19 | 1107 | 30651 | C | ADDITIVE | 0.014300 | 1.10 |
| ADAMTS19 | 1108 | 4835975 | A | RECESSIVE | 0.009838 | 1.30 |
| VDAC1 | 1110 | 2066944 | T | ADDITIVE | 0.026128 | 1.21 |
| VDAC1 | 1112 | 4958172 | A | DOMINANT | 0.022243 | 1.22 |
| TRPC7 | 1113 | 7732110 | A | ADDITIVE | 0.000694 | 1.17 |
| TRPC7 | 1114 | 3734125 | G | ADDITIVE | 0.001041 | 1.15 |
| TRPC7 | 1115 | 10045073 | G | ADDITIVE | 0.001245 | 1.14 |
| TRPC7 | 1116 | 10060256 | A | RECESSIVE | 0.022267 | 4.85 |
| TRPC7 | 1117 | 7727558 | G | ADDITIVE | 0.000761 | 1.20 |
| TRPC7 | 1118 | 4976485 | A | ADDITIVE | 0.010429 | 0.88 |
| TRPC7 | 1119 | 10070699 | G | ADDITIVE | 0.013025 | 0.87 |
| TRPC7 | 1120 | 3777145 | T | ADDITIVE | 0.015531 | 1.16 |
| TRPC7 | 1121 | 4976368 | A | ADDITIVE | 0.013223 | 0.87 |
| TRPC7 | 1122 | 3822748 | T | ADDITIVE | 0.013223 | 0.87 |
| TRPC7 | 1123 | 950714 | G | ADDITIVE | 0.015531 | 1.16 |
| TRPC7 | 1124 | 953096 | C | ADDITIVE | 0.011542 | 0.85 |
| TRPC7 | 1125 | 2649691 | A | ADDITIVE | 0.006170 | 1.16 |
| TRPC7 | 1126 | 963590 | C | ADDITIVE | 0.014941 | 0.83 |
| TRPC7 | 1127 | 2673926 | T | ADDITIVE | 0.000043 | 1.23 |
| TRPC7 | 1128 | 2673925 | T | ADDITIVE | 0.000050 | 1.24 |
| TRPC7 | 1129 | 2649696 | G | ADDITIVE | 0.000108 | 1.21 |
| GRIA1 | 1130 | 2452801 | G | ADDITIVE | 0.030501 | 1.09 |

TABLE 2-continued

Alleles and Genotypes Influencing Likelihood of Diagnosis of Bipolar or Schizophrenia

| Gene | SEQ ID NO: | NCBI RS# | Allele | Model | P | Odds Ratio |
|---|---|---|---|---|---|---|
| GRIA1 | 1132 | 778825 | A | RECESSIVE | 0.040823 | 1.24 |
| ODZ2 | 1135 | 11134468 | G | RECESSIVE | 0.006592 | 0.38 |
| ODZ2 | 1136 | 7737681 | A | RECESSIVE | 0.023441 | 0.55 |
| ODZ2 | 1137 | 1549152 | C | RECESSIVE | 0.009367 | 0.48 |
| ODZ2 | 1139 | 2546957 | C | RECESSIVE | 0.035689 | 1.26 |
| ODZ2 | 1142 | 1960425 | T | DOMINANT | 0.009361 | 1.22 |
| ODZ2 | 1143 | 10447203 | A | ADDITIVE | 0.005199 | 1.17 |
| ODZ2 | 1144 | 11748886 | G | RECESSIVE | 0.017496 | >5 |
| WWC1 | 1145 | 11748902 | G | RECESSIVE | 0.004500 | >5 |
| WWC1 | 1148 | 10038727 | A | ADDITIVE | 0.034029 | 0.91 |
| WWC1 | 1149 | 4576167 | C | ADDITIVE | 0.030218 | 0.91 |
| KCNIP1 | 1151 | 906361 | A | ADDITIVE | 0.000597 | 0.81 |
| KCNIP1 | 1152 | 906359 | G | ADDITIVE | 0.000882 | 0.81 |
| KCNIP1 | 1153 | 906358 | A | ADDITIVE | 0.000903 | 0.81 |
| KCNIP1 | 1155 | 6555913 | G | RECESSIVE | 0.007000 | 1.29 |
| EXOC2 | 1159 | 6597037 | A | ADDITIVE | 0.029028 | 1.25 |
| EXOC2 | 1160 | 9503977 | C | ADDITIVE | 0.038101 | 1.18 |
| EXOC2 | 1161 | 4959273 | A | ADDITIVE | 0.010099 | 1.23 |
| EXOC2 | 1163 | 6940427 | A | ADDITIVE | 0.038202 | 1.14 |
| EXOC2 | 1164 | 1766835 | C | ADDITIVE | 0.020589 | 1.15 |
| EXOC2 | 1165 | 4960092 | G | ADDITIVE | 0.007911 | 1.18 |
| EXOC2 | 1166 | 2013853 | G | ADDITIVE | 0.030903 | 1.14 |
| EXOC2 | 1167 | 1747586 | A | ADDITIVE | 0.016906 | 1.14 |
| SERPINB6 | 1169 | 7751676 | T | DOMINANT | 0.007640 | 1.32 |
| SERPINB6 | 1170 | 1358869 | C | ADDITIVE | 0.013337 | 1.25 |
| ATXN1 | 1186 | 2237166 | C | RECESSIVE | 0.020335 | 1.21 |
| ATXN1 | 1187 | 2237164 | G | RECESSIVE | 0.019501 | 1.22 |
| ATXN1 | 1188 | 2073516 | T | ADDITIVE | 0.034126 | 1.18 |
| ATXN1 | 1189 | 909786 | G | ADDITIVE | 0.027054 | 1.15 |
| ATXN1 | 1190 | 760882 | A | ADDITIVE | 0.002167 | 1.19 |
| ATXN1 | 1191 | 6921608 | C | DOMINANT | 0.005835 | 1.22 |
| ATXN1 | 1192 | 719316 | G | ADDITIVE | 0.000348 | 1.31 |
| ATXN1 | 1193 | 1570487 | T | DOMINANT | 0.005962 | 1.22 |
| ATXN1 | 1194 | 11754887 | C | DOMINANT | 0.013713 | 1.19 |
| ATXN1 | 1195 | 1144695 | A | ADDITIVE | 0.020507 | 1.19 |
| SLC17A4 | 1196 | 4712972 | A | DOMINANT | 0.017749 | 0.82 |
| SLC17A4 | 1197 | 1892252 | G | DOMINANT | 0.010305 | 0.81 |
| SLC17A1 | 1199 | 1324082 | A | DOMINANT | 0.014663 | 0.84 |
| SLC17A1 | 1200 | 1165196 | C | ADDITIVE | 0.040499 | 1.00 |
| SLC17A1 | 1201 | 12182983 | A | DOMINANT | 0.024179 | 0.85 |
| SLC17A1 | 1202 | 6913879 | C | DOMINANT | 0.018099 | 0.85 |
| SLC17A1 | 1203 | 6905614 | C | ADDITIVE | 0.009533 | 1.11 |
| SLC17A1 | 1204 | 1324088 | T | DOMINANT | 0.032943 | 0.84 |
| SLC17A3 | 1205 | 1182814 | G | ADDITIVE | 0.003071 | 0.82 |
| SLC17A3 | 1206 | 1165165 | A | ADDITIVE | 0.001545 | 0.80 |
| SLC17A3 | 1207 | 1165162 | A | ADDITIVE | 0.003673 | 0.83 |
| SLC17A3 | 1208 | 1165158 | T | ADDITIVE | 0.003926 | 0.83 |
| SLC17A3 | 1209 | 1165207 | A | ADDITIVE | 0.006364 | 1.09 |
| SLC17A3 | 1210 | 523383 | C | DOMINANT | 0.037395 | 0.84 |
| SLC17A3 | 1211 | 1165205 | A | ADDITIVE | 0.006296 | 1.09 |
| BTN3A1 | 1212 | 4712986 | G | RECESSIVE | 0.012582 | 1.91 |
| BTN3A1 | 1213 | 12208788 | A | RECESSIVE | 0.009747 | 2.04 |
| BTN3A1 | 1215 | 10807008 | C | ADDITIVE | 0.034023 | 1.15 |
| BTN3A1 | 1216 | 17610161 | A | RECESSIVE | 0.038234 | 2.07 |
| MSH5 | 1218 | 707937 | C | RECESSIVE | 0.019603 | 0.65 |
| LRFN2 | 1219 | 846505 | T | DOMINANT | 0.035993 | 0.85 |
| PARC | 1222 | 6938026 | G | DOMINANT | 0.034030 | 0.85 |
| TRDN | 1240 | 1890467 | C | RECESSIVE | 0.023215 | 0.49 |
| TRDN | 1241 | 9372744 | G | RECESSIVE | 0.012248 | 0.48 |
| TRDN | 1242 | 1431291 | G | RECESSIVE | 0.010469 | 0.45 |
| TRDN | 1243 | 7765003 | A | RECESSIVE | 0.015667 | 0.47 |
| TRDN | 1248 | 6931183 | A | DOMINANT | 0.019725 | 1.21 |
| NKAIN2 | 1261 | 6906607 | A | ADDITIVE | 0.042731 | 1.14 |
| EYA4 | 1262 | 2027210 | A | DOMINANT | 0.004507 | 1.25 |
| EYA4 | 1263 | 17301622 | G | DOMINANT | 0.000543 | 1.32 |
| EYA4 | 1264 | 7454561 | G | DOMINANT | 0.004285 | 1.25 |
| EYA4 | 1265 | 12524250 | A | DOMINANT | 0.004121 | 1.25 |
| PDE7B | 1269 | 9389370 | G | ADDITIVE | 0.011134 | 0.88 |
| PDE7B | 1270 | 6931460 |  | ADDITIVE | 0.031841 | 0.58 |
| PLAGL1 | 1271 | 11155338 | T | DOMINANT | 0.005488 | 1.22 |
| STX11 | 1273 | 6935462 | A | ADDITIVE | 0.006308 | 1.39 |
| UTRN | 1274 | 6906465 | G | ADDITIVE | 0.002849 | 1.23 |
| UTRN | 1275 | 9373430 | A | DOMINANT | 0.039224 | 1.16 |
| PARK2 | 1283 | 2064419 | T | RECESSIVE | 0.027128 | 1.20 |
| PARK2 | 1284 | 9364602 | A | RECESSIVE | 0.020631 | 1.25 |
| PACRG | 1285 | 2763986 | T | RECESSIVE | 0.000018 | 0.68 |

TABLE 2-continued

Alleles and Genotypes Influencing Likelihood of Diagnosis of Bipolar or Schizophrenia

| Gene | SEQ ID NO: | NCBI RS# | Allele | Model | P | Odds Ratio |
|---|---|---|---|---|---|---|
| PACRG | 1286 | 761625 | A | RECESSIVE | 0.000138 | 0.71 |
| PDE10A | 1294 | 481701 | C | RECESSIVE | 0.015732 | 2.29 |
| NXPH1 | 1298 | 10085720 | T | DOMINANT | 0.032211 | 0.86 |
| NXPH1 | 1299 | 4455737 | G | DOMINANT | 0.041509 | 0.87 |
| NXPH1 | 1300 | 7456267 | A | DOMINANT | 0.039360 | 0.86 |
| NXPH1 | 1301 | 2349499 | C | DOMINANT | 0.020655 | 0.85 |
| NXPH1 | 1302 | 10257265 | C | DOMINANT | 0.034891 | 0.86 |
| NXPH1 | 1303 | 970526 | G | DOMINANT | 0.034780 | 0.86 |
| NXPH1 | 1304 | 970527 | C | DOMINANT | 0.011590 | 0.83 |
| NXPH1 | 1305 | 3779355 | A | ADDITIVE | 0.029694 | 0.84 |
| DGKB | 1307 | 17167942 | A | DOMINANT | 0.003092 | 1.24 |
| DGKB | 1308 | 6969690 | G | DOMINANT | 0.007030 | 1.22 |
| DGKB | 1311 | 12699645 | C | ADDITIVE | 0.011602 | 0.91 |
| DGKB | 1312 | 2049447 | C | ADDITIVE | 0.007679 | 0.91 |
| DGKB | 1314 | 1981680 | T | RECESSIVE | 0.017378 | 0.73 |
| DGKB | 1316 | 10277367 | C | RECESSIVE | 0.033853 | 0.76 |
| SNX13 | 1318 | 4543441 | A | ADDITIVE | 0.027678 | 0.98 |
| SNX13 | 1319 | 4544985 | C | ADDITIVE | 0.033053 | 0.97 |
| SNX13 | 1320 | 6970593 | A | ADDITIVE | 0.030068 | 0.97 |
| STK31 | 1323 | 13244337 | G | RECESSIVE | 0.018236 | 1.55 |
| CREB5 | 1330 | 2237361 | C | DOMINANT | 0.043164 | 1.16 |
| PDE1C | 1335 | 7791180 | G | DOMINANT | 0.034376 | 1.16 |
| PDE1C | 1336 | 10951305 | T | DOMINANT | 0.049127 | 1.15 |
| PDE1C | 1337 | 4723103 | T | DOMINANT | 0.018831 | 1.18 |
| PDE1C | 1338 | 3801350 | T | DOMINANT | 0.001524 | 1.25 |
| PDE1C | 1339 | 12701142 | G | DOMINANT | 0.001375 | 1.25 |
| BMPER | 1340 | 1365883 | T | RECESSIVE | 0.029436 | 0.71 |
| BMPER | 1341 | 13244436 | A | RECESSIVE | 0.043482 | 0.73 |
| BMPER | 1342 | 2110856 | C | RECESSIVE | 0.033499 | 0.72 |
| BMPER | 1343 | 12672492 | A | RECESSIVE | 0.033499 | 0.72 |
| EEPD1 | 1345 | 2726113 | T | RECESSIVE | 0.011127 | 1.66 |
| VPS41 | 1349 | 2240355 | A | ADDITIVE | 0.029219 | 1.13 |
| VPS41 | 1350 | 10262154 | T | RECESSIVE | 0.048068 | 0.82 |
| VPS41 | 1353 | 10279367 | A | RECESSIVE | 0.004238 | 0.71 |
| VPS41 | 1360 | 4723793 | G | DOMINANT | 0.047847 | 1.15 |
| VPS41 | 1361 | 17680408 | A | RECESSIVE | 0.006066 | 0.72 |
| VPS41 | 1366 | 10951578 | C | RECESSIVE | 0.009675 | 0.77 |
| VPS41 | 1367 | 10255290 | A | RECESSIVE | 0.035368 | 0.77 |
| VPS41 | 1368 | 10255854 | T | RECESSIVE | 0.036509 | 0.77 |
| ABCA13 | 1373 | 17661073 | C | ADDITIVE | 0.009969 | 1.26 |
| ABCA13 | 1374 | 17132158 | G | ADDITIVE | 0.010967 | 1.25 |
| ABCA13 | 1377 | 17132163 | T | ADDITIVE | 0.031656 | 1.16 |
| ABCA13 | 1378 | 12113721 | A | ADDITIVE | 0.028846 | 1.20 |
| ABCA13 | 1379 | 2049514 | T | ADDITIVE | 0.030707 | 1.17 |
| ABCA13 | 1380 | 6583461 | A | DOMINANT | 0.010862 | 0.82 |
| ABCA13 | 1381 | 2049513 | A | ADDITIVE | 0.030583 | 1.19 |
| ABCA13 | 1382 | 11977113 | A | ADDITIVE | 0.039820 | 1.15 |
| ABCA13 | 1383 | 7802110 | G | ADDITIVE | 0.024160 | 0.86 |
| ABCA13 | 1384 | 7778020 | A | DOMINANT | 0.004982 | 0.77 |
| ABCA13 | 1385 | 4072503 | G | ADDITIVE | 0.026352 | 0.81 |
| ABCA13 | 1386 | 1317162 | C | ADDITIVE | 0.027645 | 0.80 |
| ABCA13 | 1387 | 12113920 | T | ADDITIVE | 0.026352 | 0.81 |
| ABCA13 | 1388 | 1918596 | T | ADDITIVE | 0.035153 | 0.81 |
| ABCA13 | 1389 | 1918588 | A | ADDITIVE | 0.022262 | 0.81 |
| ABCA13 | 1390 | 4144067 | T | ADDITIVE | 0.046224 | 0.82 |
| ABCA13 | 1391 | 7802150 | A | ADDITIVE | 0.029891 | 0.79 |
| ABCA13 | 1392 | 6965361 | T | ADDITIVE | 0.015271 | 0.76 |
| GRB10 | 1393 | 2244372 | G | DOMINANT | 0.004744 | 0.81 |
| GRB10 | 1394 | 2244353 | T | DOMINANT | 0.004277 | 0.80 |
| GRB10 | 1395 | 2244351 | G | DOMINANT | 0.004587 | 0.81 |
| GRB10 | 1396 | 2244347 | C | DOMINANT | 0.015688 | 0.84 |
| GRB10 | 1397 | 2237477 | T | DOMINANT | 0.005297 | 0.82 |
| GRB10 | 1398 | 2282931 | T | DOMINANT | 0.013027 | 0.83 |
| WBSCR17 | 1418 | 1001835 | A | ADDITIVE | 0.009100 | 1.20 |
| CALN1 | 1431 | 1914386 | T | RECESSIVE | 0.026272 | 3.24 |
| GTF2IRD1 | 1437 | 6953789 | A | DOMINANT | 0.016620 | 1.19 |
| MAGI2 | 1438 | 1860538 | G | DOMINANT | 0.013668 | 1.21 |
| MAGI2 | 1439 | 2075013 | C | DOMINANT | 0.011336 | 1.21 |
| MAGI2 | 1440 | 2075014 | T | RECESSIVE | 0.022202 | 0.80 |
| MAGI2 | 1445 | 7778707 | G | DOMINANT | 0.042255 | 0.85 |
| MAGI2 | 1446 | 1918935 | A | DOMINANT | 0.019166 | 0.83 |
| GRM3 | 1459 | 10239714 | C | ADDITIVE | 0.044664 | 1.14 |
| GRM3 | 1460 | 10280549 | A | ADDITIVE | 0.035220 | 1.16 |
| GRM3 | 1461 | 2299219 | C | ADDITIVE | 0.035472 | 1.16 |
| GRM3 | 1462 | 7804907 | T | ADDITIVE | 0.031061 | 1.19 |
| ADAM22 | 1463 | 1201841 | G | ADDITIVE | 0.041241 | 0.78 |

TABLE 2-continued

Alleles and Genotypes Influencing Likelihood of Diagnosis of Bipolar or Schizophrenia

| Gene | SEQ ID NO: | NCBI RS# | Allele | Model | P | Odds Ratio |
|---|---|---|---|---|---|---|
| ADAM22 | 1464 | 7799148 | C | RECESSIVE | 0.034290 | 1.21 |
| PPP1R9A | 1475 | 2285694 | A | RECESSIVE | 0.044675 | >5 |
| CUX1 | 1484 | 1725604 | C | ADDITIVE | 0.000141 | 1.26 |
| CUX1 | 1485 | 2257738 | A | DOMINANT | 0.000605 | 1.27 |
| NRCAM | 1487 | 409797 | C | DOMINANT | 0.011478 | 1.20 |
| NRCAM | 1488 | 441468 | C | RECESSIVE | 0.044038 | 0.60 |
| NRCAM | 1490 | 2284280 | A | DOMINANT | 0.005295 | 1.22 |
| NRCAM | 1491 | 404287 | C | DOMINANT | 0.001819 | 1.25 |
| NRCAM | 1492 | 369800 | G | DOMINANT | 0.003476 | 1.24 |
| NRCAM | 1493 | 425013 | C | DOMINANT | 0.003512 | 1.23 |
| NRCAM | 1494 | 2023503 | G | RECESSIVE | 0.021159 | 0.79 |
| KCND2 | 1498 | 802372 | C | DOMINANT | 0.009167 | 1.29 |
| KCND2 | 1499 | 10488302 | A | DOMINANT | 0.013025 | 1.30 |
| CADPS2 | 1501 | 10267604 | G | DOMINANT | 0.002823 | 0.81 |
| CADPS2 | 1502 | 1154609 | C | DOMINANT | 0.003229 | 0.81 |
| CADPS2 | 1503 | 916982 | G | DOMINANT | 0.028635 | 0.85 |
| DGKI | 1538 | 834054 | T | ADDITIVE | 0.022104 | 0.45 |
| CREB3L2 | 1541 | 1020961 | T | DOMINANT | 0.005991 | 0.82 |
| CREB3L2 | 1542 | 9757 | G | DOMINANT | 0.007309 | 0.82 |
| CREB3L2 | 1543 | 13232124 | T | RECESSIVE | 0.003506 | 0.74 |
| CREB3L2 | 1544 | 11972734 | A | RECESSIVE | 0.004367 | 0.74 |
| TBXAS1 | 1545 | 2267705 | C | ADDITIVE | 0.037511 | 1.14 |
| TBXAS1 | 1546 | 2269997 | T | ADDITIVE | 0.011752 | 1.30 |
| PTPRN2 | 1585 | 4909289 | A | ADDITIVE | 0.047024 | 1.12 |
| CSMD1 | 1587 | 688894 | G | DOMINANT | 0.028176 | 0.85 |
| MCPH1 | 1597 | 12546890 | G | RECESSIVE | 0.028336 | 1.85 |
| MCPH1 | 1601 | 11989215 | G | DOMINANT | 0.034417 | 0.86 |
| MCPH1 | 1602 | 1375668 | G | ADDITIVE | 0.002813 | 0.81 |
| MCPH1 | 1603 | 4455855 | A | ADDITIVE | 0.007836 | 0.81 |
| ANGPT2 | 1609 | 7825811 | T | ADDITIVE | 0.009640 | 0.78 |
| DLC1 | 1610 | 7824944 | C | ADDITIVE | 0.041485 | 0.89 |
| SLC7A2 | 1619 | 2720590 | T | RECESSIVE | 0.020977 | 1.38 |
| PSD3 | 1621 | 13259407 | C | RECESSIVE | 0.025522 | 1.24 |
| PSD3 | 1623 | 1386688 | C | DOMINANT | 0.000444 | 1.31 |
| PSD3 | 1624 | 7837572 | T | DOMINANT | 0.000813 | 1.29 |
| ATP6V1B2 | 1626 | 1106634 | A | ADDITIVE | 0.000158 | 1.30 |
| PEBP4 | 1637 | 2466195 | C | RECESSIVE | 0.032095 | 1.40 |
| SLC25A37 | 1639 | 3736032 | A | RECESSIVE | 0.006306 | 6.08 |
| SLC25A37 | 1640 | 10104250 | T | RECESSIVE | 0.011315 | 8.91 |
| SLC25A37 | 1641 | 10092233 | G | RECESSIVE | 0.007312 | 9.72 |
| UNC5D | 1648 | 4739429 | G | ADDITIVE | 0.035910 | 1.11 |
| UNC5D | 1649 | 2843933 | T | RECESSIVE | 0.025249 | 1.21 |
| SFRP1 | 1650 | 13276051 | G | RECESSIVE | 0.011594 | 0.71 |
| SFRP1 | 1652 | 7843510 | G | RECESSIVE | 0.039906 | 0.83 |
| PRKDC | 1653 | 7841661 | G | DOMINANT | 0.032346 | 1.28 |
| SNTG1 | 1655 | 1486258 | G | RECESSIVE | 0.015905 | 1.47 |
| SNTG1 | 1658 | 2385554 | T | RECESSIVE | 0.022557 | 1.44 |
| SNTG1 | 1666 | 900958 | T | ADDITIVE | 0.022660 | 1.10 |
| SNTG1 | 1669 | 13260265 | C | ADDITIVE | 0.044904 | 0.87 |
| SNTG1 | 1670 | 12548940 | C | RECESSIVE | 0.033654 | 0.70 |
| TOX | 1679 | 6471757 | G | RECESSIVE | 0.009022 | 1.28 |
| TOX | 1680 | 4738738 | C | DOMINANT | 0.034348 | 0.86 |
| NKAIN3 | 1684 | 1993125 | C | ADDITIVE | 0.035728 | 0.87 |
| NKAIN3 | 1686 | 11787352 | A | ADDITIVE | 0.047193 | 0.89 |
| NKAIN3 | 1687 | 9298070 | G | RECESSIVE | 0.031088 | 1.22 |
| NKAIN3 | 1688 | 10100456 | T | RECESSIVE | 0.018065 | 1.33 |
| DEPDC2 | 1689 | 1434763 | C | RECESSIVE | 0.004902 | 0.75 |
| DEPDC2 | 1690 | 1434764 | A | RECESSIVE | 0.014905 | 0.79 |
| DEPDC2 | 1691 | 1014663 | C | RECESSIVE | 0.043302 | 0.82 |
| KCNB2 | 1692 | 13251896 | G | DOMINANT | 0.034554 | 0.85 |
| MMP16 | 1709 | 10106275 | A | RECESSIVE | 0.007120 | 0.79 |
| MMP16 | 1712 | 10504845 | T | DOMINANT | 0.026150 | 1.18 |
| GRHL2 | 1716 | 6992430 | G | DOMINANT | 0.008103 | 1.22 |
| GRHL2 | 1717 | 1357984 | A | DOMINANT | 0.006790 | 1.22 |
| GRHL2 | 1718 | 13275653 | C | DOMINANT | 0.011414 | 1.21 |
| GRHL2 | 1719 | 4734567 | A | RECESSIVE | 0.001421 | 1.56 |
| GRHL2 | 1720 | 4734038 | T | RECESSIVE | 0.002126 | 1.36 |
| GRHL2 | 1721 | 4734573 | G | RECESSIVE | 0.004418 | 1.38 |
| GRHL2 | 1722 | 3735715 | G | RECESSIVE | 0.000255 | 1.43 |
| GRHL2 | 1723 | 11994917 | T | RECESSIVE | 0.000743 | 1.40 |
| NCALD | 1724 | 1131862 | G | ADDITIVE | 0.027108 | 1.14 |
| NCALD | 1725 | 4734584 | A | RECESSIVE | 0.004912 | 1.37 |
| NCALD | 1726 | 12681368 | C | RECESSIVE | 0.001008 | 1.38 |
| NCALD | 1727 | 2226401 | G | RECESSIVE | 0.023428 | 1.43 |
| NCALD | 1728 | 6468791 | C | RECESSIVE | 0.001319 | 1.37 |
| NCALD | 1729 | 7829690 | T | ADDITIVE | 0.004749 | 1.07 |

TABLE 2-continued

Alleles and Genotypes Influencing Likelihood of Diagnosis of Bipolar or Schizophrenia

| Gene | SEQ ID NO: | NCBI RS# | Allele | Model | P | Odds Ratio |
|---|---|---|---|---|---|---|
| ZFPM2 | 1730 | 7816536 | G | DOMINANT | 0.009659 | 0.83 |
| ZFPM2 | 1731 | 10464844 | G | DOMINANT | 0.010500 | 0.83 |
| ZFPM2 | 1732 | 1383591 | C | DOMINANT | 0.008786 | 0.83 |
| ZFPM2 | 1733 | 11988529 | C | DOMINANT | 0.008141 | 0.83 |
| ZFPM2 | 1734 | 1383592 | A | DOMINANT | 0.008265 | 0.83 |
| ZFPM2 | 1735 | 16873003 | C | DOMINANT | 0.003674 | 0.81 |
| ZFPM2 | 1736 | 4734863 | G | DOMINANT | 0.006262 | 0.82 |
| ZFPM2 | 1737 | 7823133 | T | DOMINANT | 0.006442 | 0.82 |
| ZFPM2 | 1738 | 6992053 | A | DOMINANT | 0.008970 | 0.83 |
| ZFPM2 | 1739 | 1481026 | T | DOMINANT | 0.008876 | 0.83 |
| ZFPM2 | 1740 | 6981187 | G | DOMINANT | 0.008594 | 0.83 |
| ZFPM2 | 1741 | 7007352 | G | RECESSIVE | 0.020585 | 0.40 |
| CSMD3 | 1763 | 4876502 | C | DOMINANT | 0.049394 | 1.17 |
| SAMD12 | 1766 | 4876815 | G | DOMINANT | 0.004186 | 0.81 |
| SAMD12 | 1767 | 13263320 | A | DOMINANT | 0.016429 | 1.20 |
| FER1L6 | 1771 | 4355755 | T | RECESSIVE | 0.009814 | 1.44 |
| FER1L6 | 1772 | 16893054 | T | RECESSIVE | 0.006023 | 1.48 |
| FER1L6 | 1773 | 4870877 | T | ADDITIVE | 0.001558 | 1.08 |
| FER1L6 | 1774 | 4871437 | C | ADDITIVE | 0.027223 | 1.06 |
| FER1L6 | 1775 | 7838453 | A | ADDITIVE | 0.034326 | 1.07 |
| FER1L6 | 1776 | 7842762 | C | ADDITIVE | 0.043442 | 1.03 |
| MTSS1 | 1781 | 3901290 | C | ADDITIVE | 0.017417 | 1.24 |
| MTSS1 | 1782 | 10956198 | G | DOMINANT | 0.017463 | 1.20 |
| COL22A1 | 1789 | 6577934 | A | DOMINANT | 0.005571 | 1.26 |
| COL22A1 | 1790 | 7017524 | A | DOMINANT | 0.010750 | 1.24 |
| COL22A1 | 1792 | 7818881 | C | RECESSIVE | 0.007364 | 0.80 |
| COL22A1 | 1793 | 10090299 | C | RECESSIVE | 0.010095 | 0.81 |
| COL22A1 | 1794 | 7838300 | C | RECESSIVE | 0.010325 | 0.81 |
| COL22A1 | 1795 | 7838450 | C | RECESSIVE | 0.010221 | 0.81 |
| SMARCA2 | 1803 | 13288443 | G | ADDITIVE | 0.022779 | 0.83 |
| SMARCA2 | 1804 | 7035991 | T | ADDITIVE | 0.024016 | 0.84 |
| SMARCA2 | 1805 | 3829070 | C | RECESSIVE | 0.028265 | 2.14 |
| SMARCA2 | 1808 | 10738600 | T | DOMINANT | 0.004771 | 0.81 |
| KIAA1797 | 1821 | 7021708 | G | RECESSIVE | 0.038416 | 1.24 |
| KIAA1797 | 1823 | 10511687 | G | RECESSIVE | 0.019549 | 1.29 |
| IFT74 | 1830 | 7035755 | G | DOMINANT | 0.015964 | 1.22 |
| IFT74 | 1831 | 7039400 | A | DOMINANT | 0.017917 | 1.22 |
| IFT74 | 1834 | 10812518 | T | RECESSIVE | 0.019272 | 1.58 |
| IFT74 | 1835 | 17694631 | C | DOMINANT | 0.013654 | 1.24 |
| IFT74 | 1836 | 2095405 | C | DOMINANT | 0.032978 | 1.17 |
| TEK | 1837 | 1591355 | G | DOMINANT | 0.037968 | 1.17 |
| PIP5K1B | 1839 | 7861710 | C | RECESSIVE | 0.026362 | 1.27 |
| PIP5K1B | 1840 | 4237268 | G | RECESSIVE | 0.049598 | 1.23 |
| TMC1 | 1857 | 7044235 | A | DOMINANT | 0.041657 | 0.85 |
| TMC1 | 1858 | 7044241 | A | DOMINANT | 0.028447 | 0.84 |
| TMC1 | 1859 | 7855743 | G | DOMINANT | 0.021116 | 0.83 |
| TMC1 | 1860 | 4373587 | T | DOMINANT | 0.030872 | 0.85 |
| TMC1 | 1861 | 13285932 | T | DOMINANT | 0.008895 | 1.21 |
| TMC1 | 1862 | 969205 | A | RECESSIVE | 0.010827 | 0.59 |
| TMC1 | 1863 | 1663740 | T | RECESSIVE | 0.008185 | 0.58 |
| TMC1 | 1864 | 1796991 | G | RECESSIVE | 0.008851 | 0.58 |
| TMC1 | 1865 | 2256491 | C | RECESSIVE | 0.008288 | 0.58 |
| TMC1 | 1866 | 2589609 | T | RECESSIVE | 0.006119 | 0.57 |
| TMC1 | 1867 | 7860172 | A | RECESSIVE | 0.014842 | 2.04 |
| TMC1 | 1868 | 12000987 | T | DOMINANT | 0.045381 | 0.78 |
| GNAQ | 1874 | 10869954 | A | DOMINANT | 0.015380 | 1.21 |
| GNAQ | 1875 | 10869955 | A | RECESSIVE | 0.003435 | 0.79 |
| GNAQ | 1876 | 12551478 | C | DOMINANT | 0.014351 | 1.19 |
| GNAQ | 1877 | 6560612 | T | DOMINANT | 0.041744 | 1.15 |
| GNAQ | 1878 | 10869960 | T | DOMINANT | 0.047659 | 1.15 |
| GNAQ | 1882 | 10781482 | T | RECESSIVE | 0.042270 | 1.41 |
| SHC3 | 1902 | 1125467 | C | ADDITIVE | 0.033919 | 1.15 |
| SHC3 | 1903 | 9410299 | C | ADDITIVE | 0.007328 | 0.86 |
| SHC3 | 1904 | 7868553 | T | RECESSIVE | 0.046564 | 1.24 |
| DIRAS2 | 1905 | 690474 | G | ADDITIVE | 0.022096 | 1.11 |
| DIRAS2 | 1907 | 7028171 | A | RECESSIVE | 0.044570 | 0.77 |
| NFIL3 | 1909 | 7038686 | A | DOMINANT | 0.016229 | 1.19 |
| GABBR2 | 1911 | 16914425 | T | ADDITIVE | 0.045254 | 1.44 |
| GRIN3A | 1915 | 9299345 | T | ADDITIVE | 0.028101 | 0.84 |
| GRIN3A | 1921 | 1853447 | T | ADDITIVE | 0.026043 | 0.87 |
| GRIN3A | 1923 | 4742823 | A | ADDITIVE | 0.028114 | 0.84 |
| GRIN3A | 1925 | 2506362 | C | ADDITIVE | 0.015761 | 0.92 |
| FKTN | 1929 | 2768290 | G | ADDITIVE | 0.031902 | 0.87 |
| FKTN | 1930 | 2768294 | G | DOMINANT | 0.046703 | 0.87 |
| FKTN | 1931 | 2518106 | A | ADDITIVE | 0.048622 | 0.87 |
| PALM2 | 1932 | 1358912 | A | ADDITIVE | 0.020090 | 1.06 |

TABLE 2-continued

Alleles and Genotypes Influencing Likelihood of Diagnosis of Bipolar or Schizophrenia

| Gene | SEQ ID NO: | NCBI RS# | Allele | Model | P | Odds Ratio |
|---|---|---|---|---|---|---|
| PALM2 | 1933 | 10739282 | A | RECESSIVE | 0.025066 | 1.24 |
| PALM2 | 1934 | 4978848 | G | ADDITIVE | 0.024272 | 1.07 |
| PALM2 | 1935 | 2025878 | A | RECESSIVE | 0.036827 | 1.21 |
| PALM2 | 1936 | 4246875 | A | RECESSIVE | 0.026623 | 1.22 |
| MUSK | 1940 | 3001115 | T | ADDITIVE | 0.026372 | 1.13 |
| MUSK | 1943 | 1184926 | T | ADDITIVE | 0.042279 | 0.85 |
| DFNB31 | 1948 | 2274160 | T | RECESSIVE | 0.005390 | 1.51 |
| DFNB31 | 1949 | 731421 | T | RECESSIVE | 0.030474 | 0.71 |
| DFNB31 | 1950 | 10817607 | G | RECESSIVE | 0.025753 | 0.70 |
| DFNB31 | 1951 | 7875262 | T | RECESSIVE | 0.033082 | 0.71 |
| DFNB31 | 1952 | 10081699 | G | RECESSIVE | 0.013955 | 1.43 |
| DFNB31 | 1953 | 10739411 | G | ADDITIVE | 0.026062 | 0.92 |
| DFNB31 | 1954 | 10982213 | A | RECESSIVE | 0.020370 | 0.70 |
| DFNB31 | 1955 | 1408527 | C | RECESSIVE | 0.015767 | 1.41 |
| PAPPA | 1963 | 10759836 | T | RECESSIVE | 0.005237 | 0.72 |
| PAPPA | 1964 | 13285093 | C | DOMINANT | 0.029229 | 1.17 |
| ASTN2 | 1976 | 10759876 | A | DOMINANT | 0.003467 | 1.24 |
| ASTN2 | 1977 | 3849144 | G | DOMINANT | 0.004674 | 1.23 |
| ASTN2 | 1978 | 12350890 | A | DOMINANT | 0.013281 | 1.25 |
| ASTN2 | 1979 | 10817968 | A | ADDITIVE | 0.026212 | 1.24 |
| ASTN2 | 1983 | 1928998 | G | ADDITIVE | 0.038135 | 1.19 |
| ASTN2 | 1984 | 10983518 | C | RECESSIVE | 0.016127 | 0.68 |
| ASTN2 | 1985 | 13298697 | A | RECESSIVE | 0.047152 | 0.72 |
| RAB14 | 1992 | 2302498 | A | RECESSIVE | 0.015476 | 0.80 |
| GSN | 1993 | 12376078 | A | DOMINANT | 0.003682 | 1.47 |
| GSN | 1994 | 10985207 | G | DOMINANT | 0.005065 | 1.46 |
| GSN | 1996 | 767770 | T | DOMINANT | 0.000187 | 1.69 |
| TTLL11 | 1998 | 10818618 | C | RECESSIVE | 0.039629 | 0.73 |
| NEK6 | 2017 | 749355 | A | ADDITIVE | 0.030480 | 1.23 |
| TSC1 | 2031 | 7874234 | T | ADDITIVE | 0.011367 | 0.84 |
| VAV2 | 2032 | 10993790 | T | DOMINANT | 0.003427 | 1.26 |
| VAV2 | 2033 | 7855899 | C | RECESSIVE | 0.003355 | 1.68 |
| VAV2 | 2034 | 3780737 | T | RECESSIVE | 0.004754 | 0.47 |
| VAV2 | 2035 | 7038256 | T | RECESSIVE | 0.025434 | 0.51 |
| VAV2 | 2036 | 7025939 | C | RECESSIVE | 0.023272 | 0.49 |
| NOTCH1 | 2041 | 11145770 | T | RECESSIVE | 0.002492 | 0.74 |
| CACNA1B | 2042 | 2168526 | T | RECESSIVE | 0.024854 | 1.69 |
| CACNA1B | 2043 | 10780196 | A | RECESSIVE | 0.027471 | 1.69 |
| CACNA1B | 2044 | 7028989 | T | RECESSIVE | 0.017789 | 1.75 |
| CACNA1B | 2045 | 12005780 | C | RECESSIVE | 0.012863 | 1.84 |
| CACNB2 | 2051 | 2357928 | G | ADDITIVE | 0.012595 | 0.91 |
| CACNB2 | 2053 | 11014484 | C | DOMINANT | 0.024884 | 0.85 |
| CACNB2 | 2054 | 12416052 | C | RECESSIVE | 0.004716 | 1.31 |
| CACNB2 | 2055 | 12257556 | G | RECESSIVE | 0.002839 | 1.29 |
| CACNB2 | 2056 | 4748474 | G | RECESSIVE | 0.007791 | 1.26 |
| CACNB2 | 2057 | 4237348 | C | DOMINANT | 0.041066 | 0.85 |
| CACNB2 | 2058 | 12764916 | T | DOMINANT | 0.031006 | 0.86 |
| CACNB2 | 2059 | 4628581 | C | DOMINANT | 0.023338 | 0.84 |
| CACNB2 | 2060 | 7910506 | G | DOMINANT | 0.014403 | 1.19 |
| CACNB2 | 2062 | 10828859 | C | RECESSIVE | 0.008707 | 1.28 |
| ARMC3 | 2063 | 10828371 | T | RECESSIVE | 0.021711 | 1.49 |
| ARMC3 | 2064 | 17440393 | A | RECESSIVE | 0.006511 | 1.67 |
| ARMC3 | 2065 | 7084413 | C | RECESSIVE | 0.018948 | 1.40 |
| MYO3A | 2068 | 1339814 | T | RECESSIVE | 0.022947 | 1.28 |
| MYO3A | 2069 | 1416860 | T | RECESSIVE | 0.025959 | 1.28 |
| MYO3A | 2070 | 7899567 | A | RECESSIVE | 0.029350 | 1.27 |
| MYO3A | 2071 | 11014934 | G | RECESSIVE | 0.017798 | 1.30 |
| MYO3A | 2072 | 12246202 | C | RECESSIVE | 0.042753 | 1.27 |
| MYO3A | 2073 | 12263990 | G | RECESSIVE | 0.046502 | 1.25 |
| MYO3A | 2074 | 7095559 | A | RECESSIVE | 0.024761 | 1.28 |
| MYO3A | 2075 | 12258453 | T | RECESSIVE | 0.026415 | 1.28 |
| PRKG1 | 2078 | 6479874 | T | RECESSIVE | 0.014762 | 1.91 |
| PRKG1 | 2084 | 293244 | A | ADDITIVE | 0.020720 | 1.21 |
| PCDH15 | 2090 | 2610922 | A | RECESSIVE | 0.018308 | 3.44 |
| PCDH15 | 2092 | 4465289 | C | RECESSIVE | 0.017216 | 1.69 |
| PCDH15 | 2093 | 1020203 | G | DOMINANT | 0.003999 | 0.79 |
| PCDH15 | 2094 | 2384413 | T | DOMINANT | 0.003476 | 0.79 |
| PCDH15 | 2095 | 7477283 | T | DOMINANT | 0.005120 | 0.80 |
| PCDH15 | 2096 | 10740578 | C | DOMINANT | 0.001890 | 0.78 |
| PCDH15 | 2097 | 7919293 | G | DOMINANT | 0.006251 | 0.80 |
| PCDH15 | 2098 | 2384419 | G | DOMINANT | 0.004336 | 0.79 |
| PCDH15 | 2099 | 2891506 | T | DOMINANT | 0.003985 | 0.79 |
| PCDH15 | 2100 | 997066 | A | DOMINANT | 0.015385 | 0.84 |
| PCDH15 | 2101 | 857374 | C | DOMINANT | 0.022635 | 0.85 |
| PCDH15 | 2102 | 1342281 | T | DOMINANT | 0.018736 | 0.85 |
| PCDH15 | 2103 | 857395 | C | DOMINANT | 0.017903 | 0.85 |

TABLE 2-continued

Alleles and Genotypes Influencing Likelihood of Diagnosis of Bipolar or Schizophrenia

| Gene | SEQ ID NO: | NCBI RS# | Allele | Model | P | Odds Ratio |
|---|---|---|---|---|---|---|
| PCDH15 | 2104 | 11004267 | A | DOMINANT | 0.009219 | 0.83 |
| PCDH15 | 2105 | 11004270 | T | DOMINANT | 0.029388 | 0.86 |
| PCDH15 | 2106 | 7069188 | C | RECESSIVE | 0.014258 | 1.46 |
| PCDH15 | 2108 | 7474541 | C | RECESSIVE | 0.016106 | 1.51 |
| PCDH15 | 2109 | 3902590 | G | RECESSIVE | 0.012226 | 1.54 |
| ANK3 | 2115 | 7907721 | A | RECESSIVE | 0.033308 | 0.79 |
| ANK3 | 2116 | 4948254 | A | RECESSIVE | 0.023395 | 1.27 |
| JMJD1C | 2124 | 10995505 | A | RECESSIVE | 0.026757 | 1.44 |
| JMJD1C | 2126 | 10761747 | G | RECESSIVE | 0.016333 | 1.50 |
| CTNNA3 | 2128 | 10509256 | A | RECESSIVE | 0.041901 | 0.68 |
| CTNNA3 | 2129 | 3911783 | A | ADDITIVE | 0.040526 | 1.09 |
| CTNNA3 | 2140 | 7893145 | C | DOMINANT | 0.000786 | 0.79 |
| CTNNA3 | 2141 | 7922094 | C | DOMINANT | 0.007206 | 1.21 |
| CTNNA3 | 2142 | 7907580 | T | DOMINANT | 0.008743 | 1.21 |
| CTNNA3 | 2143 | 10997420 | C | RECESSIVE | 0.014850 | 1.23 |
| CTNNA3 | 2144 | 1925605 | T | RECESSIVE | 0.049015 | 1.19 |
| CTNNA3 | 2154 | 2448547 | G | DOMINANT | 0.022824 | 0.75 |
| CTNNA3 | 2155 | 2616687 | G | DOMINANT | 0.011127 | 0.79 |
| KCNMA1 | 2165 | 2569360 | C | RECESSIVE | 0.027821 | 1.22 |
| KCNMA1 | 2166 | 2569361 | C | RECESSIVE | 0.021437 | 1.23 |
| KCNMA1 | 2167 | 4980107 | C | RECESSIVE | 0.041453 | 1.20 |
| KCNMA1 | 2168 | 10762731 | G | RECESSIVE | 0.024986 | 1.22 |
| KCNMA1 | 2169 | 4980113 | C | RECESSIVE | 0.032402 | 1.21 |
| KCNMA1 | 2170 | 10762732 | T | RECESSIVE | 0.034144 | 1.20 |
| KCNMA1 | 2173 | 3781158 | T | DOMINANT | 0.019022 | 0.85 |
| KCNMA1 | 2174 | 2131216 | T | DOMINANT | 0.019030 | 0.84 |
| KCNMA1 | 2175 | 10509378 | A | DOMINANT | 0.007199 | 0.83 |
| KCNMA1 | 2176 | 12219498 | T | DOMINANT | 0.015542 | 0.84 |
| NRG3 | 2184 | 1124744 | A | DOMINANT | 0.002015 | 1.29 |
| NRG3 | 2186 | 11595839 | G | ADDITIVE | 0.025402 | 1.27 |
| NRG3 | 2187 | 474496 | G | DOMINANT | 0.005874 | 1.21 |
| NRG3 | 2188 | 495978 | A | DOMINANT | 0.006781 | 1.21 |
| SORBS1 | 2190 | 11188287 | G | RECESSIVE | 0.021191 | 1.53 |
| SORBS1 | 2193 | 7080545 | C | ADDITIVE | 0.043587 | 0.86 |
| SORBS1 | 2194 | 11188327 | C | DOMINANT | 0.007510 | 1.21 |
| PIK3AP1 | 2196 | 7448 | G | RECESSIVE | 0.005100 | 1.37 |
| PIK3AP1 | 2197 | 1983831 | A | RECESSIVE | 0.006490 | 1.34 |
| PIK3AP1 | 2198 | 912480 | G | RECESSIVE | 0.002642 | 1.44 |
| PIK3AP1 | 2199 | 7914154 | C | RECESSIVE | 0.010974 | 1.33 |
| SLIT1 | 2201 | 2817688 | G | DOMINANT | 0.007821 | 1.21 |
| SLIT1 | 2202 | 2636815 | A | DOMINANT | 0.006388 | 1.23 |
| SLIT1 | 2203 | 2817666 | A | DOMINANT | 0.004951 | 0.81 |
| SORCS3 | 2209 | 1387827 | A | ADDITIVE | 0.021458 | 1.03 |
| SORCS3 | 2210 | 973190 | T | ADDITIVE | 0.016671 | 1.09 |
| SORCS3 | 2211 | 2496029 | A | ADDITIVE | 0.021204 | 1.09 |
| SORCS3 | 2213 | 2451492 | T | DOMINANT | 0.049209 | 0.87 |
| SORCS3 | 2214 | 2451498 | C | DOMINANT | 0.041030 | 0.86 |
| SORCS3 | 2215 | 2177744 | C | DOMINANT | 0.022268 | 1.18 |
| SORCS3 | 2217 | 7072425 | A | DOMINANT | 0.037455 | 1.22 |
| VTI1A | 2218 | 10509963 | A | RECESSIVE | 0.045868 | 0.78 |
| ATRNL1 | 2220 | 1264764 | C | ADDITIVE | 0.024878 | 0.87 |
| ATRNL1 | 2223 | 12767028 | C | DOMINANT | 0.017014 | 1.20 |
| ATRNL1 | 2224 | 7922670 | G | DOMINANT | 0.022609 | 1.19 |
| ATRNL1 | 2225 | 11197255 | G | DOMINANT | 0.019749 | 1.20 |
| ATRNL1 | 2228 | 11197294 | T | DOMINANT | 0.027662 | 1.19 |
| ATRNL1 | 2230 | 2804192 | A | ADDITIVE | 0.029904 | 1.14 |
| ATRNL1 | 2231 | 7095798 | T | DOMINANT | 0.034822 | 1.18 |
| ATRNL1 | 2232 | 2804204 | T | ADDITIVE | 0.031879 | 1.15 |
| ATRNL1 | 2233 | 2804207 | C | ADDITIVE | 0.032750 | 0.90 |
| ATRNL1 | 2234 | 1590734 | G | ADDITIVE | 0.026976 | 1.17 |
| ATRNL1 | 2235 | 1590733 | G | ADDITIVE | 0.025347 | 1.18 |
| ATRNL1 | 2236 | 10787584 | T | ADDITIVE | 0.008453 | 1.20 |
| ATRNL1 | 2237 | 11197337 | T | ADDITIVE | 0.027025 | 1.18 |
| ATRNL1 | 2238 | 2804249 | G | ADDITIVE | 0.026115 | 0.91 |
| ATRNL1 | 2239 | 2420098 | G | ADDITIVE | 0.029450 | 0.90 |
| HSPA12A | 2241 | 12777585 | G | RECESSIVE | 0.015733 | 1.38 |
| NANOS1 | 2244 | 9325559 | T | ADDITIVE | 0.019015 | 0.88 |
| ATE1 | 2251 | 7086628 | G | ADDITIVE | 0.038812 | 0.92 |
| ATE1 | 2252 | 1693682 | A | RECESSIVE | 0.028622 | 0.82 |
| ATE1 | 2256 | 10510102 | G | RECESSIVE | 0.020025 | 1.61 |
| EBF3 | 2265 | 10829666 | A | ADDITIVE | 0.008326 | 0.83 |
| CEND1 | 2269 | 11246327 | T | DOMINANT | 0.016652 | 0.82 |
| HCCA2 | 2270 | 11029977 | T | ADDITIVE | 0.026816 | 1.12 |
| HCCA2 | 2271 | 1554855 | C | ADDITIVE | 0.006336 | 1.15 |
| HCCA2 | 2272 | 4881740 | T | ADDITIVE | 0.003597 | 1.17 |
| HCCA2 | 2273 | 7396009 | T | ADDITIVE | 0.002743 | 1.18 |

TABLE 2-continued

Alleles and Genotypes Influencing Likelihood of Diagnosis of Bipolar or Schizophrenia

| Gene | SEQ ID NO: | NCBI RS# | Allele | Model | P | Odds Ratio |
|---|---|---|---|---|---|---|
| DUSP8 | 2274 | 1108991 | G | ADDITIVE | 0.002643 | 1.18 |
| DUSP8 | 2275 | 6578475 | C | ADDITIVE | 0.000799 | 1.29 |
| DUSP8 | 2276 | 6578476 | G | ADDITIVE | 0.003429 | 1.15 |
| DUSP8 | 2277 | 10734456 | C | DOMINANT | 0.026547 | 1.17 |
| STIM1 | 2278 | 7924984 | A | DOMINANT | 0.024698 | 1.17 |
| TRIM21 | 2279 | 10835979 | G | ADDITIVE | 0.009525 | 1.32 |
| GALNTL4 | 2281 | 7120631 | T | ADDITIVE | 0.032773 | 0.94 |
| GALNTL4 | 2283 | 901553 | C | RECESSIVE | 0.047890 | 1.23 |
| MICAL2 | 2287 | 11022241 | A | RECESSIVE | 0.045635 | 1.20 |
| MICAL2 | 2288 | 10437600 | A | RECESSIVE | 0.011587 | 0.62 |
| MICAL2 | 2290 | 12807026 | C | ADDITIVE | 0.013182 | 0.86 |
| SPON1 | 2291 | 2697852 | G | DOMINANT | 0.049783 | 0.87 |
| SPON1 | 2292 | 1969542 | C | DOMINANT | 0.007499 | 0.83 |
| SPON1 | 2293 | 7116230 | A | ADDITIVE | 0.020903 | 0.88 |
| SPON1 | 2294 | 11023051 | C | DOMINANT | 0.031882 | 0.85 |
| SPON1 | 2295 | 1528668 | C | ADDITIVE | 0.032120 | 0.89 |
| SPON1 | 2296 | 11601500 | C | ADDITIVE | 0.024398 | 0.88 |
| SPON1 | 2297 | 10832163 | T | ADDITIVE | 0.018945 | 0.88 |
| SPON1 | 2298 | 11023054 | A | ADDITIVE | 0.023861 | 0.88 |
| SPON1 | 2299 | 10832165 | A | ADDITIVE | 0.025929 | 0.89 |
| SPON1 | 2300 | 11023055 | G | ADDITIVE | 0.024619 | 0.89 |
| SPON1 | 2301 | 7112850 | A | ADDITIVE | 0.009613 | 0.86 |
| SPON1 | 2302 | 10766134 | G | ADDITIVE | 0.018251 | 0.92 |
| SPON1 | 2303 | 12283632 | A | DOMINANT | 0.024620 | 0.85 |
| SPON1 | 2304 | 11023067 | G | DOMINANT | 0.013934 | 0.84 |
| SPON1 | 2305 | 882667 | G | DOMINANT | 0.010949 | 1.22 |
| SPON1 | 2306 | 1528641 | A | DOMINANT | 0.014322 | 1.21 |
| SPON1 | 2307 | 7116296 | T | DOMINANT | 0.027466 | 1.19 |
| SPON1 | 2308 | 11023088 | T | DOMINANT | 0.025094 | 1.19 |
| SPON1 | 2309 | 1864658 | C | DOMINANT | 0.047272 | 0.87 |
| SPON1 | 2310 | 4757244 | A | DOMINANT | 0.049295 | 0.87 |
| SPON1 | 2313 | 4756787 | C | RECESSIVE | 0.010483 | 0.45 |
| USH1C | 2314 | 4756895 | T | RECESSIVE | 0.030914 | 1.22 |
| USH1C | 2315 | 1055581 | G | DOMINANT | 0.002232 | 0.78 |
| USH1C | 2316 | 2072230 | T | RECESSIVE | 0.002686 | 1.34 |
| USH1C | 2317 | 16934376 | C | RECESSIVE | 0.044775 | 0.23 |
| OTOG | 2318 | 10832822 | A | ADDITIVE | 0.011682 | 0.80 |
| PTPN5 | 2329 | 4757718 | G | ADDITIVE | 0.030868 | 1.13 |
| NAV2 | 2330 | 10500860 | C | ADDITIVE | 0.005524 | 1.18 |
| NAV2 | 2331 | 1559665 | G | RECESSIVE | 0.026395 | 1.20 |
| NAV2 | 2332 | 1559666 | C | ADDITIVE | 0.023490 | 1.09 |
| NAV2 | 2334 | 4757841 | G | ADDITIVE | 0.019763 | 0.92 |
| NAV2 | 2335 | 10766590 | A | ADDITIVE | 0.020748 | 1.06 |
| NAV2 | 2336 | 10734284 | T | ADDITIVE | 0.012674 | 1.10 |
| NAV2 | 2337 | 10741800 | C | ADDITIVE | 0.021872 | 1.08 |
| NAV2 | 2338 | 11025246 | C | RECESSIVE | 0.007488 | 1.31 |
| NAV2 | 2340 | 2255677 | A | DOMINANT | 0.019534 | 1.19 |
| NAV2 | 2341 | 10732471 | T | ADDITIVE | 0.023843 | 0.89 |
| NAV2 | 2342 | 1470254 | T | ADDITIVE | 0.039435 | 0.89 |
| NAV2 | 2343 | 1470253 | C | ADDITIVE | 0.041924 | 0.88 |
| NAV2 | 2344 | 1470251 | A | ADDITIVE | 0.025843 | 0.86 |
| SLC6A5 | 2345 | 1443548 | T | DOMINANT | 0.024295 | 1.18 |
| SLC6A5 | 2346 | 4922798 | G | RECESSIVE | 0.011680 | 1.37 |
| SLC6A5 | 2347 | 10766703 | A | RECESSIVE | 0.011211 | 1.37 |
| SLC6A5 | 2348 | 10741848 | T | RECESSIVE | 0.038041 | 1.21 |
| SLC6A5 | 2349 | 10741849 | G | RECESSIVE | 0.043513 | 1.20 |
| SLC6A5 | 2350 | 4454712 | T | RECESSIVE | 0.004974 | 1.32 |
| SLC6A5 | 2351 | 2276431 | A | RECESSIVE | 0.009040 | 1.32 |
| KCNA4 | 2353 | 11030913 | C | DOMINANT | 0.023874 | 0.84 |
| KCNA4 | 2354 | 524373 | G | ADDITIVE | 0.009368 | 1.26 |
| KCNA4 | 2355 | 10835607 | A | DOMINANT | 0.021842 | 0.84 |
| KCNA4 | 2356 | 536830 | C | ADDITIVE | 0.010851 | 1.23 |
| LRRC4C | 2357 | 2953310 | C | ADDITIVE | 0.036554 | 1.09 |
| LRRC4C | 2358 | 7943560 | G | ADDITIVE | 0.012296 | 1.17 |
| LRRC4C | 2359 | 10160235 | T | RECESSIVE | 0.040393 | 1.26 |
| LRRC4C | 2360 | 4237677 | C | DOMINANT | 0.031520 | 1.17 |
| LRRC4C | 2361 | 4237678 | G | DOMINANT | 0.000965 | 1.29 |
| LRRC4C | 2372 | 1377106 | T | DOMINANT | 0.042343 | 0.83 |
| LRRC4C | 2375 | 10837391 | G | ADDITIVE | 0.009622 | 1.14 |
| PHACS | 2379 | 7950395 | T | DOMINANT | 0.038936 | 1.19 |
| PHACS | 2380 | 113080 | G | ADDITIVE | 0.011000 | 0.89 |
| PHACS | 2381 | 2285029 | A | ADDITIVE | 0.012050 | 0.88 |
| CTNND1 | 2390 | 576859 | A | RECESSIVE | 0.018240 | 0.75 |
| CTNND1 | 2391 | 2956981 | A | DOMINANT | 0.045557 | 1.16 |
| DLG2 | 2398 | 10501540 | G | RECESSIVE | 0.047974 | 0.83 |
| DLG2 | 2399 | 11233641 | G | RECESSIVE | 0.038672 | 0.81 |

TABLE 2-continued

Alleles and Genotypes Influencing Likelihood of Diagnosis of Bipolar or Schizophrenia

| Gene | SEQ ID NO: | NCBI RS# | Allele | Model | P | Odds Ratio |
|---|---|---|---|---|---|---|
| DLG2 | 2400 | 7116939 | C | RECESSIVE | 0.049426 | 0.80 |
| DLG2 | 2405 | 635823 | G | RECESSIVE | 0.039970 | 0.81 |
| DLG2 | 2420 | 10898330 | C | DOMINANT | 0.019595 | 1.20 |
| OPCML | 2422 | 1823365 | T | DOMINANT | 0.000367 | 0.72 |
| OPCML | 2423 | 2277271 | C | DOMINANT | 0.028391 | 1.17 |
| OPCML | 2428 | 4554901 | T | RECESSIVE | 0.021988 | 0.55 |
| OPCML | 2429 | 7945576 | T | ADDITIVE | 0.041086 | 1.05 |
| WNT5B | 2430 | 10773971 | G | ADDITIVE | 0.013765 | 1.63 |
| WNT5B | 2431 | 4766401 | T | RECESSIVE | 0.016081 | 1.41 |
| TSPAN9 | 2432 | 1860431 | T | ADDITIVE | 0.044410 | 1.23 |
| TSPAN9 | 2433 | 7969363 | T | DOMINANT | 0.003161 | 1.23 |
| TMEM16B | 2437 | 10849338 | G | ADDITIVE | 0.049314 | 0.86 |
| TMEM16B | 2438 | 3782652 | G | DOMINANT | 0.023546 | 1.20 |
| TMEM16B | 2441 | 11832095 | A | DOMINANT | 0.006913 | 1.21 |
| TMEM16B | 2442 | 11063875 | T | DOMINANT | 0.008667 | 1.21 |
| STYK1 | 2443 | 10845187 | C | RECESSIVE | 0.027359 | 1.23 |
| STYK1 | 2444 | 6488316 | T | RECESSIVE | 0.048914 | 1.20 |
| STYK1 | 2445 | 2418087 | C | RECESSIVE | 0.038431 | 1.21 |
| STYK1 | 2446 | 2418088 | G | RECESSIVE | 0.045827 | 1.20 |
| STYK1 | 2447 | 7350597 | A | RECESSIVE | 0.044659 | 1.20 |
| STYK1 | 2448 | 10743918 | C | DOMINANT | 0.010106 | 0.83 |
| LOC729025 | 2449 | 7955194 | T | DOMINANT | 0.015742 | 0.83 |
| LOC729025 | 2450 | 10219493 | G | DOMINANT | 0.030417 | 0.84 |
| LOC729025 | 2451 | 3847918 | G | DOMINANT | 0.020876 | 0.83 |
| LOC729025 | 2452 | 7297251 | C | DOMINANT | 0.030287 | 0.84 |
| LOC729025 | 2453 | 7297372 | G | DOMINANT | 0.005504 | 0.81 |
| LOC729025 | 2454 | 10772915 | A | DOMINANT | 0.003516 | 0.80 |
| LOC729025 | 2455 | 1913253 | T | DOMINANT | 0.023973 | 0.83 |
| LOC729025 | 2456 | 1799491 | T | DOMINANT | 0.003693 | 0.80 |
| LOC729025 | 2457 | 3915237 | C | DOMINANT | 0.032814 | 0.86 |
| PIK3C2G | 2458 | 4491292 | T | DOMINANT | 0.026816 | 1.17 |
| PIK3C2G | 2459 | 10841014 | A | ADDITIVE | 0.003107 | 1.16 |
| PIK3C2G | 2460 | 9300118 | G | ADDITIVE | 0.009854 | 1.17 |
| PIK3C2G | 2463 | 11044130 | A | ADDITIVE | 0.043648 | 0.81 |
| ITPR2 | 2465 | 11048447 | T | DOMINANT | 0.036036 | 0.86 |
| ITPR2 | 2466 | 9442 | T | DOMINANT | 0.011697 | 0.83 |
| ITPR2 | 2467 | 2570 | C | DOMINANT | 0.014971 | 0.84 |
| ITPR2 | 2469 | 11048588 | G | ADDITIVE | 0.002640 | 0.91 |
| ITPR2 | 2470 | 2230377 | T | ADDITIVE | 0.003187 | 0.89 |
| ITPR2 | 2471 | 6487566 | A | DOMINANT | 0.013025 | 0.84 |
| LRP1 | 2472 | 7975818 | C | RECESSIVE | 0.014070 | 0.75 |
| LRP1 | 2473 | 1800176 | T | RECESSIVE | 0.019701 | 0.76 |
| LRP1 | 2474 | 1800168 | C | RECESSIVE | 0.019762 | 0.76 |
| LRP1 | 2475 | 7301155 | G | RECESSIVE | 0.019893 | 0.77 |
| CNOT2 | 2477 | 7974636 | T | DOMINANT | 0.016534 | 0.84 |
| KCNC2 | 2478 | 4309217 | A | RECESSIVE | 0.014095 | 0.75 |
| KCNC2 | 2479 | 4131954 | T | RECESSIVE | 0.012375 | 0.74 |
| CHST11 | 2487 | 11112146 | T | ADDITIVE | 0.037414 | 1.10 |
| CHST11 | 2488 | 2453161 | G | DOMINANT | 0.005432 | 0.82 |
| CHST11 | 2489 | 2468110 | A | DOMINANT | 0.004451 | 0.82 |
| CHST11 | 2490 | 2642109 | T | DOMINANT | 0.010529 | 0.83 |
| CHST11 | 2491 | 1565815 | T | DOMINANT | 0.034071 | 0.86 |
| CHST11 | 2492 | 1038968 | C | DOMINANT | 0.025751 | 0.85 |
| CHST11 | 2493 | 2696006 | T | DOMINANT | 0.021717 | 0.85 |
| CHST11 | 2494 | 2463017 | C | DOMINANT | 0.022342 | 0.85 |
| CHST11 | 2495 | 2468082 | G | DOMINANT | 0.021225 | 0.85 |
| CHST11 | 2496 | 2468083 | A | DOMINANT | 0.015754 | 0.84 |
| KIAA1853 | 2497 | 7134748 | G | RECESSIVE | 0.047235 | 1.28 |
| RIMBP2 | 2504 | 7132917 | A | ADDITIVE | 0.040625 | 0.73 |
| RIMBP2 | 2505 | 1982939 | T | ADDITIVE | 0.039930 | 0.80 |
| MTIF3 | 2515 | 7334690 | A | ADDITIVE | 0.031553 | 0.89 |
| N4BP2L2 | 2518 | 1081796 | A | RECESSIVE | 0.030849 | 1.48 |
| NBEA | 2524 | 9600580 | A | RECESSIVE | 0.035462 | 1.81 |
| KPNA3 | 2533 | 7997798 | A | ADDITIVE | 0.045890 | 0.84 |
| KPNA3 | 2534 | 4942864 | G | ADDITIVE | 0.039912 | 0.84 |
| KPNA3 | 2535 | 9535347 | G | ADDITIVE | 0.023264 | 0.86 |
| PCDH17 | 2537 | 4564470 | G | ADDITIVE | 0.003916 | 1.24 |
| SLAIN1 | 2553 | 1146920 | C | DOMINANT | 0.016112 | 1.19 |
| NALCN | 2590 | 7321815 | A | RECESSIVE | 0.000016 | 1.56 |
| NALCN | 2591 | 3751403 | T | RECESSIVE | 0.000016 | 1.61 |
| NALCN | 2592 | 12430088 | T | RECESSIVE | 0.000020 | 1.59 |
| NALCN | 2593 | 638732 | C | RECESSIVE | 0.000202 | 1.48 |
| NALCN | 2594 | 2274085 | T | RECESSIVE | 0.002256 | 1.30 |
| NALCN | 2595 | 7334863 | C | RECESSIVE | 0.000134 | 1.44 |
| NALCN | 2596 | 1289556 | G | ADDITIVE | 0.010143 | 0.89 |
| NALCN | 2597 | 9554752 | T | RECESSIVE | 0.000046 | 1.51 |

TABLE 2-continued

Alleles and Genotypes Influencing Likelihood of Diagnosis of Bipolar or Schizophrenia

| Gene | SEQ ID NO: | NCBI RS# | Allele | Model | P | Odds Ratio |
|---|---|---|---|---|---|---|
| NALCN | 2598 | 633321 | G | ADDITIVE | 0.024253 | 0.91 |
| NALCN | 2599 | 2044118 | A | RECESSIVE | 0.000020 | 1.58 |
| NALCN | 2600 | 7986657 | G | RECESSIVE | 0.000381 | 1.50 |
| ITGBL1 | 2603 | 1335589 | T | RECESSIVE | 0.018609 | 1.37 |
| ITGBL1 | 2604 | 875117 | G | RECESSIVE | 0.023042 | 1.36 |
| ITGBL1 | 2605 | 875116 | C | RECESSIVE | 0.021721 | 1.36 |
| ITGBL1 | 2606 | 3783222 | G | RECESSIVE | 0.006719 | 1.33 |
| ITGBL1 | 2608 | 17686597 | C | DOMINANT | 0.027308 | 1.20 |
| ITGBL1 | 2609 | 2281991 | G | DOMINANT | 0.020401 | 1.21 |
| ITGBL1 | 2610 | 1469855 | G | DOMINANT | 0.021955 | 1.20 |
| ITGBL1 | 2611 | 1469853 | G | DOMINANT | 0.028859 | 1.19 |
| TTC5 | 2615 | 10139180 | A | ADDITIVE | 0.013975 | 0.90 |
| WDR23 | 2627 | 6573565 | A | RECESSIVE | 0.015197 | 1.32 |
| NOVA1 | 2628 | 6574950 | C | RECESSIVE | 0.044675 | >5 |
| NOVA1 | 2629 | 178165 | C | RECESSIVE | 0.037814 | 1.28 |
| SLC25A21 | 2631 | 17105036 | T | DOMINANT | 0.001136 | 0.63 |
| SLC25A21 | 2632 | 712342 | C | ADDITIVE | 0.020794 | 0.88 |
| SLC25A21 | 2635 | 1950367 | C | ADDITIVE | 0.014648 | 0.61 |
| GNG2 | 2636 | 7158738 | C | RECESSIVE | 0.039010 | 0.84 |
| GNG2 | 2637 | 4278650 | C | ADDITIVE | 0.025528 | 1.18 |
| GNG2 | 2638 | 7148347 | G | ADDITIVE | 0.025573 | 1.16 |
| GNG2 | 2639 | 12878420 | T | RECESSIVE | 0.038410 | 0.83 |
| GNG2 | 2640 | 10131301 | T | RECESSIVE | 0.015036 | 0.80 |
| GNG2 | 2641 | 1959518 | C | DOMINANT | 0.030573 | 1.18 |
| GNG2 | 2642 | 1959517 | A | DOMINANT | 0.031171 | 1.18 |
| GNG2 | 2647 | 10873056 | C | ADDITIVE | 0.025723 | 1.43 |
| SAMD4A | 2648 | 4901520 | A | DOMINANT | 0.006420 | 1.25 |
| SAMD4A | 2649 | 6572964 | A | RECESSIVE | 0.004562 | 0.60 |
| SAMD4A | 2650 | 3813402 | A | DOMINANT | 0.012538 | 1.20 |
| DAAM1 | 2654 | 1272858 | G | ADDITIVE | 0.012202 | 0.91 |
| DAAM1 | 2655 | 2295850 | C | ADDITIVE | 0.031869 | 0.91 |
| GPR135 | 2656 | 1253165 | A | ADDITIVE | 0.048407 | 0.91 |
| GPR135 | 2657 | 11628147 | A | ADDITIVE | 0.006366 | 0.90 |
| GPR135 | 2658 | 1271183 | T | ADDITIVE | 0.007668 | 0.90 |
| GPR135 | 2659 | 1253170 | T | RECESSIVE | 0.039459 | 0.80 |
| GPR135 | 2660 | 10136708 | G | ADDITIVE | 0.018228 | 0.89 |
| PPP2R5E | 2661 | 6573507 | C | RECESSIVE | 0.036369 | 0.74 |
| PPP2R5E | 2662 | 6573508 | C | RECESSIVE | 0.037725 | 0.74 |
| PPP2R5E | 2663 | 6573522 | A | DOMINANT | 0.017188 | 1.18 |
| PPP2R5E | 2664 | 2754223 | G | DOMINANT | 0.014128 | 1.19 |
| PPP2R5E | 2665 | 10129182 | T | ADDITIVE | 0.003108 | 1.21 |
| PPP2R5E | 2666 | 964954 | G | DOMINANT | 0.011911 | 1.19 |
| PPP2R5E | 2667 | 1255771 | G | DOMINANT | 0.004338 | 1.23 |
| PPP2R5E | 2668 | 8021183 | G | ADDITIVE | 0.002841 | 1.21 |
| PPP2R5E | 2669 | 1255741 | A | DOMINANT | 0.024639 | 1.17 |
| RGS6 | 2685 | 2526896 | C | RECESSIVE | 0.023660 | 0.82 |
| KCNK10 | 2686 | 12587003 | C | RECESSIVE | 0.002115 | 1.45 |
| KCNK10 | 2687 | 11627082 | A | RECESSIVE | 0.000848 | 1.72 |
| RPS6KA5 | 2698 | 1286146 | G | DOMINANT | 0.005154 | 1.22 |
| CCDC88C | 2700 | 1970912 | T | DOMINANT | 0.012282 | 1.17 |
| CCDC88C | 2708 | 2295882 | C | ADDITIVE | 0.035938 | 0.81 |
| ATXN3 | 2710 | 8008215 | G | ADDITIVE | 0.016375 | 0.83 |
| RYR3 | 2718 | 2596229 | A | DOMINANT | 0.022549 | 0.83 |
| RYR3 | 2719 | 1560968 | G | DOMINANT | 0.016056 | 0.83 |
| RYR3 | 2720 | 2676085 | A | DOMINANT | 0.006326 | 0.82 |
| RYR3 | 2721 | 2676087 | A | DOMINANT | 0.021488 | 0.83 |
| RYR3 | 2722 | 2164249 | C | RECESSIVE | 0.030824 | 0.83 |
| RYR3 | 2723 | 2596159 | T | DOMINANT | 0.018069 | 0.83 |
| RYR3 | 2724 | 2596163 | G | DOMINANT | 0.029746 | 0.85 |
| RYR3 | 2725 | 2572189 | T | RECESSIVE | 0.006751 | 0.79 |
| RYR3 | 2726 | 2082753 | A | RECESSIVE | 0.003879 | 0.77 |
| RYR3 | 2727 | 2572175 | A | RECESSIVE | 0.003637 | 0.78 |
| RYR3 | 2728 | 2572169 | A | RECESSIVE | 0.000866 | 0.74 |
| RYR3 | 2729 | 2596175 | A | RECESSIVE | 0.005002 | 0.78 |
| RYR3 | 2730 | 744776 | C | ADDITIVE | 0.029493 | 0.70 |
| RYR3 | 2732 | 1390159 | T | RECESSIVE | 0.027798 | >5 |
| RYR3 | 2734 | 7163140 | T | DOMINANT | 0.002105 | 1.26 |
| C15ORF41 | 2736 | 1901721 | C | DOMINANT | 0.004128 | 0.75 |
| C15ORF41 | 2737 | 10518905 | C | DOMINANT | 0.004549 | 0.76 |
| C15ORF41 | 2738 | 8033760 | A | DOMINANT | 0.003999 | 0.75 |
| C15ORF41 | 2739 | 16964046 | T | DOMINANT | 0.014211 | 0.78 |
| C15ORF41 | 2740 | 16964049 | A | DOMINANT | 0.005453 | 0.76 |
| C15ORF41 | 2741 | 16964052 | G | DOMINANT | 0.006294 | 0.76 |
| MEIS2 | 2742 | 16964229 | C | DOMINANT | 0.020710 | 0.82 |
| MEIS2 | 2743 | 12900044 | T | ADDITIVE | 0.013848 | 1.12 |
| MEIS2 | 2744 | 11638361 | C | ADDITIVE | 0.021406 | 1.11 |

TABLE 2-continued

Alleles and Genotypes Influencing Likelihood of Diagnosis of Bipolar or Schizophrenia

| Gene | SEQ ID NO: | NCBI RS# | Allele | Model | P | Odds Ratio |
|---|---|---|---|---|---|---|
| MEIS2 | 2745 | 12438771 | T | RECESSIVE | 0.007917 | 1.24 |
| KIAA1370 | 2747 | 1693523 | C | RECESSIVE | 0.021736 | 1.44 |
| KIAA1370 | 2748 | 11853179 | T | RECESSIVE | 0.008002 | 1.81 |
| UNC13C | 2750 | 2115825 | A | RECESSIVE | 0.045016 | 1.19 |
| UNC13C | 2754 | 11636356 | T | DOMINANT | 0.043811 | 1.17 |
| UNC13C | 2755 | 934192 | A | DOMINANT | 0.012088 | 1.22 |
| UNC13C | 2756 | 1897069 | G | RECESSIVE | 0.001261 | 0.76 |
| UNC13C | 2757 | 12439401 | T | RECESSIVE | 0.001191 | 0.76 |
| UNC13C | 2758 | 12900128 | C | ADDITIVE | 0.001591 | 1.25 |
| UNC13C | 2759 | 4517736 | T | RECESSIVE | 0.022153 | 1.25 |
| UNC13C | 2760 | 12908083 | T | RECESSIVE | 0.030215 | 1.23 |
| UNC13C | 2761 | 7172577 | A | RECESSIVE | 0.023330 | 1.25 |
| UNC13C | 2762 | 4776220 | T | RECESSIVE | 0.026425 | 1.24 |
| UNC13C | 2763 | 4776222 | C | RECESSIVE | 0.019881 | 1.24 |
| UNC13C | 2764 | 573320 | A | RECESSIVE | 0.019152 | 1.48 |
| UNC13C | 2765 | 8040774 | T | RECESSIVE | 0.031914 | 1.22 |
| UNC13C | 2766 | 12592914 | T | DOMINANT | 0.042845 | 0.87 |
| NEDD4 | 2768 | 10518828 | A | RECESSIVE | 0.005630 | 0.35 |
| CGNL1 | 2769 | 1039979 | T | ADDITIVE | 0.048156 | 1.07 |
| CGNL1 | 2770 | 1706376 | C | ADDITIVE | 0.048780 | 1.07 |
| GRINL1A | 2775 | 16977629 | T | ADDITIVE | 0.023972 | 0.79 |
| ADAM10 | 2777 | 1427282 | T | ADDITIVE | 0.026787 | 1.05 |
| ADAM10 | 2778 | 972801 | C | ADDITIVE | 0.032827 | 1.08 |
| ADAM10 | 2780 | 514049 | A | RECESSIVE | 0.029312 | 1.23 |
| TBC1D2B | 2782 | 4591100 | C | DOMINANT | 0.020383 | 1.18 |
| TBC1D2B | 2783 | 16969397 | T | RECESSIVE | 0.012908 | 0.18 |
| ARNT2 | 2785 | 4238521 | A | RECESSIVE | 0.000302 | 0.38 |
| ARNT2 | 2788 | 11072927 | T | ADDITIVE | 0.044369 | 0.97 |
| AKAP13 | 2796 | 7180923 | A | RECESSIVE | 0.039654 | 0.83 |
| AKAP13 | 2797 | 2880765 | A | RECESSIVE | 0.032081 | 0.83 |
| AKAP13 | 2798 | 4842888 | T | RECESSIVE | 0.031967 | 0.83 |
| AKAP13 | 2799 | 3743321 | A | RECESSIVE | 0.026612 | 0.82 |
| AKAP13 | 2800 | 8026938 | T | RECESSIVE | 0.022401 | 0.82 |
| AKAP13 | 2801 | 6496055 | A | RECESSIVE | 0.020444 | 0.82 |
| AKAP13 | 2802 | 11632326 | A | RECESSIVE | 0.007324 | 0.79 |
| AKAP13 | 2804 | 10520594 | A | RECESSIVE | 0.014430 | 1.52 |
| AKAP13 | 2805 | 17571078 | G | RECESSIVE | 0.031478 | 1.45 |
| AKAP13 | 2807 | 11631015 | G | DOMINANT | 0.025944 | 0.85 |
| AKAP13 | 2810 | 12909648 | A | RECESSIVE | 0.029193 | 1.20 |
| AKAP13 | 2811 | 7181796 | C | RECESSIVE | 0.018794 | 1.49 |
| AKAP13 | 2813 | 338535 | A | ADDITIVE | 0.021891 | 0.80 |
| SLCO3A1 | 2818 | 207970 | T | RECESSIVE | 0.019343 | 0.72 |
| SLCO3A1 | 2820 | 960440 | G | DOMINANT | 0.045442 | 1.16 |
| ST8SIA2 | 2821 | 2035645 | A | RECESSIVE | 0.006841 | 1.28 |
| RGMA | 2822 | 12438714 | T | RECESSIVE | 0.011283 | 4.32 |
| A2BP1 | 2826 | 7201725 | G | DOMINANT | 0.017247 | 1.27 |
| A2BP1 | 2827 | 12443531 | A | DOMINANT | 0.018749 | 1.28 |
| A2BP1 | 2831 | 4274456 | T | RECESSIVE | 0.045300 | 0.80 |
| A2BP1 | 2836 | 7197039 | C | ADDITIVE | 0.009536 | 1.36 |
| N4BP1 | 2839 | 9933187 | T | ADDITIVE | 0.049264 | 1.13 |
| N4BP1 | 2840 | 9937623 | T | ADDITIVE | 0.047294 | 1.12 |
| GOT2 | 2841 | 6993 | T | RECESSIVE | 0.011580 | 1.33 |
| GOT2 | 2842 | 30842 | T | RECESSIVE | 0.022879 | 1.33 |
| GOT2 | 2844 | 257637 | T | ADDITIVE | 0.036785 | 1.11 |
| GOT2 | 2847 | 185397 | T | ADDITIVE | 0.049385 | 1.12 |
| GOT2 | 2848 | 11076262 | G | RECESSIVE | 0.036619 | 1.26 |
| GOT2 | 2849 | 6499976 | A | RECESSIVE | 0.026537 | 1.32 |
| GOT2 | 2850 | 1595181 | A | RECESSIVE | 0.047739 | 1.24 |
| GOT2 | 2851 | 10852565 | C | RECESSIVE | 0.019138 | 1.34 |
| GOT2 | 2852 | 4784986 | T | RECESSIVE | 0.015787 | 1.37 |
| WWOX | 2857 | 7184271 | C | RECESSIVE | 0.030927 | 0.83 |
| MPHOSPH6 | 2864 | 2967370 | A | DOMINANT | 0.020494 | 1.18 |
| MPHOSPH6 | 2865 | 1862820 | C | DOMINANT | 0.043415 | 1.15 |
| MPHOSPH6 | 2866 | 2911391 | G | DOMINANT | 0.036535 | 1.16 |
| CDH13 | 2869 | 11149556 | G | RECESSIVE | 0.013336 | 0.79 |
| CDH13 | 2870 | 9940179 | A | DOMINANT | 0.005530 | 0.81 |
| CDH13 | 2871 | 6563892 | A | DOMINANT | 0.001664 | 0.80 |
| CDH13 | 2872 | 10514579 | C | DOMINANT | 0.002875 | 0.81 |
| CDH13 | 2873 | 444881 | G | RECESSIVE | 0.022470 | 1.26 |
| CDH13 | 2874 | 4782841 | G | RECESSIVE | 0.032078 | 1.50 |
| KIAA0182 | 2879 | 1053328 | A | DOMINANT | 0.029274 | 0.85 |
| DNAH9 | 2881 | 9904592 | A | DOMINANT | 0.004777 | 1.27 |
| DNAH9 | 2883 | 1990236 | A | ADDITIVE | 0.030533 | 0.84 |
| RAB11FIP4 | 2885 | 770520 | T | ADDITIVE | 0.041981 | 0.97 |
| CA10 | 2888 | 952258 | C | DOMINANT | 0.003866 | 1.23 |
| CA10 | 2889 | 349947 | A | DOMINANT | 0.009860 | 1.20 |

TABLE 2-continued

Alleles and Genotypes Influencing Likelihood of Diagnosis of Bipolar or Schizophrenia

| Gene | SEQ ID NO: | NCBI RS# | Allele | Model | P | Odds Ratio |
|---|---|---|---|---|---|---|
| CA10 | 2890 | 349914 | G | DOMINANT | 0.009759 | 1.20 |
| CA10 | 2891 | 6504780 | T | DOMINANT | 0.024457 | 1.17 |
| CA10 | 2892 | 9916020 | G | RECESSIVE | 0.016853 | 1.28 |
| SDK2 | 2895 | 9909121 | A | DOMINANT | 0.034090 | 0.85 |
| SDK2 | 2896 | 7219778 | A | DOMINANT | 0.032294 | 0.85 |
| DLGAP1 | 2902 | 1791375 | A | ADDITIVE | 0.021983 | 0.84 |
| DLGAP1 | 2903 | 11876399 | C | ADDITIVE | 0.042241 | 0.83 |
| ZFP161 | 2904 | 9948693 | T | ADDITIVE | 0.034816 | 1.11 |
| ZFP161 | 2905 | 1539935 | C | DOMINANT | 0.023740 | 0.84 |
| ZFP161 | 2906 | 2155686 | G | DOMINANT | 0.040997 | 0.85 |
| ZFP161 | 2907 | 990072 | T | ADDITIVE | 0.037763 | 0.87 |
| ZFP161 | 2908 | 9957892 | C | RECESSIVE | 0.016403 | 1.26 |
| ZFP161 | 2909 | 11665417 | T | RECESSIVE | 0.017340 | 1.25 |
| ZFP161 | 2910 | 9945680 | A | RECESSIVE | 0.014368 | 1.26 |
| PTPRM | 2912 | 11081352 | T | DOMINANT | 0.021126 | 1.18 |
| PTPRM | 2913 | 2156236 | T | DOMINANT | 0.008387 | 1.21 |
| PTPRM | 2914 | 5000485 | T | DOMINANT | 0.009215 | 1.20 |
| PTPRM | 2915 | 1942958 | T | DOMINANT | 0.011456 | 1.20 |
| PTPRM | 2916 | 8088354 | A | DOMINANT | 0.009717 | 1.21 |
| PTPRM | 2917 | 649598 | T | DOMINANT | 0.016659 | 1.19 |
| PTPRM | 2918 | 623258 | T | DOMINANT | 0.048530 | 1.15 |
| PTPRM | 2919 | 2230601 | C | DOMINANT | 0.041904 | 1.17 |
| PTPRM | 2920 | 619379 | C | DOMINANT | 0.021461 | 1.18 |
| PTPRM | 2921 | 502843 | T | DOMINANT | 0.011208 | 1.20 |
| PTPRM | 2922 | 552448 | T | DOMINANT | 0.020617 | 1.18 |
| PTPRM | 2923 | 507445 | T | DOMINANT | 0.047780 | 1.15 |
| KIAA0802 | 2924 | 1000080 | C | ADDITIVE | 0.034821 | 0.93 |
| KIAA0802 | 2925 | 11877395 | T | ADDITIVE | 0.026018 | 0.91 |
| KIAA0802 | 2926 | 10502383 | A | ADDITIVE | 0.024860 | 0.90 |
| KIAA0802 | 2927 | 17407982 | C | ADDITIVE | 0.023943 | 0.91 |
| KIAA0802 | 2928 | 17408213 | A | ADDITIVE | 0.023207 | 0.90 |
| OSBPL1A | 2930 | 9945595 | C | DOMINANT | 0.002700 | 0.70 |
| OSBPL1A | 2931 | 275857 | C | DOMINANT | 0.004533 | 0.71 |
| FUSSEL18 | 2939 | 1434507 | T | RECESSIVE | 0.003435 | 0.66 |
| FUSSEL18 | 2940 | 1434514 | C | RECESSIVE | 0.009662 | 0.74 |
| FUSSEL18 | 2941 | 11877471 | G | RECESSIVE | 0.011304 | 0.75 |
| KIAA0427 | 2943 | 169936 | A | ADDITIVE | 0.041137 | 0.86 |
| KIAA0427 | 2944 | 1384227 | C | ADDITIVE | 0.001146 | 0.84 |
| KIAA0427 | 2945 | 1384226 | A | DOMINANT | 0.005707 | 0.82 |
| KIAA0427 | 2946 | 16949850 | G | ADDITIVE | 0.000385 | 0.83 |
| KIAA0427 | 2947 | 9947954 | C | ADDITIVE | 0.012909 | 0.86 |
| KIAA0427 | 2948 | 877885 | A | ADDITIVE | 0.000926 | 0.83 |
| DCC | 2960 | 7233997 | A | DOMINANT | 0.014859 | 0.83 |
| DCC | 2961 | 9957443 | G | DOMINANT | 0.020159 | 0.84 |
| DCC | 2963 | 2879526 | G | DOMINANT | 0.021401 | 0.85 |
| DOK6 | 2983 | 9947842 | C | RECESSIVE | 0.022893 | 1.72 |
| DOK6 | 2984 | 2364201 | T | ADDITIVE | 0.020490 | 1.15 |
| DOK6 | 2985 | 10871643 | G | ADDITIVE | 0.012735 | 1.15 |
| DOK6 | 2986 | 9964498 | T | ADDITIVE | 0.049292 | 1.05 |
| DOK6 | 2987 | 12966827 | C | ADDITIVE | 0.027862 | 1.20 |
| DOK6 | 2988 | 1550597 | C | ADDITIVE | 0.041182 | 1.18 |
| DOK6 | 2989 | 1550598 | A | ADDITIVE | 0.042207 | 1.22 |
| DOK6 | 2990 | 1992488 | C | ADDITIVE | 0.037761 | 1.20 |
| DOK6 | 2992 | 12967804 | T | RECESSIVE | 0.039890 | 1.20 |
| DOK6 | 2993 | 12968689 | A | RECESSIVE | 0.039259 | 1.20 |
| DOK6 | 2994 | 9965360 | A | DOMINANT | 0.028614 | 0.85 |
| MBP | 2996 | 12967023 | A | ADDITIVE | 0.035505 | 1.20 |
| MBP | 2997 | 17576996 | C | ADDITIVE | 0.031055 | 1.21 |
| MBP | 2998 | 7232502 | T | DOMINANT | 0.009987 | 1.21 |
| MBP | 2999 | 8085877 | G | RECESSIVE | 0.033747 | 1.27 |
| MBP | 3000 | 1868655 | C | ADDITIVE | 0.035758 | 1.09 |
| ZNF667 | 3003 | 7251105 | G | DOMINANT | 0.038115 | 0.86 |
| RNF24 | 3008 | 2143235 | A | ADDITIVE | 0.007496 | 1.24 |
| FERMT1 | 3015 | 16991765 | A | RECESSIVE | 0.001650 | 3.26 |
| FERMT1 | 3016 | 11700199 | A | RECESSIVE | 0.001192 | 4.88 |
| FERMT1 | 3017 | 11700084 | C | RECESSIVE | 0.010871 | 1.88 |
| FERMT1 | 3018 | 6516104 | T | RECESSIVE | 0.001978 | 4.07 |
| FERMT1 | 3019 | 7268391 | C | RECESSIVE | 0.002881 | 3.91 |
| PLCB1 | 3020 | 6118083 | G | RECESSIVE | 0.039048 | 0.68 |
| PLCB1 | 3026 | 1237829 | A | DOMINANT | 0.028785 | 0.86 |
| PLCB1 | 3027 | 1237071 | A | DOMINANT | 0.024043 | 0.85 |
| PLCB4 | 3033 | 6086900 | T | RECESSIVE | 0.024142 | 0.20 |
| PLCB4 | 3034 | 6077549 | T | RECESSIVE | 0.011337 | 0.65 |
| PLCB4 | 3035 | 6077552 | G | RECESSIVE | 0.043659 | 0.32 |
| MACROD2 | 3039 | 6079391 | T | RECESSIVE | 0.011533 | 1.26 |
| MACROD2 | 3041 | 2208135 | G | RECESSIVE | 0.024086 | 0.82 |

TABLE 2-continued

Alleles and Genotypes Influencing Likelihood of Diagnosis of Bipolar or Schizophrenia

| Gene | SEQ ID NO: | NCBI RS# | Allele | Model | P | Odds Ratio |
|---|---|---|---|---|---|---|
| MACROD2 | 3043 | 6074905 | A | RECESSIVE | 0.030731 | 0.82 |
| MACROD2 | 3046 | 6034296 | G | RECESSIVE | 0.033971 | 1.56 |
| MACROD2 | 3047 | 175810 | G | RECESSIVE | 0.029735 | 1.59 |
| MACROD2 | 3048 | 175805 | T | RECESSIVE | 0.039405 | 1.53 |
| MACROD2 | 3049 | 6080100 | C | DOMINANT | 0.010450 | 1.20 |
| KIF16B | 3051 | 6044021 | T | DOMINANT | 0.005183 | 0.81 |
| PTPRT | 3058 | 2223540 | T | DOMINANT | 0.042570 | 0.87 |
| KCNB1 | 3059 | 6095546 | A | DOMINANT | 0.017233 | 1.18 |
| PTGIS | 3060 | 4647 | T | DOMINANT | 0.021768 | 1.18 |
| PTGIS | 3061 | 5629 | A | DOMINANT | 0.015779 | 1.19 |
| PTGIS | 3062 | 6019876 | C | DOMINANT | 0.031979 | 1.16 |
| PTGIS | 3063 | 495146 | T | ADDITIVE | 0.044751 | 1.16 |
| BMP7 | 3065 | 6070015 | A | RECESSIVE | 0.024126 | 0.20 |
| BMP7 | 3066 | 162313 | A | DOMINANT | 0.016012 | 0.82 |
| BMP7 | 3067 | 2180782 | C | DOMINANT | 0.001178 | 0.78 |
| BMP7 | 3068 | 1015985 | A | DOMINANT | 0.013295 | 0.81 |
| BMP7 | 3069 | 6127980 | A | DOMINANT | 0.036373 | 0.84 |
| BMP7 | 3070 | 6127985 | A | DOMINANT | 0.003333 | 0.80 |
| GNAS | 3072 | 8386 | T | DOMINANT | 0.019343 | 0.60 |
| CDH4 | 3076 | 6028127 | G | RECESSIVE | 0.019399 | 0.75 |
| CDH4 | 3077 | 6061722 | C | ADDITIVE | 0.002832 | 1.11 |
| CDH4 | 3078 | 6121761 | A | DOMINANT | 0.011894 | 1.20 |
| CDH4 | 3079 | 6121764 | G | DOMINANT | 0.009310 | 1.21 |
| CDH4 | 3080 | 1317385 | C | DOMINANT | 0.006347 | 1.22 |
| CDH4 | 3082 | 2427142 | G | DOMINANT | 0.008281 | 0.82 |
| CDH4 | 3083 | 6089264 | G | DOMINANT | 0.016691 | 1.19 |
| CDH4 | 3084 | 6089476 | A | ADDITIVE | 0.018997 | 1.23 |
| CDH4 | 3085 | 6089479 | G | DOMINANT | 0.016246 | 1.19 |
| NCAM2 | 3091 | 2826349 | G | DOMINANT | 0.031339 | 0.86 |
| NCAM2 | 3092 | 2826351 | A | DOMINANT | 0.025268 | 0.85 |
| NCAM2 | 3093 | 9980583 | G | RECESSIVE | 0.002420 | 0.54 |
| PCP4 | 3110 | 1011037 | A | ADDITIVE | 0.011279 | 0.79 |
| PCP4 | 3111 | 2837283 | T | ADDITIVE | 0.034281 | 0.82 |
| PCP4 | 3112 | 2837286 | C | ADDITIVE | 0.035252 | 0.82 |
| SLC37A1 | 3114 | 228058 | A | DOMINANT | 0.023159 | 1.19 |
| SLC37A1 | 3115 | 228067 | A | DOMINANT | 0.015615 | 1.21 |
| ARVCF | 3120 | 2239395 | G | RECESSIVE | 0.017496 | >5 |
| HPS4 | 3123 | 929131 | T | ADDITIVE | 0.046458 | 0.80 |
| RIBC2 | 3141 | 5765425 | A | DOMINANT | 0.029442 | 0.85 |

Table A provides a summary of the SNPs (numbering is based on NCBI Human Genome Reference Assembly Build 36.3).

TABLE A

Summary of SNPs (NCBI Human Genome Reference Assembly Build 36.3)

| SEQ ID NO: | Gene | Chr | Position (BP) | SEQ ID NO: | Gene | Chr | Position (BP) |
|---|---|---|---|---|---|---|---|
| 1 | KIF1B | 1 | 10,323,189 | 2 | PRDM2 | 1 | 13,817,155 |
| 3 | RP1-21O18.1 | 1 | 15,149,071 | 4 | RP1-21O18.1 | 1 | 15,160,805 |
| 5 | RP1-21O18.1 | 1 | 15,278,076 | 6 | RP1-21O18.1 | 1 | 15,281,743 |
| 7 | RP1-21O18.1 | 1 | 15,284,856 | 8 | RP1-21O18.1 | 1 | 15,287,000 |
| 9 | EPHB2 | 1 | 23,091,301 | 10 | EPHB2 | 1 | 23,092,613 |
| 11 | CLIC4 | 1 | 24,939,035 | 12 | CLIC4 | 1 | 25,040,711 |
| 13 | AGBL4-C1ORF165 | 1 | 49,010,181 | 14 | AGBL4-C1ORF165 | 1 | 49,013,544 |
| 15 | AGBL4-C1ORF165 | 1 | 49,021,571 | 16 | AGBL4-C1ORF165 | 1 | 49,025,043 |
| 17 | AGBL4-C1ORF165 | 1 | 49,046,634 | 18 | AGBL4-C1ORF165 | 1 | 49,109,043 |
| 19 | AGBL4-C1ORF165 | 1 | 49,214,610 | 20 | AGBL4-C1ORF165 | 1 | 49,219,672 |
| 21 | AGBL4-C1ORF165 | 1 | 49,223,291 | 22 | AGBL4-C1ORF165 | 1 | 49,236,388 |
| 23 | AGBL4-C1ORF165 | 1 | 49,239,649 | 24 | AGBL4-C1ORF165 | 1 | 49,240,612 |
| 25 | AGBL4-C1ORF165 | 1 | 49,243,353 | 26 | AGBL4-C1ORF165 | 1 | 49,255,290 |
| 27 | AGBL4-C1ORF165 | 1 | 49,278,082 | 28 | LRP8 | 1 | 53,480,541 |
| 29 | LRP8 | 1 | 53,484,323 | 30 | LRP8 | 1 | 53,486,137 |
| 31 | LRP8 | 1 | 53,495,778 | 32 | LRP8 | 1 | 53,495,937 |
| 33 | LRP8 | 1 | 53,504,903 | 34 | LRP8 | 1 | 53,519,183 |
| 35 | LRP8 | 1 | 53,524,198 | 36 | LRP8 | 1 | 53,581,281 |
| 37 | LRP8 | 1 | 53,584,530 | 38 | LRP8 | 1 | 53,584,799 |
| 39 | PRKACB | 1 | 84,421,173 | 40 | SLC6A17 | 1 | 110,525,368 |
| 41 | SLC6A17 | 1 | 110,533,656 | 42 | SLC16A4 | 1 | 110,706,448 |
| 43 | SLC16A4 | 1 | 110,711,920 | 44 | SLC16A4 | 1 | 110,723,238 |

TABLE A-continued

Summary of SNPs (NCBI Human Genome Reference Assembly Build 36.3)

| SEQ ID NO: | Gene | Chr | Position (BP) | SEQ ID NO: | Gene | Chr | Position (BP) |
|---|---|---|---|---|---|---|---|
| 45 | KCNA10 | 1 | 110,862,534 | 46 | SYT6 | 1 | 114,452,599 |
| 47 | NGF | 1 | 115,662,788 | 48 | NGF | 1 | 115,668,794 |
| 49 | NGF | 1 | 115,674,570 | 50 | NGF | 1 | 115,677,168 |
| 51 | NGF | 1 | 115,679,147 | 52 | SLC22A15 | 1 | 116,328,295 |
| 53 | SLC22A15 | 1 | 116,328,591 | 54 | SLC22A15 | 1 | 116,406,946 |
| 55 | PTGFRN | 1 | 117,277,238 | 56 | PTGFRN | 1 | 117,316,638 |
| 57 | PTGFRN | 1 | 117,324,524 | 58 | PTGFRN | 1 | 117,333,336 |
| 59 | CGN | 1 | 149,743,817 | 60 | CGN | 1 | 149,743,936 |
| 61 | CGN | 1 | 149,763,826 | 62 | CGN | 1 | 149,776,650 |
| 63 | ATF6 | 1 | 160,007,898 | 64 | ATF6 | 1 | 160,014,680 |
| 65 | ATF6 | 1 | 160,038,140 | 66 | ATF6 | 1 | 160,052,935 |
| 67 | ATF6 | 1 | 160,058,351 | 68 | ATF6 | 1 | 160,062,520 |
| 69 | ATF6 | 1 | 160,076,775 | 70 | ATF6 | 1 | 160,101,070 |
| 71 | ATF6 | 1 | 160,102,111 | 72 | ATF6 | 1 | 160,107,168 |
| 73 | ATF6 | 1 | 160,118,977 | 74 | ATF6 | 1 | 160,166,085 |
| 75 | ATF6 | 1 | 160,166,355 | 76 | ATF6 | 1 | 160,173,294 |
| 77 | ATF6 | 1 | 160,176,223 | 78 | ATF6 | 1 | 160,176,587 |
| 79 | ATF6 | 1 | 160,197,100 | 80 | OLFML2B | 1 | 160,230,231 |
| 81 | OLFML2B | 1 | 160,230,414 | 82 | OLFML2B | 1 | 160,231,160 |
| 83 | OLFML2B | 1 | 160,231,641 | 84 | OLFML2B | 1 | 160,233,911 |
| 85 | FAM78B | 1 | 164,307,179 | 86 | FAM78B | 1 | 164,382,610 |
| 87 | FAM78B | 1 | 164,385,520 | 88 | FAM78B | 1 | 164,388,390 |
| 89 | FAM78B | 1 | 164,392,047 | 90 | DPT | 1 | 166,961,651 |
| 91 | SEC16B | 1 | 176,201,673 | 92 | CACNA1E | 1 | 179,723,323 |
| 93 | CACNA1E | 1 | 179,726,011 | 94 | CACNA1E | 1 | 179,745,206 |
| 95 | CACNA1E | 1 | 179,746,806 | 96 | CACNA1E | 1 | 179,845,854 |
| 97 | CACNA1E | 1 | 179,913,657 | 98 | CACNA1E | 1 | 179,939,026 |
| 99 | CACNA1E | 1 | 179,941,514 | 100 | CACNA1E | 1 | 179,980,795 |
| 101 | CACNA1E | 1 | 179,993,896 | 102 | CACNA1E | 1 | 180,019,653 |
| 103 | LAMC1 | 1 | 181,258,040 | 104 | LAMC1 | 1 | 181,290,319 |
| 105 | LAMC1 | 1 | 181,295,593 | 106 | LAMC1 | 1 | 181,299,851 |
| 107 | LAMC1 | 1 | 181,319,156 | 108 | LAMC1 | 1 | 181,342,355 |
| 109 | LAMC1 | 1 | 181,342,401 | 110 | LAMC1 | 1 | 181,343,643 |
| 111 | LAMC1 | 1 | 181,344,420 | 112 | LAMC1 | 1 | 181,344,519 |
| 113 | LAMC1 | 1 | 181,348,490 | 114 | LAMC1 | 1 | 181,352,319 |
| 115 | LAMC1 | 1 | 181,352,378 | 116 | LAMC1 | 1 | 181,359,123 |
| 117 | LAMC1 | 1 | 181,359,651 | 118 | LAMC1 | 1 | 181,366,003 |
| 119 | LAMC1 | 1 | 181,374,069 | 120 | LAMC1 | 1 | 181,375,234 |
| 121 | PLA2G4A | 1 | 185,146,514 | 122 | KCNH1 | 1 | 209,006,965 |
| 123 | KCNH1 | 1 | 209,007,097 | 124 | KCNH1 | 1 | 209,024,314 |
| 125 | KCNH1 | 1 | 209,149,546 | 126 | KCNH1 | 1 | 209,219,982 |
| 127 | KCNH1 | 1 | 209,229,662 | 128 | KCNH1 | 1 | 209,339,441 |
| 129 | KCNH1 | 1 | 209,361,502 | 130 | KCNK2 | 1 | 213,245,368 |
| 131 | KCNK2 | 1 | 213,266,926 | 132 | KCNK2 | 1 | 213,312,765 |
| 133 | KCNK2 | 1 | 213,428,830 | 134 | KCNK2 | 1 | 213,444,580 |
| 135 | KCNK2 | 1 | 213,453,686 | 136 | KCNK2 | 1 | 213,456,232 |
| 137 | KCNK2 | 1 | 213,474,680 | 138 | USH2A | 1 | 213,507,653 |
| 139 | USH2A | 1 | 213,585,997 | 140 | USH2A | 1 | 213,857,628 |
| 141 | USH2A | 1 | 213,883,311 | 142 | USH2A | 1 | 214,020,229 |
| 143 | ESRRG | 1 | 214,908,407 | 144 | ESRRG | 1 | 214,962,423 |
| 145 | SLC35F3 | 1 | 232,337,540 | 146 | SLC35F3 | 1 | 232,338,040 |
| 147 | SLC35F3 | 1 | 232,344,068 | 148 | SLC35F3 | 1 | 232,348,338 |
| 149 | SLC35F3 | 1 | 232,349,217 | 150 | SLC35F3 | 1 | 232,515,592 |
| 151 | GNG4 | 1 | 233,794,439 | 152 | GNG4 | 1 | 233,869,010 |
| 153 | GNG4 | 1 | 233,869,096 | 154 | RYR2 | 1 | 235,313,686 |
| 155 | RYR2 | 1 | 235,400,588 | 156 | RYR2 | 1 | 235,593,923 |
| 157 | RYR2 | 1 | 235,793,735 | 158 | RYR2 | 1 | 235,795,490 |
| 159 | CHRM3 | 1 | 237,867,474 | 160 | FMN2 | 1 | 238,486,712 |
| 161 | FMN2 | 1 | 238,494,888 | 162 | FMN2 | 1 | 238,564,221 |
| 163 | FMN2 | 1 | 238,564,870 | 164 | FMN2 | 1 | 238,575,081 |
| 165 | FMN2 | 1 | 238,575,190 | 166 | RGS7 | 1 | 239,432,765 |
| 167 | PLD5 | 1 | 240,696,081 | 168 | PLD5 | 1 | 240,696,530 |
| 169 | C2ORF46Â | 2 | 8,256,296 | 170 | C2ORF46Â | 2 | 8,262,682 |
| 171 | C2ORF46Â | 2 | 8,276,150 | 172 | DDEF2 | 2 | 9,293,513 |
| 173 | DDEF2 | 2 | 9,309,142 | 174 | DDEF2 | 2 | 9,320,439 |
| 175 | DDEF2 | 2 | 9,335,725 | 176 | DDEF2 | 2 | 9,347,069 |
| 177 | DDEF2 | 2 | 9,347,151 | 178 | DDEF2 | 2 | 9,351,380 |
| 179 | DDEF2 | 2 | 9,352,262 | 180 | DDEF2 | 2 | 9,352,592 |
| 181 | DDEF2 | 2 | 9,356,883 | 182 | DDEF2 | 2 | 9,358,353 |
| 183 | DDEF2 | 2 | 9,361,294 | 184 | DDEF2 | 2 | 9,375,632 |
| 185 | DDEF2 | 2 | 9,375,911 | 186 | DDEF2 | 2 | 9,376,857 |
| 187 | DDEF2 | 2 | 9,377,685 | 188 | DDEF2 | 2 | 9,383,138 |
| 189 | DDEF2 | 2 | 9,392,788 | 190 | DDEF2 | 2 | 9,398,018 |
| 191 | DDEF2 | 2 | 9,431,301 | 192 | KCNF1 | 2 | 10,935,452 |
| 193 | NAG | 2 | 15,335,505 | 194 | NAG | 2 | 15,368,097 |

TABLE A-continued

Summary of SNPs (NCBI Human Genome Reference Assembly Build 36.3)

| SEQ ID NO: | Gene | Chr | Position (BP) | SEQ ID NO: | Gene | Chr | Position (BP) |
|---|---|---|---|---|---|---|---|
| 195 | HS1BP3 | 2 | 20,680,974 | 196 | HS1BP3 | 2 | 20,681,154 |
| 197 | HS1BP3 | 2 | 20,702,827 | 198 | KLHL29 | 2 | 23,469,562 |
| 199 | KLHL29 | 2 | 23,482,236 | 200 | KLHL29 | 2 | 23,503,207 |
| 201 | KLHL29 | 2 | 23,504,556 | 202 | KLHL29 | 2 | 23,504,709 |
| 203 | KLHL29 | 2 | 23,504,805 | 204 | KLHL29 | 2 | 23,512,565 |
| 205 | KLHL29 | 2 | 23,518,985 | 206 | KLHL29 | 2 | 23,519,201 |
| 207 | KLHL29 | 2 | 23,529,537 | 208 | KLHL29 | 2 | 23,554,108 |
| 209 | KLHL29 | 2 | 23,554,609 | 210 | ASXL2 | 2 | 25,823,233 |
| 211 | ASXL2 | 2 | 25,859,983 | 212 | ASXL2 | 2 | 25,871,731 |
| 213 | CIB4 | 2 | 26,718,111 | 214 | KCNK3 | 2 | 26,806,502 |
| 215 | DPYSL5 | 2 | 26,936,063 | 216 | DPYSL5 | 2 | 26,936,993 |
| 217 | BRE | 2 | 27,955,442 | 218 | BRE | 2 | 28,059,085 |
| 219 | BRE | 2 | 28,085,591 | 220 | BRE | 2 | 28,094,029 |
| 221 | BRE | 2 | 28,121,971 | 222 | BRE | 2 | 28,377,338 |
| 223 | CRIM1 | 2 | 36,532,532 | 224 | CRIM1 | 2 | 36,535,123 |
| 225 | CRIM1 | 2 | 36,545,455 | 226 | CRIM1 | 2 | 36,549,124 |
| 227 | CRIM1 | 2 | 36,553,482 | 228 | CRIM1 | 2 | 36,554,084 |
| 229 | CRIM1 | 2 | 36,557,648 | 230 | CRIM1 | 2 | 36,558,502 |
| 231 | CRIM1 | 2 | 36,581,523 | 232 | CRIM1 | 2 | 36,581,946 |
| 233 | CRIM1 | 2 | 36,592,075 | 234 | CRIM1 | 2 | 36,594,147 |
| 235 | CRIM1 | 2 | 36,598,516 | 236 | CRIM1 | 2 | 36,610,853 |
| 237 | CRIM1 | 2 | 36,611,604 | 238 | FEZ2 | 2 | 36,632,391 |
| 239 | FEZ2 | 2 | 36,634,053 | 240 | FEZ2 | 2 | 36,634,284 |
| 241 | FEZ2 | 2 | 36,634,524 | 242 | FEZ2 | 2 | 36,634,642 |
| 243 | FEZ2 | 2 | 36,634,905 | 244 | FEZ2 | 2 | 36,644,730 |
| 245 | FEZ2 | 2 | 36,645,798 | 246 | FEZ2 | 2 | 36,655,361 |
| 247 | FEZ2 | 2 | 36,657,394 | 248 | FEZ2 | 2 | 36,663,977 |
| 249 | FEZ2 | 2 | 36,672,274 | 250 | FEZ2 | 2 | 36,673,724 |
| 251 | CDC42EP3 | 2 | 37,718,574 | 252 | CDC42EP3 | 2 | 37,726,375 |
| 253 | SLC8A1 | 2 | 40,381,169 | 254 | SLC8A1 | 2 | 40,406,693 |
| 255 | SLC8A1 | 2 | 40,409,237 | 256 | HAAO | 2 | 42,900,658 |
| 257 | HAAO | 2 | 42,911,782 | 258 | PLEKHH2 | 2 | 43,817,582 |
| 259 | PLEKHH2 | 2 | 43,839,444 | 260 | PLEKHH2 | 2 | 43,846,952 |
| 261 | C2ORF34 | 2 | 44,443,570 | 262 | C2ORF34 | 2 | 44,446,479 |
| 263 | C2ORF34 | 2 | 44,457,570 | 264 | C2ORF34 | 2 | 44,458,445 |
| 265 | C2ORF34 | 2 | 44,474,546 | 266 | C2ORF34 | 2 | 44,497,761 |
| 267 | C2ORF34 | 2 | 44,499,415 | 268 | C2ORF34 | 2 | 44,500,542 |
| 269 | C2ORF34 | 2 | 44,501,551 | 270 | C2ORF34 | 2 | 44,503,622 |
| 271 | C2ORF34 | 2 | 44,503,754 | 272 | C2ORF34 | 2 | 44,508,409 |
| 273 | C2ORF34 | 2 | 44,514,120 | 274 | C2ORF34 | 2 | 44,516,656 |
| 275 | C2ORF34 | 2 | 44,524,500 | 276 | C2ORF34 | 2 | 44,524,913 |
| 277 | C2ORF34 | 2 | 44,525,669 | 278 | C2ORF34 | 2 | 44,527,954 |
| 279 | C2ORF34 | 2 | 44,529,327 | 280 | C2ORF34 | 2 | 44,529,730 |
| 281 | C2ORF34 | 2 | 44,532,789 | 282 | C2ORF34 | 2 | 44,536,723 |
| 283 | C2ORF34 | 2 | 44,538,657 | 284 | C2ORF34 | 2 | 44,539,189 |
| 285 | C2ORF34 | 2 | 44,546,928 | 286 | C2ORF34 | 2 | 44,556,482 |
| 287 | C2ORF34 | 2 | 44,574,451 | 288 | C2ORF34 | 2 | 44,576,627 |
| 289 | C2ORF34 | 2 | 44,584,000 | 290 | C2ORF34 | 2 | 44,584,081 |
| 291 | C2ORF34 | 2 | 44,588,327 | 292 | C2ORF34 | 2 | 44,588,942 |
| 293 | C2ORF34 | 2 | 44,589,457 | 294 | C2ORF34 | 2 | 44,593,376 |
| 295 | C2ORF34 | 2 | 44,599,767 | 296 | C2ORF34 | 2 | 44,610,492 |
| 297 | C2ORF34 | 2 | 44,613,163 | 298 | C2ORF34 | 2 | 44,621,606 |
| 299 | C2ORF34 | 2 | 44,631,967 | 300 | C2ORF34 | 2 | 44,635,233 |
| 301 | C2ORF34 | 2 | 44,643,689 | 302 | C2ORF34 | 2 | 44,645,848 |
| 303 | C2ORF34 | 2 | 44,648,280 | 304 | C2ORF34 | 2 | 44,815,520 |
| 305 | C2ORF34 | 2 | 44,834,212 | 306 | C2ORF34 | 2 | 44,846,991 |
| 307 | PRKCE | 2 | 45,955,890 | 308 | PRKCE | 2 | 45,979,919 |
| 309 | PRKCE | 2 | 46,065,162 | 310 | PRKCE | 2 | 46,141,058 |
| 311 | EPAS1 | 2 | 46,449,937 | 312 | EPAS1 | 2 | 46,451,331 |
| 313 | EPAS1 | 2 | 46,462,046 | 314 | PSME4 | 2 | 53,987,248 |
| 315 | ACYP2 | 2 | 54,216,479 | 316 | CCDC85A | 2 | 56,457,489 |
| 317 | COMMD1 | 2 | 62,054,981 | 318 | COMMD1 | 2 | 62,127,627 |
| 319 | COMMD1 | 2 | 62,193,184 | 320 | COMMD1 | 2 | 62,221,224 |
| 321 | AAK1 | 2 | 69,569,349 | 322 | AAK1 | 2 | 69,630,234 |
| 323 | AAK1 | 2 | 69,635,501 | 324 | AAK1 | 2 | 69,637,782 |
| 325 | AAK1 | 2 | 69,685,140 | 326 | AAK1 | 2 | 69,832,899 |
| 327 | CTNNA2 | 2 | 79,635,253 | 328 | CTNNA2 | 2 | 79,726,512 |
| 329 | CTNNA2 | 2 | 79,826,944 | 330 | CTNNA2 | 2 | 80,167,469 |
| 331 | CTNNA2 | 2 | 80,218,704 | 332 | CTNNA2 | 2 | 80,251,439 |
| 333 | CTNNA2 | 2 | 80,252,218 | 334 | CTNNA2 | 2 | 80,266,636 |
| 335 | CTNNA2 | 2 | 80,266,949 | 336 | CTNNA2 | 2 | 80,274,207 |
| 337 | CTNNA2 | 2 | 80,274,788 | 338 | CTNNA2 | 2 | 80,287,912 |
| 339 | CTNNA2 | 2 | 80,288,147 | 340 | CTNNA2 | 2 | 80,299,023 |
| 341 | CTNNA2 | 2 | 80,304,589 | 342 | CTNNA2 | 2 | 80,304,695 |
| 343 | CTNNA2 | 2 | 80,305,615 | 344 | CTNNA2 | 2 | 80,313,674 |

TABLE A-continued

Summary of SNPs (NCBI Human Genome Reference Assembly Build 36.3)

| SEQ ID NO: | Gene | Chr | Position (BP) | SEQ ID NO: | Gene | Chr | Position (BP) |
|---|---|---|---|---|---|---|---|
| 345 | INPP4A | 2 | 98,530,592 | 346 | NAP5 | 2 | 133,502,847 |
| 347 | NAP5 | 2 | 133,546,849 | 348 | NAP5 | 2 | 133,547,260 |
| 349 | NAP5 | 2 | 133,589,500 | 350 | NAP5 | 2 | 134,042,993 |
| 351 | RAB3GAP1 | 2 | 135,513,693 | 352 | RAB3GAP1 | 2 | 135,520,236 |
| 353 | RAB3GAP1 | 2 | 135,535,377 | 354 | RAB3GAP1 | 2 | 135,607,078 |
| 355 | RAB3GAP1 | 2 | 135,624,316 | 356 | ZRANB3 | 2 | 135,867,882 |
| 357 | LRP1B | 2 | 140,711,565 | 358 | LRP1B | 2 | 140,749,675 |
| 359 | LRP1B | 2 | 141,253,166 | 360 | LRP1B | 2 | 141,287,799 |
| 361 | LRP1B | 2 | 141,480,634 | 362 | LRP1B | 2 | 141,495,066 |
| 363 | LRP1B | 2 | 141,495,534 | 364 | LRP1B | 2 | 142,281,762 |
| 365 | LRP1B | 2 | 142,298,733 | 366 | LRP1B | 2 | 142,358,098 |
| 367 | LRP1B | 2 | 142,360,248 | 368 | LRP1B | 2 | 142,363,092 |
| 369 | LRP1B | 2 | 142,363,404 | 370 | LRP1B | 2 | 142,371,205 |
| 371 | LRP1B | 2 | 142,518,411 | 372 | LRP1B | 2 | 142,529,079 |
| 373 | LRP1B | 2 | 142,529,190 | 374 | LRP1B | 2 | 142,530,425 |
| 375 | LRP1B | 2 | 142,537,344 | 376 | LRP1B | 2 | 142,544,454 |
| 377 | LRP1B | 2 | 142,568,099 | 378 | LRP1B | 2 | 142,572,993 |
| 379 | LRP1B | 2 | 142,590,723 | 380 | LRP1B | 2 | 142,591,415 |
| 381 | LRP1B | 2 | 142,592,521 | 382 | KYNU | 2 | 143,365,273 |
| 383 | KYNU | 2 | 143,436,812 | 384 | KYNU | 2 | 143,474,395 |
| 385 | ARHGAP15 | 2 | 143,773,914 | 386 | ARHGAP15 | 2 | 143,999,263 |
| 387 | ARHGAP15 | 2 | 144,018,166 | 388 | ARHGAP15 | 2 | 144,025,496 |
| 389 | ARHGAP15 | 2 | 144,034,639 | 390 | ARHGAP15 | 2 | 144,059,774 |
| 391 | ARHGAP15 | 2 | 144,264,615 | 392 | ARHGAP15 | 2 | 144,283,468 |
| 393 | ARHGAP15 | 2 | 144,294,622 | 394 | CACNB4 | 2 | 152,552,320 |
| 395 | FMNL2 | 2 | 153,113,840 | 396 | FMNL2 | 2 | 153,122,655 |
| 397 | FMNL2 | 2 | 153,123,190 | 398 | FMNL2 | 2 | 153,153,555 |
| 399 | KCNJ3 | 2 | 155,340,539 | 400 | PKP4 | 2 | 159,101,556 |
| 401 | PKP4 | 2 | 159,208,949 | 402 | PLA2R1 | 2 | 160,516,560 |
| 403 | PLA2R1 | 2 | 160,543,237 | 404 | PLA2R1 | 2 | 160,594,118 |
| 405 | PLA2R1 | 2 | 160,598,673 | 406 | PLA2R1 | 2 | 160,599,255 |
| 407 | PLA2R1 | 2 | 160,599,934 | 408 | KCNH7 | 2 | 163,243,409 |
| 409 | KCNH7 | 2 | 163,253,109 | 410 | KCNH7 | 2 | 163,256,031 |
| 411 | SCN3A | 2 | 165,694,177 | 412 | SCN2A | 2 | 165,846,854 |
| 413 | SCN2A | 2 | 165,927,516 | 414 | SCN2A | 2 | 165,927,991 |
| 415 | SCN2A | 2 | 165,948,264 | 416 | SCN1A | 2 | 166,626,965 |
| 417 | SCN1A | 2 | 166,628,663 | 418 | SCN1A | 2 | 166,629,033 |
| 419 | SCN1A | 2 | 166,632,718 | 420 | SCN1A | 2 | 166,633,217 |
| 421 | SCN1A | 2 | 166,633,417 | 422 | SCN9A | 2 | 166,764,674 |
| 423 | SCN9A | 2 | 166,814,951 | 424 | SCN9A | 2 | 166,844,835 |
| 425 | SCN9A | 2 | 166,853,220 | 426 | SCN7A | 2 | 166,970,242 |
| 427 | SCN7A | 2 | 166,991,078 | 428 | SCN7A | 2 | 167,027,829 |
| 429 | SCN7A | 2 | 167,034,898 | 430 | SCN7A | 2 | 167,056,881 |
| 431 | SCN7A | 2 | 167,057,716 | 432 | CERKL | 2 | 182,228,354 |
| 433 | PDE1A | 2 | 182,874,241 | 434 | PDE1A | 2 | 182,910,657 |
| 435 | PDE1A | 2 | 182,918,516 | 436 | PDE1A | 2 | 182,919,054 |
| 437 | PDE1A | 2 | 182,919,225 | 438 | PDE1A | 2 | 182,932,372 |
| 439 | PDE1A | 2 | 182,970,373 | 440 | PDE1A | 2 | 182,971,998 |
| 441 | NAB1 | 2 | 191,177,207 | 442 | TMEFF2 | 2 | 192,701,461 |
| 443 | TMEFF2 | 2 | 192,712,421 | 444 | TMEFF2 | 2 | 192,715,868 |
| 445 | TMEFF2 | 2 | 192,740,989 | 446 | TMEFF2 | 2 | 192,743,968 |
| 447 | ALS2Â | 2 | 202,269,099 | 448 | ABI2 | 2 | 203,952,004 |
| 449 | ABI2 | 2 | 203,985,853 | 450 | PARD3B | 2 | 205,237,235 |
| 451 | PARD3B | 2 | 205,244,163 | 452 | PARD3B | 2 | 205,538,236 |
| 453 | PARD3B | 2 | 206,182,257 | 454 | PARD3B | 2 | 206,188,103 |
| 455 | NRP2 | 2 | 206,300,940 | 456 | NRP2 | 2 | 206,301,486 |
| 457 | NRP2 | 2 | 206,318,296 | 458 | PIP5K3 | 2 | 208,843,584 |
| 459 | ERBB4 | 2 | 211,945,133 | 460 | ERBB4 | 2 | 213,507,240 |
| 461 | ERBB4 | 2 | 213,507,896 | 462 | IRS1 | 2 | 227,304,756 |
| 463 | IRS1 | 2 | 227,307,777 | 464 | IRS1 | 2 | 227,310,525 |
| 465 | IRS1 | 2 | 227,322,249 | 466 | IRS1 | 2 | 227,322,481 |
| 467 | IRS1 | 2 | 227,385,837 | 468 | IRS1 | 2 | 227,388,355 |
| 469 | COL4A4 | 2 | 227,575,963 | 470 | COL4A4 | 2 | 227,581,239 |
| 471 | COL4A4 | 2 | 227,583,201 | 472 | COL4A4 | 2 | 227,583,604 |
| 473 | COL4A4 | 2 | 227,591,892 | 474 | COL4A4 | 2 | 227,597,803 |
| 475 | COL4A4 | 2 | 227,600,105 | 476 | COL4A4 | 2 | 227,601,261 |
| 477 | COL4A4 | 2 | 227,604,676 | 478 | COL4A4 | 2 | 227,604,896 |
| 479 | COL4A4 | 2 | 227,606,678 | 480 | COL4A4 | 2 | 227,608,663 |
| 481 | COL4A4 | 2 | 227,613,183 | 482 | COL4A4 | 2 | 227,664,311 |
| 483 | COL4A3 | 2 | 227,857,351 | 484 | COL4A3 | 2 | 227,864,201 |
| 485 | COL4A3 | 2 | 227,864,848 | 486 | COL4A3 | 2 | 227,885,723 |
| 487 | COL4A3 | 2 | 227,886,069 | 488 | DNER | 2 | 229,964,830 |
| 489 | DNER | 2 | 229,972,935 | 490 | DNER | 2 | 230,109,326 |
| 491 | DNER | 2 | 230,110,447 | 492 | DNER | 2 | 230,145,109 |
| 493 | ECEL1 | 2 | 233,017,310 | 494 | CHRND | 2 | 233,088,264 |

TABLE A-continued

Summary of SNPs (NCBI Human Genome Reference Assembly Build 36.3)

| SEQ ID NO: | Gene | Chr | Position (BP) | SEQ ID NO: | Gene | Chr | Position (BP) |
|---|---|---|---|---|---|---|---|
| 495 | SAG | 2 | 233,912,247 | 496 | SAG | 2 | 233,912,366 |
| 497 | SAG | 2 | 233,912,663 | 498 | CENTG2 | 2 | 236,372,905 |
| 499 | CENTG2 | 2 | 236,487,308 | 500 | CENTG2 | 2 | 236,601,492 |
| 501 | CNTN6 | 3 | 1,206,334 | 502 | CNTN6 | 3 | 1,222,859 |
| 503 | CNTN6 | 3 | 1,372,069 | 504 | CNTN6 | 3 | 1,372,414 |
| 505 | CNTN6 | 3 | 1,396,673 | 506 | CNTN6 | 3 | 1,396,885 |
| 507 | CNTN6 | 3 | 1,396,900 | 508 | CNTN6 | 3 | 1,399,718 |
| 509 | CNTN6 | 3 | 1,399,850 | 510 | CNTN6 | 3 | 1,400,168 |
| 511 | CNTN6 | 3 | 1,400,506 | 512 | CNTN6 | 3 | 1,417,951 |
| 513 | CNTN4 | 3 | 2,461,763 | 514 | CNTN4 | 3 | 2,462,786 |
| 515 | CNTN4 | 3 | 2,584,580 | 516 | CNTN4 | 3 | 2,588,001 |
| 517 | CNTN4 | 3 | 2,729,042 | 518 | CNTN4 | 3 | 2,733,163 |
| 519 | CNTN4 | 3 | 2,734,283 | 520 | CNTN4 | 3 | 2,751,927 |
| 521 | CNTN4 | 3 | 3,044,773 | 522 | CNTN4 | 3 | 3,068,277 |
| 523 | CNTN4 | 3 | 3,071,927 | 524 | CNTN4 | 3 | 3,073,041 |
| 525 | ITPR1 | 3 | 4,527,968 | 526 | ITPR1 | 3 | 4,536,649 |
| 527 | ITPR1 | 3 | 4,646,029 | 528 | ITPR1 | 3 | 4,646,393 |
| 529 | ITPR1 | 3 | 4,651,285 | 530 | ITPR1 | 3 | 4,688,093 |
| 531 | IRAK2 | 3 | 10,216,875 | 532 | IRAK2 | 3 | 10,247,181 |
| 533 | IRAK2 | 3 | 10,251,163 | 534 | ATP2B2 | 3 | 10,388,601 |
| 535 | SLC6A11 | 3 | 10,844,124 | 536 | SLC6A1 | 3 | 11,055,169 |
| 537 | SLC6A6 | 3 | 14,503,422 | 538 | GADL1 | 3 | 30,846,244 |
| 539 | FBXL2 | 3 | 33,268,762 | 540 | CLASP2 | 3 | 33,516,308 |
| 541 | CLASP2 | 3 | 33,516,362 | 542 | CLASP2 | 3 | 33,584,334 |
| 543 | CLASP2 | 3 | 33,628,626 | 544 | CLASP2 | 3 | 33,712,097 |
| 545 | CLASP2 | 3 | 33,726,022 | 546 | ARPP-21 | 3 | 35,699,600 |
| 547 | ARPP-21 | 3 | 35,754,086 | 548 | ARPP-21 | 3 | 35,754,754 |
| 549 | ARPP-21 | 3 | 35,756,766 | 550 | ARPP-21 | 3 | 35,760,300 |
| 551 | ARPP-21 | 3 | 35,760,612 | 552 | STAC | 3 | 36,407,617 |
| 553 | ULK4 | 3 | 41,276,512 | 554 | ULK4 | 3 | 41,276,538 |
| 555 | ULK4 | 3 | 41,278,091 | 556 | ULK4 | 3 | 41,280,179 |
| 557 | ULK4 | 3 | 41,347,094 | 558 | ULK4 | 3 | 41,353,625 |
| 559 | ULK4 | 3 | 41,395,796 | 560 | ULK4 | 3 | 41,430,367 |
| 561 | ZNF445 | 3 | 44,472,605 | 562 | GPX1 | 3 | 49,853,082 |
| 563 | GPX1 | 3 | 49,865,617 | 564 | CAMKV | 3 | 49,877,164 |
| 565 | SEMA3F | 3 | 50,171,422 | 566 | SEMA3F | 3 | 50,200,033 |
| 567 | CACNA2D2 | 3 | 50,404,286 | 568 | CACNA2D2 | 3 | 50,406,198 |
| 569 | CACNA2D2 | 3 | 50,406,414 | 570 | CACNA2D2 | 3 | 50,424,066 |
| 571 | CACNA2D2 | 3 | 50,432,231 | 572 | CACNA2D2 | 3 | 50,436,244 |
| 573 | CACNA2D2 | 3 | 50,451,382 | 574 | CACNA2D2 | 3 | 50,458,441 |
| 575 | CACNA2D2 | 3 | 50,496,406 | 576 | CACNA2D2 | 3 | 50,499,225 |
| 577 | CACNA2D2 | 3 | 50,499,562 | 578 | CACNA2D2 | 3 | 50,500,021 |
| 579 | CACNA2D2 | 3 | 50,523,899 | 580 | CACNA2D3 | 3 | 54,123,584 |
| 581 | CACNA2D3 | 3 | 54,986,416 | 582 | CACNA2D3 | 3 | 54,986,679 |
| 583 | CACNA2D3 | 3 | 54,996,262 | 584 | CACNA2D3 | 3 | 55,011,390 |
| 585 | CACNA2D3 | 3 | 55,019,916 | 586 | ERC2 | 3 | 55,776,128 |
| 587 | ERC2 | 3 | 55,924,525 | 588 | FLNB | 3 | 58,083,555 |
| 589 | FLNB | 3 | 58,144,512 | 590 | FHIT | 3 | 59,814,275 |
| 591 | FHIT | 3 | 59,921,424 | 592 | FHIT | 3 | 59,928,545 |
| 593 | FHIT | 3 | 59,941,593 | 594 | FHIT | 3 | 59,956,110 |
| 595 | FHIT | 3 | 59,957,080 | 596 | FHIT | 3 | 59,966,929 |
| 597 | FHIT | 3 | 59,968,262 | 598 | FHIT | 3 | 60,123,563 |
| 599 | FHIT | 3 | 60,334,358 | 600 | FHIT | 3 | 60,350,356 |
| 601 | FHIT | 3 | 60,755,919 | 602 | FHIT | 3 | 60,769,257 |
| 603 | PTPRG | 3 | 62,219,610 | 604 | CADPS | 3 | 62,747,546 |
| 605 | CADPS | 3 | 62,780,447 | 606 | CADPS | 3 | 62,828,479 |
| 607 | CADPS | 3 | 62,838,021 | 608 | CADPS | 3 | 62,838,356 |
| 609 | CADPS | 3 | 62,846,542 | 610 | CADPS | 3 | 62,851,173 |
| 611 | SYNPR | 3 | 63,450,516 | 612 | SYNPR | 3 | 63,451,187 |
| 613 | SYNPR | 3 | 63,505,317 | 614 | PRICKLE2 | 3 | 64,159,383 |
| 615 | PRICKLE2 | 3 | 64,159,437 | 616 | PRICKLE2 | 3 | 64,184,717 |
| 617 | PRICKLE2 | 3 | 64,186,645 | 618 | MAGI1 | 3 | 65,576,514 |
| 619 | MAGI1 | 3 | 65,821,824 | 620 | MAGI1 | 3 | 65,836,434 |
| 621 | MAGI1 | 3 | 65,839,896 | 622 | FAM19A1 | 3 | 68,075,588 |
| 623 | FAM19A1 | 3 | 68,409,920 | 624 | ROBO2 | 3 | 77,392,802 |
| 625 | ROBO2 | 3 | 77,405,024 | 626 | ROBO1 | 3 | 78,987,206 |
| 627 | ROBO1 | 3 | 78,987,766 | 628 | ROBO1 | 3 | 79,258,557 |
| 629 | ROBO1 | 3 | 79,273,280 | 630 | ROBO1 | 3 | 79,280,400 |
| 631 | ROBO1 | 3 | 79,615,785 | 632 | GBE1 | 3 | 81,677,271 |
| 633 | EPHA3 | 3 | 89,604,354 | 634 | EPHA6 | 3 | 98,039,176 |
| 635 | CBLB | 3 | 106,905,095 | 636 | CBLB | 3 | 106,947,879 |
| 637 | CBLB | 3 | 106,982,063 | 638 | CBLB | 3 | 107,007,179 |
| 639 | CBLB | 3 | 107,007,800 | 640 | PLCXD2 | 3 | 112,846,428 |
| 641 | PLCXD2 | 3 | 112,878,258 | 642 | PLCXD2 | 3 | 112,883,336 |
| 643 | KALRN | 3 | 125,279,449 | 644 | KALRN | 3 | 125,453,554 |

TABLE A-continued

Summary of SNPs (NCBI Human Genome Reference Assembly Build 36.3)

| SEQ ID NO: | Gene | Chr | Position (BP) | SEQ ID NO: | Gene | Chr | Position (BP) |
|---|---|---|---|---|---|---|---|
| 645 | KALRN | 3 | 125,461,439 | 646 | KALRN | 3 | 125,649,153 |
| 647 | KALRN | 3 | 125,675,364 | 648 | KALRN | 3 | 125,678,784 |
| 649 | KALRN | 3 | 125,685,686 | 650 | KALRN | 3 | 125,904,630 |
| 651 | ZXDC | 3 | 127,661,080 | 652 | ZXDC | 3 | 127,665,610 |
| 653 | CPNE4 | 3 | 132,705,653 | 654 | CPNE4 | 3 | 132,886,287 |
| 655 | CPNE4 | 3 | 133,106,102 | 656 | CPNE4 | 3 | 133,142,633 |
| 657 | CPNE4 | 3 | 133,145,979 | 658 | EPHB1 | 3 | 135,954,344 |
| 659 | EPHB1 | 3 | 136,150,537 | 660 | EPHB1 | 3 | 136,150,839 |
| 661 | EPHB1 | 3 | 136,151,449 | 662 | EPHB1 | 3 | 136,152,557 |
| 663 | EPHB1 | 3 | 136,153,214 | 664 | EPHB1 | 3 | 136,154,213 |
| 665 | EPHB1 | 3 | 136,154,774 | 666 | EPHB1 | 3 | 136,154,975 |
| 667 | EPHB1 | 3 | 136,156,084 | 668 | EPHB1 | 3 | 136,158,491 |
| 669 | EPHB1 | 3 | 136,166,312 | 670 | EPHB1 | 3 | 136,166,631 |
| 671 | EPHB1 | 3 | 136,396,640 | 672 | SPSB4 | 3 | 142,238,268 |
| 673 | SPSB4 | 3 | 142,241,400 | 674 | SPSB4 | 3 | 142,332,653 |
| 675 | SERPINI1 | 3 | 168,993,166 | 676 | SLC7A14 | 3 | 171,664,127 |
| 677 | SLC7A14 | 3 | 171,793,139 | 678 | SLC7A14 | 3 | 171,815,650 |
| 679 | TNIK | 3 | 172,281,618 | 680 | TNIK | 3 | 172,426,406 |
| 681 | TNIK | 3 | 172,713,965 | 682 | PLD1 | 3 | 172,783,931 |
| 683 | PLD1 | 3 | 172,784,300 | 684 | PLD1 | 3 | 172,784,760 |
| 685 | PLD1 | 3 | 172,785,096 | 686 | PLD1 | 3 | 172,786,345 |
| 687 | PLD1 | 3 | 172,790,287 | 688 | PLD1 | 3 | 172,790,551 |
| 689 | PLD1 | 3 | 172,791,538 | 690 | PLD1 | 3 | 172,792,846 |
| 691 | PLD1 | 3 | 172,802,921 | 692 | PLD1 | 3 | 172,804,008 |
| 693 | PLD1 | 3 | 172,820,931 | 694 | PLD1 | 3 | 172,852,470 |
| 695 | PLD1 | 3 | 172,862,868 | 696 | PLD1 | 3 | 172,886,817 |
| 697 | PLD1 | 3 | 172,887,172 | 698 | PLD1 | 3 | 172,892,297 |
| 699 | PLD1 | 3 | 172,937,882 | 700 | PLD1 | 3 | 172,960,647 |
| 701 | PLD1 | 3 | 172,965,677 | 702 | NLGN1 | 3 | 175,040,531 |
| 703 | NLGN1 | 3 | 175,046,630 | 704 | NLGN1 | 3 | 175,512,036 |
| 705 | NLGN1 | 3 | 175,522,551 | 706 | NLGN1 | 3 | 175,541,245 |
| 707 | HTR3D | 3 | 185,244,358 | 708 | LEPREL1 | 3 | 191,232,932 |
| 709 | LEPREL1 | 3 | 191,232,980 | 710 | IL1RAP | 3 | 191,715,994 |
| 711 | IL1RAP | 3 | 191,716,369 | 712 | IL1RAP | 3 | 191,716,532 |
| 713 | IL1RAP | 3 | 191,719,452 | 714 | IL1RAP | 3 | 191,721,842 |
| 715 | IL1RAP | 3 | 191,836,940 | 716 | IL1RAP | 3 | 191,902,235 |
| 717 | IL1RAP | 3 | 191,914,335 | 718 | CENTB2 | 3 | 196,488,549 |
| 719 | SLC2A9 | 4 | 9,525,278 | 720 | SLC2A9 | 4 | 9,525,760 |
| 721 | SLC2A9 | 4 | 9,551,057 | 722 | SLC2A9 | 4 | 9,596,422 |
| 723 | SLC2A9 | 4 | 9,605,950 | 724 | SLC2A9 | 4 | 9,606,822 |
| 725 | SLC2A9 | 4 | 9,611,763 | 726 | LDB2 | 4 | 16,086,960 |
| 727 | LDB2 | 4 | 16,088,861 | 728 | LDB2 | 4 | 16,104,049 |
| 729 | LDB2 | 4 | 16,197,827 | 730 | LDB2 | 4 | 16,207,495 |
| 731 | LDB2 | 4 | 16,390,278 | 732 | LDB2 | 4 | 16,399,413 |
| 733 | LDB2 | 4 | 16,410,139 | 734 | LDB2 | 4 | 16,417,600 |
| 735 | KCNIP4 | 4 | 20,299,155 | 736 | KCNIP4 | 4 | 20,342,368 |
| 737 | KCNIP4 | 4 | 20,364,338 | 738 | KCNIP4 | 4 | 20,368,712 |
| 739 | KCNIP4 | 4 | 20,369,781 | 740 | SOD3 | 4 | 24,400,244 |
| 741 | PI4K2B | 4 | 24,837,015 | 742 | KIAA1239 | 4 | 37,121,710 |
| 743 | KIAA1239 | 4 | 37,161,668 | 744 | UBE2K | 4 | 39,394,605 |
| 745 | N4BP2 | 4 | 39,736,870 | 746 | LIMCH1 | 4 | 41,032,178 |
| 747 | LIMCH1 | 4 | 41,183,247 | 748 | LIMCH1 | 4 | 41,212,305 |
| 749 | LIMCH1 | 4 | 41,213,350 | 750 | LIMCH1 | 4 | 41,213,408 |
| 751 | LIMCH1 | 4 | 41,215,951 | 752 | LIMCH1 | 4 | 41,219,683 |
| 753 | LIMCH1 | 4 | 41,221,260 | 754 | LIMCH1 | 4 | 41,221,506 |
| 755 | LIMCH1 | 4 | 41,221,779 | 756 | LIMCH1 | 4 | 41,223,320 |
| 757 | LIMCH1 | 4 | 41,226,429 | 758 | LIMCH1 | 4 | 41,235,876 |
| 759 | LIMCH1 | 4 | 41,306,332 | 760 | LIMCH1 | 4 | 41,308,688 |
| 761 | LIMCH1 | 4 | 41,310,447 | 762 | LIMCH1 | 4 | 41,314,999 |
| 763 | LIMCH1 | 4 | 41,317,805 | 764 | LIMCH1 | 4 | 41,376,499 |
| 765 | LIMCH1 | 4 | 41,394,864 | 766 | LPHN3 | 4 | 62,506,258 |
| 767 | LPHN3 | 4 | 62,528,085 | 768 | LPHN3 | 4 | 62,708,418 |
| 769 | LPHN3 | 4 | 62,719,919 | 770 | NPFFR2 | 4 | 73,122,046 |
| 771 | NPFFR2 | 4 | 73,122,182 | 772 | NPFFR2 | 4 | 73,143,891 |
| 773 | NPFFR2 | 4 | 73,145,571 | 774 | NPFFR2 | 4 | 73,145,990 |
| 775 | NPFFR2 | 4 | 73,147,681 | 776 | NPFFR2 | 4 | 73,153,403 |
| 777 | NPFFR2 | 4 | 73,160,673 | 778 | NPFFR2 | 4 | 73,161,337 |
| 779 | NPFFR2 | 4 | 73,199,922 | 780 | NPFFR2 | 4 | 73,200,677 |
| 781 | NPFFR2 | 4 | 73,263,574 | 782 | NPFFR2 | 4 | 73,283,790 |
| 783 | NPFFR2 | 4 | 73,291,379 | 784 | SCARB2 | 4 | 77,296,450 |
| 785 | SCARB2 | 4 | 77,296,499 | 786 | SHROOM3 | 4 | 77,850,449 |
| 787 | SHROOM3 | 4 | 77,850,911 | 788 | SHROOM3 | 4 | 77,855,667 |
| 789 | SHROOM3 | 4 | 77,859,641 | 790 | SCD5 | 4 | 83,785,141 |
| 791 | GPRIN3 | 4 | 90,386,804 | 792 | GPRIN3 | 4 | 90,388,948 |
| 793 | GPRIN3 | 4 | 90,399,512 | 794 | GPRIN3 | 4 | 90,438,516 |

TABLE A-continued

Summary of SNPs (NCBI Human Genome Reference Assembly Build 36.3)

| SEQ ID NO: | Gene | Chr | Position (BP) | SEQ ID NO: | Gene | Chr | Position (BP) |
|---|---|---|---|---|---|---|---|
| 795 | GPRIN3 | 4 | 90,442,126 | 796 | GRID2 | 4 | 93,686,509 |
| 797 | GRID2 | 4 | 93,747,063 | 798 | GRID2 | 4 | 93,758,555 |
| 799 | GRID2 | 4 | 94,519,182 | 800 | GRID2 | 4 | 94,577,046 |
| 801 | GRID2 | 4 | 94,605,786 | 802 | GRID2 | 4 | 94,706,340 |
| 803 | GRID2 | 4 | 94,760,264 | 804 | GRID2 | 4 | 94,760,609 |
| 805 | GRID2 | 4 | 94,768,297 | 806 | GRID2 | 4 | 94,776,578 |
| 807 | GRID2 | 4 | 94,872,717 | 808 | GRID2 | 4 | 94,911,369 |
| 809 | GRID2 | 4 | 94,919,018 | 810 | GRID2 | 4 | 94,919,599 |
| 811 | UNC5C | 4 | 96,459,368 | 812 | UNC5C | 4 | 96,604,340 |
| 813 | UNC5C | 4 | 96,610,041 | 814 | UNC5C | 4 | 96,620,115 |
| 815 | UNC5C | 4 | 96,624,936 | 816 | UNC5C | 4 | 96,626,563 |
| 817 | UNC5C | 4 | 96,626,795 | 818 | UNC5C | 4 | 96,633,345 |
| 819 | UNC5C | 4 | 96,656,785 | 820 | ADH1C | 4 | 100,261,126 |
| 821 | PPP3CA | 4 | 102,128,589 | 822 | PPP3CA | 4 | 102,143,083 |
| 823 | PPP3CA | 4 | 102,187,634 | 824 | PPP3CA | 4 | 102,189,271 |
| 825 | PPP3CA | 4 | 102,198,890 | 826 | PPP3CA | 4 | 102,368,237 |
| 827 | PAPSS1 | 4 | 108,754,784 | 828 | PAPSS1 | 4 | 108,829,312 |
| 829 | PAPSS1 | 4 | 108,831,390 | 830 | PAPSS1 | 4 | 108,831,450 |
| 831 | PAPSS1 | 4 | 108,834,075 | 832 | PAPSS1 | 4 | 108,843,216 |
| 833 | PAPSS1 | 4 | 108,843,960 | 834 | PAPSS1 | 4 | 108,855,111 |
| 835 | COL25A1 | 4 | 109,985,739 | 836 | COL25A1 | 4 | 109,987,393 |
| 837 | COL25A1 | 4 | 110,067,552 | 838 | COL25A1 | 4 | 110,400,686 |
| 839 | COL25A1 | 4 | 110,409,320 | 840 | COL25A1 | 4 | 110,413,733 |
| 841 | COL25A1 | 4 | 110,474,589 | 842 | ANK2 | 4 | 114,190,823 |
| 843 | ANK2 | 4 | 114,328,632 | 844 | ANK2 | 4 | 114,329,042 |
| 845 | ANK2 | 4 | 114,329,441 | 846 | ANK2 | 4 | 114,340,609 |
| 847 | ANK2 | 4 | 114,429,212 | 848 | ANK2 | 4 | 114,437,446 |
| 849 | CAMK2D | 4 | 114,656,174 | 850 | CAMK2D | 4 | 114,715,574 |
| 851 | PRSS12 | 4 | 119,488,872 | 852 | PRSS12 | 4 | 119,498,546 |
| 853 | PRSS12 | 4 | 119,518,526 | 854 | MAML3 | 4 | 140,896,430 |
| 855 | MAML3 | 4 | 141,044,880 | 856 | MAML3 | 4 | 141,051,231 |
| 857 | MAML3 | 4 | 141,099,379 | 858 | MAML3 | 4 | 141,130,298 |
| 859 | MAML3 | 4 | 141,138,533 | 860 | MAML3 | 4 | 141,140,107 |
| 861 | MAML3 | 4 | 141,142,480 | 862 | MAML3 | 4 | 141,196,186 |
| 863 | MAML3 | 4 | 141,273,298 | 864 | MAML3 | 4 | 141,383,990 |
| 865 | IL15 | 4 | 142,737,011 | 866 | INPP4B | 4 | 143,274,371 |
| 867 | INPP4B | 4 | 143,288,240 | 868 | INPP4B | 4 | 143,292,058 |
| 869 | INPP4B | 4 | 143,296,851 | 870 | INPP4B | 4 | 143,300,521 |
| 871 | INPP4B | 4 | 143,314,721 | 872 | INPP4B | 4 | 143,392,444 |
| 873 | INPP4B | 4 | 143,414,201 | 874 | INPP4B | 4 | 143,421,104 |
| 875 | INPP4B | 4 | 143,436,841 | 876 | INPP4B | 4 | 143,437,563 |
| 877 | INPP4B | 4 | 143,508,343 | 878 | INPP4B | 4 | 143,516,488 |
| 879 | INPP4B | 4 | 143,524,042 | 880 | INPP4B | 4 | 143,547,226 |
| 881 | INPP4B | 4 | 143,563,055 | 882 | INPP4B | 4 | 143,566,886 |
| 883 | POU4F2 | 4 | 147,726,913 | 884 | POU4F2 | 4 | 147,731,368 |
| 885 | POU4F2 | 4 | 147,737,119 | 886 | POU4F2 | 4 | 147,739,219 |
| 887 | POU4F2 | 4 | 147,748,659 | 888 | POU4F2 | 4 | 147,758,283 |
| 889 | DCLK2 | 4 | 151,204,307 | 890 | DCLK2 | 4 | 151,235,111 |
| 891 | DCLK2 | 4 | 151,346,175 | 892 | DCLK2 | 4 | 151,366,761 |
| 893 | CTSO | 4 | 157,073,518 | 894 | CTSO | 4 | 157,090,787 |
| 895 | CTSO | 4 | 157,091,152 | 896 | CTSO | 4 | 157,092,343 |
| 897 | FSTL5 | 4 | 163,159,232 | 898 | FSTL5 | 4 | 163,172,602 |
| 899 | FSTL5 | 4 | 163,198,742 | 900 | FSTL5 | 4 | 163,204,852 |
| 901 | FSTL5 | 4 | 163,274,800 | 902 | FSTL5 | 4 | 163,275,058 |
| 903 | FSTL5 | 4 | 163,281,294 | 904 | FSTL5 | 4 | 163,282,207 |
| 905 | FSTL5 | 4 | 163,306,761 | 906 | FSTL5 | 4 | 163,316,993 |
| 907 | FSTL5 | 4 | 163,355,152 | 908 | FSTL5 | 4 | 163,369,235 |
| 909 | FSTL5 | 4 | 163,379,495 | 910 | TLL1 | 4 | 167,169,368 |
| 911 | TLL1 | 4 | 167,239,774 | 912 | PALLD | 4 | 169,650,759 |
| 913 | PALLD | 4 | 169,666,940 | 914 | PALLD | 4 | 169,678,372 |
| 915 | PALLD | 4 | 169,684,095 | 916 | PALLD | 4 | 169,759,910 |
| 917 | PALLD | 4 | 169,828,987 | 918 | PALLD | 4 | 169,855,143 |
| 919 | PALLD | 4 | 169,866,028 | 920 | PALLD | 4 | 169,894,890 |
| 921 | PALLD | 4 | 169,910,404 | 922 | PALLD | 4 | 170,065,920 |
| 923 | PALLD | 4 | 170,082,830 | 924 | PALLD | 4 | 170,113,748 |
| 925 | PALLD | 4 | 170,117,820 | 926 | PALLD | 4 | 170,118,492 |
| 927 | PALLD | 4 | 170,135,598 | 928 | GPM6A | 4 | 176,811,484 |
| 929 | GPM6A | 4 | 177,178,625 | 930 | ODZ3 | 4 | 183,917,599 |
| 931 | ODZ3 | 4 | 183,918,042 | 932 | ODZ3 | 4 | 183,918,858 |
| 933 | ENPP6 | 4 | 185,228,598 | 934 | ENPP6 | 4 | 185,266,961 |
| 935 | CASP3 | 4 | 185,808,551 | 936 | SLC6A3 | 5 | 1,415,793 |
| 937 | SLC6A3 | 5 | 1,480,803 | 938 | SLC6A3 | 5 | 1,481,011 |
| 939 | SLC6A3 | 5 | 1,481,514 | 940 | SLC6A3 | 5 | 1,496,728 |
| 941 | SEMA5A | 5 | 9,243,404 | 942 | SEMA5A | 5 | 9,495,994 |
| 943 | SEMA5A | 5 | 9,611,762 | 944 | SEMA5A | 5 | 9,612,903 |

TABLE A-continued

Summary of SNPs (NCBI Human Genome Reference Assembly Build 36.3)

| SEQ ID NO: | Gene | Chr | Position (BP) | SEQ ID NO: | Gene | Chr | Position (BP) |
|---|---|---|---|---|---|---|---|
| 945 | SEMA5A | 5 | 9,613,249 | 946 | CTNND2 | 5 | 11,160,238 |
| 947 | CTNND2 | 5 | 11,207,447 | 948 | CTNND2 | 5 | 11,250,495 |
| 949 | CTNND2 | 5 | 11,252,301 | 950 | CTNND2 | 5 | 11,271,488 |
| 951 | CTNND2 | 5 | 11,351,223 | 952 | CTNND2 | 5 | 11,476,628 |
| 953 | CTNND2 | 5 | 11,478,745 | 954 | CTNND2 | 5 | 11,975,555 |
| 955 | CTNND2 | 5 | 11,975,628 | 956 | CTNND2 | 5 | 11,982,913 |
| 957 | CTNND2 | 5 | 12,002,210 | 958 | CTNND2 | 5 | 12,002,315 |
| 959 | DNAH5 | 5 | 13,774,378 | 960 | DNAH5 | 5 | 13,957,400 |
| 961 | DNAH5 | 5 | 13,963,535 | 962 | MYO10 | 5 | 16,711,524 |
| 963 | MYO10 | 5 | 17,022,392 | 964 | BASP1 | 5 | 17,264,649 |
| 965 | BASP1 | 5 | 17,266,319 | 966 | BASP1 | 5 | 17,266,365 |
| 967 | CDH10 | 5 | 24,643,409 | 968 | CDH10 | 5 | 24,645,127 |
| 969 | CDH10 | 5 | 24,674,827 | 970 | C1QTNF3 | 5 | 34,051,438 |
| 971 | C1QTNF3 | 5 | 34,054,261 | 972 | C1QTNF3 | 5 | 34,058,118 |
| 973 | C1QTNF3 | 5 | 34,091,777 | 974 | SLC1A3 | 5 | 36,637,612 |
| 975 | SLC1A3 | 5 | 36,668,160 | 976 | EGFLAM | 5 | 38,301,820 |
| 977 | EGFLAM | 5 | 38,357,801 | 978 | EGFLAM | 5 | 38,386,400 |
| 979 | ITGA1 | 5 | 52,111,244 | 980 | ITGA1 | 5 | 52,114,759 |
| 981 | ITGA1 | 5 | 52,130,669 | 982 | ITGA1 | 5 | 52,134,676 |
| 983 | ITGA1 | 5 | 52,185,208 | 984 | ITGA1 | 5 | 52,185,286 |
| 985 | ITGA1 | 5 | 52,190,752 | 986 | ITGA1 | 5 | 52,285,233 |
| 987 | ITGA1 | 5 | 52,294,108 | 988 | ITGA2 | 5 | 52,369,177 |
| 989 | ITGA2 | 5 | 52,376,821 | 990 | ITGA2 | 5 | 52,388,971 |
| 991 | ITGA2 | 5 | 52,394,644 | 992 | ITGA2 | 5 | 52,394,794 |
| 993 | ITGA2 | 5 | 52,406,189 | 994 | ITGA2 | 5 | 52,417,975 |
| 995 | ITGA2 | 5 | 52,418,412 | 996 | ITGA2 | 5 | 52,418,682 |
| 997 | PDE4D | 5 | 58,406,595 | 998 | PDE4D | 5 | 58,429,089 |
| 999 | PDE4D | 5 | 58,511,874 | 1000 | PDE4D | 5 | 58,669,849 |
| 1001 | PDE4D | 5 | 58,895,884 | 1002 | PDE4D | 5 | 58,935,951 |
| 1003 | PDE4D | 5 | 58,937,131 | 1004 | PDE4D | 5 | 58,941,526 |
| 1005 | ELOVL7 | 5 | 60,099,268 | 1006 | ELOVL7 | 5 | 60,102,082 |
| 1007 | ELOVL7 | 5 | 60,131,029 | 1008 | ELOVL7 | 5 | 60,132,254 |
| 1009 | ELOVL7 | 5 | 60,152,959 | 1010 | ELOVL7 | 5 | 60,171,719 |
| 1011 | ELOVL7 | 5 | 60,201,944 | 1012 | PIK3R1 | 5 | 67,558,478 |
| 1013 | PIK3R1 | 5 | 67,564,947 | 1014 | MAP1B | 5 | 71,528,490 |
| 1015 | TNPO1 | 5 | 72,201,677 | 1016 | TNPO1 | 5 | 72,268,268 |
| 1017 | FCHO2 | 5 | 72,359,464 | 1018 | FCHO2 | 5 | 72,382,846 |
| 1019 | FCHO2 | 5 | 72,397,388 | 1020 | FCHO2 | 5 | 72,397,906 |
| 1021 | FCHO2 | 5 | 72,401,612 | 1022 | FCHO2 | 5 | 72,413,771 |
| 1023 | FCHO2 | 5 | 72,429,851 | 1024 | PDE8B | 5 | 76,535,298 |
| 1025 | PDE8B | 5 | 76,549,775 | 1026 | PDE8B | 5 | 76,656,410 |
| 1027 | PDE8B | 5 | 76,659,055 | 1028 | PDE8B | 5 | 76,676,601 |
| 1029 | PDE8B | 5 | 76,707,804 | 1030 | PDE8B | 5 | 76,712,714 |
| 1031 | PDE8B | 5 | 76,728,438 | 1032 | PDE8B | 5 | 76,753,826 |
| 1033 | PDE8B | 5 | 76,761,338 | 1034 | SCAMP1 | 5 | 77,716,826 |
| 1035 | SCAMP1 | 5 | 77,744,823 | 1036 | SCAMP1 | 5 | 77,754,972 |
| 1037 | SCAMP1 | 5 | 77,755,075 | 1038 | SCAMP1 | 5 | 77,775,583 |
| 1039 | SCAMP1 | 5 | 77,780,932 | 1040 | SCAMP1 | 5 | 77,781,293 |
| 1041 | SCAMP1 | 5 | 77,804,758 | 1042 | SCAMP1 | 5 | 77,818,845 |
| 1043 | SCAMP1 | 5 | 77,822,520 | 1044 | CMYA5 | 5 | 79,056,182 |
| 1045 | CMYA5 | 5 | 79,058,467 | 1046 | CMYA5 | 5 | 79,060,490 |
| 1047 | CMYA5 | 5 | 79,073,027 | 1048 | CMYA5 | 5 | 79,073,240 |
| 1049 | CMYA5 | 5 | 79,074,951 | 1050 | CMYA5 | 5 | 79,076,813 |
| 1051 | CMYA5 | 5 | 79,136,873 | 1052 | MEF2C | 5 | 88,039,159 |
| 1053 | MEF2C | 5 | 88,074,146 | 1054 | MEF2C | 5 | 88,078,052 |
| 1055 | MEF2C | 5 | 88,090,048 | 1056 | MEF2C | 5 | 88,090,519 |
| 1057 | MEF2C | 5 | 88,156,944 | 1058 | MEF2C | 5 | 88,159,879 |
| 1059 | MEF2C | 5 | 88,161,609 | 1060 | MEF2C | 5 | 88,173,798 |
| 1061 | GPR98 | 5 | 89,883,625 | 1062 | GPR98 | 5 | 89,893,330 |
| 1063 | GPR98 | 5 | 90,010,394 | 1064 | GPR98 | 5 | 90,058,163 |
| 1065 | GPR98 | 5 | 90,064,161 | 1066 | GPR98 | 5 | 90,071,845 |
| 1067 | GPR98 | 5 | 90,379,334 | 1068 | GPR98 | 5 | 90,420,854 |
| 1069 | GPR98 | 5 | 90,428,377 | 1070 | FBXL17 | 5 | 107,377,610 |
| 1071 | FBXL17 | 5 | 107,380,193 | 1072 | FBXL17 | 5 | 107,381,014 |
| 1073 | FBXL17 | 5 | 107,420,461 | 1074 | FBXL17 | 5 | 107,423,133 |
| 1075 | FBXL17 | 5 | 107,428,404 | 1076 | FBXL17 | 5 | 107,429,502 |
| 1077 | FBXL17 | 5 | 107,433,375 | 1078 | FBXL17 | 5 | 107,522,936 |
| 1079 | FBXL17 | 5 | 107,546,460 | 1080 | FBXL17 | 5 | 107,564,803 |
| 1081 | PJA2 | 5 | 108,686,797 | 1082 | PJA2 | 5 | 108,694,666 |
| 1083 | PJA2 | 5 | 108,727,060 | 1084 | PJA2 | 5 | 108,727,773 |
| 1085 | PJA2 | 5 | 108,758,672 | 1086 | PJA2 | 5 | 108,776,974 |
| 1087 | PJA2 | 5 | 108,780,765 | 1088 | PJA2 | 5 | 108,781,038 |
| 1089 | PJA2 | 5 | 108,782,510 | 1090 | PJA2 | 5 | 108,784,484 |
| 1091 | PJA2 | 5 | 108,787,364 | 1092 | PJA2 | 5 | 108,803,710 |
| 1093 | PJA2 | 5 | 108,812,698 | 1094 | KCNN2 | 5 | 113,836,032 |

TABLE A-continued

Summary of SNPs (NCBI Human Genome Reference Assembly Build 36.3)

| SEQ ID NO: | Gene | Chr | Position (BP) | SEQ ID NO: | Gene | Chr | Position (BP) |
|---|---|---|---|---|---|---|---|
| 1095 | KCNN2 | 5 | 113,836,263 | 1096 | SEMA6A | 5 | 115,855,255 |
| 1097 | SEMA6A | 5 | 115,855,306 | 1098 | ADAMTS19 | 5 | 128,915,938 |
| 1099 | ADAMTS19 | 5 | 128,968,517 | 1100 | ADAMTS19 | 5 | 128,968,799 |
| 1101 | ADAMTS19 | 5 | 128,986,841 | 1102 | ADAMTS19 | 5 | 129,018,892 |
| 1103 | ADAMTS19 | 5 | 129,019,131 | 1104 | ADAMTS19 | 5 | 129,024,772 |
| 1105 | ADAMTS19 | 5 | 129,033,634 | 1106 | ADAMTS19 | 5 | 129,034,142 |
| 1107 | ADAMTS19 | 5 | 129,039,887 | 1108 | ADAMTS19 | 5 | 129,078,440 |
| 1109 | VDAC1 | 5 | 133,335,005 | 1110 | VDAC1 | 5 | 133,355,058 |
| 1111 | VDAC1 | 5 | 133,356,459 | 1112 | VDAC1 | 5 | 133,405,061 |
| 1113 | TRPC7 | 5 | 135,547,908 | 1114 | TRPC7 | 5 | 135,551,643 |
| 1115 | TRPC7 | 5 | 135,557,803 | 1116 | TRPC7 | 5 | 135,660,209 |
| 1117 | TRPC7 | 5 | 135,674,104 | 1118 | TRPC7 | 5 | 135,678,197 |
| 1119 | TRPC7 | 5 | 135,679,839 | 1120 | TRPC7 | 5 | 135,680,121 |
| 1121 | TRPC7 | 5 | 135,689,800 | 1122 | TRPC7 | 5 | 135,693,248 |
| 1123 | TRPC7 | 5 | 135,708,380 | 1124 | TRPC7 | 5 | 135,712,132 |
| 1125 | TRPC7 | 5 | 135,713,994 | 1126 | TRPC7 | 5 | 135,724,949 |
| 1127 | TRPC7 | 5 | 135,725,523 | 1128 | TRPC7 | 5 | 135,733,573 |
| 1129 | TRPC7 | 5 | 135,734,750 | 1130 | GRIA1 | 5 | 152,884,137 |
| 1131 | GRIA1 | 5 | 152,949,087 | 1132 | GRIA1 | 5 | 152,956,518 |
| 1133 | GRIA1 | 5 | 153,167,666 | 1134 | ODZ2 | 5 | 166,910,625 |
| 1135 | ODZ2 | 5 | 167,105,972 | 1136 | ODZ2 | 5 | 167,177,338 |
| 1137 | ODZ2 | 5 | 167,189,249 | 1138 | ODZ2 | 5 | 167,313,056 |
| 1139 | ODZ2 | 5 | 167,345,783 | 1140 | ODZ2 | 5 | 167,400,913 |
| 1141 | ODZ2 | 5 | 167,601,421 | 1142 | ODZ2 | 5 | 167,604,683 |
| 1143 | ODZ2 | 5 | 167,611,516 | 1144 | ODZ2 | 5 | 167,634,619 |
| 1145 | WWC1 | 5 | 167,641,813 | 1146 | WWC1 | 5 | 167,785,852 |
| 1147 | WWC1 | 5 | 167,818,328 | 1148 | WWC1 | 5 | 167,819,115 |
| 1149 | WWC1 | 5 | 167,819,275 | 1150 | WWC1 | 5 | 167,820,009 |
| 1151 | KCNIP1 | 5 | 169,709,852 | 1152 | KCNIP1 | 5 | 169,709,936 |
| 1153 | KCNIP1 | 5 | 169,710,014 | 1154 | KCNIP1 | 5 | 170,021,180 |
| 1155 | KCNIP1 | 5 | 170,078,162 | 1156 | KCNIP1 | 5 | 170,095,949 |
| 1157 | STK10 | 5 | 171,538,167 | 1158 | EXOC2 | 6 | 417,807 |
| 1159 | EXOC2 | 6 | 418,248 | 1160 | EXOC2 | 6 | 420,154 |
| 1161 | EXOC2 | 6 | 420,810 | 1162 | EXOC2 | 6 | 441,555 |
| 1163 | EXOC2 | 6 | 536,765 | 1164 | EXOC2 | 6 | 541,042 |
| 1165 | EXOC2 | 6 | 542,871 | 1166 | EXOC2 | 6 | 555,542 |
| 1167 | EXOC2 | 6 | 559,375 | 1168 | EXOC2 | 6 | 577,061 |
| 1169 | SERPINB6 | 6 | 2,876,878 | 1170 | SERPINB6 | 6 | 2,926,223 |
| 1171 | PHACTR1 | 6 | 12,837,251 | 1172 | PHACTR1 | 6 | 13,386,732 |
| 1173 | JARID2 | 6 | 15,355,372 | 1174 | JARID2 | 6 | 15,499,187 |
| 1175 | JARID2 | 6 | 15,503,960 | 1176 | JARID2 | 6 | 15,505,614 |
| 1177 | JARID2 | 6 | 15,512,229 | 1178 | JARID2 | 6 | 15,516,507 |
| 1179 | JARID2 | 6 | 15,537,710 | 1180 | JARID2 | 6 | 15,545,369 |
| 1181 | JARID2 | 6 | 15,567,913 | 1182 | JARID2 | 6 | 15,598,338 |
| 1183 | ATXN1 | 6 | 16,595,223 | 1184 | ATXN1 | 6 | 16,595,385 |
| 1185 | ATXN1 | 6 | 16,681,514 | 1186 | ATXN1 | 6 | 16,755,137 |
| 1187 | ATXN1 | 6 | 16,762,029 | 1188 | ATXN1 | 6 | 16,766,596 |
| 1189 | ATXN1 | 6 | 16,767,074 | 1190 | ATXN1 | 6 | 16,767,110 |
| 1191 | ATXN1 | 6 | 16,779,315 | 1192 | ATXN1 | 6 | 16,780,739 |
| 1193 | ATXN1 | 6 | 16,791,838 | 1194 | ATXN1 | 6 | 16,799,821 |
| 1195 | ATXN1 | 6 | 16,850,744 | 1196 | SLC17A4 | 6 | 25,880,026 |
| 1197 | SLC17A4 | 6 | 25,880,618 | 1198 | SLC17A4 | 6 | 25,887,371 |
| 1199 | SLC17A1 | 6 | 25,909,950 | 1200 | SLC17A1 | 6 | 25,921,129 |
| 1201 | SLC17A1 | 6 | 25,926,734 | 1202 | SLC17A1 | 6 | 25,928,407 |
| 1203 | SLC17A1 | 6 | 25,948,464 | 1204 | SLC17A1 | 6 | 25,949,101 |
| 1205 | SLC17A3 | 6 | 25,967,533 | 1206 | SLC17A3 | 6 | 25,970,445 |
| 1207 | SLC17A3 | 6 | 25,971,584 | 1208 | SLC17A3 | 6 | 25,972,877 |
| 1209 | SLC17A3 | 6 | 25,973,245 | 1210 | SLC17A3 | 6 | 25,977,827 |
| 1211 | SLC17A3 | 6 | 25,978,521 | 1212 | BTN3A1 | 6 | 26,504,182 |
| 1213 | BTN3A1 | 6 | 26,506,534 | 1214 | BTN3A1 | 6 | 26,512,353 |
| 1215 | BTN3A1 | 6 | 26,513,243 | 1216 | BTN3A1 | 6 | 26,513,969 |
| 1217 | MSH5 | 6 | 31,826,581 | 1218 | MSH5 | 6 | 31,838,993 |
| 1219 | LRFN2 | 6 | 40,635,612 | 1220 | LRFN2 | 6 | 40,640,871 |
| 1221 | KLC4 | 6 | 43,131,349 | 1222 | PARC | 6 | 43,293,711 |
| 1223 | TJAP1 | 6 | 43,598,787 | 1224 | XPO5 | 6 | 43,606,651 |
| 1225 | XPO5 | 6 | 43,621,785 | 1226 | XPO5 | 6 | 43,636,419 |
| 1227 | XPO5 | 6 | 43,648,904 | 1228 | TMEM63B | 6 | 44,201,720 |
| 1229 | ELOVL5 | 6 | 53,213,187 | 1230 | ELOVL5 | 6 | 53,282,407 |
| 1231 | ELOVL5 | 6 | 53,341,053 | 1232 | ELOVL5 | 6 | 53,350,763 |
| 1233 | ELOVL5 | 6 | 53,362,070 | 1234 | RIMS1 | 6 | 72,866,546 |
| 1235 | RIMS1 | 6 | 72,932,594 | 1236 | HTR1B | 6 | 78,228,979 |
| 1237 | HTR1B | 6 | 78,247,981 | 1238 | GABRR2 | 6 | 90,031,297 |
| 1239 | GABRR2 | 6 | 90,052,273 | 1240 | TRDN | 6 | 123,681,714 |
| 1241 | TRDN | 6 | 123,707,645 | 1242 | TRDN | 6 | 123,730,952 |
| 1243 | TRDN | 6 | 123,731,764 | 1244 | TRDN | 6 | 123,747,133 |

TABLE A-continued

Summary of SNPs (NCBI Human Genome Reference Assembly Build 36.3)

| SEQ ID NO: | Gene | Chr | Position (BP) | SEQ ID NO: | Gene | Chr | Position (BP) |
|---|---|---|---|---|---|---|---|
| 1245 | TRDN | 6 | 123,749,431 | 1246 | TRDN | 6 | 123,753,539 |
| 1247 | TRDN | 6 | 123,790,942 | 1248 | TRDN | 6 | 123,878,251 |
| 1249 | TRDN | 6 | 123,963,305 | 1250 | TRDN | 6 | 123,982,387 |
| 1251 | TRDN | 6 | 123,983,371 | 1252 | TRDN | 6 | 123,983,783 |
| 1253 | TRDN | 6 | 123,991,308 | 1254 | TRDN | 6 | 123,992,112 |
| 1255 | TRDN | 6 | 124,006,657 | 1256 | TRDN | 6 | 124,007,196 |
| 1257 | TRDN | 6 | 124,008,072 | 1258 | TRDN | 6 | 124,011,033 |
| 1259 | NKAIN2 | 6 | 124,074,609 | 1260 | NKAIN2 | 6 | 124,085,957 |
| 1261 | NKAIN2 | 6 | 124,977,809 | 1262 | EYA4 | 6 | 133,668,941 |
| 1263 | EYA4 | 6 | 133,672,254 | 1264 | EYA4 | 6 | 133,678,316 |
| 1265 | EYA4 | 6 | 133,684,611 | 1266 | PDE7B | 6 | 136,337,547 |
| 1267 | PDE7B | 6 | 136,391,000 | 1268 | PDE7B | 6 | 136,402,540 |
| 1269 | PDE7B | 6 | 136,472,958 | 1270 | PDE7B | 6 | 136,555,234 |
| 1271 | PLAGL1 | 6 | 144,345,925 | 1272 | PLAGL1 | 6 | 144,355,380 |
| 1273 | STX11 | 6 | 144,554,694 | 1274 | UTRN | 6 | 144,943,208 |
| 1275 | UTRN | 6 | 145,213,578 | 1276 | SYNE1 | 6 | 152,534,210 |
| 1277 | SYNE1 | 6 | 152,534,429 | 1278 | SYNE1 | 6 | 152,535,158 |
| 1279 | SYNE1 | 6 | 152,535,230 | 1280 | SYNE1 | 6 | 152,549,890 |
| 1281 | SLC22A3 | 6 | 160,664,141 | 1282 | SLC22A3 | 6 | 160,701,723 |
| 1283 | PARK2 | 6 | 161,894,294 | 1284 | PARK2 | 6 | 161,894,946 |
| 1285 | PACRG | 6 | 163,512,225 | 1286 | PACRG | 6 | 163,523,252 |
| 1287 | PACRG | 6 | 163,571,731 | 1288 | PACRG | 6 | 163,656,492 |
| 1289 | PDE10A | 6 | 165,656,576 | 1290 | PDE10A | 6 | 165,657,424 |
| 1291 | PDE10A | 6 | 165,659,019 | 1292 | PDE10A | 6 | 165,711,808 |
| 1293 | PDE10A | 6 | 165,865,960 | 1294 | PDE10A | 6 | 165,868,876 |
| 1295 | SDK1 | 7 | 4,133,862 | 1296 | SDK1 | 7 | 4,141,415 |
| 1297 | SDK1 | 7 | 4,142,841 | 1298 | NXPH1 | 7 | 8,633,152 |
| 1299 | NXPH1 | 7 | 8,633,615 | 1300 | NXPH1 | 7 | 8,637,519 |
| 1301 | NXPH1 | 7 | 8,642,990 | 1302 | NXPH1 | 7 | 8,647,759 |
| 1303 | NXPH1 | 7 | 8,662,332 | 1304 | NXPH1 | 7 | 8,662,442 |
| 1305 | NXPH1 | 7 | 8,758,143 | 1306 | ETV1 | 7 | 13,882,768 |
| 1307 | DGKB | 7 | 14,179,937 | 1308 | DGKB | 7 | 14,181,086 |
| 1309 | DGKB | 7 | 14,213,223 | 1310 | DGKB | 7 | 14,213,591 |
| 1311 | DGKB | 7 | 14,557,877 | 1312 | DGKB | 7 | 14,663,822 |
| 1313 | DGKB | 7 | 14,795,170 | 1314 | DGKB | 7 | 14,816,578 |
| 1315 | DGKB | 7 | 14,817,686 | 1316 | DGKB | 7 | 14,818,142 |
| 1317 | TSPAN13 | 7 | 16,770,515 | 1318 | SNX13 | 7 | 17,949,822 |
| 1319 | SNX13 | 7 | 17,950,332 | 1320 | SNX13 | 7 | 17,955,884 |
| 1321 | STK31 | 7 | 23,712,523 | 1322 | STK31 | 7 | 23,790,538 |
| 1323 | STK31 | 7 | 23,796,703 | 1324 | STK31 | 7 | 23,844,516 |
| 1325 | STK31 | 7 | 23,859,520 | 1326 | SKAP2 | 7 | 26,814,684 |
| 1327 | SKAP2 | 7 | 26,825,824 | 1328 | SKAP2 | 7 | 26,830,698 |
| 1329 | SKAP2 | 7 | 26,862,761 | 1330 | CREB5 | 7 | 28,798,822 |
| 1331 | CREB5 | 7 | 28,808,592 | 1332 | PLEKHA8 | 7 | 30,037,069 |
| 1333 | PLEKHA8 | 7 | 30,081,142 | 1334 | CRHR2 | 7 | 30,665,429 |
| 1335 | PDE1C | 7 | 31,821,130 | 1336 | PDE1C | 7 | 31,822,595 |
| 1337 | PDE1C | 7 | 31,835,138 | 1338 | PDE1C | 7 | 31,838,385 |
| 1339 | PDE1C | 7 | 31,841,400 | 1340 | BMPER | 7 | 34,020,913 |
| 1341 | BMPER | 7 | 34,057,259 | 1342 | BMPER | 7 | 34,067,083 |
| 1343 | BMPER | 7 | 34,077,746 | 1344 | BMPER | 7 | 34,159,287 |
| 1345 | EEPD1 | 7 | 36,145,203 | 1346 | EEPD1 | 7 | 36,235,809 |
| 1347 | VPS41 | 7 | 38,708,501 | 1348 | VPS41 | 7 | 38,738,392 |
| 1349 | VPS41 | 7 | 38,750,276 | 1350 | VPS41 | 7 | 38,757,077 |
| 1351 | VPS41 | 7 | 38,757,472 | 1352 | VPS41 | 7 | 38,759,768 |
| 1353 | VPS41 | 7 | 38,761,292 | 1354 | VPS41 | 7 | 38,776,517 |
| 1355 | VPS41 | 7 | 38,784,656 | 1356 | VPS41 | 7 | 38,798,095 |
| 1357 | VPS41 | 7 | 38,798,875 | 1358 | VPS41 | 7 | 38,800,593 |
| 1359 | VPS41 | 7 | 38,806,116 | 1360 | VPS41 | 7 | 38,812,386 |
| 1361 | VPS41 | 7 | 38,820,297 | 1362 | VPS41 | 7 | 38,820,469 |
| 1363 | VPS41 | 7 | 38,828,636 | 1364 | VPS41 | 7 | 38,836,969 |
| 1365 | VPS41 | 7 | 38,850,065 | 1366 | VPS41 | 7 | 38,882,602 |
| 1367 | VPS41 | 7 | 38,925,791 | 1368 | VPS41 | 7 | 38,926,367 |
| 1369 | VPS41 | 7 | 38,936,691 | 1370 | IGFBP3 | 7 | 45,875,519 |
| 1371 | IGFBP3 | 7 | 45,916,971 | 1372 | IGFBP3 | 7 | 46,061,993 |
| 1373 | ABCA13 | 7 | 48,240,607 | 1374 | ABCA13 | 7 | 48,245,100 |
| 1375 | ABCA13 | 7 | 48,250,081 | 1376 | ABCA13 | 7 | 48,250,147 |
| 1377 | ABCA13 | 7 | 48,253,360 | 1378 | ABCA13 | 7 | 48,256,966 |
| 1379 | ABCA13 | 7 | 48,261,753 | 1380 | ABCA13 | 7 | 48,262,848 |
| 1381 | ABCA13 | 7 | 48,263,650 | 1382 | ABCA13 | 7 | 48,275,993 |
| 1383 | ABCA13 | 7 | 48,415,696 | 1384 | ABCA13 | 7 | 48,427,057 |
| 1385 | ABCA13 | 7 | 48,537,723 | 1386 | ABCA13 | 7 | 48,538,115 |
| 1387 | ABCA13 | 7 | 48,549,904 | 1388 | ABCA13 | 7 | 48,551,488 |
| 1389 | ABCA13 | 7 | 48,576,570 | 1390 | ABCA13 | 7 | 48,577,426 |
| 1391 | ABCA13 | 7 | 48,642,999 | 1392 | ABCA13 | 7 | 48,664,499 |
| 1393 | GRB10 | 7 | 50,706,645 | 1394 | GRB10 | 7 | 50,706,949 |

TABLE A-continued

Summary of SNPs (NCBI Human Genome Reference Assembly Build 36.3)

| SEQ ID NO: | Gene | Chr | Position (BP) | SEQ ID NO: | Gene | Chr | Position (BP) |
|---|---|---|---|---|---|---|---|
| 1395 | GRB10 | 7 | 50,707,020 | 1396 | GRB10 | 7 | 50,707,082 |
| 1397 | GRB10 | 7 | 50,712,801 | 1398 | GRB10 | 7 | 50,723,008 |
| 1399 | GRB10 | 7 | 50,727,714 | 1400 | GRB10 | 7 | 50,735,647 |
| 1401 | GRB10 | 7 | 50,750,413 | 1402 | GRB10 | 7 | 50,752,942 |
| 1403 | GRB10 | 7 | 50,753,544 | 1404 | GRB10 | 7 | 50,769,928 |
| 1405 | GRB10 | 7 | 50,775,527 | 1406 | GRB10 | 7 | 50,775,581 |
| 1407 | GRB10 | 7 | 50,777,265 | 1408 | GRB10 | 7 | 50,790,805 |
| 1409 | GRB10 | 7 | 50,791,895 | 1410 | GRB10 | 7 | 50,797,467 |
| 1411 | GRB10 | 7 | 50,803,980 | 1412 | GRB10 | 7 | 50,807,550 |
| 1413 | GRB10 | 7 | 50,820,922 | 1414 | GRB10 | 7 | 50,823,003 |
| 1415 | GRB10 | 7 | 50,823,341 | 1416 | GRB10 | 7 | 50,839,403 |
| 1417 | GRB10 | 7 | 50,839,923 | 1418 | WBSCR17 | 7 | 70,218,616 |
| 1419 | WBSCR17 | 7 | 70,314,044 | 1420 | WBSCR17 | 7 | 70,765,881 |
| 1421 | WBSCR17 | 7 | 70,771,838 | 1422 | CALN1 | 7 | 70,886,612 |
| 1423 | CALN1 | 7 | 70,889,691 | 1424 | CALN1 | 7 | 71,180,137 |
| 1425 | CALN1 | 7 | 71,196,919 | 1426 | CALN1 | 7 | 71,206,186 |
| 1427 | CALN1 | 7 | 71,212,064 | 1428 | CALN1 | 7 | 71,214,046 |
| 1429 | CALN1 | 7 | 71,235,264 | 1430 | CALN1 | 7 | 71,235,395 |
| 1431 | CALN1 | 7 | 71,377,109 | 1432 | CALN1 | 7 | 71,446,681 |
| 1433 | CALN1 | 7 | 71,464,567 | 1434 | CALN1 | 7 | 71,472,868 |
| 1435 | CALN1 | 7 | 71,475,237 | 1436 | CALN1 | 7 | 71,505,190 |
| 1437 | GTF2IRD1 | 7 | 73,545,909 | 1438 | MAGI2 | 7 | 77,807,229 |
| 1439 | MAGI2 | 7 | 77,811,392 | 1440 | MAGI2 | 7 | 77,811,723 |
| 1441 | MAGI2 | 7 | 78,083,120 | 1442 | MAGI2 | 7 | 78,087,129 |
| 1443 | MAGI2 | 7 | 78,735,107 | 1444 | MAGI2 | 7 | 78,753,565 |
| 1445 | MAGI2 | 7 | 78,817,962 | 1446 | MAGI2 | 7 | 78,824,996 |
| 1447 | MAGI2 | 7 | 78,825,573 | 1448 | MAGI2 | 7 | 78,829,240 |
| 1449 | CACNA2D1 | 7 | 81,438,378 | 1450 | CACNA2D1 | 7 | 81,442,364 |
| 1451 | PCLO | 7 | 82,393,605 | 1452 | PCLO | 7 | 82,395,097 |
| 1453 | PCLO | 7 | 82,401,047 | 1454 | PCLO | 7 | 82,401,452 |
| 1455 | PCLO | 7 | 82,411,459 | 1456 | PCLO | 7 | 82,454,771 |
| 1457 | PCLO | 7 | 82,650,074 | 1458 | PCLO | 7 | 82,659,120 |
| 1459 | GRM3 | 7 | 86,189,153 | 1460 | GRM3 | 7 | 86,254,957 |
| 1461 | GRM3 | 7 | 86,255,781 | 1462 | GRM3 | 7 | 86,266,144 |
| 1463 | ADAM22 | 7 | 87,469,462 | 1464 | ADAM22 | 7 | 87,539,714 |
| 1465 | ADAM22 | 7 | 87,590,464 | 1466 | PPP1R9A | 7 | 94,589,831 |
| 1467 | PPP1R9A | 7 | 94,632,721 | 1468 | PPP1R9A | 7 | 94,733,892 |
| 1469 | PPP1R9A | 7 | 94,734,041 | 1470 | PPP1R9A | 7 | 94,742,812 |
| 1471 | PPP1R9A | 7 | 94,746,827 | 1472 | PPP1R9A | 7 | 94,747,431 |
| 1473 | PPP1R9A | 7 | 94,747,598 | 1474 | PPP1R9A | 7 | 94,748,184 |
| 1475 | PPP1R9A | 7 | 94,750,340 | 1476 | DYNC1I1 | 7 | 95,258,613 |
| 1477 | DYNC1I1 | 7 | 95,325,994 | 1478 | DYNC1I1 | 7 | 95,336,462 |
| 1479 | DYNC1I1 | 7 | 95,386,677 | 1480 | ZNF3 | 7 | 99,429,354 |
| 1481 | ZNF3 | 7 | 99,480,681 | 1482 | EMID2 | 7 | 100,868,518 |
| 1483 | EMID2 | 7 | 100,878,190 | 1484 | CUX1 | 7 | 101,700,855 |
| 1485 | CUX1 | 7 | 101,712,058 | 1486 | CUX1 | 7 | 101,758,636 |
| 1487 | NRCAM | 7 | 107,585,096 | 1488 | NRCAM | 7 | 107,587,783 |
| 1489 | NRCAM | 7 | 107,588,905 | 1490 | NRCAM | 7 | 107,598,938 |
| 1491 | NRCAM | 7 | 107,621,970 | 1492 | NRCAM | 7 | 107,626,668 |
| 1493 | NRCAM | 7 | 107,628,207 | 1494 | NRCAM | 7 | 107,654,504 |
| 1495 | NRCAM | 7 | 107,657,867 | 1496 | NRCAM | 7 | 107,731,054 |
| 1497 | KCND2 | 7 | 119,693,426 | 1498 | KCND2 | 7 | 119,956,552 |
| 1499 | KCND2 | 7 | 119,967,907 | 1500 | KCND2 | 7 | 120,089,523 |
| 1501 | CADPS2 | 7 | 121,760,839 | 1502 | CADPS2 | 7 | 121,767,778 |
| 1503 | CADPS2 | 7 | 121,805,395 | 1504 | CADPS2 | 7 | 122,314,434 |
| 1505 | SLC13A1 | 7 | 122,533,104 | 1506 | SLC13A1 | 7 | 122,557,321 |
| 1507 | SLC13A1 | 7 | 122,560,268 | 1508 | SLC13A1 | 7 | 122,590,060 |
| 1509 | SLC13A1 | 7 | 122,594,916 | 1510 | SLC13A1 | 7 | 122,595,280 |
| 1511 | SLC13A1 | 7 | 122,596,347 | 1512 | GRM8 | 7 | 125,866,380 |
| 1513 | GRM8 | 7 | 125,872,156 | 1514 | GRM8 | 7 | 125,880,817 |
| 1515 | GRM8 | 7 | 125,918,108 | 1516 | GRM8 | 7 | 125,923,221 |
| 1517 | GRM8 | 7 | 125,938,463 | 1518 | GRM8 | 7 | 125,940,799 |
| 1519 | GRM8 | 7 | 125,941,472 | 1520 | GRM8 | 7 | 125,959,757 |
| 1521 | GRM8 | 7 | 125,979,607 | 1522 | GRM8 | 7 | 126,435,292 |
| 1523 | GRM8 | 7 | 126,436,133 | 1524 | GRM8 | 7 | 126,444,781 |
| 1525 | GRM8 | 7 | 126,483,848 | 1526 | GRM8 | 7 | 126,499,299 |
| 1527 | GRM8 | 7 | 126,499,423 | 1528 | GRM8 | 7 | 126,504,393 |
| 1529 | GRM8 | 7 | 126,521,407 | 1530 | GRM8 | 7 | 126,581,967 |
| 1531 | GRM8 | 7 | 126,624,857 | 1532 | DGKI | 7 | 136,749,535 |
| 1533 | DGKI | 7 | 136,757,487 | 1534 | DGKI | 7 | 136,769,973 |
| 1535 | DGKI | 7 | 136,780,737 | 1536 | DGKI | 7 | 136,782,783 |
| 1537 | DGKI | 7 | 136,787,596 | 1538 | DGKI | 7 | 136,885,223 |
| 1539 | DGKI | 7 | 136,888,628 | 1540 | DGKI | 7 | 136,888,749 |
| 1541 | CREB3L2 | 7 | 137,203,650 | 1542 | CREB3L2 | 7 | 137,211,237 |
| 1543 | CREB3L2 | 7 | 137,342,248 | 1544 | CREB3L2 | 7 | 137,343,428 |

TABLE A-continued

Summary of SNPs (NCBI Human Genome Reference Assembly Build 36.3)

| SEQ ID NO: | Gene | Chr | Position (BP) | SEQ ID NO: | Gene | Chr | Position (BP) |
|---|---|---|---|---|---|---|---|
| 1545 | TBXAS1 | 7 | 139,342,717 | 1546 | TBXAS1 | 7 | 139,369,869 |
| 1547 | CNTNAP2 | 7 | 146,670,511 | 1548 | CNTNAP2 | 7 | 146,671,711 |
| 1549 | CNTNAP2 | 7 | 146,671,930 | 1550 | CNTNAP2 | 7 | 146,673,648 |
| 1551 | CNTNAP2 | 7 | 146,706,249 | 1552 | CNTNAP2 | 7 | 146,723,973 |
| 1553 | CNTNAP2 | 7 | 146,724,262 | 1554 | CNTNAP2 | 7 | 146,782,515 |
| 1555 | CNTNAP2 | 7 | 146,786,412 | 1556 | CNTNAP2 | 7 | 146,786,448 |
| 1557 | CNTNAP2 | 7 | 146,788,290 | 1558 | CNTNAP2 | 7 | 146,791,664 |
| 1559 | CNTNAP2 | 7 | 146,791,891 | 1560 | CNTNAP2 | 7 | 146,792,055 |
| 1561 | CNTNAP2 | 7 | 146,792,712 | 1562 | CNTNAP2 | 7 | 146,794,158 |
| 1563 | CNTNAP2 | 7 | 146,795,212 | 1564 | CNTNAP2 | 7 | 146,795,377 |
| 1565 | CNTNAP2 | 7 | 146,795,593 | 1566 | CNTNAP2 | 7 | 146,798,866 |
| 1567 | CNTNAP2 | 7 | 146,800,067 | 1568 | CNTNAP2 | 7 | 146,800,208 |
| 1569 | CNTNAP2 | 7 | 146,816,270 | 1570 | CNTNAP2 | 7 | 146,816,456 |
| 1571 | CNTNAP2 | 7 | 147,067,210 | 1572 | CNTNAP2 | 7 | 147,088,310 |
| 1573 | CNTNAP2 | 7 | 147,748,379 | 1574 | ACCN3 | 7 | 150,382,999 |
| 1575 | DPP6 | 7 | 154,100,079 | 1576 | DPP6 | 7 | 154,132,604 |
| 1577 | DPP6 | 7 | 154,143,043 | 1578 | HTR5A | 7 | 154,513,733 |
| 1579 | HTR5A | 7 | 154,518,336 | 1580 | PTPRN2 | 7 | 157,055,372 |
| 1581 | PTPRN2 | 7 | 157,060,284 | 1582 | PTPRN2 | 7 | 157,062,744 |
| 1583 | PTPRN2 | 7 | 157,509,808 | 1584 | PTPRN2 | 7 | 157,519,106 |
| 1585 | PTPRN2 | 7 | 157,647,665 | 1586 | CSMD1 | 8 | 2,793,553 |
| 1587 | CSMD1 | 8 | 2,795,939 | 1588 | CSMD1 | 8 | 3,202,280 |
| 1589 | CSMD1 | 8 | 3,202,904 | 1590 | CSMD1 | 8 | 3,218,544 |
| 1591 | CSMD1 | 8 | 3,228,881 | 1592 | CSMD1 | 8 | 3,242,988 |
| 1593 | CSMD1 | 8 | 3,245,103 | 1594 | CSMD1 | 8 | 3,246,122 |
| 1595 | CSMD1 | 8 | 3,248,205 | 1596 | CSMD1 | 8 | 3,252,146 |
| 1597 | MCPH1 | 8 | 6,305,755 | 1598 | MCPH1 | 8 | 6,355,722 |
| 1599 | MCPH1 | 8 | 6,357,338 | 1600 | MCPH1 | 8 | 6,362,452 |
| 1601 | MCPH1 | 8 | 6,383,317 | 1602 | MCPH1 | 8 | 6,384,278 |
| 1603 | MCPH1 | 8 | 6,384,838 | 1604 | MCPH1 | 8 | 6,402,090 |
| 1605 | MCPH1 | 8 | 6,407,942 | 1606 | MCPH1 | 8 | 6,407,982 |
| 1607 | MCPH1 | 8 | 6,414,463 | 1608 | MCPH1 | 8 | 6,480,594 |
| 1609 | ANGPT2 | 8 | 6,522,454 | 1610 | DLC1 | 8 | 13,033,085 |
| 1611 | SGCZ | 8 | 14,292,030 | 1612 | SGCZ | 8 | 14,297,725 |
| 1613 | SGCZ | 8 | 14,303,019 | 1614 | SGCZ | 8 | 14,567,685 |
| 1615 | SGCZ | 8 | 14,594,527 | 1616 | SGCZ | 8 | 14,594,583 |
| 1617 | SGCZ | 8 | 14,603,034 | 1618 | SGCZ | 8 | 14,619,388 |
| 1619 | SLC7A2 | 8 | 17,456,102 | 1620 | SLC7A2 | 8 | 17,480,172 |
| 1621 | PSD3 | 8 | 18,467,203 | 1622 | PSD3 | 8 | 18,469,732 |
| 1623 | PSD3 | 8 | 18,708,574 | 1624 | PSD3 | 8 | 18,709,420 |
| 1625 | PSD3 | 8 | 18,819,182 | 1626 | ATP6V1B2 | 8 | 20,110,329 |
| 1627 | ATP6V1B2 | 8 | 20,116,050 | 1628 | XPO7 | 8 | 21,934,553 |
| 1629 | PPP3CC | 8 | 22,390,555 | 1630 | PPP3CC | 8 | 22,391,033 |
| 1631 | PPP3CC | 8 | 22,416,883 | 1632 | PPP3CC | 8 | 22,417,197 |
| 1633 | PPP3CC | 8 | 22,421,890 | 1634 | PPP3CC | 8 | 22,438,725 |
| 1635 | PPP3CC | 8 | 22,451,254 | 1636 | PPP3CC | 8 | 22,451,454 |
| 1637 | PEBP4 | 8 | 22,872,629 | 1638 | SLC25A37 | 8 | 23,454,180 |
| 1639 | SLC25A37 | 8 | 23,479,642 | 1640 | SLC25A37 | 8 | 23,487,137 |
| 1641 | SLC25A37 | 8 | 23,490,677 | 1642 | UNC5D | 8 | 35,523,511 |
| 1643 | UNC5D | 8 | 35,531,300 | 1644 | UNC5D | 8 | 35,534,179 |
| 1645 | UNC5D | 8 | 35,534,272 | 1646 | UNC5D | 8 | 35,543,336 |
| 1647 | UNC5D | 8 | 35,855,073 | 1648 | UNC5D | 8 | 36,042,355 |
| 1649 | UNC5D | 8 | 36,055,367 | 1650 | SFRP1 | 8 | 41,221,920 |
| 1651 | SFRP1 | 8 | 41,238,711 | 1652 | SFRP1 | 8 | 41,254,926 |
| 1653 | PRKDC | 8 | 48,805,431 | 1654 | PRKDC | 8 | 49,014,881 |
| 1655 | SNTG1 | 8 | 50,990,529 | 1656 | SNTG1 | 8 | 50,990,561 |
| 1657 | SNTG1 | 8 | 50,996,988 | 1658 | SNTG1 | 8 | 51,010,187 |
| 1659 | SNTG1 | 8 | 51,028,383 | 1660 | SNTG1 | 8 | 51,035,846 |
| 1661 | SNTG1 | 8 | 51,042,787 | 1662 | SNTG1 | 8 | 51,049,706 |
| 1663 | SNTG1 | 8 | 51,054,533 | 1664 | SNTG1 | 8 | 51,058,990 |
| 1665 | SNTG1 | 8 | 51,082,766 | 1666 | SNTG1 | 8 | 51,102,449 |
| 1667 | SNTG1 | 8 | 51,173,297 | 1668 | SNTG1 | 8 | 51,234,295 |
| 1669 | SNTG1 | 8 | 51,235,510 | 1670 | SNTG1 | 8 | 51,320,466 |
| 1671 | SNTG1 | 8 | 51,527,844 | 1672 | SNTG1 | 8 | 51,542,530 |
| 1673 | LYN | 8 | 56,942,219 | 1674 | LYN | 8 | 57,038,773 |
| 1675 | LYN | 8 | 57,039,144 | 1676 | LYN | 8 | 57,039,314 |
| 1677 | LYN | 8 | 57,045,025 | 1678 | LYN | 8 | 57,068,622 |
| 1679 | TOX | 8 | 59,968,292 | 1680 | TOX | 8 | 60,006,808 |
| 1681 | NKAIN3 | 8 | 63,276,675 | 1682 | NKAIN3 | 8 | 63,524,869 |
| 1683 | NKAIN3 | 8 | 63,553,374 | 1684 | NKAIN3 | 8 | 63,555,581 |
| 1685 | NKAIN3 | 8 | 63,588,448 | 1686 | NKAIN3 | 8 | 63,644,314 |
| 1687 | NKAIN3 | 8 | 64,033,212 | 1688 | NKAIN3 | 8 | 64,033,505 |
| 1689 | DEPDC2 | 8 | 69,166,435 | 1690 | DEPDC2 | 8 | 69,176,632 |
| 1691 | DEPDC2 | 8 | 69,177,796 | 1692 | KCNB2 | 8 | 73,754,111 |
| 1693 | KCNB2 | 8 | 73,756,664 | 1694 | KCNB2 | 8 | 73,762,984 |

TABLE A-continued

Summary of SNPs (NCBI Human Genome Reference Assembly Build 36.3)

| SEQ ID NO: | Gene | Chr | Position (BP) | SEQ ID NO: | Gene | Chr | Position (BP) |
|---|---|---|---|---|---|---|---|
| 1695 | KCNB2 | 8 | 73,771,914 | 1696 | KCNB2 | 8 | 73,776,211 |
| 1697 | KCNB2 | 8 | 73,780,154 | 1698 | KCNB2 | 8 | 73,783,806 |
| 1699 | KCNB2 | 8 | 73,798,241 | 1700 | KCNB2 | 8 | 73,799,263 |
| 1701 | KCNB2 | 8 | 73,811,601 | 1702 | KCNB2 | 8 | 73,818,016 |
| 1703 | KCNB2 | 8 | 73,901,806 | 1704 | KCNB2 | 8 | 73,905,902 |
| 1705 | KCNB2 | 8 | 73,906,242 | 1706 | KCNB2 | 8 | 73,906,305 |
| 1707 | KCNB2 | 8 | 74,001,540 | 1708 | KCNB2 | 8 | 74,006,869 |
| 1709 | MMP16 | 8 | 89,115,235 | 1710 | MMP16 | 8 | 89,379,684 |
| 1711 | MMP16 | 8 | 89,413,738 | 1712 | MMP16 | 8 | 89,414,303 |
| 1713 | MMP16 | 8 | 89,421,430 | 1714 | GRHL2 | 8 | 102,684,162 |
| 1715 | GRHL2 | 8 | 102,689,866 | 1716 | GRHL2 | 8 | 102,701,749 |
| 1717 | GRHL2 | 8 | 102,702,489 | 1718 | GRHL2 | 8 | 102,718,857 |
| 1719 | GRHL2 | 8 | 102,736,242 | 1720 | GRHL2 | 8 | 102,744,463 |
| 1721 | GRHL2 | 8 | 102,746,981 | 1722 | GRHL2 | 8 | 102,749,085 |
| 1723 | GRHL2 | 8 | 102,759,164 | 1724 | NCALD | 8 | 102,769,504 |
| 1725 | NCALD | 8 | 102,781,373 | 1726 | NCALD | 8 | 102,801,328 |
| 1727 | NCALD | 8 | 102,812,988 | 1728 | NCALD | 8 | 102,815,103 |
| 1729 | NCALD | 8 | 102,815,612 | 1730 | ZFPM2 | 8 | 106,488,701 |
| 1731 | ZFPM2 | 8 | 106,488,930 | 1732 | ZFPM2 | 8 | 106,489,004 |
| 1733 | ZFPM2 | 8 | 106,497,198 | 1734 | ZFPM2 | 8 | 106,499,852 |
| 1735 | ZFPM2 | 8 | 106,505,157 | 1736 | ZFPM2 | 8 | 106,507,154 |
| 1737 | ZFPM2 | 8 | 106,507,756 | 1738 | ZFPM2 | 8 | 106,521,287 |
| 1739 | ZFPM2 | 8 | 106,530,047 | 1740 | ZFPM2 | 8 | 106,688,431 |
| 1741 | ZFPM2 | 8 | 106,888,057 | 1742 | CSMD3 | 8 | 113,274,947 |
| 1743 | CSMD3 | 8 | 113,288,783 | 1744 | CSMD3 | 8 | 113,335,045 |
| 1745 | CSMD3 | 8 | 113,337,274 | 1746 | CSMD3 | 8 | 113,338,203 |
| 1747 | CSMD3 | 8 | 113,352,390 | 1748 | CSMD3 | 8 | 113,373,346 |
| 1749 | CSMD3 | 8 | 113,387,234 | 1750 | CSMD3 | 8 | 113,443,580 |
| 1751 | CSMD3 | 8 | 113,443,849 | 1752 | CSMD3 | 8 | 113,445,071 |
| 1753 | CSMD3 | 8 | 113,449,291 | 1754 | CSMD3 | 8 | 113,451,969 |
| 1755 | CSMD3 | 8 | 113,452,014 | 1756 | CSMD3 | 8 | 113,452,239 |
| 1757 | CSMD3 | 8 | 113,469,659 | 1758 | CSMD3 | 8 | 113,470,832 |
| 1759 | CSMD3 | 8 | 113,473,493 | 1760 | CSMD3 | 8 | 113,474,100 |
| 1761 | CSMD3 | 8 | 113,539,247 | 1762 | CSMD3 | 8 | 113,554,111 |
| 1763 | CSMD3 | 8 | 114,099,667 | 1764 | CSMD3 | 8 | 114,104,594 |
| 1765 | CSMD3 | 8 | 114,526,293 | 1766 | SAMD12 | 8 | 119,448,826 |
| 1767 | SAMD12 | 8 | 119,517,329 | 1768 | FBXO32 | 8 | 124,585,035 |
| 1769 | FER1L6 | 8 | 124,966,104 | 1770 | FER1L6 | 8 | 124,991,846 |
| 1771 | FER1L6 | 8 | 124,996,892 | 1772 | FER1L6 | 8 | 124,997,443 |
| 1773 | FER1L6 | 8 | 125,002,201 | 1774 | FER1L6 | 8 | 125,010,633 |
| 1775 | FER1L6 | 8 | 125,011,048 | 1776 | FER1L6 | 8 | 125,015,766 |
| 1777 | FER1L6 | 8 | 125,053,616 | 1778 | MTSS1 | 8 | 125,688,384 |
| 1779 | MTSS1 | 8 | 125,690,229 | 1780 | MTSS1 | 8 | 125,708,636 |
| 1781 | MTSS1 | 8 | 125,771,942 | 1782 | MTSS1 | 8 | 125,793,473 |
| 1783 | MTSS1 | 8 | 125,952,323 | 1784 | MTSS1 | 8 | 125,954,015 |
| 1785 | DDEF1 | 8 | 131,325,860 | 1786 | ADCY8 | 8 | 132,056,557 |
| 1787 | ADCY8 | 8 | 132,057,744 | 1788 | ADCY8 | 8 | 132,057,791 |
| 1789 | COL22A1 | 8 | 139,662,848 | 1790 | COL22A1 | 8 | 139,662,978 |
| 1791 | COL22A1 | 8 | 139,743,805 | 1792 | COL22A1 | 8 | 139,888,333 |
| 1793 | COL22A1 | 8 | 139,890,241 | 1794 | COL22A1 | 8 | 139,892,274 |
| 1795 | COL22A1 | 8 | 139,892,385 | 1796 | COL22A1 | 8 | 139,895,678 |
| 1797 | COL22A1 | 8 | 139,908,094 | 1798 | COL22A1 | 8 | 139,972,905 |
| 1799 | COL22A1 | 8 | 139,975,270 | 1800 | COL22A1 | 8 | 139,976,026 |
| 1801 | KCNK9 | 8 | 140,740,112 | 1802 | PTP4A3 | 8 | 142,469,282 |
| 1803 | SMARCA2 | 9 | 2,063,292 | 1804 | SMARCA2 | 9 | 2,084,908 |
| 1805 | SMARCA2 | 9 | 2,113,639 | 1806 | SMARCA2 | 9 | 2,118,165 |
| 1807 | SMARCA2 | 9 | 2,170,694 | 1808 | SMARCA2 | 9 | 2,176,460 |
| 1809 | SMARCA2 | 9 | 2,181,725 | 1810 | SLC1A1 | 9 | 4,452,265 |
| 1811 | SLC1A1 | 9 | 4,483,526 | 1812 | SLC1A1 | 9 | 4,572,082 |
| 1813 | SLC1A1 | 9 | 4,588,748 | 1814 | PTPRD | 9 | 8,415,422 |
| 1815 | ADAMTSL1 | 9 | 18,718,689 | 1816 | ASAH3L | 9 | 19,438,473 |
| 1817 | KIAA1797 | 9 | 20,682,438 | 1818 | KIAA1797 | 9 | 20,686,043 |
| 1819 | KIAA1797 | 9 | 20,725,284 | 1820 | KIAA1797 | 9 | 20,730,433 |
| 1821 | KIAA1797 | 9 | 20,732,210 | 1822 | KIAA1797 | 9 | 20,753,840 |
| 1823 | KIAA1797 | 9 | 20,754,870 | 1824 | KIAA1797 | 9 | 20,833,841 |
| 1825 | KIAA1797 | 9 | 20,872,525 | 1826 | KIAA1797 | 9 | 20,873,199 |
| 1827 | KIAA1797 | 9 | 20,873,713 | 1828 | KIAA1797 | 9 | 20,882,952 |
| 1829 | KIAA1797 | 9 | 20,989,646 | 1830 | IFT74 | 9 | 26,935,976 |
| 1831 | IFT74 | 9 | 26,936,249 | 1832 | IFT74 | 9 | 26,999,738 |
| 1833 | IFT74 | 9 | 27,022,385 | 1834 | IFT74 | 9 | 27,031,676 |
| 1835 | IFT74 | 9 | 27,056,070 | 1836 | IFT74 | 9 | 27,063,650 |
| 1837 | TEK | 9 | 27,065,883 | 1838 | TEK | 9 | 27,142,292 |
| 1839 | PIP5K1B | 9 | 70,643,121 | 1840 | PIP5K1B | 9 | 70,647,996 |
| 1841 | PIP5K1B | 9 | 70,673,848 | 1842 | PIP5K1B | 9 | 70,687,329 |
| 1843 | PIP5K1B | 9 | 70,691,508 | 1844 | PIP5K1B | 9 | 70,700,570 |

TABLE A-continued

Summary of SNPs (NCBI Human Genome Reference Assembly Build 36.3)

| SEQ ID NO: | Gene | Chr | Position (BP) | SEQ ID NO: | Gene | Chr | Position (BP) |
|---|---|---|---|---|---|---|---|
| 1845 | PIP5K1B | 9 | 70,814,515 | 1846 | MAMDC2 | 9 | 71,887,859 |
| 1847 | MAMDC2 | 9 | 71,896,167 | 1848 | MAMDC2 | 9 | 71,913,927 |
| 1849 | MAMDC2 | 9 | 71,917,647 | 1850 | MAMDC2 | 9 | 71,998,782 |
| 1851 | TRPM3 | 9 | 72,637,875 | 1852 | TRPM3 | 9 | 72,644,103 |
| 1853 | TRPM3 | 9 | 72,648,924 | 1854 | TRPM3 | 9 | 72,649,911 |
| 1855 | TRPM3 | 9 | 72,652,604 | 1856 | TRPM3 | 9 | 72,662,180 |
| 1857 | TMC1 | 9 | 74,317,350 | 1858 | TMC1 | 9 | 74,317,363 |
| 1859 | TMC1 | 9 | 74,317,668 | 1860 | TMC1 | 9 | 74,320,797 |
| 1861 | TMC1 | 9 | 74,401,423 | 1862 | TMC1 | 9 | 74,503,133 |
| 1863 | TMC1 | 9 | 74,507,002 | 1864 | TMC1 | 9 | 74,507,694 |
| 1865 | TMC1 | 9 | 74,531,851 | 1866 | TMC1 | 9 | 74,537,387 |
| 1867 | TMC1 | 9 | 74,610,051 | 1868 | TMC1 | 9 | 74,686,641 |
| 1869 | TRPM6 | 9 | 76,540,404 | 1870 | TRPM6 | 9 | 76,543,120 |
| 1871 | TRPM6 | 9 | 76,566,467 | 1872 | TRPM6 | 9 | 76,567,230 |
| 1873 | TRPM6 | 9 | 76,570,941 | 1874 | GNAQ | 9 | 79,481,827 |
| 1875 | GNAQ | 9 | 79,483,477 | 1876 | GNAQ | 9 | 79,494,080 |
| 1877 | GNAQ | 9 | 79,517,988 | 1878 | GNAQ | 9 | 79,536,340 |
| 1879 | GNAQ | 9 | 79,827,513 | 1880 | GNAQ | 9 | 79,845,641 |
| 1881 | GNAQ | 9 | 79,868,777 | 1882 | GNAQ | 9 | 79,874,660 |
| 1883 | GNAQ | 9 | 79,878,161 | 1884 | NTRK2 | 9 | 86,457,519 |
| 1885 | NTRK2 | 9 | 86,464,568 | 1886 | NTRK2 | 9 | 86,472,347 |
| 1887 | NTRK2 | 9 | 86,479,100 | 1888 | NTRK2 | 9 | 86,542,608 |
| 1889 | NTRK2 | 9 | 86,553,021 | 1890 | NTRK2 | 9 | 86,571,296 |
| 1891 | NTRK2 | 9 | 86,573,597 | 1892 | NTRK2 | 9 | 86,577,727 |
| 1893 | NTRK2 | 9 | 86,579,987 | 1894 | NTRK2 | 9 | 86,598,770 |
| 1895 | NTRK2 | 9 | 86,598,798 | 1896 | NTRK2 | 9 | 86,625,557 |
| 1897 | NTRK2 | 9 | 86,631,295 | 1898 | NTRK2 | 9 | 86,635,476 |
| 1899 | DAPK1 | 9 | 89,446,457 | 1900 | DAPK1 | 9 | 89,466,486 |
| 1901 | DAPK1 | 9 | 89,518,960 | 1902 | SHC3 | 9 | 90,813,631 |
| 1903 | SHC3 | 9 | 90,829,608 | 1904 | SHC3 | 9 | 90,846,224 |
| 1905 | DIRAS2 | 9 | 92,391,092 | 1906 | DIRAS2 | 9 | 92,432,152 |
| 1907 | DIRAS2 | 9 | 92,432,978 | 1908 | DIRAS2 | 9 | 92,453,078 |
| 1909 | NFIL3 | 9 | 93,283,388 | 1910 | ZNF169 | 9 | 96,065,119 |
| 1911 | GABBR2 | 9 | 100,075,165 | 1912 | GABBR2 | 9 | 100,094,975 |
| 1913 | GABBR2 | 9 | 100,101,460 | 1914 | GABBR2 | 9 | 100,102,891 |
| 1915 | GRIN3A | 9 | 103,379,633 | 1916 | GRIN3A | 9 | 103,429,073 |
| 1917 | GRIN3A | 9 | 103,440,380 | 1918 | GRIN3A | 9 | 103,457,375 |
| 1919 | GRIN3A | 9 | 103,467,085 | 1920 | GRIN3A | 9 | 103,467,403 |
| 1921 | GRIN3A | 9 | 103,468,661 | 1922 | GRIN3A | 9 | 103,476,464 |
| 1923 | GRIN3A | 9 | 103,481,593 | 1924 | GRIN3A | 9 | 103,491,159 |
| 1925 | GRIN3A | 9 | 103,516,083 | 1926 | GRIN3A | 9 | 103,520,656 |
| 1927 | GRIN3A | 9 | 103,535,011 | 1928 | GRIN3A | 9 | 103,578,372 |
| 1929 | FKTN | 9 | 107,361,938 | 1930 | FKTN | 9 | 107,409,195 |
| 1931 | FKTN | 9 | 107,435,753 | 1932 | PALM2 | 9 | 111,481,826 |
| 1933 | PALM2 | 9 | 111,488,202 | 1934 | PALM2 | 9 | 111,560,947 |
| 1935 | PALM2 | 9 | 111,561,356 | 1936 | PALM2 | 9 | 111,561,384 |
| 1937 | PALM2 | 9 | 111,975,567 | 1938 | SVEP1Â | 9 | 112,294,525 |
| 1939 | SVEP1Â | 9 | 112,396,284 | 1940 | MUSK | 9 | 112,443,667 |
| 1941 | MUSK | 9 | 112,562,853 | 1942 | MUSK | 9 | 112,600,135 |
| 1943 | MUSK | 9 | 112,615,167 | 1944 | RGS3 | 9 | 115,354,739 |
| 1945 | RGS3 | 9 | 115,368,771 | 1946 | ZNF618 | 9 | 115,840,427 |
| 1947 | DFNB31 | 9 | 116,203,827 | 1948 | DFNB31 | 9 | 116,210,131 |
| 1949 | DFNB31 | 9 | 116,216,770 | 1950 | DFNB31 | 9 | 116,219,043 |
| 1951 | DFNB31 | 9 | 116,221,058 | 1952 | DFNB31 | 9 | 116,222,299 |
| 1953 | DFNB31 | 9 | 116,222,970 | 1954 | DFNB31 | 9 | 116,229,014 |
| 1955 | DFNB31 | 9 | 116,250,139 | 1956 | DFNB31 | 9 | 116,287,408 |
| 1957 | DFNB31 | 9 | 116,290,214 | 1958 | DFNB31 | 9 | 116,312,260 |
| 1959 | DFNB31 | 9 | 116,327,990 | 1960 | DFNB31 | 9 | 116,345,761 |
| 1961 | PAPPA | 9 | 118,151,091 | 1962 | PAPPA | 9 | 118,185,562 |
| 1963 | PAPPA | 9 | 118,198,635 | 1964 | PAPPA | 9 | 118,211,325 |
| 1965 | ASTN2 | 9 | 118,293,293 | 1966 | ASTN2 | 9 | 118,298,008 |
| 1967 | ASTN2 | 9 | 118,300,987 | 1968 | ASTN2 | 9 | 118,342,138 |
| 1969 | ASTN2 | 9 | 118,421,106 | 1970 | ASTN2 | 9 | 118,443,189 |
| 1971 | ASTN2 | 9 | 118,446,482 | 1972 | ASTN2 | 9 | 118,449,459 |
| 1973 | ASTN2 | 9 | 118,450,577 | 1974 | ASTN2 | 9 | 118,493,276 |
| 1975 | ASTN2 | 9 | 118,514,893 | 1976 | ASTN2 | 9 | 118,750,592 |
| 1977 | ASTN2 | 9 | 118,752,154 | 1978 | ASTN2 | 9 | 118,767,325 |
| 1979 | ASTN2 | 9 | 118,767,524 | 1980 | ASTN2 | 9 | 118,780,289 |
| 1981 | ASTN2 | 9 | 118,782,752 | 1982 | ASTN2 | 9 | 118,783,350 |
| 1983 | ASTN2 | 9 | 118,786,221 | 1984 | ASTN2 | 9 | 118,898,790 |
| 1985 | ASTN2 | 9 | 118,900,774 | 1986 | ASTN2 | 9 | 119,192,376 |
| 1987 | ASTN2 | 9 | 119,198,404 | 1988 | ASTN2 | 9 | 119,233,626 |
| 1989 | CDK5RAP2 | 9 | 122,266,946 | 1990 | CDK5RAP2 | 9 | 122,315,206 |
| 1991 | CDK5RAP2 | 9 | 122,377,819 | 1992 | RAB14 | 9 | 122,976,150 |
| 1993 | GSN | 9 | 123,122,996 | 1994 | GSN | 9 | 123,123,769 |

TABLE A-continued

Summary of SNPs (NCBI Human Genome Reference Assembly Build 36.3)

| SEQ ID NO: | Gene | Chr | Position (BP) | SEQ ID NO: | Gene | Chr | Position (BP) |
|---|---|---|---|---|---|---|---|
| 1995 | GSN | 9 | 123,135,092 | 1996 | GSN | 9 | 123,138,356 |
| 1997 | TTLL11 | 9 | 123,780,890 | 1998 | TTLL11 | 9 | 123,839,061 |
| 1999 | TTLL11 | 9 | 123,904,206 | 2000 | TTLL11 | 9 | 123,908,883 |
| 2001 | LHX6 | 9 | 123,995,743 | 2002 | DENND1A | 9 | 125,236,746 |
| 2003 | DENND1A | 9 | 125,237,968 | 2004 | DENND1A | 9 | 125,259,527 |
| 2005 | DENND1A | 9 | 125,273,650 | 2006 | DENND1A | 9 | 125,274,235 |
| 2007 | DENND1A | 9 | 125,278,391 | 2008 | DENND1A | 9 | 125,391,244 |
| 2009 | DENND1A | 9 | 125,406,711 | 2010 | DENND1A | 9 | 125,457,338 |
| 2011 | DENND1A | 9 | 125,677,182 | 2012 | DENND1A | 9 | 125,701,433 |
| 2013 | DENND1A | 9 | 125,714,335 | 2014 | NEK6 | 9 | 126,050,083 |
| 2015 | NEK6 | 9 | 126,050,327 | 2016 | NEK6 | 9 | 126,050,695 |
| 2017 | NEK6 | 9 | 126,129,943 | 2018 | ABL1 | 9 | 132,590,178 |
| 2019 | ABL1 | 9 | 132,601,560 | 2020 | ABL1 | 9 | 132,603,386 |
| 2021 | ABL1 | 9 | 132,607,062 | 2022 | ABL1 | 9 | 132,610,819 |
| 2023 | ABL1 | 9 | 132,611,325 | 2024 | ABL1 | 9 | 132,611,594 |
| 2025 | ABL1 | 9 | 132,613,270 | 2026 | ABL1 | 9 | 132,625,367 |
| 2027 | ABL1 | 9 | 132,690,607 | 2028 | TSC1 | 9 | 134,739,894 |
| 2029 | TSC1 | 9 | 134,765,855 | 2030 | TSC1 | 9 | 134,773,990 |
| 2031 | TSC1 | 9 | 134,802,822 | 2032 | VAV2 | 9 | 135,614,363 |
| 2033 | VAV2 | 9 | 135,655,129 | 2034 | VAV2 | 9 | 135,722,588 |
| 2035 | VAV2 | 9 | 135,725,041 | 2036 | VAV2 | 9 | 135,726,939 |
| 2037 | VAV2 | 9 | 135,737,060 | 2038 | KCNT1 | 9 | 137,739,699 |
| 2039 | INPP5E | 9 | 138,461,433 | 2040 | NOTCH1 | 9 | 138,521,325 |
| 2041 | NOTCH1 | 9 | 138,546,887 | 2042 | CACNA1B | 9 | 140,019,421 |
| 2043 | CACNA1B | 9 | 140,019,503 | 2044 | CACNA1B | 9 | 140,031,491 |
| 2045 | CACNA1B | 9 | 140,040,905 | 2046 | CACNA1B | 9 | 140,106,414 |
| 2047 | CACNA1B | 9 | 140,131,345 | 2048 | PITRM1 | 10 | 3,163,364 |
| 2049 | PITRM1 | 10 | 3,173,747 | 2050 | PRKCQ | 10 | 7,132,955 |
| 2051 | CACNB2 | 10 | 18,589,647 | 2052 | CACNB2 | 10 | 18,751,294 |
| 2053 | CACNB2 | 10 | 18,819,330 | 2054 | CACNB2 | 10 | 18,829,273 |
| 2055 | CACNB2 | 10 | 18,830,509 | 2056 | CACNB2 | 10 | 18,830,733 |
| 2057 | CACNB2 | 10 | 18,838,209 | 2058 | CACNB2 | 10 | 18,839,230 |
| 2059 | CACNB2 | 10 | 18,839,896 | 2060 | CACNB2 | 10 | 18,847,063 |
| 2061 | CACNB2 | 10 | 18,861,080 | 2062 | CACNB2 | 10 | 18,862,348 |
| 2063 | ARMC3 | 10 | 23,233,970 | 2064 | ARMC3 | 10 | 23,277,574 |
| 2065 | ARMC3 | 10 | 23,314,154 | 2066 | MYO3A | 10 | 26,222,334 |
| 2067 | MYO3A | 10 | 26,256,474 | 2068 | MYO3A | 10 | 26,352,830 |
| 2069 | MYO3A | 10 | 26,353,343 | 2070 | MYO3A | 10 | 26,383,203 |
| 2071 | MYO3A | 10 | 26,385,264 | 2072 | MYO3A | 10 | 26,419,059 |
| 2073 | MYO3A | 10 | 26,447,414 | 2074 | MYO3A | 10 | 26,493,174 |
| 2075 | MYO3A | 10 | 26,504,528 | 2076 | SLC18A3 | 10 | 50,438,238 |
| 2077 | SLC18A3 | 10 | 50,491,249 | 2078 | PRKG1 | 10 | 52,459,361 |
| 2079 | PRKG1 | 10 | 52,577,528 | 2080 | PRKG1 | 10 | 52,585,849 |
| 2081 | PRKG1 | 10 | 52,585,942 | 2082 | PRKG1 | 10 | 52,586,179 |
| 2083 | PRKG1 | 10 | 52,619,168 | 2084 | PRKG1 | 10 | 52,869,416 |
| 2085 | PRKG1 | 10 | 52,901,690 | 2086 | PRKG1 | 10 | 52,904,054 |
| 2087 | PRKG1 | 10 | 53,550,571 | 2088 | PRKG1 | 10 | 53,562,357 |
| 2089 | PCDH15 | 10 | 55,284,858 | 2090 | PCDH15 | 10 | 55,334,011 |
| 2091 | PCDH15 | 10 | 55,468,894 | 2092 | PCDH15 | 10 | 55,502,506 |
| 2093 | PCDH15 | 10 | 55,631,926 | 2094 | PCDH15 | 10 | 55,633,952 |
| 2095 | PCDH15 | 10 | 55,635,312 | 2096 | PCDH15 | 10 | 55,636,727 |
| 2097 | PCDH15 | 10 | 55,639,211 | 2098 | PCDH15 | 10 | 55,639,890 |
| 2099 | PCDH15 | 10 | 55,639,938 | 2100 | PCDH15 | 10 | 55,709,225 |
| 2101 | PCDH15 | 10 | 55,743,087 | 2102 | PCDH15 | 10 | 55,746,766 |
| 2103 | PCDH15 | 10 | 55,759,269 | 2104 | PCDH15 | 10 | 55,806,859 |
| 2105 | PCDH15 | 10 | 55,817,364 | 2106 | PCDH15 | 10 | 56,237,672 |
| 2107 | PCDH15 | 10 | 56,285,230 | 2108 | PCDH15 | 10 | 56,287,963 |
| 2109 | PCDH15 | 10 | 56,288,058 | 2110 | PCDH15 | 10 | 56,873,024 |
| 2111 | PCDH15 | 10 | 56,960,734 | 2112 | PCDH15 | 10 | 57,003,485 |
| 2113 | PCDH15 | 10 | 57,005,770 | 2114 | ANK3 | 10 | 61,466,096 |
| 2115 | ANK3 | 10 | 61,490,495 | 2116 | ANK3 | 10 | 61,569,339 |
| 2117 | ANK3 | 10 | 61,585,961 | 2118 | ANK3 | 10 | 61,594,867 |
| 2119 | ANK3 | 10 | 61,740,656 | 2120 | ANK3 | 10 | 61,746,842 |
| 2121 | JMJD1C | 10 | 64,618,690 | 2122 | JMJD1C | 10 | 64,732,014 |
| 2123 | JMJD1C | 10 | 64,736,192 | 2124 | JMJD1C | 10 | 64,761,165 |
| 2125 | JMJD1C | 10 | 64,771,213 | 2126 | JMJD1C | 10 | 64,778,162 |
| 2127 | CTNNA3 | 10 | 67,462,579 | 2128 | CTNNA3 | 10 | 67,487,829 |
| 2129 | CTNNA3 | 10 | 67,515,886 | 2130 | CTNNA3 | 10 | 67,516,561 |
| 2131 | CTNNA3 | 10 | 67,564,825 | 2132 | CTNNA3 | 10 | 67,577,247 |
| 2133 | CTNNA3 | 10 | 67,595,330 | 2134 | CTNNA3 | 10 | 67,634,469 |
| 2135 | CTNNA3 | 10 | 67,637,097 | 2136 | CTNNA3 | 10 | 67,695,250 |
| 2137 | CTNNA3 | 10 | 67,698,152 | 2138 | CTNNA3 | 10 | 67,713,848 |
| 2139 | CTNNA3 | 10 | 67,725,533 | 2140 | CTNNA3 | 10 | 68,131,872 |
| 2141 | CTNNA3 | 10 | 68,283,754 | 2142 | CTNNA3 | 10 | 68,283,801 |
| 2143 | CTNNA3 | 10 | 68,285,636 | 2144 | CTNNA3 | 10 | 68,506,311 |

TABLE A-continued

Summary of SNPs (NCBI Human Genome Reference Assembly Build 36.3)

| SEQ ID NO: | Gene | Chr | Position (BP) | SEQ ID NO: | Gene | Chr | Position (BP) |
|---|---|---|---|---|---|---|---|
| 2145 | CTNNA3 | 10 | 68,600,561 | 2146 | CTNNA3 | 10 | 68,609,647 |
| 2147 | CTNNA3 | 10 | 68,611,041 | 2148 | CTNNA3 | 10 | 68,617,000 |
| 2149 | CTNNA3 | 10 | 68,622,864 | 2150 | CTNNA3 | 10 | 68,626,505 |
| 2151 | CTNNA3 | 10 | 68,628,119 | 2152 | CTNNA3 | 10 | 68,628,572 |
| 2153 | CTNNA3 | 10 | 68,631,498 | 2154 | CTNNA3 | 10 | 68,742,873 |
| 2155 | CTNNA3 | 10 | 68,750,082 | 2156 | CTNNA3 | 10 | 69,048,122 |
| 2157 | CTNNA3 | 10 | 69,088,276 | 2158 | CTNNA3 | 10 | 69,106,914 |
| 2159 | CTNNA3 | 10 | 69,118,295 | 2160 | CTNNA3 | 10 | 69,123,347 |
| 2161 | CTNNA3 | 10 | 69,163,784 | 2162 | CTNNA3 | 10 | 69,193,368 |
| 2163 | CDH23 | 10 | 73,076,605 | 2164 | KCNMA1 | 10 | 78,232,825 |
| 2165 | KCNMA1 | 10 | 78,258,751 | 2166 | KCNMA1 | 10 | 78,259,743 |
| 2167 | KCNMA1 | 10 | 78,286,204 | 2168 | KCNMA1 | 10 | 78,297,136 |
| 2169 | KCNMA1 | 10 | 78,299,801 | 2170 | KCNMA1 | 10 | 78,300,503 |
| 2171 | KCNMA1 | 10 | 78,358,158 | 2172 | KCNMA1 | 10 | 78,372,877 |
| 2173 | KCNMA1 | 10 | 78,426,444 | 2174 | KCNMA1 | 10 | 78,426,609 |
| 2175 | KCNMA1 | 10 | 78,446,565 | 2176 | KCNMA1 | 10 | 78,447,710 |
| 2177 | KCNMA1 | 10 | 78,587,494 | 2178 | KCNMA1 | 10 | 78,598,169 |
| 2179 | KCNMA1 | 10 | 78,865,698 | 2180 | KCNMA1 | 10 | 78,865,774 |
| 2181 | KCNMA1 | 10 | 78,872,456 | 2182 | KCNMA1 | 10 | 79,086,473 |
| 2183 | NRG3 | 10 | 83,532,551 | 2184 | NRG3 | 10 | 83,626,423 |
| 2185 | NRG3 | 10 | 84,141,992 | 2186 | NRG3 | 10 | 84,195,058 |
| 2187 | NRG3 | 10 | 84,604,364 | 2188 | NRG3 | 10 | 84,616,939 |
| 2189 | SORBS1 | 10 | 97,061,998 | 2190 | SORBS1 | 10 | 97,097,088 |
| 2191 | SORBS1 | 10 | 97,111,958 | 2192 | SORBS1 | 10 | 97,112,231 |
| 2193 | SORBS1 | 10 | 97,136,438 | 2194 | SORBS1 | 10 | 97,214,150 |
| 2195 | SORBS1 | 10 | 97,313,525 | 2196 | PIK3AP1 | 10 | 98,343,203 |
| 2197 | PIK3AP1 | 10 | 98,361,738 | 2198 | PIK3AP1 | 10 | 98,368,240 |
| 2199 | PIK3AP1 | 10 | 98,370,534 | 2200 | PIK3AP1 | 10 | 98,468,439 |
| 2201 | SLIT1 | 10 | 98,840,790 | 2202 | SLIT1 | 10 | 98,868,371 |
| 2203 | SLIT1 | 10 | 98,923,843 | 2204 | SLIT1 | 10 | 98,956,872 |
| 2205 | SLIT1 | 10 | 98,961,015 | 2206 | SORCS3 | 10 | 106,355,057 |
| 2207 | SORCS3 | 10 | 106,371,034 | 2208 | SORCS3 | 10 | 106,511,862 |
| 2209 | SORCS3 | 10 | 106,518,456 | 2210 | SORCS3 | 10 | 106,543,829 |
| 2211 | SORCS3 | 10 | 106,546,794 | 2212 | SORCS3 | 10 | 106,586,272 |
| 2213 | SORCS3 | 10 | 106,618,988 | 2214 | SORCS3 | 10 | 106,622,111 |
| 2215 | SORCS3 | 10 | 106,703,623 | 2216 | SORCS3 | 10 | 106,934,094 |
| 2217 | SORCS3 | 10 | 107,025,958 | 2218 | VTI1A | 10 | 114,226,855 |
| 2219 | VTI1A | 10 | 114,228,361 | 2220 | ATRNL1 | 10 | 116,937,138 |
| 2221 | ATRNL1 | 10 | 117,018,254 | 2222 | ATRNL1 | 10 | 117,193,379 |
| 2223 | ATRNL1 | 10 | 117,251,493 | 2224 | ATRNL1 | 10 | 117,257,300 |
| 2225 | ATRNL1 | 10 | 117,261,885 | 2226 | ATRNL1 | 10 | 117,267,663 |
| 2227 | ATRNL1 | 10 | 117,280,076 | 2228 | ATRNL1 | 10 | 117,301,088 |
| 2229 | ATRNL1 | 10 | 117,305,474 | 2230 | ATRNL1 | 10 | 117,329,513 |
| 2231 | ATRNL1 | 10 | 117,341,209 | 2232 | ATRNL1 | 10 | 117,341,891 |
| 2233 | ATRNL1 | 10 | 117,342,514 | 2234 | ATRNL1 | 10 | 117,348,909 |
| 2235 | ATRNL1 | 10 | 117,348,932 | 2236 | ATRNL1 | 10 | 117,350,294 |
| 2237 | ATRNL1 | 10 | 117,352,824 | 2238 | ATRNL1 | 10 | 117,385,627 |
| 2239 | ATRNL1 | 10 | 117,404,353 | 2240 | ATRNL1 | 10 | 117,628,480 |
| 2241 | HSPA12A | 10 | 118,434,753 | 2242 | HSPA12A | 10 | 118,437,365 |
| 2243 | HSPA12A | 10 | 118,438,068 | 2244 | NANOS1 | 10 | 120,811,615 |
| 2245 | GRK5 | 10 | 121,222,444 | 2246 | ATE1 | 10 | 123,421,505 |
| 2247 | ATE1 | 10 | 123,426,686 | 2248 | ATE1 | 10 | 123,427,197 |
| 2249 | ATE1 | 10 | 123,427,443 | 2250 | ATE1 | 10 | 123,428,103 |
| 2251 | ATE1 | 10 | 123,432,831 | 2252 | ATE1 | 10 | 123,453,723 |
| 2253 | ATE1 | 10 | 123,484,634 | 2254 | ATE1 | 10 | 123,573,965 |
| 2255 | ATE1 | 10 | 123,614,295 | 2256 | ATE1 | 10 | 123,615,180 |
| 2257 | ATE1 | 10 | 123,627,690 | 2258 | ATE1 | 10 | 123,630,511 |
| 2259 | ATE1 | 10 | 123,634,335 | 2260 | ATE1 | 10 | 123,648,119 |
| 2261 | ATE1 | 10 | 123,659,245 | 2262 | ATE1 | 10 | 123,666,737 |
| 2263 | ATE1 | 10 | 123,669,674 | 2264 | EBF3 | 10 | 131,490,856 |
| 2265 | EBF3 | 10 | 131,645,661 | 2266 | EBF3 | 10 | 131,740,881 |
| 2267 | DEAF1 | 11 | 723,609 | 2268 | CEND1 | 11 | 762,982 |
| 2269 | CEND1 | 11 | 830,034 | 2270 | HCCA2 | 11 | 1,451,351 |
| 2271 | HCCA2 | 11 | 1,455,660 | 2272 | HCCA2 | 11 | 1,476,557 |
| 2273 | HCCA2 | 11 | 1,489,585 | 2274 | DUSP8 | 11 | 1,494,093 |
| 2275 | DUSP8 | 11 | 1,501,758 | 2276 | DUSP8 | 11 | 1,501,827 |
| 2277 | DUSP8 | 11 | 1,563,922 | 2278 | STIM1 | 11 | 3,931,164 |
| 2279 | TRIM21 | 11 | 4,352,761 | 2280 | TRIM21 | 11 | 4,365,143 |
| 2281 | GALNTL4 | 11 | 11,215,705 | 2282 | GALNTL4 | 11 | 11,219,194 |
| 2283 | GALNTL4 | 11 | 11,310,922 | 2284 | GALNTL4 | 11 | 11,591,325 |
| 2285 | GALNTL4 | 11 | 11,611,548 | 2286 | MICAL2 | 11 | 12,148,237 |
| 2287 | MICAL2 | 11 | 12,165,670 | 2288 | MICAL2 | 11 | 12,172,022 |
| 2289 | MICAL2 | 11 | 12,179,624 | 2290 | MICAL2 | 11 | 12,187,248 |
| 2291 | SPON1 | 11 | 13,978,590 | 2292 | SPON1 | 11 | 13,991,391 |
| 2293 | SPON1 | 11 | 13,992,156 | 2294 | SPON1 | 11 | 13,992,537 |

TABLE A-continued

Summary of SNPs (NCBI Human Genome Reference Assembly Build 36.3)

| SEQ ID NO: | Gene | Chr | Position (BP) | SEQ ID NO: | Gene | Chr | Position (BP) |
|---|---|---|---|---|---|---|---|
| 2295 | SPON1 | 11 | 13,994,054 | 2296 | SPON1 | 11 | 13,995,954 |
| 2297 | SPON1 | 11 | 14,004,879 | 2298 | SPON1 | 11 | 14,005,230 |
| 2299 | SPON1 | 11 | 14,005,260 | 2300 | SPON1 | 11 | 14,005,745 |
| 2301 | SPON1 | 11 | 14,008,775 | 2302 | SPON1 | 11 | 14,014,762 |
| 2303 | SPON1 | 11 | 14,014,854 | 2304 | SPON1 | 11 | 14,031,836 |
| 2305 | SPON1 | 11 | 14,039,110 | 2306 | SPON1 | 11 | 14,043,034 |
| 2307 | SPON1 | 11 | 14,070,335 | 2308 | SPON1 | 11 | 14,075,677 |
| 2309 | SPON1 | 11 | 14,213,020 | 2310 | SPON1 | 11 | 14,215,231 |
| 2311 | SPON1 | 11 | 14,221,555 | 2312 | SPON1 | 11 | 14,233,507 |
| 2313 | SPON1 | 11 | 14,248,953 | 2314 | USH1C | 11 | 17,470,828 |
| 2315 | USH1C | 11 | 17,472,244 | 2316 | USH1C | 11 | 17,475,101 |
| 2317 | USH1C | 11 | 17,499,779 | 2318 | OTOG | 11 | 17,615,741 |
| 2319 | SERGEF | 11 | 17,761,574 | 2320 | SERGEF | 11 | 17,767,536 |
| 2321 | SERGEF | 11 | 17,772,558 | 2322 | IGSF22 | 11 | 18,643,492 |
| 2323 | IGSF22 | 11 | 18,646,229 | 2324 | IGSF22 | 11 | 18,646,965 |
| 2325 | IGSF22 | 11 | 18,689,422 | 2326 | PTPN5 | 11 | 18,732,258 |
| 2327 | PTPN5 | 11 | 18,732,276 | 2328 | PTPN5 | 11 | 18,732,907 |
| 2329 | PTPN5 | 11 | 18,761,510 | 2330 | NAV2 | 11 | 19,700,849 |
| 2331 | NAV2 | 11 | 19,707,031 | 2332 | NAV2 | 11 | 19,707,122 |
| 2333 | NAV2 | 11 | 19,713,624 | 2334 | NAV2 | 11 | 19,724,190 |
| 2335 | NAV2 | 11 | 19,727,563 | 2336 | NAV2 | 11 | 19,732,967 |
| 2337 | NAV2 | 11 | 19,733,236 | 2338 | NAV2 | 11 | 19,743,216 |
| 2339 | NAV2 | 11 | 19,916,723 | 2340 | NAV2 | 11 | 20,071,925 |
| 2341 | NAV2 | 11 | 20,077,485 | 2342 | NAV2 | 11 | 20,077,810 |
| 2343 | NAV2 | 11 | 20,078,033 | 2344 | NAV2 | 11 | 20,078,168 |
| 2345 | SLC6A5 | 11 | 20,579,618 | 2346 | SLC6A5 | 11 | 20,597,598 |
| 2347 | SLC6A5 | 11 | 20,598,252 | 2348 | SLC6A5 | 11 | 20,599,698 |
| 2349 | SLC6A5 | 11 | 20,599,788 | 2350 | SLC6A5 | 11 | 20,601,656 |
| 2351 | SLC6A5 | 11 | 20,609,196 | 2352 | NELL1 | 11 | 20,763,894 |
| 2353 | KCNA4 | 11 | 29,964,590 | 2354 | KCNA4 | 11 | 29,983,650 |
| 2355 | KCNA4 | 11 | 29,984,859 | 2356 | KCNA4 | 11 | 29,987,012 |
| 2357 | LRRC4C | 11 | 40,094,119 | 2358 | LRRC4C | 11 | 40,098,953 |
| 2359 | LRRC4C | 11 | 40,131,206 | 2360 | LRRC4C | 11 | 40,149,430 |
| 2361 | LRRC4C | 11 | 40,149,688 | 2362 | LRRC4C | 11 | 40,194,755 |
| 2363 | LRRC4C | 11 | 40,198,084 | 2364 | LRRC4C | 11 | 40,209,366 |
| 2365 | LRRC4C | 11 | 40,211,317 | 2366 | LRRC4C | 11 | 40,212,327 |
| 2367 | LRRC4C | 11 | 40,216,303 | 2368 | LRRC4C | 11 | 40,216,724 |
| 2369 | LRRC4C | 11 | 40,217,071 | 2370 | LRRC4C | 11 | 40,229,850 |
| 2371 | LRRC4C | 11 | 40,231,418 | 2372 | LRRC4C | 11 | 40,231,636 |
| 2373 | LRRC4C | 11 | 40,262,733 | 2374 | LRRC4C | 11 | 40,306,179 |
| 2375 | LRRC4C | 11 | 40,359,450 | 2376 | PHACS | 11 | 44,050,194 |
| 2377 | PHACS | 11 | 44,050,992 | 2378 | PHACS | 11 | 44,057,118 |
| 2379 | PHACS | 11 | 44,057,694 | 2380 | PHACS | 11 | 44,058,383 |
| 2381 | PHACS | 11 | 44,062,444 | 2382 | PHACS | 11 | 44,067,266 |
| 2383 | SYT13 | 11 | 45,220,853 | 2384 | SYT13 | 11 | 45,226,820 |
| 2385 | SYT13 | 11 | 45,233,558 | 2386 | SYT13 | 11 | 45,234,779 |
| 2387 | SYT13 | 11 | 45,234,893 | 2388 | SYT13 | 11 | 45,242,661 |
| 2389 | SYT13 | 11 | 45,254,175 | 2390 | CTNND1 | 11 | 57,237,199 |
| 2391 | CTNND1 | 11 | 57,257,758 | 2392 | CTNND1 | 11 | 57,312,346 |
| 2393 | CTNND1 | 11 | 57,350,416 | 2394 | CTNND1 | 11 | 57,353,641 |
| 2395 | CTNND1 | 11 | 57,353,850 | 2396 | CTNND1 | 11 | 57,380,391 |
| 2397 | DLG2 | 11 | 82,852,684 | 2398 | DLG2 | 11 | 82,866,094 |
| 2399 | DLG2 | 11 | 82,881,713 | 2400 | DLG2 | 11 | 82,882,102 |
| 2401 | DLG2 | 11 | 82,910,180 | 2402 | DLG2 | 11 | 82,913,481 |
| 2403 | DLG2 | 11 | 82,935,775 | 2404 | DLG2 | 11 | 82,970,299 |
| 2405 | DLG2 | 11 | 82,982,760 | 2406 | DLG2 | 11 | 83,004,627 |
| 2407 | DLG2 | 11 | 83,018,046 | 2408 | DLG2 | 11 | 83,018,663 |
| 2409 | DLG2 | 11 | 83,018,964 | 2410 | DLG2 | 11 | 83,036,277 |
| 2411 | DLG2 | 11 | 83,065,789 | 2412 | DLG2 | 11 | 83,083,527 |
| 2413 | DLG2 | 11 | 83,086,000 | 2414 | DLG2 | 11 | 83,086,089 |
| 2415 | DLG2 | 11 | 83,098,203 | 2416 | DLG2 | 11 | 83,099,929 |
| 2417 | DLG2 | 11 | 83,120,827 | 2418 | DLG2 | 11 | 84,210,011 |
| 2419 | DLG2 | 11 | 84,254,292 | 2420 | DLG2 | 11 | 84,307,983 |
| 2421 | ELMOD1 | 11 | 107,036,969 | 2422 | OPCML | 11 | 131,716,323 |
| 2423 | OPCML | 11 | 131,904,482 | 2424 | OPCML | 11 | 132,032,722 |
| 2425 | OPCML | 11 | 132,037,815 | 2426 | OPCML | 11 | 132,624,713 |
| 2427 | OPCML | 11 | 132,795,217 | 2428 | OPCML | 11 | 132,905,489 |
| 2429 | OPCML | 11 | 133,105,149 | 2430 | WNT5B | 12 | 1,610,432 |
| 2431 | WNT5B | 12 | 1,611,877 | 2432 | TSPAN9 | 12 | 3,053,288 |
| 2433 | TSPAN9 | 12 | 3,173,346 | 2434 | TSPAN9 | 12 | 3,257,542 |
| 2435 | TSPAN9 | 12 | 3,258,265 | 2436 | TMEM16B | 12 | 5,755,581 |
| 2437 | TMEM16B | 12 | 5,760,697 | 2438 | TMEM16B | 12 | 5,776,400 |
| 2439 | TMEM16B | 12 | 5,781,725 | 2440 | TMEM16B | 12 | 5,786,611 |
| 2441 | TMEM16B | 12 | 5,793,628 | 2442 | TMEM16B | 12 | 5,794,409 |
| 2443 | STYK1 | 12 | 10,676,279 | 2444 | STYK1 | 12 | 10,696,179 |

TABLE A-continued

Summary of SNPs (NCBI Human Genome Reference Assembly Build 36.3)

| SEQ ID NO: | Gene | Chr | Position (BP) | SEQ ID NO: | Gene | Chr | Position (BP) |
|---|---|---|---|---|---|---|---|
| 2445 | STYK1 | 12 | 10,697,552 | 2446 | STYK1 | 12 | 10,697,609 |
| 2447 | STYK1 | 12 | 10,697,767 | 2448 | STYK1 | 12 | 10,711,189 |
| 2449 | LOC729025 | 12 | 16,235,442 | 2450 | LOC729025 | 12 | 16,236,620 |
| 2451 | LOC729025 | 12 | 16,237,633 | 2452 | LOC729025 | 12 | 16,237,876 |
| 2453 | LOC729025 | 12 | 16,288,678 | 2454 | LOC729025 | 12 | 16,297,957 |
| 2455 | LOC729025 | 12 | 16,298,403 | 2456 | LOC729025 | 12 | 16,302,981 |
| 2457 | LOC729025 | 12 | 16,310,672 | 2458 | PIK3C2G | 12 | 18,212,721 |
| 2459 | PIK3C2G | 12 | 18,349,706 | 2460 | PIK3C2G | 12 | 18,356,504 |
| 2461 | PIK3C2G | 12 | 18,393,150 | 2462 | PIK3C2G | 12 | 18,459,343 |
| 2463 | PIK3C2G | 12 | 18,506,439 | 2464 | PIK3C2G | 12 | 18,701,315 |
| 2465 | ITPR2 | 12 | 26,335,364 | 2466 | ITPR2 | 12 | 26,379,772 |
| 2467 | ITPR2 | 12 | 26,383,105 | 2468 | ITPR2 | 12 | 26,476,845 |
| 2469 | ITPR2 | 12 | 26,621,910 | 2470 | ITPR2 | 12 | 26,641,098 |
| 2471 | ITPR2 | 12 | 26,650,941 | 2472 | LRP1 | 12 | 55,844,772 |
| 2473 | LRP1 | 12 | 55,847,718 | 2474 | LRP1 | 12 | 55,878,824 |
| 2475 | LRP1 | 12 | 55,909,088 | 2476 | CNOT2 | 12 | 68,893,334 |
| 2477 | CNOT2 | 12 | 68,954,824 | 2478 | KCNC2 | 12 | 73,597,214 |
| 2479 | KCNC2 | 12 | 73,597,675 | 2480 | KCNC2 | 12 | 73,855,015 |
| 2481 | NAV3 | 12 | 77,041,541 | 2482 | NAV3 | 12 | 77,042,099 |
| 2483 | NAV3 | 12 | 77,070,387 | 2484 | GAS2L3 | 12 | 99,494,084 |
| 2485 | GAS2L3 | 12 | 99,494,793 | 2486 | GAS2L3 | 12 | 99,495,794 |
| 2487 | CHST11 | 12 | 103,575,899 | 2488 | CHST11 | 12 | 103,669,570 |
| 2489 | CHST11 | 12 | 103,676,521 | 2490 | CHST11 | 12 | 103,681,081 |
| 2491 | CHST11 | 12 | 103,685,709 | 2492 | CHST11 | 12 | 103,685,984 |
| 2493 | CHST11 | 12 | 103,692,809 | 2494 | CHST11 | 12 | 103,696,050 |
| 2495 | CHST11 | 12 | 103,702,696 | 2496 | CHST11 | 12 | 103,704,275 |
| 2497 | KIAA1853 | 12 | 118,035,761 | 2498 | KIAA1853 | 12 | 118,052,804 |
| 2499 | KIAA1853 | 12 | 118,053,104 | 2500 | KIAA1853 | 12 | 118,054,044 |
| 2501 | KIAA1853 | 12 | 118,054,167 | 2502 | KIAA1853 | 12 | 118,054,447 |
| 2503 | PLA2G1B | 12 | 119,247,148 | 2504 | RIMBP2 | 12 | 129,432,804 |
| 2505 | RIMBP2 | 12 | 129,433,601 | 2506 | RIMBP2 | 12 | 129,529,219 |
| 2507 | STX2 | 12 | 129,846,370 | 2508 | STX2 | 12 | 129,854,397 |
| 2509 | STX2 | 12 | 129,879,750 | 2510 | STX2 | 12 | 129,885,052 |
| 2511 | KIAA1545 | 12 | 131,667,713 | 2512 | KIAA1545 | 12 | 131,671,419 |
| 2513 | MTIF3 | 13 | 26,909,686 | 2514 | MTIF3 | 13 | 26,939,055 |
| 2515 | MTIF3 | 13 | 26,979,535 | 2516 | UBL3 | 13 | 29,235,331 |
| 2517 | N4BP2L2 | 13 | 31,897,951 | 2518 | N4BP2L2 | 13 | 31,934,759 |
| 2519 | N4BP2L2 | 13 | 31,953,620 | 2520 | NBEA | 13 | 34,550,806 |
| 2521 | NBEA | 13 | 34,773,125 | 2522 | NBEA | 13 | 34,784,368 |
| 2523 | NBEA | 13 | 34,796,208 | 2524 | NBEA | 13 | 34,827,043 |
| 2525 | NBEA | 13 | 34,952,510 | 2526 | NBEA | 13 | 34,980,142 |
| 2527 | NBEA | 13 | 35,070,686 | 2528 | TRPC4 | 13 | 37,108,100 |
| 2529 | TRPC4 | 13 | 37,203,414 | 2530 | TRPC4 | 13 | 37,212,640 |
| 2531 | TRPC4 | 13 | 37,243,920 | 2532 | TRPC4 | 13 | 37,282,014 |
| 2533 | KPNA3 | 13 | 49,167,094 | 2534 | KPNA3 | 13 | 49,231,388 |
| 2535 | KPNA3 | 13 | 49,279,103 | 2536 | KPNA3 | 13 | 49,341,559 |
| 2537 | PCDH17 | 13 | 56,739,785 | 2538 | PCDH17 | 13 | 57,113,143 |
| 2539 | PCDH17 | 13 | 57,113,277 | 2540 | PCDH17 | 13 | 57,124,943 |
| 2541 | PCDH17 | 13 | 57,130,775 | 2542 | PCDH20 | 13 | 60,868,943 |
| 2543 | PCDH20 | 13 | 60,932,538 | 2544 | PCDH20 | 13 | 60,964,632 |
| 2545 | LMO7 | 13 | 75,283,739 | 2546 | LMO7 | 13 | 75,308,726 |
| 2547 | SLAIN1 | 13 | 77,123,666 | 2548 | SLAIN1 | 13 | 77,130,842 |
| 2549 | SLAIN1 | 13 | 77,131,233 | 2550 | SLAIN1 | 13 | 77,159,020 |
| 2551 | SLAIN1 | 13 | 77,192,498 | 2552 | SLAIN1 | 13 | 77,192,550 |
| 2553 | SLAIN1 | 13 | 77,232,218 | 2554 | GPC5 | 13 | 90,781,911 |
| 2555 | GPC5 | 13 | 90,792,026 | 2556 | GPC5 | 13 | 90,811,414 |
| 2557 | GPC5 | 13 | 90,811,945 | 2558 | GPC5 | 13 | 90,813,978 |
| 2559 | GPC5 | 13 | 90,817,618 | 2560 | GPC5 | 13 | 90,818,043 |
| 2561 | GPC5 | 13 | 92,100,968 | 2562 | GPC5 | 13 | 92,117,688 |
| 2563 | GPC5 | 13 | 92,117,738 | 2564 | GPC5 | 13 | 92,121,147 |
| 2565 | GPC5 | 13 | 92,121,270 | 2566 | GPC6 | 13 | 92,948,013 |
| 2567 | GPC6 | 13 | 93,081,095 | 2568 | GPC6 | 13 | 93,115,588 |
| 2569 | GPC6 | 13 | 93,183,430 | 2570 | GPC6 | 13 | 93,185,878 |
| 2571 | GPC6 | 13 | 93,196,895 | 2572 | GPC6 | 13 | 93,196,981 |
| 2573 | GPC6 | 13 | 93,197,927 | 2574 | GPC6 | 13 | 93,235,757 |
| 2575 | GPC6 | 13 | 93,235,896 | 2576 | GPC6 | 13 | 93,243,178 |
| 2577 | GPC6 | 13 | 93,243,273 | 2578 | GPC6 | 13 | 93,244,881 |
| 2579 | GPC6 | 13 | 93,249,369 | 2580 | GPC6 | 13 | 93,253,982 |
| 2581 | GPC6 | 13 | 93,254,425 | 2582 | GPC6 | 13 | 93,254,940 |
| 2583 | GPC6 | 13 | 93,259,422 | 2584 | GPC6 | 13 | 93,288,101 |
| 2585 | GPC6 | 13 | 93,289,027 | 2586 | GPC6 | 13 | 93,317,951 |
| 2587 | GPC6 | 13 | 93,340,807 | 2588 | GPC6 | 13 | 93,341,695 |
| 2589 | GPC6 | 13 | 93,863,160 | 2590 | NALCN | 13 | 100,499,428 |
| 2591 | NALCN | 13 | 100,499,748 | 2592 | NALCN | 13 | 100,502,077 |
| 2593 | NALCN | 13 | 100,507,599 | 2594 | NALCN | 13 | 100,510,427 |

TABLE A-continued

Summary of SNPs (NCBI Human Genome Reference Assembly Build 36.3)

| SEQ ID NO: | Gene | Chr | Position (BP) | SEQ ID NO: | Gene | Chr | Position (BP) |
|---|---|---|---|---|---|---|---|
| 2595 | NALCN | 13 | 100,511,470 | 2596 | NALCN | 13 | 100,518,301 |
| 2597 | NALCN | 13 | 100,524,314 | 2598 | NALCN | 13 | 100,524,587 |
| 2599 | NALCN | 13 | 100,530,564 | 2600 | NALCN | 13 | 100,535,000 |
| 2601 | NALCN | 13 | 100,595,841 | 2602 | NALCN | 13 | 100,742,753 |
| 2603 | ITGBL1 | 13 | 100,956,004 | 2604 | ITGBL1 | 13 | 100,973,881 |
| 2605 | ITGBL1 | 13 | 100,973,899 | 2606 | ITGBL1 | 13 | 101,140,742 |
| 2607 | ITGBL1 | 13 | 101,146,706 | 2608 | ITGBL1 | 13 | 101,163,997 |
| 2609 | ITGBL1 | 13 | 101,164,826 | 2610 | ITGBL1 | 13 | 101,165,404 |
| 2611 | ITGBL1 | 13 | 101,165,489 | 2612 | FGF14 | 13 | 101,224,288 |
| 2613 | FGF14 | 13 | 101,249,030 | 2614 | FGF14 | 13 | 101,881,550 |
| 2615 | TTC5 | 14 | 19,786,681 | 2616 | TTC5 | 14 | 19,826,727 |
| 2617 | TTC5 | 14 | 19,827,644 | 2618 | TTC5 | 14 | 19,833,934 |
| 2619 | TTC5 | 14 | 19,834,425 | 2620 | TTC5 | 14 | 19,837,458 |
| 2621 | TTC5 | 14 | 19,839,876 | 2622 | TTC5 | 14 | 19,845,685 |
| 2623 | TEP1 | 14 | 19,921,869 | 2624 | TEP1 | 14 | 19,922,610 |
| 2625 | TEP1 | 14 | 19,922,657 | 2626 | TEP1 | 14 | 19,945,109 |
| 2627 | WDR23 | 14 | 23,664,573 | 2628 | NOVA1 | 14 | 25,943,292 |
| 2629 | NOVA1 | 14 | 26,098,029 | 2630 | NOVA1 | 14 | 26,159,322 |
| 2631 | SLC25A21 | 14 | 36,224,345 | 2632 | SLC25A21 | 14 | 36,352,544 |
| 2633 | SLC25A21 | 14 | 36,558,361 | 2634 | SLC25A21 | 14 | 36,619,169 |
| 2635 | SLC25A21 | 14 | 36,727,597 | 2636 | GNG2 | 14 | 51,393,655 |
| 2637 | GNG2 | 14 | 51,394,658 | 2638 | GNG2 | 14 | 51,395,147 |
| 2639 | GNG2 | 14 | 51,406,432 | 2640 | GNG2 | 14 | 51,419,524 |
| 2641 | GNG2 | 14 | 51,422,662 | 2642 | GNG2 | 14 | 51,422,700 |
| 2643 | GNG2 | 14 | 51,428,644 | 2644 | GNG2 | 14 | 51,480,711 |
| 2645 | GNG2 | 14 | 51,480,818 | 2646 | GNG2 | 14 | 51,486,162 |
| 2647 | GNG2 | 14 | 51,520,930 | 2648 | SAMD4A | 14 | 54,092,204 |
| 2649 | SAMD4A | 14 | 54,169,379 | 2650 | SAMD4A | 14 | 54,327,340 |
| 2651 | DAAM1 | 14 | 58,765,383 | 2652 | DAAM1 | 14 | 58,768,753 |
| 2653 | DAAM1 | 14 | 58,874,752 | 2654 | DAAM1 | 14 | 58,883,684 |
| 2655 | DAAM1 | 14 | 58,899,726 | 2656 | GPR135 | 14 | 58,952,891 |
| 2657 | GPR135 | 14 | 58,954,960 | 2658 | GPR135 | 14 | 58,961,544 |
| 2659 | GPR135 | 14 | 58,963,400 | 2660 | GPR135 | 14 | 58,997,129 |
| 2661 | PPP2R5E | 14 | 62,856,367 | 2662 | PPP2R5E | 14 | 62,856,493 |
| 2663 | PPP2R5E | 14 | 63,040,607 | 2664 | PPP2R5E | 14 | 63,044,719 |
| 2665 | PPP2R5E | 14 | 63,050,455 | 2666 | PPP2R5E | 14 | 63,050,484 |
| 2667 | PPP2R5E | 14 | 63,060,864 | 2668 | PPP2R5E | 14 | 63,078,186 |
| 2669 | PPP2R5E | 14 | 63,099,534 | 2670 | PPP2R5E | 14 | 63,125,605 |
| 2671 | RGS6 | 14 | 71,433,141 | 2672 | RGS6 | 14 | 71,436,529 |
| 2673 | RGS6 | 14 | 71,727,478 | 2674 | RGS6 | 14 | 71,785,834 |
| 2675 | RGS6 | 14 | 71,789,406 | 2676 | RGS6 | 14 | 71,792,071 |
| 2677 | RGS6 | 14 | 71,793,717 | 2678 | RGS6 | 14 | 71,796,649 |
| 2679 | RGS6 | 14 | 71,801,725 | 2680 | RGS6 | 14 | 71,889,437 |
| 2681 | RGS6 | 14 | 71,979,491 | 2682 | RGS6 | 14 | 71,990,360 |
| 2683 | RGS6 | 14 | 72,012,929 | 2684 | RGS6 | 14 | 72,024,776 |
| 2685 | RGS6 | 14 | 72,124,860 | 2686 | KCNK10 | 14 | 87,843,799 |
| 2687 | KCNK10 | 14 | 87,844,293 | 2688 | KCNK10 | 14 | 87,869,850 |
| 2689 | KCNK10 | 14 | 87,874,319 | 2690 | KCNK10 | 14 | 87,874,519 |
| 2691 | KCNK10 | 14 | 87,877,121 | 2692 | KCNK10 | 14 | 87,878,632 |
| 2693 | KCNK10 | 14 | 87,881,781 | 2694 | KCNK10 | 14 | 87,887,777 |
| 2695 | KCNK13 | 14 | 89,678,960 | 2696 | KCNK13 | 14 | 89,686,350 |
| 2697 | KCNK13 | 14 | 89,697,368 | 2698 | RPS6KA5 | 14 | 90,544,201 |
| 2699 | RPS6KA5 | 14 | 90,576,018 | 2700 | CCDC88C | 14 | 90,843,321 |
| 2701 | CCDC88C | 14 | 90,862,073 | 2702 | CCDC88C | 14 | 90,914,886 |
| 2703 | CCDC88C | 14 | 90,916,433 | 2704 | CCDC88C | 14 | 90,918,598 |
| 2705 | CCDC88C | 14 | 90,919,949 | 2706 | CCDC88C | 14 | 90,920,049 |
| 2707 | CCDC88C | 14 | 90,926,910 | 2708 | CCDC88C | 14 | 90,944,709 |
| 2709 | CCDC88C | 14 | 90,960,430 | 2710 | ATXN3 | 14 | 91,626,364 |
| 2711 | ATP10A | 15 | 23,496,768 | 2712 | ATP10A | 15 | 23,504,291 |
| 2713 | ATP10A | 15 | 23,505,611 | 2714 | ATP10A | 15 | 23,507,697 |
| 2715 | ATP10A | 15 | 23,513,151 | 2716 | ATP10A | 15 | 23,653,372 |
| 2717 | ATP10A | 15 | 23,829,032 | 2718 | RYR3 | 15 | 31,507,942 |
| 2719 | RYR3 | 15 | 31,533,192 | 2720 | RYR3 | 15 | 31,534,443 |
| 2721 | RYR3 | 15 | 31,536,045 | 2722 | RYR3 | 15 | 31,542,264 |
| 2723 | RYR3 | 15 | 31,542,373 | 2724 | RYR3 | 15 | 31,545,132 |
| 2725 | RYR3 | 15 | 31,550,764 | 2726 | RYR3 | 15 | 31,551,413 |
| 2727 | RYR3 | 15 | 31,564,997 | 2728 | RYR3 | 15 | 31,566,783 |
| 2729 | RYR3 | 15 | 31,567,171 | 2730 | RYR3 | 15 | 31,623,922 |
| 2731 | RYR3 | 15 | 31,646,227 | 2732 | RYR3 | 15 | 31,744,674 |
| 2733 | RYR3 | 15 | 31,803,566 | 2734 | RYR3 | 15 | 31,921,882 |
| 2735 | C15ORF41 | 15 | 34,771,254 | 2736 | C15ORF41 | 15 | 34,847,872 |
| 2737 | C15ORF41 | 15 | 34,859,591 | 2738 | C15ORF41 | 15 | 34,862,071 |
| 2739 | C15ORF41 | 15 | 34,863,762 | 2740 | C15ORF41 | 15 | 34,863,820 |
| 2741 | C15ORF41 | 15 | 34,864,057 | 2742 | MEIS2 | 15 | 34,955,596 |
| 2743 | MEIS2 | 15 | 35,081,084 | 2744 | MEIS2 | 15 | 35,086,366 |

TABLE A-continued

Summary of SNPs (NCBI Human Genome Reference Assembly Build 36.3)

| SEQ ID NO: | Gene | Chr | Position (BP) | SEQ ID NO: | Gene | Chr | Position (BP) |
|---|---|---|---|---|---|---|---|
| 2745 | MEIS2 | 15 | 35,091,425 | 2746 | RASGRP1 | 15 | 36,656,958 |
| 2747 | KIAA1370 | 15 | 50,614,631 | 2748 | KIAA1370 | 15 | 50,617,081 |
| 2749 | UNC13C | 15 | 52,127,362 | 2750 | UNC13C | 15 | 52,127,720 |
| 2751 | UNC13C | 15 | 52,134,616 | 2752 | UNC13C | 15 | 52,176,418 |
| 2753 | UNC13C | 15 | 52,178,602 | 2754 | UNC13C | 15 | 52,179,635 |
| 2755 | UNC13C | 15 | 52,182,570 | 2756 | UNC13C | 15 | 52,222,738 |
| 2757 | UNC13C | 15 | 52,224,076 | 2758 | UNC13C | 15 | 52,243,049 |
| 2759 | UNC13C | 15 | 52,337,529 | 2760 | UNC13C | 15 | 52,337,770 |
| 2761 | UNC13C | 15 | 52,338,559 | 2762 | UNC13C | 15 | 52,357,520 |
| 2763 | UNC13C | 15 | 52,357,746 | 2764 | UNC13C | 15 | 52,465,606 |
| 2765 | UNC13C | 15 | 52,658,396 | 2766 | UNC13C | 15 | 52,682,121 |
| 2767 | UNC13C | 15 | 52,708,142 | 2768 | NEDD4 | 15 | 53,987,004 |
| 2769 | CGNL1 | 15 | 55,460,127 | 2770 | CGNL1 | 15 | 55,460,219 |
| 2771 | CGNL1 | 15 | 55,501,043 | 2772 | GRINL1A | 15 | 55,689,523 |
| 2773 | GRINL1A | 15 | 55,692,212 | 2774 | GRINL1A | 15 | 55,705,948 |
| 2775 | GRINL1A | 15 | 55,713,128 | 2776 | GRINL1A | 15 | 55,718,309 |
| 2777 | ADAM10 | 15 | 56,701,618 | 2778 | ADAM10 | 15 | 56,708,490 |
| 2779 | ADAM10 | 15 | 56,810,507 | 2780 | ADAM10 | 15 | 56,829,655 |
| 2781 | CLK3 | 15 | 72,702,941 | 2782 | TBC1D2B | 15 | 75,940,905 |
| 2783 | TBC1D2B | 15 | 76,083,890 | 2784 | TBC1D2B | 15 | 76,098,398 |
| 2785 | ARNT2 | 15 | 78,583,183 | 2786 | ARNT2 | 15 | 78,673,568 |
| 2787 | ARNT2 | 15 | 78,674,561 | 2788 | ARNT2 | 15 | 78,694,359 |
| 2789 | AKAP13 | 15 | 83,807,339 | 2790 | AKAP13 | 15 | 83,811,108 |
| 2791 | AKAP13 | 15 | 83,840,475 | 2792 | AKAP13 | 15 | 83,841,141 |
| 2793 | AKAP13 | 15 | 83,841,398 | 2794 | AKAP13 | 15 | 83,847,837 |
| 2795 | AKAP13 | 15 | 83,848,290 | 2796 | AKAP13 | 15 | 83,851,894 |
| 2797 | AKAP13 | 15 | 83,857,466 | 2798 | AKAP13 | 15 | 83,864,137 |
| 2799 | AKAP13 | 15 | 83,865,972 | 2800 | AKAP13 | 15 | 83,870,122 |
| 2801 | AKAP13 | 15 | 83,871,692 | 2802 | AKAP13 | 15 | 83,880,838 |
| 2803 | AKAP13 | 15 | 83,921,005 | 2804 | AKAP13 | 15 | 83,929,645 |
| 2805 | AKAP13 | 15 | 83,941,483 | 2806 | AKAP13 | 15 | 83,961,445 |
| 2807 | AKAP13 | 15 | 84,001,703 | 2808 | AKAP13 | 15 | 84,017,421 |
| 2809 | AKAP13 | 15 | 84,019,771 | 2810 | AKAP13 | 15 | 84,025,574 |
| 2811 | AKAP13 | 15 | 84,034,013 | 2812 | AKAP13 | 15 | 84,052,538 |
| 2813 | AKAP13 | 15 | 84,052,594 | 2814 | AKAP13 | 15 | 84,060,543 |
| 2815 | AKAP13 | 15 | 84,061,704 | 2816 | SV2B | 15 | 89,609,732 |
| 2817 | SLCO3A1 | 15 | 90,284,500 | 2818 | SLCO3A1 | 15 | 90,441,591 |
| 2819 | SLCO3A1 | 15 | 90,464,205 | 2820 | SLCO3A1 | 15 | 90,499,647 |
| 2821 | ST8SIA2 | 15 | 90,747,330 | 2822 | RGMA | 15 | 91,386,979 |
| 2823 | IGF1R | 15 | 97,045,310 | 2824 | IGF1R | 15 | 97,046,853 |
| 2825 | IGF1R | 15 | 97,049,391 | 2826 | A2BP1 | 16 | 6,249,617 |
| 2827 | A2BP1 | 16 | 6,251,202 | 2828 | A2BP1 | 16 | 6,253,029 |
| 2829 | A2BP1 | 16 | 6,657,066 | 2830 | A2BP1 | 16 | 6,688,743 |
| 2831 | A2BP1 | 16 | 7,419,133 | 2832 | A2BP1 | 16 | 7,628,696 |
| 2833 | A2BP1 | 16 | 7,629,108 | 2834 | A2BP1 | 16 | 7,630,524 |
| 2835 | A2BP1 | 16 | 7,632,187 | 2836 | A2BP1 | 16 | 7,706,480 |
| 2837 | TMC5 | 16 | 19,254,444 | 2838 | TMC5 | 16 | 19,378,267 |
| 2839 | N4BP1 | 16 | 47,114,074 | 2840 | N4BP1 | 16 | 47,129,091 |
| 2841 | GOT2 | 16 | 57,298,868 | 2842 | GOT2 | 16 | 57,300,955 |
| 2843 | GOT2 | 16 | 57,314,899 | 2844 | GOT2 | 16 | 57,317,440 |
| 2845 | GOT2 | 16 | 57,318,951 | 2846 | GOT2 | 16 | 57,319,081 |
| 2847 | GOT2 | 16 | 57,319,812 | 2848 | GOT2 | 16 | 57,360,362 |
| 2849 | GOT2 | 16 | 57,361,735 | 2850 | GOT2 | 16 | 57,361,866 |
| 2851 | GOT2 | 16 | 57,362,682 | 2852 | GOT2 | 16 | 57,394,412 |
| 2853 | GOT2 | 16 | 57,421,815 | 2854 | WWOX | 16 | 76,669,764 |
| 2855 | WWOX | 16 | 76,671,254 | 2856 | WWOX | 16 | 76,673,175 |
| 2857 | WWOX | 16 | 76,674,781 | 2858 | PLCG2 | 16 | 80,579,047 |
| 2859 | MPHOSPH6 | 16 | 80,702,549 | 2860 | MPHOSPH6 | 16 | 80,726,886 |
| 2861 | MPHOSPH6 | 16 | 80,728,226 | 2862 | MPHOSPH6 | 16 | 80,743,884 |
| 2863 | MPHOSPH6 | 16 | 80,757,604 | 2864 | MPHOSPH6 | 16 | 80,763,959 |
| 2865 | MPHOSPH6 | 16 | 80,765,783 | 2866 | MPHOSPH6 | 16 | 80,765,856 |
| 2867 | MPHOSPH6 | 16 | 80,820,057 | 2868 | CDH13 | 16 | 81,812,818 |
| 2869 | CDH13 | 16 | 81,896,946 | 2870 | CDH13 | 16 | 81,904,078 |
| 2871 | CDH13 | 16 | 81,905,756 | 2872 | CDH13 | 16 | 81,917,154 |
| 2873 | CDH13 | 16 | 82,328,997 | 2874 | CDH13 | 16 | 82,331,866 |
| 2875 | KIAA0182 | 16 | 84,248,252 | 2876 | KIAA0182 | 16 | 84,260,191 |
| 2877 | KIAA0182 | 16 | 84,263,548 | 2878 | KIAA0182 | 16 | 84,264,134 |
| 2879 | KIAA0182 | 16 | 84,269,361 | 2880 | GAS7 | 17 | 9,747,805 |
| 2881 | DNAH9 | 17 | 11,408,733 | 2882 | DNAH9 | 17 | 11,776,046 |
| 2883 | DNAH9 | 17 | 11,806,187 | 2884 | RAB11FIP4 | 17 | 26,867,375 |
| 2885 | RAB11FIP4 | 17 | 27,004,572 | 2886 | RAB11FIP4 | 17 | 27,005,299 |
| 2887 | CA10 | 17 | 47,587,715 | 2888 | CA10 | 17 | 47,983,984 |
| 2889 | CA10 | 17 | 48,008,209 | 2890 | CA10 | 17 | 48,026,031 |
| 2891 | CA10 | 17 | 48,122,155 | 2892 | CA10 | 17 | 48,154,827 |
| 2893 | MSI2 | 17 | 53,002,826 | 2894 | MSI2 | 17 | 53,007,065 |

TABLE A-continued

Summary of SNPs (NCBI Human Genome Reference Assembly Build 36.3)

| SEQ ID NO: | Gene | Chr | Position (BP) | SEQ ID NO: | Gene | Chr | Position (BP) |
|---|---|---|---|---|---|---|---|
| 2895 | SDK2 | 17 | 68,953,741 | 2896 | SDK2 | 17 | 68,954,425 |
| 2897 | DNAH17 | 17 | 73,954,236 | 2898 | DNAH17 | 17 | 74,016,132 |
| 2899 | DNAH17 | 17 | 74,017,503 | 2900 | HRNBP3 | 17 | 75,313,177 |
| 2901 | HRNBP3 | 17 | 75,313,214 | 2902 | DLGAP1 | 18 | 3,603,827 |
| 2903 | DLGAP1 | 18 | 3,605,943 | 2904 | ZFP161 | 18 | 5,237,432 |
| 2905 | ZFP161 | 18 | 5,240,346 | 2906 | ZFP161 | 18 | 5,251,246 |
| 2907 | ZFP161 | 18 | 5,280,198 | 2908 | ZFP161 | 18 | 5,283,875 |
| 2909 | ZFP161 | 18 | 5,283,943 | 2910 | ZFP161 | 18 | 5,284,323 |
| 2911 | PTPRM | 18 | 7,978,643 | 2912 | PTPRM | 18 | 8,000,444 |
| 2913 | PTPRM | 18 | 8,012,573 | 2914 | PTPRM | 18 | 8,013,359 |
| 2915 | PTPRM | 18 | 8,021,623 | 2916 | PTPRM | 18 | 8,024,067 |
| 2917 | PTPRM | 18 | 8,040,886 | 2918 | PTPRM | 18 | 8,042,261 |
| 2919 | PTPRM | 18 | 8,059,868 | 2920 | PTPRM | 18 | 8,068,553 |
| 2921 | PTPRM | 18 | 8,070,357 | 2922 | PTPRM | 18 | 8,075,047 |
| 2923 | PTPRM | 18 | 8,086,608 | 2924 | KIAA0802 | 18 | 8,832,312 |
| 2925 | KIAA0802 | 18 | 8,833,160 | 2926 | KIAA0802 | 18 | 8,839,087 |
| 2927 | KIAA0802 | 18 | 8,840,062 | 2928 | KIAA0802 | 18 | 8,844,132 |
| 2929 | OSBPL1A | 18 | 20,042,294 | 2930 | OSBPL1A | 18 | 20,076,380 |
| 2931 | OSBPL1A | 18 | 20,093,929 | 2932 | CHST9 | 18 | 22,940,363 |
| 2933 | CHST9 | 18 | 22,960,659 | 2934 | CHST9 | 18 | 22,965,754 |
| 2935 | CHST9 | 18 | 23,000,286 | 2936 | CHST9 | 18 | 23,010,213 |
| 2937 | CHST9 | 18 | 23,012,354 | 2938 | CHST9 | 18 | 23,015,926 |
| 2939 | FUSSEL18 | 18 | 43,092,404 | 2940 | FUSSEL18 | 18 | 43,096,405 |
| 2941 | FUSSEL18 | 18 | 43,105,881 | 2942 | KIAA0427 | 18 | 44,356,926 |
| 2943 | KIAA0427 | 18 | 44,410,788 | 2944 | KIAA0427 | 18 | 44,488,963 |
| 2945 | KIAA0427 | 18 | 44,489,439 | 2946 | KIAA0427 | 18 | 44,494,468 |
| 2947 | KIAA0427 | 18 | 44,494,709 | 2948 | KIAA0427 | 18 | 44,495,161 |
| 2949 | KIAA0427 | 18 | 44,594,841 | 2950 | KIAA0427 | 18 | 44,622,539 |
| 2951 | DCC | 18 | 48,523,497 | 2952 | DCC | 18 | 48,581,071 |
| 2953 | DCC | 18 | 48,606,324 | 2954 | DCC | 18 | 48,607,209 |
| 2955 | DCC | 18 | 48,608,936 | 2956 | DCC | 18 | 48,609,120 |
| 2957 | DCC | 18 | 48,609,275 | 2958 | DCC | 18 | 48,609,314 |
| 2959 | DCC | 18 | 48,709,007 | 2960 | DCC | 18 | 48,872,357 |
| 2961 | DCC | 18 | 48,876,855 | 2962 | DCC | 18 | 48,877,638 |
| 2963 | DCC | 18 | 49,023,541 | 2964 | DCC | 18 | 49,067,285 |
| 2965 | DCC | 18 | 49,159,204 | 2966 | DCC | 18 | 49,159,355 |
| 2967 | DCC | 18 | 49,159,861 | 2968 | DCC | 18 | 49,160,029 |
| 2969 | DCC | 18 | 49,311,296 | 2970 | NEDD4L | 18 | 53,901,050 |
| 2971 | NEDD4L | 18 | 53,910,209 | 2972 | NEDD4L | 18 | 53,913,025 |
| 2973 | NEDD4L | 18 | 54,257,576 | 2974 | CCBE1 | 18 | 55,266,769 |
| 2975 | TXNDC10 | 18 | 64,472,145 | 2976 | TXNDC10 | 18 | 64,477,750 |
| 2977 | TXNDC10 | 18 | 64,478,795 | 2978 | TXNDC10 | 18 | 64,483,488 |
| 2979 | TXNDC10 | 18 | 64,509,383 | 2980 | TXNDC10 | 18 | 64,531,445 |
| 2981 | TXNDC10 | 18 | 64,536,945 | 2982 | TXNDC10 | 18 | 64,644,387 |
| 2983 | DOK6 | 18 | 65,007,777 | 2984 | DOK6 | 18 | 65,239,042 |
| 2985 | DOK6 | 18 | 65,284,947 | 2986 | DOK6 | 18 | 65,290,269 |
| 2987 | DOK6 | 18 | 65,297,738 | 2988 | DOK6 | 18 | 65,312,795 |
| 2989 | DOK6 | 18 | 65,312,915 | 2990 | DOK6 | 18 | 65,323,078 |
| 2991 | DOK6 | 18 | 65,324,331 | 2992 | DOK6 | 18 | 65,413,042 |
| 2993 | DOK6 | 18 | 65,421,361 | 2994 | DOK6 | 18 | 65,437,247 |
| 2995 | DOK6 | 18 | 65,637,817 | 2996 | MBP | 18 | 72,849,372 |
| 2997 | MBP | 18 | 72,851,555 | 2998 | MBP | 18 | 72,856,606 |
| 2999 | MBP | 18 | 73,014,458 | 3000 | MBP | 18 | 73,015,500 |
| 3001 | LDLR | 19 | 11,097,804 | 3002 | ZNF667 | 19 | 61,676,582 |
| 3003 | ZNF667 | 19 | 61,678,984 | 3004 | ATRN | 20 | 3,553,336 |
| 3005 | RNF24 | 20 | 3,865,215 | 3006 | RNF24 | 20 | 3,865,397 |
| 3007 | RNF24 | 20 | 3,882,766 | 3008 | RNF24 | 20 | 3,941,491 |
| 3009 | PRNT | 20 | 4,653,718 | 3010 | PRNT | 20 | 4,653,865 |
| 3011 | PRNT | 20 | 4,667,449 | 3012 | PRNT | 20 | 4,679,109 |
| 3013 | PRNT | 20 | 4,679,377 | 3014 | FERMT1 | 20 | 5,998,478 |
| 3015 | FERMT1 | 20 | 6,010,641 | 3016 | FERMT1 | 20 | 6,025,907 |
| 3017 | FERMT1 | 20 | 6,033,216 | 3018 | FERMT1 | 20 | 6,037,513 |
| 3019 | FERMT1 | 20 | 6,037,952 | 3020 | PLCB1 | 20 | 8,062,704 |
| 3021 | PLCB1 | 20 | 8,082,140 | 3022 | PLCB1 | 20 | 8,092,135 |
| 3023 | PLCB1 | 20 | 8,109,126 | 3024 | PLCB1 | 20 | 8,198,182 |
| 3025 | PLCB1 | 20 | 8,198,311 | 3026 | PLCB1 | 20 | 8,318,230 |
| 3027 | PLCB1 | 20 | 8,340,262 | 3028 | PLCB4 | 20 | 9,114,332 |
| 3029 | PLCB4 | 20 | 9,119,736 | 3030 | PLCB4 | 20 | 9,129,662 |
| 3031 | PLCB4 | 20 | 9,137,987 | 3032 | PLCB4 | 20 | 9,142,973 |
| 3033 | PLCB4 | 20 | 9,411,693 | 3034 | PLCB4 | 20 | 9,418,063 |
| 3035 | PLCB4 | 20 | 9,419,575 | 3036 | JAG1 | 20 | 10,587,841 |
| 3037 | JAG1 | 20 | 10,589,470 | 3038 | JAG1 | 20 | 10,589,575 |

TABLE A-continued

Summary of SNPs (NCBI Human Genome Reference Assembly Build 36.3)

| SEQ ID NO: | Gene | Chr | Position (BP) | SEQ ID NO: | Gene | Chr | Position (BP) |
|---|---|---|---|---|---|---|---|
| 3039 | MACROD2 | 20 | 14,254,953 | 3040 | MACROD2 | 20 | 15,085,117 |
| 3041 | MACROD2 | 20 | 15,413,513 | 3042 | MACROD2 | 20 | 15,414,269 |
| 3043 | MACROD2 | 20 | 15,424,726 | 3044 | MACROD2 | 20 | 15,438,760 |
| 3045 | MACROD2 | 20 | 15,443,389 | 3046 | MACROD2 | 20 | 15,756,444 |
| 3047 | MACROD2 | 20 | 15,775,930 | 3048 | MACROD2 | 20 | 15,780,282 |
| 3049 | MACROD2 | 20 | 15,951,406 | 3050 | KIF16B | 20 | 16,200,981 |
| 3051 | KIF16B | 20 | 16,418,749 | 3052 | PTPRT | 20 | 40,087,340 |
| 3053 | PTPRT | 20 | 40,173,455 | 3054 | PTPRT | 20 | 40,508,810 |
| 3055 | PTPRT | 20 | 40,510,165 | 3056 | PTPRT | 20 | 40,515,646 |
| 3057 | PTPRT | 20 | 40,714,518 | 3058 | PTPRT | 20 | 40,781,649 |
| 3059 | KCNB1 | 20 | 47,550,362 | 3060 | PTGIS | 20 | 47,554,184 |
| 3061 | PTGIS | 20 | 47,563,113 | 3062 | PTGIS | 20 | 47,563,394 |
| 3063 | PTGIS | 20 | 47,563,735 | 3064 | PTGIS | 20 | 47,600,610 |
| 3065 | BMP7 | 20 | 55,192,062 | 3066 | BMP7 | 20 | 55,237,584 |
| 3067 | BMP7 | 20 | 55,238,534 | 3068 | BMP7 | 20 | 55,243,363 |
| 3069 | BMP7 | 20 | 55,257,169 | 3070 | BMP7 | 20 | 55,258,167 |
| 3071 | GNAS | 20 | 56,912,202 | 3072 | GNAS | 20 | 56,919,207 |
| 3073 | CDH4 | 20 | 59,236,556 | 3074 | CDH4 | 20 | 59,263,242 |
| 3075 | CDH4 | 20 | 59,287,333 | 3076 | CDH4 | 20 | 59,349,681 |
| 3077 | CDH4 | 20 | 59,408,443 | 3078 | CDH4 | 20 | 59,409,551 |
| 3079 | CDH4 | 20 | 59,410,397 | 3080 | CDH4 | 20 | 59,411,482 |
| 3081 | CDH4 | 20 | 59,439,102 | 3082 | CDH4 | 20 | 59,513,826 |
| 3083 | CDH4 | 20 | 59,708,684 | 3084 | CDH4 | 20 | 59,709,160 |
| 3085 | CDH4 | 20 | 59,710,358 | 3086 | CDH4 | 20 | 59,832,199 |
| 3087 | CDH4 | 20 | 59,852,651 | 3088 | CDH4 | 20 | 59,854,564 |
| 3089 | CDH4 | 20 | 59,855,625 | 3090 | NCAM2 | 21 | 20,820,603 |
| 3091 | NCAM2 | 21 | 20,822,764 | 3092 | NCAM2 | 21 | 20,823,179 |
| 3093 | NCAM2 | 21 | 21,401,668 | 3094 | NCAM2 | 21 | 21,485,064 |
| 3095 | NCAM2 | 21 | 21,654,800 | 3096 | NCAM2 | 21 | 21,654,816 |
| 3097 | NCAM2 | 21 | 21,658,511 | 3098 | NCAM2 | 21 | 21,664,277 |
| 3099 | NCAM2 | 21 | 21,667,058 | 3100 | NCAM2 | 21 | 21,670,625 |
| 3101 | NCAM2 | 21 | 21,677,311 | 3102 | NCAM2 | 21 | 21,686,082 |
| 3103 | NCAM2 | 21 | 21,692,759 | 3104 | NCAM2 | 21 | 21,706,609 |
| 3105 | NCAM2 | 21 | 21,717,043 | 3106 | NCAM2 | 21 | 21,722,038 |
| 3107 | NCAM2 | 21 | 21,770,148 | 3108 | NCAM2 | 21 | 21,772,362 |
| 3109 | ERG | 21 | 38,829,307 | 3110 | PCP4 | 21 | 40,190,608 |
| 3111 | PCP4 | 21 | 40,196,614 | 3112 | PCP4 | 21 | 40,198,160 |
| 3113 | SLC37A1 | 21 | 42,826,920 | 3114 | SLC37A1 | 21 | 42,829,968 |
| 3115 | SLC37A1 | 21 | 42,833,146 | 3116 | SLC37A1 | 21 | 42,895,327 |
| 3117 | PDE9A | 21 | 42,977,018 | 3118 | PDE9A | 21 | 42,990,494 |
| 3119 | PDE9A | 21 | 43,064,200 | 3120 | ARVCF | 22 | 18,342,203 |
| 3121 | ASPHD2 | 22 | 25,171,390 | 3122 | ASPHD2 | 22 | 25,171,643 |
| 3123 | HPS4 | 22 | 25,174,769 | 3124 | TTLL1 | 22 | 41,800,470 |
| 3125 | EFCAB6 | 22 | 42,373,315 | 3126 | EFCAB6 | 22 | 42,397,103 |
| 3127 | EFCAB6 | 22 | 42,417,370 | 3128 | EFCAB6 | 22 | 42,454,850 |
| 3129 | EFCAB6 | 22 | 42,521,911 | 3130 | SULT4A1 | 22 | 42,542,231 |
| 3131 | SULT4A1 | 22 | 42,551,476 | 3132 | SULT4A1 | 22 | 42,570,832 |
| 3133 | SULT4A1 | 22 | 42,580,796 | 3134 | SULT4A1 | 22 | 42,581,963 |
| 3135 | SULT4A1 | 22 | 42,582,522 | 3136 | SULT4A1 | 22 | 42,603,569 |
| 3137 | SULT4A1 | 22 | 42,603,783 | 3138 | RIBC2 | 22 | 44,257,648 |
| 3139 | RIBC2 | 22 | 44,258,667 | 3140 | RIBC2 | 22 | 44,265,997 |
| 3141 | RIBC2 | 22 | 44,271,097 | | | | |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08129117B2). An electronic copy of the "Sequence Listing" will also be available from the USPTO upon request and payment of the fee set forth in 37 CFR 1.19(b)(3).

What is claimed is:

1. A method of determining relative risk of developing bipolar disorder (BD) versus schizophrenia (SZ) in a human subject, the method comprising:
obtaining a sample comprising genomic DNA from the subject;
determining the identity of an allele of a single nucleotide polymorphism (SNP) at rs2291100 in the sample; and
identifying a subject who has a cytosine (C) allele at rs2291100 as having an increased risk of developing SZ instead of BD, as compared to a subject lacking a C allele at rs2291100.

2. The method of claim 1, wherein determining the identity of an allele at rs2291100 comprises:
contacting the sample with a probe specific for an allele at rs2291100; and
detecting the formation of complexes between the probe and the allele,
wherein the formation of complexes between the probe and the allele indicates the presence of the selected allele in the sample.

3. The method of claim 1, wherein determining the identity of an allele at rs2291100 comprises determining the identity of the nucleotide at position 31 of SEQ ID NO: 509.

4. The method of claim 1, wherein the subject is a patient having or suspected of having BD or SZ.

5. The method of claim 1, wherein the subject has one or more risk factors associated with BD or SZ.

6. The method of claim 5, wherein the risk factors associated with BD or SZ include one or more of: a relative afflicted with BD or SZ; and a genetically based phenotypic trait associated with risk for BD or SZ.

7. The method of claim 1, wherein the subject has exhibited or exhibits symptoms of psychosis.

8. The method of claim 1, further comprising selecting or excluding a subject for enrollment in a clinical trial based on the identity of the allele.

9. The method of claim 1, further comprising stratifying a subject population for analysis of a clinical trial based on the identity of the allele in the subjects.

10. The method of claim 1, further comprising confirming a diagnosis of SZ or BD using psychometric instruments.

11. The method of claim 1, further comprising selecting a treatment for BD if the allele in the subject indicates that the subject has an increased risk of developing BD, or selecting a treatment for SZ if an allele in the subject indicates that the subject has an increased risk of developing SZ.

12. The method of claim 11, further comprising administering the selected treatment to the subject.

13. The method of claim 11, wherein the treatment is psychotherapy.

14. The method of claim 7, wherein the psychosis is associated with BD or SZ.

15. The method of claim 1, further comprising recording the identity of the allele in a tangible medium.

16. The method of claim 15, wherein the tangible medium comprises a computer-readable disk, a solid state memory device, or an optical storage device.

17. The method of claim 1, comprising determining the identity of both alleles at rs2291100 in the sample, and identifying a subject who has two C alleles at rs2291100 as having an increased risk of developing SZ instead of BD, as compared to a subject having one C allele at rs2291100 or lacking a C allele at rs2291100.

* * * * *

UNITED STATES PATENT AND TRADEMARK OFFICE
CERTIFICATE OF CORRECTION

PATENT NO. : 8,129,117 B2  
APPLICATION NO. : 12/612521  
DATED : March 6, 2012  
INVENTOR(S) : Mark David Brennan et al.

Page 1 of 1

It is certified that error appears in the above-identified patent and that said Letters Patent is hereby corrected as shown below:

Title Page, Col. 2, Line 2, Item [56] Other Publications, delete "Curent" and insert -- Current --

Title Page, Col. 2, Line 2, Item [56] Other Publications, delete "Pharamacology" and insert -- Pharmacology --

In the Claims

Col. 153, Line 13, Claim 2, delete "1," and insert -- 1, --

Col. 153, Line 21, Claim 2, after "presence of the" delete "selected"

Col. 153, Line 28, Claim 5, delete "1," and insert -- 1, --

Signed and Sealed this  
Sixteenth Day of April, 2013

Teresa Stanek Rea  
*Acting Director of the United States Patent and Trademark Office*